US009718840B2

(12) United States Patent
Ikuma et al.

(10) Patent No.: US 9,718,840 B2
(45) Date of Patent: Aug. 1, 2017

(54) CONDENSED 5-OXAZOLIDINONE DERIVATIVE

(71) Applicant: SUMITOMO DAINIPPON PHARMA CO., LTD., Osaka-shi, Osaka (JP)

(72) Inventors: Yohei Ikuma, Osaka (JP); Masato Iwata, Osaka (JP); Chongkwang Lee, Osaka (JP)

(73) Assignee: SUMITOMO DAINIPPON PHARMA CO., LTD., Osaka-shi (JP)

( * ) Notice: Subject to any disclaimer, the term of this patent is extended or adjusted under 35 U.S.C. 154(b) by 0 days.

(21) Appl. No.: 15/110,811

(22) PCT Filed: Sep. 12, 2014

(86) PCT No.: PCT/JP2014/074768
§ 371 (c)(1),
(2) Date: Sep. 26, 2016

(87) PCT Pub. No.: WO2015/107724
PCT Pub. Date: Jul. 23, 2015

(65) Prior Publication Data

US 2017/0022218 A1 Jan. 26, 2017

(30) Foreign Application Priority Data

Jan. 14, 2014 (JP) ................................ 2014-004252

(51) Int. Cl.
*C07D 498/04* (2006.01)
*A61K 31/424* (2006.01)
(Continued)

(52) U.S. Cl.
CPC .......... *C07D 498/04* (2013.01); *A61K 31/404* (2013.01); *A61K 31/424* (2013.01);
(Continued)

(58) Field of Classification Search
None
See application file for complete search history.

(56) References Cited

U.S. PATENT DOCUMENTS

2005/0080367 A1 4/2005 March et al.
2006/0183739 A1 8/2006 Tsaklakidis et al.
(Continued)

FOREIGN PATENT DOCUMENTS

JP 2006522033 A 9/2006
JP 2006527708 A 12/2006
(Continued)

OTHER PUBLICATIONS

Jonas Emsley, et al. "Structure and function of factor XI", Blood, 2010; vol. 115 (13): pp. 2569-2577.
(Continued)

*Primary Examiner* — Karl J Puttlitz
(74) *Attorney, Agent, or Firm* — Sughrue Mion, PLLC

(57) ABSTRACT

Provided are condensed 5-oxazolidinone derivatives and pharmaceutically permissible salts thereof, which have excellent anticoagulant effects, are well absorbed orally, and are useful as therapeutic drugs for thrombosis, etc. Compounds represented by formula (1) and pharmaceutically permissible salts thereof. [In the formula, L represents a $C_1$-$C_4$ alkylene group that may be substituted; $R^{11}$ and $R^{12}$ each independently represent a hydrogen atom or $C_1$-$C_6$ alkyl group, etc. that may be substituted; $X^1$ represents N or $CR^1$; $R^1$ and $R^2$ each independently represent a hydrogen atom, halogen atom, or $C_1$-$C_6$ alkyl group; $R^a$ represents a $C_4$-$C_7$ cycloalkyl group, etc. that may be substituted; and $R^b$ represents a hydrogen atom, etc.]

31 Claims, 2 Drawing Sheets

(51) Int. Cl.

| | |
|---|---|
| ***A61K 31/454*** | (2006.01) |
| ***A61K 45/06*** | (2006.01) |
| ***A61K 31/404*** | (2006.01) |
| ***C07B 59/00*** | (2006.01) |
| ***C07D 401/14*** | (2006.01) |
| ***C07D 403/12*** | (2006.01) |
| ***C12P 17/16*** | (2006.01) |
| ***C12P 17/18*** | (2006.01) |

(52) U.S. Cl.
CPC ............ *A61K 31/454* (2013.01); *A61K 45/06* (2013.01); *C07B 59/002* (2013.01); *C07D 401/14* (2013.01); *C07D 403/12* (2013.01); *C12P 17/165* (2013.01); *C12P 17/188* (2013.01); *C07B 2200/05* (2013.01)

(56) References Cited

U.S. PATENT DOCUMENTS

| | | | |
|---|---|---|---|
| 2007/0093472 | A1 | 4/2007 | Mederski et al. |
| 2008/0003214 | A1 | 1/2008 | Cezanne et al. |
| 2015/0152048 | A1 | 6/2015 | Imagawa et al. |

FOREIGN PATENT DOCUMENTS

| | | | |
|---|---|---|---|
| JP | 2008513387 | A | 5/2008 |
| WO | 2005080367 | A1 | 9/2005 |
| WO | 2013118805 | A1 | 8/2013 |
| WO | 2013174937 | A1 | 11/2013 |

OTHER PUBLICATIONS

William A. Schumacher, et al. “Inhibition of Factor Xla as a New Approach to Anticoagulation”, Arterioscler. Thromb. Vasc. Biol., 2010; 30: pp. 388-392.

X. Wang, et al. “Effects of factor XI deficiency on ferric chloride-induced vena cava thrombosis in mice”; J Thromb Haemost 2006; 4: pp. 1982-1988.

International Search Report, issued by International Searching Authority in corresponding International Application No. PCT/JP2014/074768, on Jan. 13, 2015.

Alan R. Katritzky, et al. “Novel Synthesis of Bicycles with Fused Pyrrole, Indole, Oxazole, and Imidazole Rings”, Journal of Organic Chemistry, 2004, vol. 69, No. 26, pp. 9313-9315.

Written Opinion of the International Searching Authority, issued in corresponding International Application No. PCT/JP2014/0747687, on Jan. 13, 2015.

International Preliminary Report on Patentability issued from the International Bureau in counterpart International Application No. PCT/JP2014/074768, issued on Jul. 19, 2016.

CONDENSED 5-OXAZOLIDINONE DERIVATIVE

CROSS REFERENCE TO RELATED APPLICATIONS

This application is a National Stage of International Application No. PCT/JP2014/074768 filed Sep. 12, 2014, claiming priority based on Japanese Patent Application No. 2014-004252 filed Jan. 14, 2014, the contents of all of which are incorporated herein by reference in their entirety.

TECHNICAL FIELD

The present invention relates to a novel condensed 5-oxazolidinone derivative or a pharmaceutically acceptable salt thereof which can be orally administered as an anticoagulant.

BACKGROUND ART

Atherothrombosis which induces myocardial infarction, brain infarction, or the like and develops due to arteriosclerosis, and deep venous thrombosis which induces pulmonary embolism is are leading causes of human deaths. Warfarin, which is currently most used as an anticoagulant with the indication for the "treatment and prevention of thromboembolism (venous thrombosis, myocardial infarction, pulmonary embolism, brain embolism, slowly progressive cerebral thrombosis, etc.)", exhibits an excellent antithrombotic effect, whereas this anticoagulant disadvantageously hinders arrest of bleeding and causes hemorrhagic complications as severe adverse reaction. Against this backdrop, there has been a strong demand for the development of therapeutic and prophylactic agents for thrombosis or thromboembolism having a novel mechanism of action that suppresses the growth of pathological thrombus and does not influence arrest of bleeding from vascular vessels.

Many blood coagulation factors (cascade) are known to participate in arrest of bleeding and thrombus formation. Accordingly, if a particular blood coagulation factor can be controlled by elucidating the mechanisms of action of individual blood coagulation factors, this may work as a promising approach to solve the problems described above. In recent years, factor XI (FXI), which is one of the intrinsic blood coagulation factors, has been found to be greatly involved in the growth of pathological thrombus (see Non Patent Literatures 1 and 2). Specifically, it has been revealed that the enhanced blood coagulation cascade that yields activated factor XI (FXIa) from FXI plays an important role in the course of growth of pathological thrombus. It has been further revealed that FXI is not involved in the mechanism underlying arrest of bleeding. In actuality, research using FXI-knockout mice has confirmed an antithrombogenic effect in venous thrombus models and demonstrated that this effect does not influence the time required for arrest of bleeding (see Non Patent Literature 3). Thus, the inhibition of the functions of FXIa (hereinafter, also referred to as FXIa inhibition) is a very attractive approach to solve the problems described above.

Patent Literature 1 discloses that a 3-substituted proline derivative represented by the following formula has excellent FXIa inhibition activity and is useful as a drug for treating thrombosis and thromboembolism:

(1)

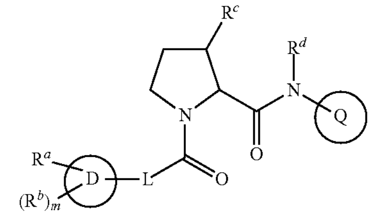

(3a')

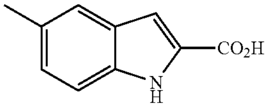

wherein ring D represents a phenyl ring or a 5- or 6-membered heteroaryl ring; m represents 0, 1, or 2; $R^a$ represents an optionally substituted 5- to 10-membered heteroaryl group or the like; a plurality of $R^b$ moieties each independently represent a halogen atom or the like; L represents $—CR^{61}═CR^{71}—$, $—CR^{61}R^{62}—CR^{71}R^{72}—$, $—NR^{61}—C(═O)—$, or $—CR^{61}R^{62}—NR^{71}—$ wherein $R^{61}$, $R^{62}$, $R^{71}$, and $R^{72}$ each independently represent a hydrogen atom or the like; $R^c$ represents an optionally substituted $C_{6-10}$ aryl group or the like; Rd represents a hydrogen atom or the like; and ring Q represents a group represented by formula (3a') or the like.

Patent Literature 2 discloses that a pyrrolidine derivative represented by the following formula (I) has selective FXIa inhibition activity and is useful as a drug for treating thromboembolism:

[Formula 2]

(I)

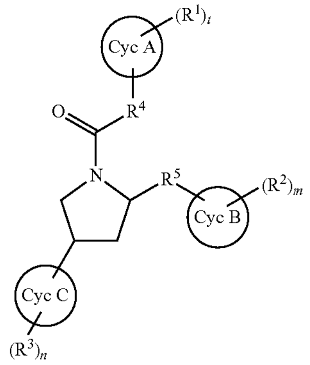

wherein Cyc A represents $C_3$-$C_8$ cycloalkyl or the like; Cyc B represents $C_6$-$C_{10}$ aryl, 5- to 10-membered heteroaryl, or the like; Cyc C represents $C_3$-$C_8$ cycloalkyl or the like; $R^1$ represents —C1-4 alkylene-$NH_2$ or the like; t represents 0 to 6; $R^2$ represents —COOH or the like; m represents 0 to 6; $R^3$ represents —CO—$NH_2$ or the like; n represents 0 to 6; $R^4$ represents a single bond or the like; and $R^5$ represents —CO—NH— or the like.

CITATION LIST

Patent Literature

Patent Literature 1: International Publication No. WO 2013/118805

Patent Literature 2: International Publication No. WO 2013/174937

Non Patent Literature

Non Patent Literature 1: Blood 2010, 115, 2569.
Non Patent Literature 2: Arterioscler Thromb Vasc Biol 2010, 30, 388.
Non Patent Literature 3: J. Thromb. Haemost. 2006, 4, 1982.

SUMMARY OF INVENTION

Technical Problem

In clinical setting, it is desirable that some administration routes should be selectable for medication, because of therapeutic purposes, patients' circumstances, etc. Particularly, oral agents are clinically very important because the oral agents, compared with injections, are administered easily and conveniently and can also be administered at home. Thus, there has been a strong demand for the development of anticoagulants having excellent oral absorbability.

An object of the present invention is to provide a novel compound that has an excellent anticoagulant effect and oral absorbability and is useful as a drug for treating thrombosis, thromboembolism, or the like.

Solution to Problem

The present inventors have conducted diligent studies to attain the object and consequently completed the present invention by finding that a compound represented by formula (1) given below and a pharmaceutically acceptable salt thereof (hereinafter, also collectively referred to as the "present compound") is a novel compound that differs structurally from the pyrrolidine derivatives represented by the formulas shown in Patent Literatures 1 and 2 in terms of having a tricyclic condensed oxazolidinone ring at the terminal portion of its side chain, and this compound exhibits excellent oral absorbability and acts as a prodrug that is converted to a carboxylic form having strong FXIa inhibition activity through in vivo metabolism.

Specifically, the present invention is as follows:

[1] A compound represented by formula (1) or a pharmaceutically acceptable salt thereof:

[Formula 3]

(1)

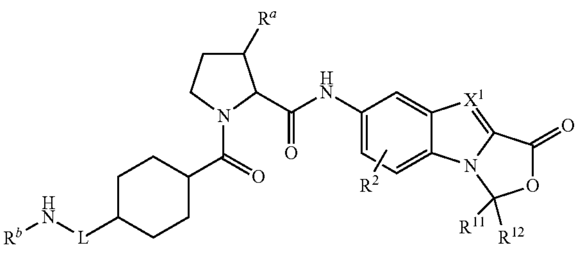

wherein

L represents an optionally substituted $C_{1-4}$ alkylene group;

$R^{11}$ and $R^{12}$ each independently represent a hydrogen atom, an optionally substituted $C_{1-6}$ alkyl group, an optionally substituted $C_3$ cycloalkyl group, an optionally substituted phenyl group, an optionally substituted 5- or 6-membered heteroaryl group, or an optionally substituted 3- to 8-membered saturated heterocyclic group, or together form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of a halogen atom, hydroxy, cyano, $C_{1-6}$ alkoxy, and $C_{1-6}$ alkyl;

$X^1$ represents N or $CR^1$;

$R^1$ and $R^2$ each independently represent a hydrogen atom, a halogen atom, a $C_{1-6}$ alkoxy group, or a $C_{1-6}$ alkyl group;

$R^a$ represents an optionally substituted $C_{4-7}$ cycloalkyl group, an optionally substituted phenyl group, an optionally substituted pyridyl group, an optionally substituted 4- to 7-membered saturated heterocyclic group, an optionally substituted $C_{1-6}$ alkoxy group, an optionally substituted $C_{4-7}$ cycloalkoxy group, an optionally substituted phenoxy group, or an optionally substituted 4- to 7-membered saturated heterocyclyloxy group; and $R^b$ represents a hydrogen atom, a $C_{1-6}$ alkoxycarbonyl group, a group represented by the following formula (2a):

[Formula 4]

(2a)

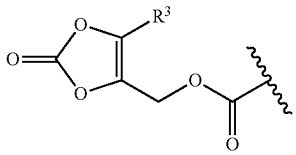

wherein $R^3$ represents a hydrogen atom or a $C_{1-6}$ alkyl group, or a group represented by the following formula (2b):

[Formula 5]

(2b)

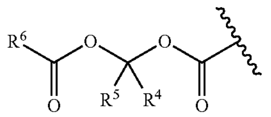

wherein $R^4$ and $R^5$ each independently represent a hydrogen atom or a $C_{1-6}$ alkyl group; and $R^6$ represents a $C_{1-6}$ alkyl group.

[2] The compound according to [1] or a pharmaceutically acceptable salt thereof, wherein L is a $C_{1-4}$ alkylene group which may be optionally substituted by 1 to 3 identical or different groups selected from the group consisting of a halogen atom, an oxo group, a hydroxy group, and a $C_{1-6}$ alkoxy group;

$R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the $C_{3-8}$ cycloalkyl group (3), or (6) a 3- to 8-membered saturated heterocyclic group which may be optionally substituted by 1 to 4 identical or different groups selected from the group consisting of the substituents (a) to (f) in the $C_{3-8}$ cycloalkyl group (3), or $R^{11}$ and $R^{12}$ together form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_3$ cycloalkyl group (3); and $R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (2) a phenyl group which may be optionally substituted by 1 to 4 identical or different groups selected from the group consisting of the substituents (a) to (e) in the $C_{4-7}$ cycloalkyl (1), (3) a pyridyl group which may be optionally substituted by 1 to 4 identical or different groups selected from the group consisting of the substituents (a) to (e) in the $C_{4-7}$ cycloalkyl (1), (4) a 4- to 7-membered saturated heterocyclic group which may be optionally substituted by 1 to 4 identical or different groups selected from the group consisting of the substituents (a) to (f) in the $C_{4-7}$ cycloalkyl (1), or (5) a $C_{1-6}$ alkoxy group which may be optionally substituted by (a) a halogen atom, (b) $C_{1-6}$ alkoxy, (c) $C_{4-7}$ cycloalkyl which may be optionally substituted by 1 to 4 identical or different groups selected from the group consisting of the substituents (a) to (f) in the $C_{4-7}$ cycloalkyl (1), (d) phenyl which may be optionally substituted by 1 to 4 identical or different groups selected from the group consisting of the substituents (a) to (e) in the $C_{4-7}$ cycloalkyl (1), (e) pyridyl which may be optionally substituted by 1 to 3 identical or different groups selected from the group consisting of the substituents (a) to (e) in the $C_{4-7}$ cycloalkyl (1), or (f) a 4- to 7-membered saturated heterocyclic ring which may be optionally substituted by 1 to 4 identical or different groups selected from the group consisting of the substituents (a) to (f) in the $C_{4-7}$ cycloalkyl (1), (6) a $C_{4-7}$ cycloalkoxy group which may be optionally substituted by 1 to 4 identical or different groups selected from the group consisting of the substituents (a) to (f) in the $C_{4-7}$ cycloalkyl (1), (7) a phenoxy group which may be optionally substituted by 1 to 4 identical or different groups selected from the group consisting of the substituents (a) to (e) in the $C_{4-7}$ cycloalkyl (1), or (8) a 4- to 7-membered saturated heterocyclyloxy group which may be optionally substituted by 1 to 4 identical or different groups selected from the group consisting of the substituents (a) to (f) in the $C_{4-7}$ cycloalkyl (1).

[3] The compound according to [1] or a pharmaceutically acceptable salt thereof, wherein L is a $C_{1-4}$ alkylene group which may be optionally substituted by 1 to 3 identical or different groups selected from the group consisting of a halogen atom, an oxo group, a hydroxy group, and a $C_{1-6}$ alkoxy group;

$R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the $C_{3-8}$ cycloalkyl group (3), or (6) a 3- to 8-membered saturated heterocyclic group which may be optionally substituted by 1 to 4 identical or different groups selected from the group consisting of the substituents (a) to (e) in the $C_{3-8}$ cycloalkyl group (3), or $R^{11}$ and $R^{12}$ together form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_{3-8}$ cycloalkyl group (3); and $R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (2) a phenyl group which may be optionally substituted by 1 to 4 identical or different groups selected from the group consisting of the substituents (a) to (e) in the $C_{4-7}$ cycloalkyl (1), (3) a pyridyl group which may be optionally substituted by 1 to 4 identical or different groups selected from the group consisting of the substituents (a) to (e) in the $C_{4-7}$ cycloalkyl (1), (4) a 4- to 7-membered saturated heterocyclic group which may be optionally substituted by 1 to 4 identical or different groups selected from the group consisting of the substituents (a) to (e) in the $C_{4-7}$ cycloalkyl (1), (5) a $C_{1-6}$ alkoxy group which may be optionally substituted by (a) a halogen atom, (b) $C_{1-6}$ alkoxy, (c) $C_{4-7}$ cycloalkyl which may be optionally substituted by 1 to 4 identical or different groups selected from the group consisting of the substituents (a) to (e) in the $C_{4-7}$ cycloalkyl (1), (d) phenyl which may be optionally substituted by 1 to 4 identical or different groups selected from the group consisting of the substituents (a) to (e) in the $C_{4-7}$ cycloalkyl (1), (e) pyridyl which may be optionally substituted by 1 to 3 identical or different groups selected from the group consisting of the substituents (a) to (e) in the $C_{4-7}$ cycloalkyl (1), or (f) a 4- to 7-membered saturated heterocyclic ring which may be optionally substituted by 1 to 4 identical or different groups selected from the group consisting of the substituents (a) to (e) in the $C_{4-7}$ cycloalkyl (1), (6) a $C_{4-7}$ cycloalkoxy group which may be optionally substituted by 1 to 4 identical or different groups selected from the group consisting of the substituents (a) to (e) in the $C_{4-7}$ cycloalkyl (1), (7) a phenoxy group which may be optionally substituted by 1 to 4 identical or different groups selected from the group consisting of the substituents (a) to (e) in the $C_{4-7}$ cycloalkyl (1), or (8) a 4- to 7-membered saturated heterocyclyloxy group which may be optionally substituted by 1 to 4 identical or different groups selected from the group consisting of the substituents (a) to (e) in the $C_{4-7}$ cycloalkyl (1).

[4] The compound according to any one of [1] to [3] or a pharmaceutically acceptable salt thereof, wherein L is a $C_{1-4}$ alkylene group which may be optionally substituted by 1 to 3 fluorine atoms.

[5] The compound according to any one of [1] to [4] or a pharmaceutically acceptable salt thereof, wherein $R^b$ is a hydrogen atom or a group represented by the following formula (2a):

[Formula 6]

(2a)

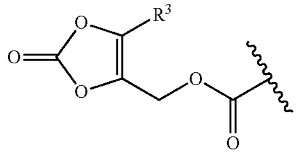

wherein $R^3$ represents a hydrogen atom or a $C_{1-6}$ alkyl group.

[6] The compound according to any one of [1] to [5] or a pharmaceutically acceptable salt thereof, wherein $R^a$ is (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, (2) a phenyl group which may be optionally substituted by 1 to 4 identical or different groups selected from the group consisting of the substituents (a) to (c) in the $C_{4-7}$ cycloalkyl group (1), or (3) a 4- to 7-membered saturated heterocyclic group which may be optionally substituted by 1 to 4 identical or different groups selected from the group consisting of the substituents (a) to (c) in the $C_{4-7}$ cycloalkyl group (1).

[7] The compound according to any one of [1] to [6] or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3).

[8] The compound according to any one of [1] to [7] or a pharmaceutically acceptable salt thereof, wherein $R^{11}$ and $R^{12}$ are each independently a hydrogen atom or a $C_{1-6}$ alkyl group which may be optionally substituted by 1 to 3 identical or different halogen atoms.

[9] The compound according to any one of [1] to [6] or a pharmaceutically acceptable salt thereof, wherein $R^{11}$ and $R^{12}$ form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and $C_{1-6}$ alkyl.

[10] The compound according to any one of [1] to [9] or a pharmaceutically acceptable salt thereof, wherein L is a $C_{1-4}$ alkylene group substituted by 1 to 3 fluorine atoms.

[11] The compound according to [1] or a pharmaceutically acceptable salt thereof, wherein the compound is represented by formula (2):

[Formula 7]

(2)

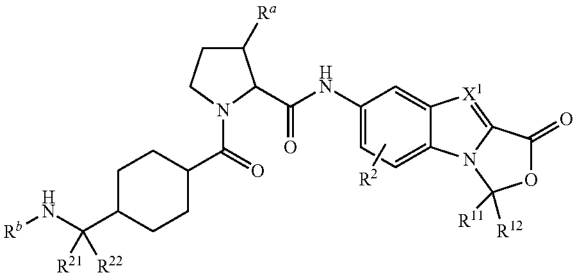

wherein $R^{11}$, $R^{12}$, $R^a$, $R^b$, $X^1$ and $R^2$ are the same as defined in [1], and $R^{21}$ and $R^{22}$ each independently represent a hydrogen atom, a fluorine atom, or a methyl group which may be optionally substituted by 1 to 3 fluorine atoms.

[12] The compound according to [11] or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the $C_{3-8}$ cycloalkyl group (3), or (6) a 3- to 8-membered saturated heterocyclic group which may be optionally substituted by 1 to 4 identical or different groups selected from the group consisting of the substituents (a) to (f) in the $C_3$ cycloalkyl group (3), or $R^{11}$ and $R^{12}$ optionally form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_3$ cycloalkyl group (3), and $R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (2) a phenyl group which may be optionally substituted by 1 to 4 identical or different groups selected from the group consisting of the substituents (a) to (e) in the $C_{4-7}$ cycloalkyl group (1), (3) a pyridyl group which may be optionally substituted by 1 to 4 identical or different groups selected from the group consisting of the substituents (a) to (e) in the $C_{4-7}$ cycloalkyl group (1), (4) a 4- to 7-membered saturated heterocyclic group which may be optionally substituted by 1 to 4 identical or different groups selected from the group consisting of the substituents (a) to (f) in the $C_{4-7}$ cycloalkyl group (1), (5) a $C_{4-7}$ cycloalkoxy group which may be optionally substituted by 1 to 4 identical or different groups selected from the group consisting of the substituents (a) to (f) in the $C_{4-7}$ cycloalkyl group (1), or (6) a phenoxy group which may be optionally substituted by 1 to 4 identical or different groups selected from the group consisting of the substituents (a) to (e) in the $C_{4-7}$ cycloalkyl group (1).

[13] The compound according to [11] or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the Cm cycloalkyl group (3), or (6) a 3- to 8-membered saturated heterocyclic group which may be optionally substituted by 1 to 4 identical or different groups selected from the group consisting of the substituents (a) to (e) in the $C_{3-8}$ cycloalkyl group (3), or $R^{11}$ and $R^{12}$ optionally form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_{3-8}$ cycloalkyl group (3); and $R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (2) a phenyl group which may be optionally substituted by 1 to 4 identical or different groups selected from the group consisting of the substituents (a) to (e) in the $C_{4-7}$ cycloalkyl group (1), (3) a pyridyl group which may be optionally substituted by 1 to 4 identical or different groups selected from the group consisting of the substituents (a) to (e) in the $C_{4-7}$ cycloalkyl group (1), (4) a 4- to 7-membered saturated heterocyclic group which may be optionally substituted by 1 to 4 identical or different groups selected from the group consisting of the substituents (a) to (e) in the $C_{4-7}$ cycloalkyl group (1), (5) a $C_{4-7}$ cycloalkoxy group which may be optionally substituted by 1 to 4 identical or different groups selected from the group consisting of the substituents (a) to (e) in the $C_{4-7}$ cycloalkyl group (1), or (6) a phenoxy group which may be optionally substituted by 1 to 4 identical or different groups selected from the group consisting of the substituents (a) to (e) in the $C_{4-7}$ cycloalkyl group (1).

[14] The compound according to any one of [11] to [13] or a pharmaceutically acceptable salt thereof, wherein $R^a$ is (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, (2) a phenyl group which may be optionally substituted by 1 to 4 identical or different groups selected from the group consisting of the substituents (a) to (c) in the $C_{4-7}$ cycloalkyl group (1), or (3) a 4- to 7-membered saturated heterocyclic group which may be optionally substituted by 1 to 4 identical or different groups selected from the group consisting of the substituents (a) to (c) in the $C_{4-7}$ cycloalkyl group (1).

[15] The compound according to any one of [11] to [14] or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3).

[16] The compound according to any one of [11] to [14] or a pharmaceutically acceptable salt thereof, wherein $R^{11}$ and $R^{12}$ are each independently a hydrogen atom or a $C_{1-6}$ alkyl group which may be optionally substituted by 1 to 3 identical or different halogen atoms.

[17] The compound according to any one of [11] to [14] or a pharmaceutically acceptable salt thereof, wherein $R^{11}$ and $R^{12}$ form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and $C_{1-6}$ alkyl.

[18] The compound according to any one of [11] to [17] or a pharmaceutically acceptable salt thereof, wherein $R^b$ is a hydrogen atom or a group represented by the following formula (2a):

[Formula 8]

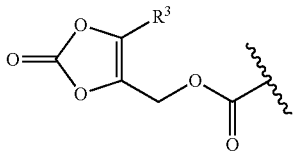

(2a)

wherein $R^3$ represents a hydrogen atom or a $C_{1-6}$ alkyl group.

[19] The compound according to any one of [11] to [18] or a pharmaceutically acceptable salt thereof, wherein $R^{21}$ is a hydrogen atom, and $R^{22}$ is a methyl group substituted by 1 to 3 fluorine atoms.

[20] The compound according to any one of [1] to [19] or a pharmaceutically acceptable salt thereof, wherein $X^1$ is $CR^1$, and each of $R^1$ and $R^2$ is a hydrogen atom.

[21] The compound according to [1] or a pharmaceutically acceptable salt thereof, wherein the compound is represented by formula (3):

[Formula 9]

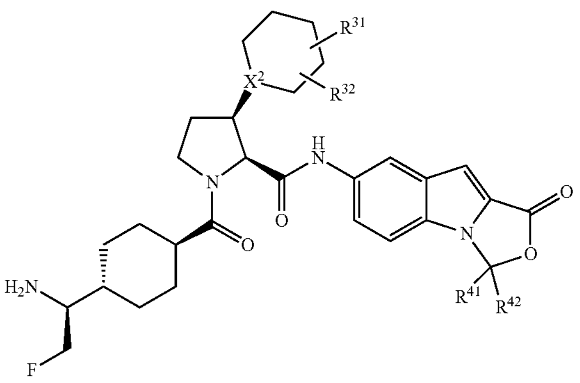

(3)

wherein $R^{41}$ and $R^{42}$ each independently represent (1) a hydrogen atom, (2) a $C_{1-6}$ alkyl group which may be optionally substituted by 1 to 4 identical or different groups selected from the group consisting of (a) a halogen atom,
(b) $C_{1-6}$ alkoxy, and
(c) $C_{4-7}$ cycloalkyl, or
(3) a $C_{3-8}$ cycloalkyl group which may be optionally substituted by 1 to 4 identical or different groups selected from the group consisting of
(a) a halogen atom,
(b) $C_{1-6}$ alkoxy, and
(c) $C_{1-6}$ alkyl, or $R^{41}$ and $R^{42}$ together form, together with the carbon atom bonded thereto, a 4- to 7-membered cycloalkane ring or a 4- to 6-membered saturated heterocyclic ring wherein the 4- to 7-membered cycloalkane ring and the 4- to 6-membered saturated heterocyclic ring may be each optionally substituted by 1 to 4 identical or different groups selected from the group consisting of the substituents (a) to (c) in the $C_{3-8}$ cycloalkyl group (3);

$X^2$ represents N or CH; and $R^{31}$ and $R^{32}$ each independently represent a hydrogen atom, a halogen atom, a $C_{1-6}$ alkoxy group, or a $C_{1-6}$ alkyl group.

[22] The compound according to [21] or a pharmaceutically acceptable salt thereof, wherein $R^{41}$ and $R^{42}$ are each independently a hydrogen atom or a $C_{1-6}$ alkyl group which may be optionally substituted by 1 to 3 identical or different halogen atoms.

[23] The compound according to [21] or a pharmaceutically acceptable salt thereof, wherein $R^{41}$ and $R^{42}$ together form, together with the carbon atom bonded thereto, a 4- to 6-membered cycloalkane ring or a 4- to 6-membered saturated heterocyclic ring wherein the 4- to 6-membered cycloalkane ring and the 4- to 6-membered saturated heterocyclic ring may be each optionally substituted by 1 to 4 identical or different groups selected from the group consisting of a halogen atom and $C_{1-6}$ alkyl.

[24] The compound according to [23] or a pharmaceutically acceptable salt thereof, wherein $R^{41}$ and $R^{42}$ together form, together with the carbon atom bonded thereto, a 4- to 6-membered cycloalkane ring which may be optionally substituted by 1 to 4 fluorine atoms.

[25] The compound according to any one of [21] to [24] or a pharmaceutically acceptable salt thereof, wherein $X^2$ is CH.

[26] The compound according to any one of [21] to [25] or a pharmaceutically acceptable salt thereof, wherein $R^{31}$ and $R^{32}$ are each independently a hydrogen atom or a methoxy group.

[27] The compound according to [1] or a pharmaceutically acceptable salt thereof, wherein the compound is selected from the following compounds: (2S,3S)-1-({trans-4-[(1 S)-1-amino-2-fluoroethyl]cyclohexyl}carbonyl)-N-(3,3-dimethyl-1-oxo-1H-[1,3]oxazolo[3,4-a]indol-7-yl)-3-cyclohexylpyrrolidine-2-carboxamide, (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-cyclohexyl-L-prolinamide, (3S)-1-({trans-4-[(1S)-1-amino-2-fluoroethyl]cyclohexyl}carbonyl)-3-cyclohexyl-N-(1'-oxo-1'H-spiro[cyclobutane-1,3'-[1,3]oxazolo[3,4-a]indol]-7'-yl)-L-prolinamide, (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-(trans-4-methoxycyclohexyl)-L-prolinamide, (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-(trans-4-methoxycyclohexyl)-L-prolinamide, (3S)-1-({trans-4-[(1S)-1-amino-2-fluoroethyl]cyclohexyl}carbonyl)-3-(trans-4-methoxycyclohexyl)-N-(1'-oxo-1'H-spiro[cyclobutane-1,3'-[1,3]oxazolo[3,4-a]indol]-7'-yl)-L-prolinamide, (3S)-1-{[trans-4-(aminomethyl)cyclohexyl]carbonyl}-3-cyclohexyl-N-(3,3-dimethyl-1-oxo-1H-[1,3]oxazolo[3,4-a]indol-7-yl)-L-prolinamide, (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-phenyl-L-prolinamide, (3R)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-phenyl-L-prolinamide, and (3R)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-phenyl-L-prolinamide.

[28] The compound according to [1] or a pharmaceutically acceptable salt thereof, wherein the compound is selected from the following compounds: (2S,3S)-1-({trans-4-[(1 S)-1-amino-2-fluoroethyl]cyclohexyl}carbonyl)-N-(3,3-dimethyl-1-oxo-1H-[1,3]oxazolo[3,4-a]indol-7-yl)-3-cyclohexylpyrrolidine-2-carboxamide, (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-cyclohexyl-L-prolinamide, (3S)-1-({trans-4-[(1S)-1-amino-2-fluoroethyl]cyclohexyl})carbonyl)-3-cyclohexyl-N-(1'-oxo-1'H-spiro[cyclobutane-1,3'-[1,3]oxazolo[3,4-a]indol]-7'-yl)-L-prolinamide, (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-(trans-4-methoxycyclohexyl)-L-prolinamide, and (3S)-1-({trans-4-[(1S)-1-amino-2-fluoroethyl]cyclohexyl}carbonyl)-3-(trans-4-methoxycyclohexyl)-N-(1'-oxo-1'H-spiro[cyclobutane-1,3'-[1,3]oxazolo[3,4-a]indol]-7'-yl)-L-prolinamide.

[29] The compound according to [1] or a pharmaceutically acceptable salt thereof, wherein the compound is (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-cyclohexyl-L-prolinamide.

[30] The compound according to [1] or a pharmaceutically acceptable salt thereof, wherein the compound is (3S)-1-({trans-4-[(1S)-1-amino-2-fluoroethyl]cyclohexyl}carbonyl)-3-cyclohexyl-N-(1'-oxo-1'H-spiro[cyclobutane-1,3'-[1,3]oxazolo[3,4-a]indol]-7'-yl)-L-prolinamide.

[31] The compound according to [1] or a pharmaceutically acceptable salt thereof, wherein the compound is (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-(trans-4-methoxycyclohexyl)-L-prolinamide.

[32] The compound according to [1], wherein the compound is (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-cyclohexyl-L-prolinamide hydrochloride.

[33] The compound according to [1], wherein the compound is (3S)-1-({trans-4-[(1S)-1-amino-2-fluoroethyl]cyclohexyl}carbonyl)-3-cyclohexyl-N-(1'-oxo-1'H-spiro[cyclobutane-1,3'-[1,3]oxazolo[3,4-a]indol]-7'-yl)-L-prolinamide hydrochloride.

[34] The compound according to [1], wherein the compound is (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-(trans-4-methoxycyclohexyl)-L-prolinamide hydrochloride.

[35] A compound represented by any of the following formulas or a pharmaceutically acceptable salt thereof:

[Formula 10]

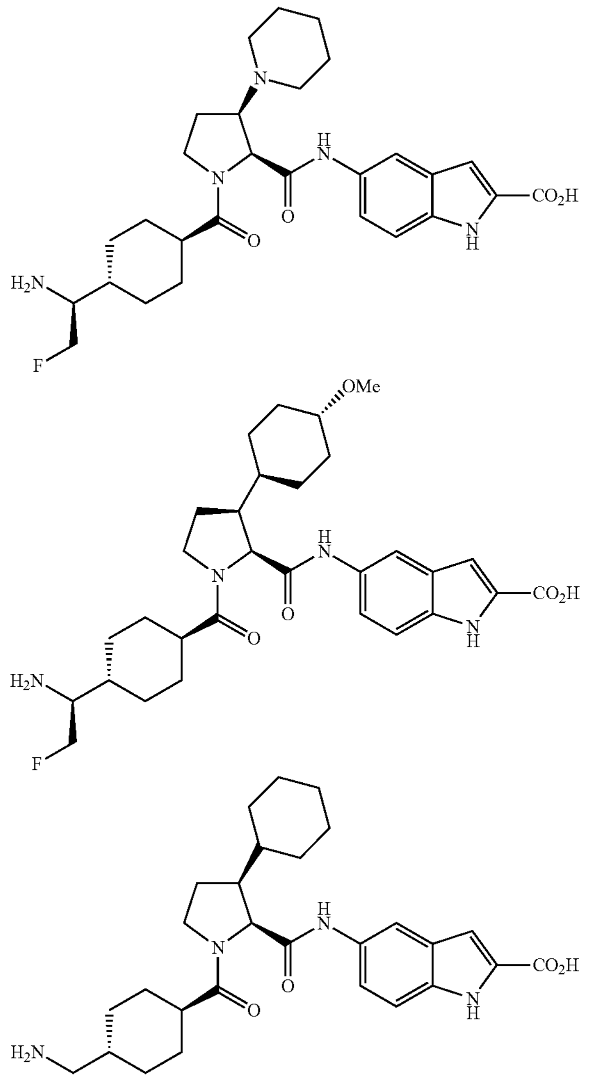

[36] A method for producing a compound represented by formula (8), comprising converting a compound according to any one of [1] to [34] or a pharmaceutically acceptable salt thereof to the compound represented by formula (8) through enzymatic reaction in plasma:

(8)

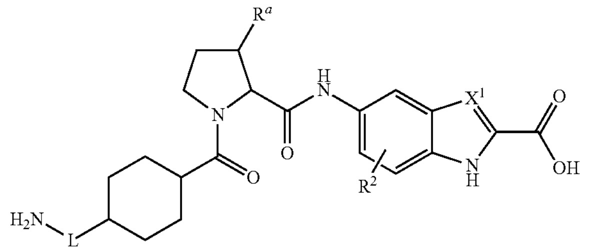

[37] A medicament comprising a compound according to any one of [1] to [35] or a pharmaceutically acceptable salt thereof as an active ingredient.

[38] An FXIa inhibitor comprising a compound according to any one of [1] to [35] or a pharmaceutically acceptable salt thereof as an active ingredient.

[39] An anticoagulant comprising a compound according to any one of [1] to [35] or a pharmaceutically acceptable salt thereof as an active ingredient.

[40] A therapeutic agent for thrombosis, comprising a compound according to any one of [1] to [35] or a pharmaceutically acceptable salt thereof as an active ingredient.

[41] A therapeutic agent for thromboembolism, comprising a compound according to any one of [1] to [35] or a pharmaceutically acceptable salt thereof as an active ingredient.

[42] A pharmaceutical composition comprising a compound according to any one of [1] to [35] or a pharmaceutically acceptable salt thereof.

[43] A therapeutic and/or prophylactic agent for a disease caused by abnormal blood coagulation involving FXIa, comprising a compound according to any one of [1] to [35] or a pharmaceutically acceptable salt thereof as an active ingredient.

[44] The therapeutic and/or prophylactic agent according to [43], wherein the disease caused by abnormal blood coagulation involving FXIa is thromboembolism.

[45] The therapeutic and/or prophylactic agent according to [43], wherein the thromboembolism is venous thrombosis, myocardial infarction, pulmonary embolism, brain embolism, or slowly progressive cerebral thrombosis.

[46] A method for treating and/or preventing a disease caused by abnormal blood coagulation involving FXIa, comprising administering a therapeutically effective amount of a compound according to any one of [1] to [35] or a pharmaceutically acceptable salt thereof to a patient in need of treatment.

[47] The method according to [45], wherein the disease caused by abnormal blood coagulation involving FXIa is thromboembolism.

[48] The method according to [46], wherein the thromboembolism is venous thrombosis, myocardial infarction, pulmonary embolism, brain embolism, or slowly progressive cerebral thrombosis.

[49] Use of a compound according to any one of [1] to [35] or a pharmaceutically acceptable salt thereof for producing a therapeutic and/or prophylactic agent for a disease caused by abnormal blood coagulation involving FXIa, an FXIa inhibitor, or an anticoagulant.

[50] A pharmaceutical composition for use in the treatment of a disease caused by abnormal blood coagulation involving FXIa, comprising a compound according to any one of [1] to [35] or a pharmaceutically acceptable salt thereof.

[51] A medicament comprising a compound according to any one of [1] to [35] or a pharmaceutically acceptable salt thereof and at least one drug selected from an anticoagulant and an antiplatelet agent.

[52] A medicament comprising a compound according to any one of [1] to [35] or a pharmaceutically acceptable salt thereof for administration in combination with at least one drug selected from an anticoagulant and an antiplatelet agent.

[53] A method for treating and/or preventing a disease caused by abnormal blood coagulation involving FXIa, comprising administering a medicament comprising a compound according to any one of [1] to [35] or a pharmaceutically acceptable salt thereof and at least one drug selected from an anticoagulant and an antiplatelet agent, to a patient in need of treatment.

[54] The method according to [51], wherein the disease caused by abnormal blood coagulation involving FXIa is thromboembolism.

[55] The method according to [52], wherein the thromboembolism is venous thrombosis, myocardial infarction, pulmonary embolism, brain embolism, or slowly progressive cerebral thrombosis.

[56] The medicament, the FXIa inhibitor, the anticoagulant, the pharmaceutical composition, or the therapeutic or prophylactic agent according to any one of [37] to [45] and [50] to [52] which is intended for oral administration.

[57] The method according to any one of [46] to [48] and [53] to [55], wherein the compound or the pharmaceutically acceptable salt thereof is orally administered.

[58] The use according to [49], wherein the therapeutic and/or prophylactic agent is intended for oral administration.

Advantageous Effects of Invention

The present compound has an excellent anticoagulant effect and oral absorbability and as such, is useful as a therapeutic and/or prophylactic agent for thrombosis, thromboembolism, or the like.

DESCRIPTION OF EMBODIMENTS

Figure 1:
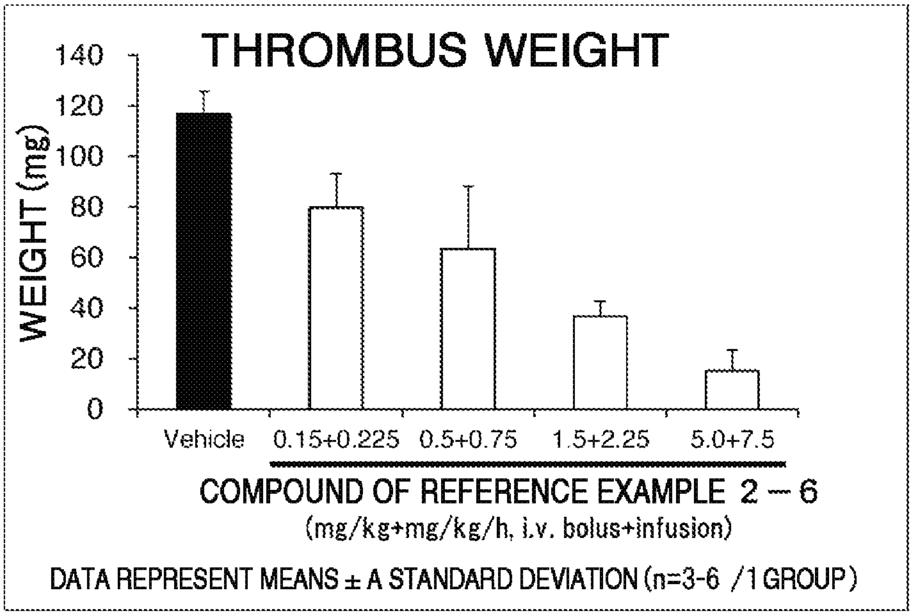
FIG. 1 shows change in thrombus weight by the administration of a compound of Reference Example 2-6 (Test Example 4).

Hereinafter, the present invention will be described in more detail. In the present specification, the number of carbon atoms in the definition of each "substituent" may be indicated by, for example, "$C_{1-6}$". In this case, the term "$C_{1-6}$ alkyl" means an alkyl group having 1 to 6 carbon atoms.

A group associated with the phrase "optionally substituted" is defined as being able to be substituted at replaceable positions by a possible number of substituent(s) unless the number of substituent(s) is otherwise specified. For example, when an optionally substituted $C_{1-6}$ alkyl group is a methyl group, the number of substituents by which the methyl group can be substituted is in the range of 1 to 3. When an optionally substituted $C_{6-10}$ aryl group is a phenyl group, the number of substituents by which the phenyl group can be substituted is in the range of 1 to 5. When substituents are two or more, they may be the same with or different from each other. The detail of each group is also applied in the case where the group is a moiety or a substituent of another group, unless otherwise specified.

The term "trans" means trans, and the term "cis" means cis.

Examples of the "halogen atom" include a fluorine atom, a chlorine atom, a bromine atom, and an iodine atom. Preferred examples thereof include a fluorine atom and a chlorine atom.

The "$C_{1-6}$ alkyl group" refers to a linear or branched saturated hydrocarbon group having 1 to 6 carbon atoms. The $C_{1-6}$ alkyl group is preferably a "$C_{1-4}$ alkyl group". Specific examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl. Specific examples of the "$C_{1-4}$ alkyl" include methyl, ethyl, propyl, isopropyl, butyl, isobutyl, sec-butyl, and tert-butyl.

The "$C_{1-4}$ alkylene group" refers to a linear or branched saturated hydrocarbon group having 1 to 4 carbon atoms, or a saturated hydrocarbon group containing a cyclic structure having 3 or 4 carbon atoms.

Specific examples of the linear or branched "$C_{1-4}$ alkylene group" include methylene, ethylene, propylene, butylene, 1-methylmethylene, 1-ethylmethylene, 1-propylmethylene, 1-methylethylene, 2-methylethylene, and 1-ethylethylene and preferably include 1-methylmethylene, methylene, and ethylene.

Specific examples of the "$C_{1-4}$ alkylene group" containing a cyclic structure include groups represented by the following group:

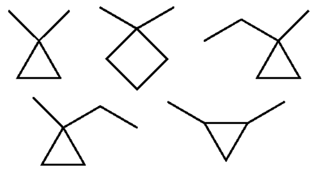

The "$C_{3-8}$ cycloalkyl group" refers to a 3- to 8-membered monocyclic saturated hydrocarbon group. The $C_3$ cycloalkyl group is preferably a "$C_{4-7}$ cycloalkyl group". Specific examples of the "Cu cycloalkyl group" include cyclopropyl, cyclobutyl, cyclopentyl, cyclohexyl, cycloheptyl, and cyclooctyl. Specific examples of the "$C_{4-7}$ cycloalkyl group" include cyclobutyl, cyclopentyl, cyclohexyl, and cycloheptyl.

The "$C_{3-8}$ cycloalkyl group" also encompasses a saturated bicyclo ring. Specific examples thereof include groups represented by the following group:

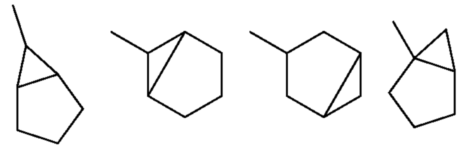

The "5- or 6-membered heteroaryl group" refers to a 5- or 6-membered monocyclic aromatic group containing one or more (e.g., 1 to 4) identical or different heteroatoms selected from a nitrogen atom, a sulfur atom, and an oxygen atom. Specific examples of the "5- or 6-membered heteroaryl group" include pyridyl, pyrazyl, pyrimidinyl, pyridazinyl, triazinyl, pyrrolyl, furyl, thienyl, imidazolyl, oxazolyl, thiazolyl, pyrazolyl, isoxazolyl, isothiazolyl, oxadiazolyl, thiadiazolyl, triazolyl, and tetrazolyl. Preferred examples of the 5- or 6-membered heteroaryl group include pyridyl, pyrazyl, pyrimidinyl, and pyridazinyl.

Examples of the "3- to 8-membered saturated heterocyclic group" include a 3- to 8-membered monocyclic saturated heterocyclic group having 1 to 3 identical or different atoms selected from a nitrogen atom, an oxygen atom, and a sulfur atom. All of the nitrogen atom, the oxygen atom, and the sulfur atom are atoms constituting the ring. The heterocyclic group may be saturated or partially unsaturated. The heterocyclic group is preferably a 4- to 7-membered saturated heterocyclic group, more preferably a 4- to 6-membered saturated heterocyclic group, further preferably a 5- or 6-membered saturated heterocyclic group. Specific examples thereof include pyranyl, dihydropyranyl, tetrahydropyranyl, tetrahydrofuryl, azetidinyl, pyrrolidinyl, imidazolidinyl, piperidinyl, azepanyl, morpholinyl, thiomorpholinyl, dioxothiomorpholinyl, hexamethyleneiminyl, oxazolidinyl, thiazolidinyl, imidazolidinyl, tetrahydrofuranyl, oxooxazolidinyl, dioxooxazolidinyl, dioxothiazolidinyl, tetrahydropyranyl, 5-oxo-1,2,4-oxadiazol-3-yl, 5-oxo-1,2,4-thiadiazol-3-yl, and 5-thioxo-1,2,4-oxadiazol-3-yl. Among them, preferred examples thereof include piperidinyl and tetrahydropyranyl.

In the "3- to 8-membered saturated heterocyclic group", the nitrogen atom constituting the ring may serve as a bond for a "group". Specifically, the group also encompasses, for example, azetidino, pyrrolidine, piperidino, azepano, morpholino, thiomorpholino, thiomorpholino-oxido, thiomorpholino-dioxido, and piperazino. Preferred examples thereof include a piperidino group.

The "4- to 6-membered saturated heterocyclic group" also encompasses a saturated bicyclo ring group and a saturated spiro ring group having the "4- to 6-membered saturated heterocyclic ring" as a backbone, in addition to the examples listed above. Specific examples thereof include "groups" represented by the following group:

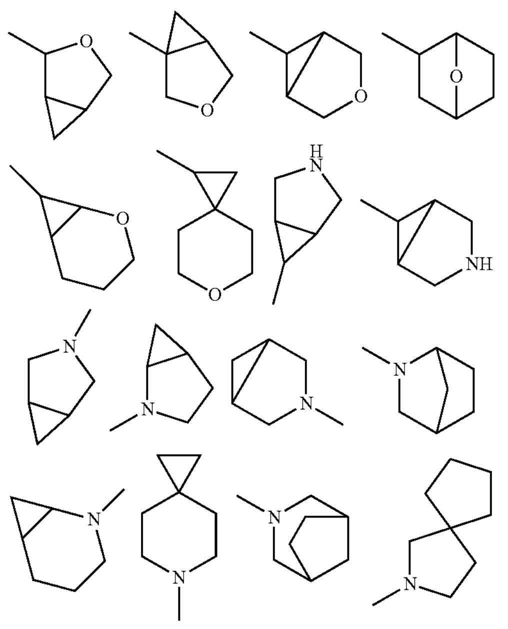

The "saturated heterocyclic group" may form a condensed ring with phenyl or 6-membered heteroaryl. The condensed ring also encompasses, for example, condensed ring groups of the 4- to 6-membered saturated heterocyclic group listed above with phenyl or 6-membered heteroaryl. Examples of the 6-membered heteroaryl include pyridine, pyrimidine, and pyridazine. Specific examples of the condensed ring include dihydroindolyl, dihydroisoindolyl, dihydropurinyl, dihydrothiazolopyrimidinyl, dihydrobenzodioxanyl, isoindolinyl, tetrahydroquinolinyl, decahydroquinolinyl, tetrahydroisoquinolinyl, decahydroisoquinolinyl, tetrahydronaphthyridinyl, and tetrahydropyridoazepinyl. Substituent(s) by which the phenyl or 6-membered heteroaryl thereof may be optionally substituted includes the substituents which the "optionally substituted phenyl group" and the "optionally substituted 5- or 6-membered heteroaryl group" may have.

The "$C_{1-6}$ alkoxy group" is the same as a "$C_{1-6}$ alkyloxy group", and its "$C_{1-6}$ alkyl" moiety is the same as defined in the "$C_{1-6}$ alkyl". The $C_{1-6}$ alkoxy group is preferably a "$C_{1-4}$ alkoxy group". Specific examples of the "$C_{1-6}$ alkoxy group" include methoxy, ethoxy, propoxy, isopropoxy, butoxy, isobutoxy, sec-butoxy, and tert-butoxy.

The "$C_{4-7}$ cycloalkyl" moiety of the "$C_{4-7}$ cycloalkoxy group" is the same as defined in the "$C_{4-7}$ cycloalkyl". Specific examples thereof include cyclobutyloxy, cyclopentyloxy, cyclohexyloxy, and cycloheptyloxy.

The "saturated heterocyclic" moiety of the "4- to 7-membered saturated heterocyclyloxy group" is the same as defined in the "saturated heterocyclic" ring. The 4- to 7-membered saturated heterocyclyloxy group is preferably a "5- or 6-membered saturated heterocyclyloxy group". Specific examples of the "4- to 7-membered saturated heterocyclyloxy group" include tetrahydropyranyloxy, tetrahydrofuryloxy, pyrrolidinyloxy, imidazolidinyloxy, piperidinyloxy, and morpholinyloxy.

Examples of the substituent(s) which the "optionally substituted alkylene group" may have, include a halogen atom, an oxo group, a hydroxyl group, and a $C_{1-6}$ alkoxy group.

Preferred examples thereof include a $C_{1-4}$ alkylene group substituted by 1 to 3 fluorine atoms. More preferred examples thereof include a 1-methylmethylene group substituted by 1 to 3 fluorine atoms.

Examples of the substituent(s) which the "optionally substituted alkyl group" and the "optionally substituted alkoxy group" may have, include (1) a halogen atom, (2) a $C_{1-6}$ alkoxy group which may be optionally substituted by 1 to 3 halogen atoms, (3) a cyano group, (4) an amino group which may be optionally substituted by 1 or 2 identical or different groups selected from the group consisting of $C_{1-6}$ alkyl and $C_{3-7}$ cycloalkyl, (5) an oxo group, (6) a hydroxy group, (7) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (8) a phenyl group which may be optionally substituted by 1 to 4 identical or different groups selected from the group consisting of the substituents (a) to (e) in the $C_{3-8}$ cycloalkyl group (7), (9) a 5- or 6-membered heteroaryl group which may be optionally substituted by 1 to 4 identical or different groups selected from the group consisting of the substituents (a) to (e) in the $C_{3-8}$ cycloalkyl group (7), and

(10) a 3- to 8-membered saturated heterocyclic group which may be optionally substituted by 1 to 4 identical or different groups selected from the group consisting of the substituents (a) to (e) in the $C_{3-8}$ cycloalkyl group (7).

Preferred examples of the substituent(s) include a halogen atom, a $C_{3-7}$ cycloalkyl group, a $C_{1-6}$ alkoxy group which may be optionally substituted by 1 to 3 halogen atoms, a phenyl group, a 5- or 6-membered heteroaryl group, and a 3- to 8-membered saturated heterocyclic group.

More preferred examples of the substituent(s) include a halogen atom, a $C_{3-7}$ cycloalkyl group, and a $C_{1-6}$ alkoxy group which may be optionally substituted by 1 to 3 halogen atoms.

Further preferred examples of the substituent include a fluorine atom and a $C_{1-6}$ alkoxy group.

Examples of the substituent(s) which the "optionally substituted $C_{3-8}$ cycloalkyl group", the "optionally substituted phenyl group", the "optionally substituted 5- or 6-membered heteroaryl group", the "optionally substituted pyridyl group", and the "optionally substituted 3- to 8-membered saturated heterocyclic group" my have, include (1) a halogen atom, (2) a $C_{1-6}$ alkyl group which may be optionally substituted by 1 to 3 halogen atoms, (3) a $C_{1-6}$ alkoxy group which may be optionally substituted by 1 to 3 halogen atoms, (4) a cyano group, (5) an amino group which may be optionally substituted by 1 or 2 identical or different groups selected from the group consisting of $C_{1-6}$ alkyl and $C_{3-7}$ cycloalkyl, (6) a hydroxy group, (7) a $C_{1-6}$ alkylcarbonyl group which may be optionally substituted by 1 to 3 halogen atoms, (8) a $C_{1-6}$ alkoxycarbonyl group which may be optionally substituted by 1 to 3 halogen atoms, (9) an aminocarbonyl group wherein the amino moiety may be optionally substituted by 1 or 2 identical or different groups selected from the group consisting of $C_{1-6}$ alkyl and $C_{3-7}$ cycloalkyl,

(10) a $C_{1-6}$ alkylsulfonyl group which may be optionally substituted by 1 to 3 halogen atoms,

(11) an aminosulfonyl group wherein the amino moiety may be optionally substituted by 1 or 2 identical or different groups selected from the group consisting of $C_{1-6}$ alkyl and $C_{3-7}$ cycloalkyl, and

(12) an oxo group which is a substituent only for the "optionally substituted $C_3$ cycloalkyl group".

Preferred examples of the substituent(s) include a halogen atom, a $C_{1-6}$ alkyl group which may be optionally substituted by 1 to 3 halogen atoms, a $C_{1-6}$ alkoxy group which may be optionally substituted by 1 to 3 halogen atoms, a cyano group, and an amino group which may be optionally substituted by 1 or 2 groups selected from the group consisting of $C_{1-6}$ alkyl and $C_{3-7}$ cycloalkyl.

More preferred examples of the substituent(s) include a halogen atom, a $C_{1-6}$ alkyl group which may be optionally substituted by 1 to 3 halogen atoms, and a $C_{1-6}$ alkoxy group which may be optionally substituted by 1 to 3 halogen atoms.

Further preferred examples of the substituent(s) include a fluorine atom, a $C_{1-6}$ alkyl group which may be optionally substituted by 1 to 3 fluorine atoms, and a $C_{1-6}$ alkoxy group which may be optionally substituted by 1 to 3 fluorine atoms.

In the formulas (1), (2), and (3), L, $R^1$, $R^2$, $R^{11}$, $R^{12}$, $R^{21}$, $R^{22}$, $R^{31}$, $R^{32}$, $R^{41}$, $R^{42}$, $X^1$, $X^2$, $R^a$, and $R^b$ are preferably as described below. However, the technical scope of the present invention is not limited to the description below.

L is preferably a $C_{1-4}$ alkylene group which may be optionally substituted by 1 to 3 fluorine atoms, more preferably a $C_{1-4}$ alkylene group substituted by 1 to 3 fluorine atoms, and further preferably a 1-methylmethylene group substituted by 1 to 3 fluorine atoms.

$R^1$ and $R^2$ are preferably each independently a hydrogen atom, a halogen atom, a $C_{1-6}$ alkoxy group, or a $C_{1-6}$ alkyl group; and more preferably each independently a hydrogen atom, a fluorine atom, or a $C_{1-6}$ alkoxy group. Further preferably, each of $R^1$ and $R^2$ is a hydrogen atom.

$R^{11}$ and $R^{12}$ are preferably each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the Cm cycloalkyl group (3), or (6) a 3- to 8-membered saturated heterocyclic group which may be optionally substituted by 1 to 4 identical or different groups selected from the group consisting of the substituents (a) to (f) in the $C_{3-8}$ cycloalkyl group (3), or $R^{11}$ and $R^{12}$ preferably form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the group (3).

More preferably, $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3), or $R^{11}$ and $R^{12}$ form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_{3-8}$ cycloalkyl group (3).

Further preferably, $R^{11}$ and $R^{12}$ are each independently a hydrogen atom or a $C_{1-6}$ alkyl group which may be optionally substituted by 1 to 3 identical or different halogen atoms, or $R^{11}$ and $R^{12}$ form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and $C_{1-6}$ alkyl.

Most preferably, $R^{11}$ and $R^{12}$ form, together with the carbon atom bonded thereto, a 4- to 6-membered cycloalkane ring which may be optionally substituted by 1 to 4 fluorine atoms.

$R^{41}$ and $R^{42}$ are preferably each independently (1) a hydrogen atom, (2) a $C_{1-6}$ alkyl group which may be optionally substituted by 1 to 4 identical or different groups selected from the group consisting of (a) a halogen atom, (b) $C_{1-6}$ alkoxy, and (c) $C_{4-7}$ cycloalkyl, or (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or $R^{41}$ and $R^{42}$ preferably form, together with the carbon atom bonded thereto, a 4- to 7-membered cycloalkane ring or a 4- to 6-membered saturated heterocyclic ring wherein the 4- to 7-membered cycloalkane ring and the 4- to 6-membered saturated heterocyclic ring may be each optionally substituted by 1 to 4 identical or different groups selected from the group consisting of the substituents (a) to (c) in the $C_{3-8}$ cycloalkyl group (3).

More preferably, $R^{41}$ and $R^{42}$ are each independently a hydrogen atom or a $C_{1-6}$ alkyl group which may be optionally substituted by 1 to 3 identical or different halogen atoms, or $R^{41}$ and $R^{42}$ form, together with the carbon atom bonded thereto, a 4- to 6-membered cycloalkane ring or a 4- to 6-membered saturated heterocyclic ring wherein the 4- to 6-membered cycloalkane ring and the 4- to 6-membered saturated heterocyclic ring may be each optionally substituted by 1 to 4 identical or different groups selected from the group consisting of a halogen atom and a C1-6 alkyl group.

Most preferably, $R^{41}$ and $R^{42}$ form, together with the carbon atom bonded thereto, a 4- to 6-membered cycloalkane ring which may be optionally substituted by 1 to 4 fluorine atoms.

$R^{21}$ and $R^{22}$ are preferably each independently a hydrogen atom, a fluorine atom, or a methyl group which may be optionally substituted by 1 to 3 fluorine atoms. More preferably, $R^{21}$ is a hydrogen atom, and $R^{22}$ is a methyl group substituted by 1 to 3 fluorine atoms.

$R^{31}$ and $R^{32}$ are preferably each independently a hydrogen atom, a halogen atom, a $C_{1-6}$ alkoxy group, or a $C_{1-6}$ alkyl group. More preferably, $R^{31}$ and $R^{32}$ are each independently a hydrogen atom or a methoxy group. Further preferably, each of $R^{31}$ and $R^{32}$ is a hydrogen atom.

$X^1$ is preferably N or $CR^1$, more preferably N or CH, and further preferably CH.

$X^2$ is preferably N or CH, and more preferably CH.

$R^a$ is preferably (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo;

(2) a phenyl group which may be optionally substituted by 1 to 4 identical or different groups selected from the group consisting of the substituents (a) to (e) in the $C_{4-7}$ cycloalkyl group (1);

(3) a pyridyl group which may be optionally substituted by 1 to 4 identical or different groups selected from the group consisting of the substituents (a) to (e) in the $C_{4-7}$ cycloalkyl group (1);

(4) a 4- to 7-membered saturated heterocyclic group which may be optionally substituted by 1 to 4 identical or different groups selected from the group consisting of the substituents (a) to (f) in the $C_{4-7}$ cycloalkyl group (1); or (5) a $C_{1-6}$ alkoxy group which may be optionally substituted by (a) a halogen atom, (b) $C_{1-6}$ alkoxy, (c) $C_{4-7}$ cycloalkyl which may be optionally substituted by 1 to 4 identical or different groups selected from the group consisting of the substituents (a) to (e) in the $C_{4-7}$ cycloalkyl group (1), (d) phenyl which may be optionally substituted by 1 to 4 identical or different groups selected from the group consisting of the substituents (a) to (e) in the $C_{4-7}$ cycloalkyl group (1), (e) pyridyl which may be optionally substituted by 1 to 4 identical or different groups selected from the group consisting of the substituents (a) to (e) in the $C_{4-7}$ cycloalkyl group (1), or (f) a 4- to 7-membered saturated heterocyclic ring which may be optionally substituted by 1 to 3 identical or different groups selected from the group consisting of the substituents (a) to (e) in the $C_{4-7}$ cycloalkyl group (1);

(6) a $C_{4-7}$ cycloalkoxy group which may be optionally substituted by 1 to 4 identical or different groups selected from the group consisting of the substituents (a) to (e) in the $C_{4-7}$ cycloalkyl group (1);

(7) a phenoxy group which may be optionally substituted by 1 to 4 identical or different groups selected from the group consisting of the substituents (a) to (e) in the $C_{4-7}$ cycloalkyl group (1); or (8) a 4- to 7-membered saturated heterocyclyloxy group which may be optionally substituted by 1 to 4 identical or different groups selected from the group consisting of the substituents (a) to (e) in the $C_{4-7}$ cycloalkyl group (1).

$R^a$ is more preferably (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl;

(2) a phenyl group which may be optionally substituted by 1 to 4 identical or different groups selected from the group consisting of the substituents (a) to (e) in the $C_{4-7}$ cycloalkyl group (1);

(3) a pyridyl group which may be optionally substituted by 1 to 4 identical or different groups selected from the group consisting of the substituents (a) to (e) in the $C_{4-7}$ cycloalkyl group (1);

(4) a 4- to 7-membered saturated heterocyclic group which may be optionally substituted by 1 to 4 identical or different groups selected from the group consisting of the substituents (a) to (e) in the $C_{4-7}$ cycloalkyl group (1);

(5) a $C_{4-7}$ cycloalkoxy group which may be optionally substituted by 1 to 4 identical or different groups selected from the group consisting of the substituents (a) to (e) in the $C_{4-7}$ cycloalkyl group (1); or (6) a phenoxy group which may be optionally substituted by 1 to 4 identical or different groups selected from the group consisting of the substituents (a) to (e) in the group (1).

$R^a$ is further preferably (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl;

(2) a phenyl group which may be optionally substituted by 1 to 4 identical or different groups selected from the group consisting of the substituents (a) to (c) in the $C_{4-7}$ cycloalkyl group (1); or (3) a 4- to 7-membered saturated heterocyclic group which may be optionally substituted by 1 to 4 identical or different groups selected from the group consisting of the substituents (a) to (c) in the $C_{4-7}$ cycloalkyl group (1).

$R^a$ is most preferably cyclohexyl, piperidinyl, or a phenyl group wherein the cyclohexyl, the piperidinyl, or the phenyl group may be each optionally substituted by 1 to 4 identical or different groups selected from a fluorine atom and a methoxy group.

$R^b$ is preferably (1) a hydrogen atom, (2) a $C_{1-6}$ alkoxycarbonyl group, (3) a group represented by the following formula (2a):

(2a)

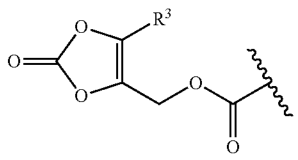

wherein $R^3$ represents a hydrogen atom or a $C_{1-6}$ alkyl group, or (4) a group represented by the following formula (2b):

(2b)

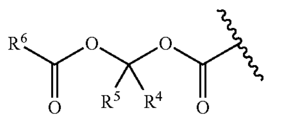

wherein $R^4$ and $R^5$ each independently represent a hydrogen atom or a $C_{1-6}$ alkyl group; and $R^6$ represents a $C_{1-6}$ alkyl group.

$R^b$ is more preferably a hydrogen atom or a group represented by the following formula (2a):

(2a)

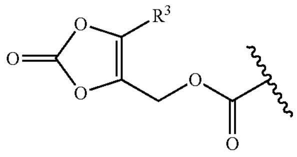

wherein $R^3$ represents a hydrogen atom or a $C_{1-6}$ alkyl group.

$R^b$ is further preferably a hydrogen atom.

Preferred examples of the compound represented by formula (1) include compounds as described below or pharmaceutically acceptable salts thereof.

Of the compounds represented by formula (1), a preferred one is the following (A):

(A) a compound or a pharmaceutically acceptable salt thereof, wherein

L is a $C_{1-4}$ alkylene group which may be optionally substituted by 1 to 3 fluorine atoms;

$R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3), or (5) $R^{11}$ and $R^{12}$ together form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (c) in the $C_{3-8}$ cycloalkyl group (3);

$X^1$ is N or $CR^1$;

$R^1$ and $R^2$ are each independently a hydrogen atom, a halogen atom, a $C_{1-6}$ alkoxy group, or a $C_{1-6}$ alkyl group;

$R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (2) a phenyl group which may be optionally substituted by 1 to 4 identical or different groups selected from the group consisting of the substituents (a) to (e) in the $C_{4-7}$ cycloalkyl group (1), (3) a pyridyl group which may be optionally substituted by 1 to 4 identical or different groups selected from the group consisting of the substituents (a) to (e) in the $C_{4-7}$ cycloalkyl group (1), (4) a 4- to 7-membered saturated heterocyclic group which may be optionally substituted by 1 to 4 identical or different groups selected from the group consisting of the substituents (a) to (e) in the $C_{4-7}$ cycloalkyl group (1), (5) a $C_{4-7}$ cycloalkoxy group which may be optionally substituted by 1 to 4 identical or different groups selected from the group consisting of the substituents (a) to (e) in the $C_{4-7}$ cycloalkyl group (1), or (6) a phenoxy group which may be optionally substituted by 1 to 4 identical or different groups selected from the group consisting of the substituents (a) to (e) in the $C_{4-7}$ cycloalkyl group (1); and $R^b$ is (1) a hydrogen atom, (2) a $C_{1-6}$ alkoxycarbonyl group, (3) a group represented by the following formula (2a):

(2a)

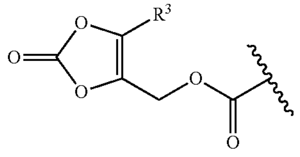

wherein $R^3$ represents a hydrogen atom or a $C_{1-6}$ alkyl group, or (4) a group represented by the following formula (2b):

(2b)

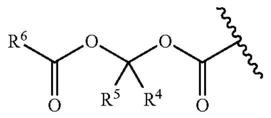

wherein $R^4$ and $R^5$ each independently represent a hydrogen atom or a $C_{1-6}$ alkyl group; and $R^6$ represents a $C_{1-6}$ alkyl group.

Of the compounds represented by formula (1), a more preferred one is the following (B):

(B) a compound or a pharmaceutically acceptable salt thereof, wherein

L is a $C_{1-4}$ alkylene group substituted by 1 to 3 fluorine atoms;

$R^{11}$ and $R^{12}$ are each independently a hydrogen atom or a $C_{1-6}$ alkyl group which may be optionally substituted by 1 to 3 halogen atoms, or $R^{11}$ and $R^{12}$ together form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and a C1-6 alkyl group;

$X^1$ is N or CH;

$R^1$ and $R^2$ are each independently a hydrogen atom, a fluorine atom, or a $C_{1-6}$ alkoxy group;

$R^a$ is (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, (2) a phenyl group which may be optionally substituted by 1 to 4 identical or different groups selected from the group consisting of the substituents (a) to (c) in the $C_{4-7}$ cycloalkyl group (1), or (3) a 4- to 7-membered saturated heterocyclic group which may be optionally substituted by 1 to 4 identical or different groups selected from the group consisting of the substituents (a) to (c) in the $C_{4-7}$ cycloalkyl group (1); and $R^b$ is a hydrogen atom or a group represented by the following formula (2a):

(2a)

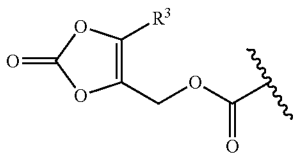

wherein $R^3$ represents a hydrogen atom or a $C_{1-6}$ alkyl group.

Of the compounds represented by formula (1) a further preferred one is the following (C):

(C) a compound or a pharmaceutically acceptable salt thereof, wherein

L is a 1-methylmethylene group substituted by 1 to 3 fluorine atoms;

$R^{11}$ and $R^{12}$ together form, together with the carbon atom bonded thereto, a 4- to 6-membered cycloalkane ring which may be optionally substituted by 1 to 4 fluorine atoms;

$X^1$ is CH;

each of $R^1$ and $R^2$ is a hydrogen atom;

$R^a$ is cyclohexane, piperidine, or a phenyl group wherein the cyclohexane, the piperidine, or the phenyl group may be each optionally substituted by 1 to 4 identical or different groups selected from a fluorine atom and a methoxy group; and $R^b$ is a hydrogen atom.

Preferred examples of the compound represented by formula (2) include compounds as described below or pharmaceutically acceptable salts thereof.

Of the compounds represented by formula (2), a preferred one is the following (D):

(D) a compound or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3), or $R^{11}$ and $R^{12}$ together form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (c) in the $C_{3-8}$ cycloalkyl group (3);

$X^1$ is N or $CR^1$;

$R^1$ and $R^2$ are each independently a hydrogen atom, a halogen atom, a $C_{1-6}$ alkoxy group, or a $C_{1-6}$ alkyl group;

$R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, and (e) $C_{1-6}$ alkyl, (2) a phenyl group which may be optionally substituted by 1 to 4 identical or different groups selected from the group consisting of the substituents (a) to (e) in the $C_{4-7}$ cycloalkyl group (1), (3) a pyridyl group which may be optionally substituted by 1 to 4 identical or different groups selected from the group consisting of the substituents (a) to (e) in the $C_{4-7}$ cycloalkyl group (1), (4) a 4- to 7-membered saturated heterocyclic group which may be optionally substituted by 1 to 4 identical or different groups selected from the group consisting of the substituents (a) to (e) in the $C_{4-7}$ cycloalkyl group (1), (5) a $C_{4-7}$ cycloalkoxy group which may be optionally substituted by 1 to 4 identical or different groups selected from the group consisting of the substituents (a) to (e) in the $C_{4-7}$ cycloalkyl group (1), or (6) a phenoxy group which may be optionally substituted by 1 to 4 identical or different groups selected from the group consisting of the substituents (a) to (e) in the $C_{4-7}$ cycloalkyl group (1);

$R^b$ is (1) a hydrogen atom, (2) a $C_{1-6}$ alkoxy carbonyl group, (3) a group represented by the following formula (2a):

(2a)

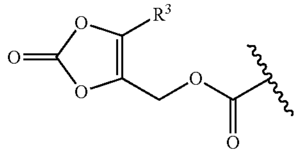

wherein $R^3$ represents a hydrogen atom or a $C_{1-6}$ alkyl group, or (4) a group represented by the following formula (2b):

(2b)

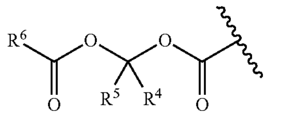

wherein $R^4$ and $R^5$ each independently represent a hydrogen atom or a $C_{1-6}$ alkyl group, and $R^6$ represents a $C_{1-6}$ alkyl group, and each of $R^{21}$ and $R^{22}$ is a hydrogen atom, a fluorine atom, or a methyl group which may be optionally substituted by 1 to 3 fluorine atoms.

Of the compounds represented by formula (2), a more preferred form is the following (E):

(E) a compound or a pharmaceutically acceptable salt thereof, wherein $R^{11}$ and $R^{12}$ are each independently a hydrogen atom or a $C_{1-6}$ alkyl group which may be optionally substituted by 1 to 3 halogen atoms, or $R^{11}$ and $R^{12}$ together form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and C1-6 alkyl;

$X^1$ is N or CH;

$R^1$ and $R^2$ are each independently a hydrogen atom, a fluorine atom, or a $C_{1-6}$ alkoxy group;

$R^a$ is (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, (2) a phenyl group which may be optionally substituted by 1 to 4 identical or different groups selected from the group consisting of the substituents (a) to (c) in the $C_{4-7}$ cycloalkyl group (1), or (3) a 4- to 7-membered saturated heterocyclic group which may be optionally substituted by 1 to 4 identical or different groups selected from the group consisting of the substituents (a) to (c) in the $C_{4-7}$ cycloalkyl group (1); and $R^b$ is a hydrogen atom or a group represented by the following formula (2a):

(2a)

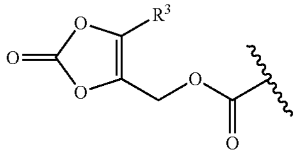

wherein $R^3$ represents a hydrogen atom or a $C_{1-6}$ alkyl group, $R^{21}$ is a hydrogen atom, and $R^{22}$ is a methyl group substituted by 1 to 3 fluorine atoms.

Of the compounds represented by formula (2), a further preferred one is the following (F):

(F) a compound or a pharmaceutically acceptable salt thereof, wherein $R^{11}$ and $R^{12}$ together form, together with the carbon atom bonded thereto, a 4- to 6-membered cycloalkane ring which may be optionally substituted by 1 to 4 fluorine atoms;

$X^1$ is CH;

each of $R^1$ and $R^2$ is a hydrogen atom;

$R^a$ is a cyclohexane, a piperidine, or a phenyl group wherein the cyclohexane, the piperidine, or the phenyl group may be each optionally substituted by 1 to 4 identical or different groups selected from a fluorine atom and a methoxy group;

$R^b$ is a hydrogen atom;

$R^{21}$ is a hydrogen atom; and $R^{22}$ is a methyl group substituted by 1 to 3 fluorine atoms.

Of the compounds represented by formula (3), a preferred one is the following (G):

(G) a compound or a pharmaceutically acceptable salt thereof, wherein $R^{31}$ and $R^{32}$ are each independently a hydrogen atom, a halogen atom, a $C_{1-6}$ alkoxy group, or a $C_{1-6}$ alkyl group;

$R^{41}$ and $R^{42}$ are each independently (1) a hydrogen atom, (2) a $C_{1-6}$ alkyl group which may be optionally substituted by 1 to 4 identical or different groups selected from the group consisting of (a) a halogen atom, (b) $C_{1-6}$ alkoxy, and (c) $C_{4-7}$ cycloalkyl, or (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) $R^{41}$ and $R^{42}$ together form, together with the carbon atom bonded thereto, a 4- to 7-membered cycloalkane ring or a 4- to 6-membered saturated heterocyclic ring wherein the 4- to 7-membered cycloalkane ring and the 4- to 6-membered saturated heterocyclic ring may be each optionally substituted by 1 to 4 identical or different groups selected from the group consisting of the substituents (a) to (c) in the $C_{3-8}$ cycloalkyl group (3); and $X^2$ is N or CH.

Of the compounds represented by formula (3), a more preferred one is the following (H):

(H) a compound or a pharmaceutically acceptable salt thereof, wherein $R^{31}$ and $R^{32}$ are each independently a hydrogen atom or a methoxy group;

$R^{41}$ and $R^{42}$ are each independently a hydrogen atom or a $C_{1-6}$ alkyl group which may be optionally substituted by 1 to 3 halogen atoms, or $R^{11}$ and $R^{12}$ together form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and C1-6 alkyl; and $X^2$ is CH.

Of the compounds represented by formula (3), a further preferred one is the following (I):

(I) a compound or a pharmaceutically acceptable salt thereof, wherein each of $R^{31}$ and $R^{32}$ is a hydrogen atom;

$R^{41}$ and $R^{42}$ together form, together with the carbon atom bonded thereto, a 4- to 6-membered cycloalkane ring which may be optionally substituted by 1 to 4 fluorine atoms; and $X^2$ is CH.

The compound represented by formula (1) and the pharmaceutically acceptable salt thereof may exist in the forms of hydrates and/or solvates. Therefore, these hydrates and/or solvates (e.g., ethanol solvate) are also included in the present compound. Furthermore, the present compound also encompasses every crystal form.

When the compound represented by formula (1) has an acidic functional group, examples of the pharmaceutically acceptable salt include: alkali metal salts such as sodium salt and potassium salt; alkaline earth metal salts such as calcium salt and magnesium salt; inorganic metal salts such as zinc salt; and salts of organic bases such as triethylamine, triethanolamine, trihydroxymethylaminomethane, and amino acids.

When the compound represented by formula (1) has a basic functional group, examples of the pharmaceutically acceptable salt include: inorganic acid salts such as hydrochloride, hydrobromide, sulfate, phosphate, and nitrate; and organic acid salts such as acetate, propionate, succinate, lactate, malate, tartrate, citrate, maleate, fumarate, methanesulfonate, p-toluenesulfonate, benzenesulfonate, and ascorbate.

The compound (1) represented by formula (1) may exist as a tautomer. Thus, the present compound also encompasses tautomers of the compound represented by formula (1).

The compound represented by formula (1) has at least two asymmetric carbon atoms. Thus, the present compound also encompasses stereoisomers of the compounds, and their mixtures. The present compound also encompasses racemates of the compound represented by formula (1), and optically active forms of the compound.

When the compound represented by formula (1) or a compound described in each Reference Example is a racemate, this racemate is illustrated as follows:

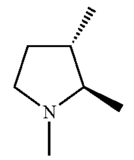
trans

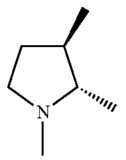
trans

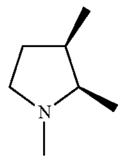
cis

Also, the compound represented by formula (1) or a compound described in each Reference Example, if the absolute configurations of asymmetric carbon atoms are known, is illustrated, for example, as follows:

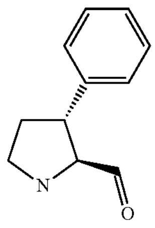
(2S,3R)

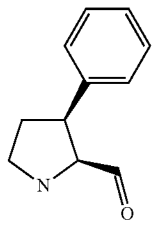
(2S,3S)

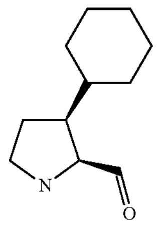
(2S,3S)

-continued

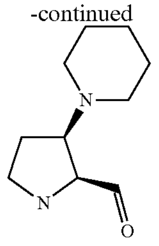

(2S,3R)

Also, the compound represented by formula (1) or a compound described in each Reference Example, if the configuration thereof is known, is illustrated, for example, as follows:

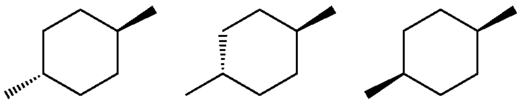

trans trans cis

Further, the compound represented by formula (1) may produce atropisomerism based on axial or planar chirality resulting from the restriction of intramolecular rotation. Thus, the present compound also encompasses stereoisomers of these compounds, and their mixtures.

Moreover, a deuterated form of the compound represented by formula (1) by the conversion of any one or two or more $^{1}H$ atoms to $^{2}H(D)$ is also encompassed with the compound represented by formula (1).

When the compound represented by the general formula (1) and the pharmaceutically acceptable salt thereof are obtained as crystals, crystal polymorphs thereof may exist. Thus, the compound of the present invention includes every crystal form.

Hereinafter, methods for producing the present compound will be described by taking some examples. However, the present invention is not intended to be limited by these examples by any means. In the present specification, the following abbreviations may be used for simple description:

Boc group: tert-butoxycarbonyl group
Cbz group: benzyloxycarbonyl group
Alloc group: allyloxycarbonyl group
Fmoc group: 9-fluorenylmethyloxycarbonyl group
THF: tetrahydrofuran
DMF: N,N-dimethylformamide Production Method The present compound is synthesized by any of production methods shown below, or by using compounds known in the art and synthesis methods known in the art in combination.

Each compound used as a starting compound may be used as a salt. The reactions shown below are given merely for illustrative purposes, and the present compound can also be appropriately produced by any of other methods based on the knowledge of those skilled in organic synthesis.

In each production method described below, a functional group that needs to be protected, if present, is protected according to the need, even if use of a protective group is not specifically described. After the completion of the reaction or after a series of reactions, the compound of interest may be obtained by deprotection.

Ordinary protective groups described in the literature (T. W. Greene and P. G. M. Wuts, "Protective Groups in Organic Synthesis", 3rd Ed., John Wiley and Sons, Inc., New York (1999)) or the like can be used as a protective group. Further specific examples thereof can include: protective groups for amino groups, such as benzyloxycarbonyl, tert-butoxycarbonyl, acetyl, and benzyl; and protective groups for hydroxy groups, such as trialkylsilyl, acetyl, and benzyl.

The protective group can be introduced and eliminated by methods routinely used in organic synthetic chemistry (e.g., methods described in T. W. Greene and P. G. M. Wuts, "Protective Groups in Organic Synthesis", 3rd Ed., John Wiley and Sons, Inc., New York (1999)) or methods equivalent thereto.

Production Method 1

The compound represented by formula (1) is produced by forming a bond at each of the sites a, b, c, and d.

(1)

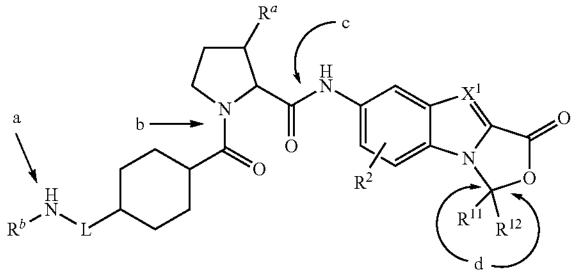

wherein L, $R^a$, $R^b$, $R^{11}$, $R^{12}$, $R^2$, and $X^1$ are the same as defined above in [1].

An exemplary method for forming a bond at each of the sites a, b, and c can be shown below, and an exemplary method for forming a bond at the site d can be shown in production method 7. However, the order in which these bonds are formed can be appropriately changed.

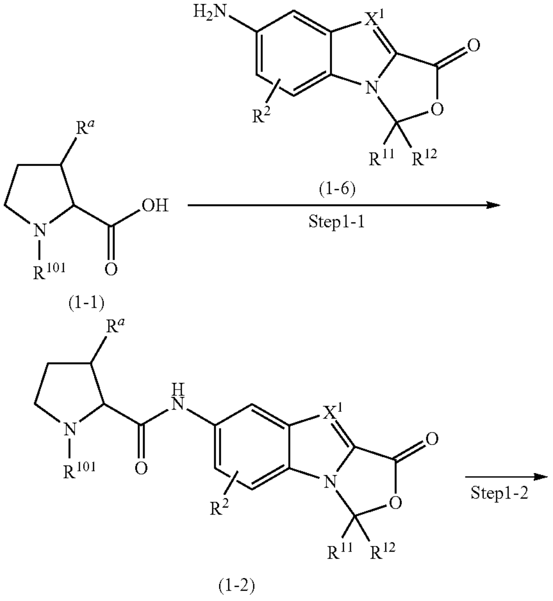

(1-6)
(1-1)
(1-2)

-continued

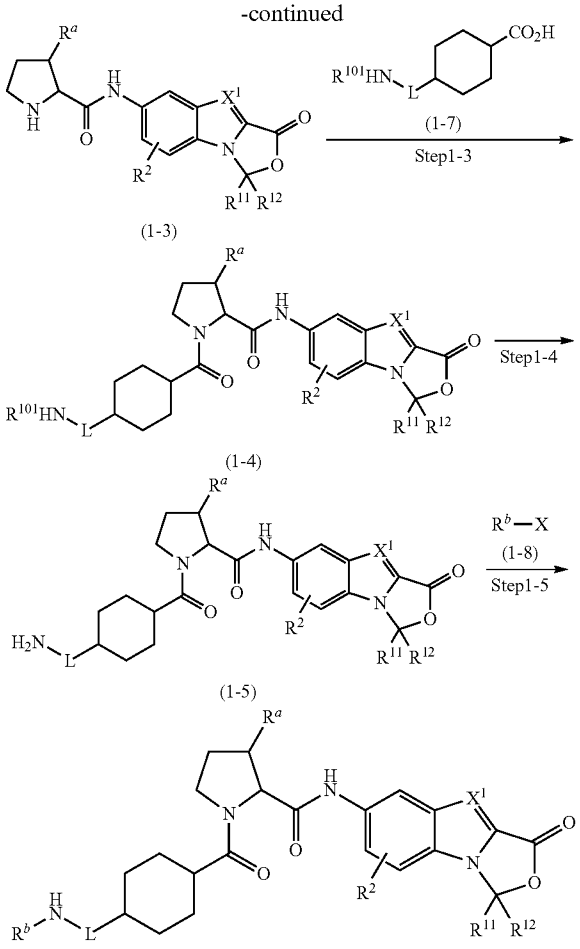

(1-3)

(1-4)

(1-5)

(1)

wherein L, $R^a$, $R^b$, $R^{11}$, $R^{12}$, $R^2$, and $X^1$ are the same as defined above in [1], $R^{101}$ represents a Cbz group, a Boc group, an Alloc group, a benzyl group, or an Fmoc group, and X represents a halogen atom or a 4-nitrophenoxy group.

The compound represented by formula (1-1) can be a commercially available product or can be produced by a known synthesis method (e.g., Tetrahedron Lett. 2010, 51, 6745, Org. Lett. 2009, 11, 4056, and Bioorg. Med. Chem. 2011, 19, 5833).

Step 1-1: Step of Producing Compound (1-2)

Compound (1-2) is produced by reacting compound (1-1) with compound (1-6) using a condensing agent, if necessary in the presence of a base, in an inert solvent.

The base is not particularly limited as long as the base can be used in usual reaction. Examples thereof include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline; and inorganic bases such as sodium bicarbonate, potassium bicarbonate, sodium carbonate, potassium carbonate, sodium hydroxide, and sodium hydride. The amount of the base used is usually 0.1 to 100 equivalents, preferably 1 to 5 equivalents, with respect to compound (1-1).

Examples of the condensing agent include those described in Experimental Chemistry (edited by The Chemical Society of Japan, Maruzen Co., Ltd.), Vol. 22. Examples thereof include: phosphoric acid esters such as diethyl cyanophosphate and diphenylphosphorylazide; carbodiimides such as 1-ethyl-3-(3-dimethylaminopropyl)-carbodiimide hydrochloride (WSC.HCl) and dicyclohexylcarbodiimide (DCC); combinations of disulfides such as 2,2'-dipyridyl disulfide and phosphines such as triphenylphosphine; phosphorus halides such as N,N'-bis(2-oxo-3-oxazolidinyl)phosphinic chloride (BOPCl); combinations of azodicarboxylic acid diesters such as diethyl azodicarboxylate and phosphines such as triphenylphosphine; 2-halo-1-lower alkylpyridinium halides such as 2-chloro-1-methylpyridinium iodide; 1,1'-carbonyldiimidazole (CDI); diphenylphosphorylazide (DPPA); diethylphosphorylcyanide (DEPC); tetrafluoroborates such as 2-(1H-benzotriazol-1-yl)-1,1,3,3-tetramethyluronium tetrafluoroborate (TBTU) and 2-chloro-1,3-dimethylimidazolidinium tetrafluoroborate (CIB); and phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino) phosphonium hexafluorophosphate (PYBOP), and 2-(7-aza-1H-benzotriazol-1-yl)-1,1,3,3-tetramethyluronium hexafluorophosphate (HATU).

In this reaction, a phase transfer catalyst can also be added, if necessary. Examples of the phase transfer catalyst include: quaternary ammonium salts such as tetrabutyl ammonium bromide and benzyl triethyl ammonium bromide; and crown ethers such as 18-crown-6-ether. The amount of the phase transfer catalyst used is usually 0.01 to 100 equivalents, preferably 0.1 to 3 equivalents, with respect to compound (1-1).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; ketone solvents such as acetone; and aprotic solvents such as acetonitrile, N,N-dimethylformamide, dimethyl sulfoxide, and hexamethylenephosphoramide. A mixed solvent thereof may be used.

The reaction temperature is not particularly limited and is preferably selected from the range of approximately −70° C. to 100° C., more preferably 0° C. to 80° C.

Compound (1-2) is also produced by reacting compound (1-1) with a halogenating reagent (e.g. 1-chloro-N,N,2-trimethylpropenylamine, phosphorus oxychloride, phosphorus trichloride, thionyl chloride, phosphorus pentachloride, and oxalyl chloride) to produce an acid halide and then reacting the acid halide with compound (1-6) in an inert solvent, and if necessary in the presence of a base.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; ester solvents such as ethyl acetate and isopropyl acetate; ketone solvents such as methyl ethyl ketone and acetone; and aprotic solvents such as acetonitrile, N,N-dimethylformamide, dimethyl sulfoxide, and hexamethylenephosphoramide.

Examples of the base include organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline.

The halogenating reagent is used at 0.1 to 100 equivalents, and preferably 0.8 to 3 equivalents, with respect to compound (1-1). The reaction temperature is not particularly limited but is preferably selected from the range of approximately −30° C. to 60° C.

Step 1-2: Step of Producing Compound (1-3)

Compound (1-3) is produced by treating compound (1-2) according to a method described in the literature (e.g., Protective Groups in Organic Synthesis 3rd Edition (John Wiley & Sons, Inc.)).

Step 1-3: Step of Producing Compound (1-4)

Compound (1-4) is produced in the same way as in step 1-1 using compound (1-3) and compound (1-7).

Step 1-4: Step of Producing Compound (1-5)

Compound (1-5) is produced by treating compound (1-4) in the same way as in step 1-2.

Step 1-5: Step of Producing Compound (1)

Compound (1) is produced by reacting compound (1-5) with compound (1-8) in the presence of an additive and a base in an inert solvent.

Examples of the base include: organic bases such as triethylamine, N-methylmorpholine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine, dimethylaminopyridine, and picoline; and inorganic bases such as cesium carbonate, sodium bicarbonate, potassium bicarbonate, sodium carbonate, and potassium carbonate.

Examples of the inert solvent include: ether solvents such as tetrahydrofuran and 1,4-dioxane; aprotic solvents such as dimethylformamide and dimethyl sulfoxide; and halogenated hydrocarbon solvents such as chloroform, dichloromethane, and dichloroethane. A mixed solvent thereof may be used.

The reaction temperature is not particularly limited and is preferably selected from the range of approximately −20° C. to approximately 60° C. Examples of the additive include dimethylaminopyridine.

Production Method 2

Among the compounds represented by formula (1-1), an optically active 3-substituted pyrrolidine-2-carboxylic acid derivative represented by formula (2-9) or (2-11) is produced by, for example, a method described in Patent Literature 1.

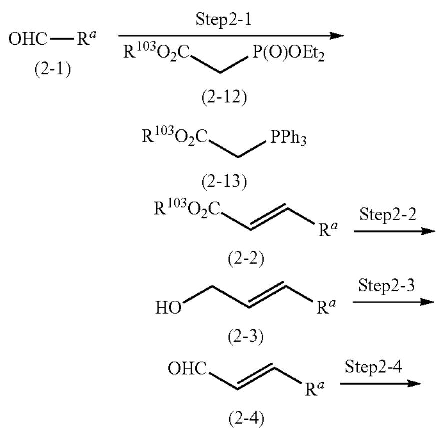

(2-1) (2-12) (2-13) (2-2) (2-3) (2-4)

-continued

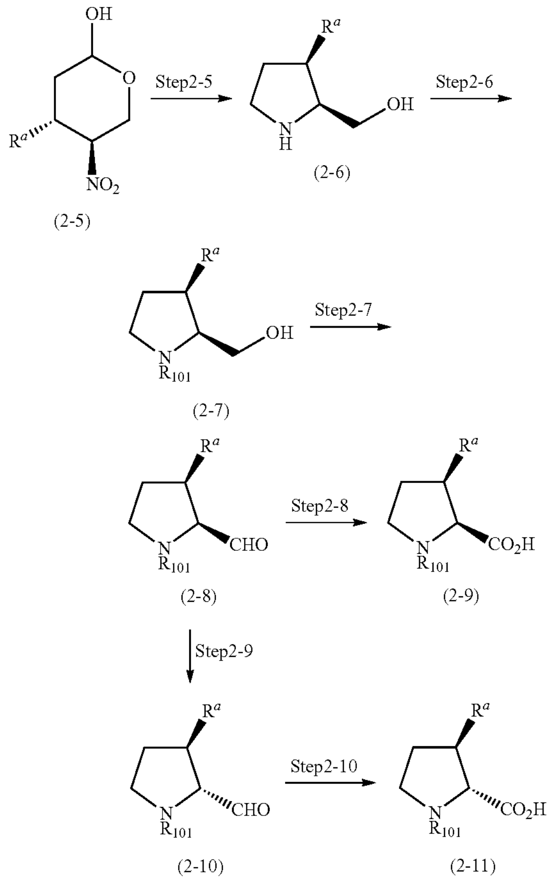

(2-5) (2-6) (2-7) (2-8) (2-9) (2-10) (2-11)

wherein $R^a$ is the same as defined above in [1], $R^{103}$ represents $C_{1-4}$ alkyl or benzyl, and $R^{101}$ represents a Cbz group, a Boc group, an Alloc group, a benzyl group, or an Fmoc group.

Production Method 3

Among the compounds represented by formula (1-1), a 3-substituted pyrrolidine-2-carboxylic acid derivative (racemate) represented by formula (3-5) is produced by, for example, a method shown below.

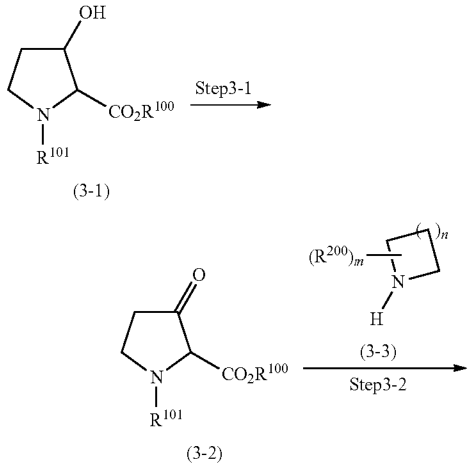

(3-1) (3-2) (3-3)

-continued

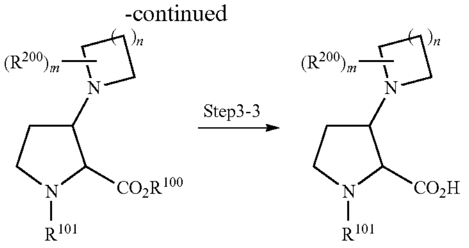

(3-4) (3-5)

wherein $R^{100}$ represents a $C_{1-4}$ alkyl group or a benzyl group, n represents 0 to 4, m represents 0 to 4, $R^{200}$ represents a halogen atom, hydroxy, cyano, $C_{1-6}$ alkoxy, or $C_{1-6}$ alkyl, and $R^{101}$ represents a Cbz group, a Boc group, an Alloc group, a benzyl group, or an Fmoc group.

The compound represented by formula (3-1) can be prepared by appropriately protecting a functional group of 3-hydroxyproline commercially available by a production method known in the art (e.g., Protective Groups in Organic Synthesis $3^{rd}$ Edition (John Wiley & Sons, Inc.)).

Step 3-1: Step of Producing Compound (3-2)

Compound (3-2) is produced by oxidizing compound (3-1) in the same way as a method known in the art (e.g., Comprehensive Organic Trans Formation, R. C. Larock et al., VCH publisher Inc., 1989). Dess-Martin oxidation, Swern oxidation, Parikh-Doering oxidation, TPAP oxidation, PCC oxidation, or the like is preferably used as the oxidation method.

Step 3-2: Step of Producing Compound (3-4)

Compound (3-4) is produced in the same way as a method known in the art (e.g., Comprehensive Organic Trans Formation, R. C. Larock, VCH publisher Inc., 1989) using compound (3-2) and compound (3-3). Possible conversion methods are, for example, reductive amination reaction or imination reaction and subsequent reduction reaction. In this step, cis and trans geometric isomers may be formed. In this case, these isomers may be resolved by a method such as various column chromatography techniques or crystallization and used in the next reaction. Examples of the reducing agent for the reductive amination reaction or the reduction reaction include lithium aluminum hydride, sodium borohydride, sodium triacetoxyborohydride, sodium cyanoborohydride, diisobutyl aluminum hydride, lithium tri(sec-butyl) borohydride, sodium tri(sec-butyl)borohydride, potassium tri(sec-butyl)borohydride, borane-dimethyl sulfide complexes, borane-tetrahydrofuran complexes, lithium triethylborohydride, and ammonium formate. Alternatively, hydrogenation reaction using a metal catalyst such as palladium-carbon or palladium oxide may be carried out. Examples of the additive for the reductive amination reaction or the reduction reaction include: organic acids such as acetic acid, hydrochloric acid, trifluoroacetic acid, and methanesulfonic acid; dehydrating agents such as tetramethyl orthosilicate and methyl orthoformate; and Lewis acids such as zinc chloride, titanium tetrachloride, lanthanum sulfate, magnesium sulfate-pyridinium p-toluenesulfonate, magnesium bromide, indium chloride, zirconium chloride, magnesium triflate, ytterbium(III) triflate, scandium triflate, alumina, copper sulfate, titanium tetraisopropoxide, and titanium tetraethoxide.

Step 3-3: Step of Producing Compound (3-5)

Compound (3-5) is produced by hydrolyzing compound (3-4) in the same way as a method known in the art (e.g., Protective Groups in Organic Synthesis $3^{rd}$ Edition (John Wiley & Sons, Inc.), and Comprehensive Organic Trans Formation, R. C. Larock et al., VCH publisher Inc., 1989). In this step, cis and trans isomers may be formed. In this case, these isomers may be resolved by a method such as various column chromatography techniques or crystallization and used in the next reaction.

Production Method 4

Among the compounds represented by formula (1-7), a compound represented by formula (4-8) is produced by, for example, a method shown below.

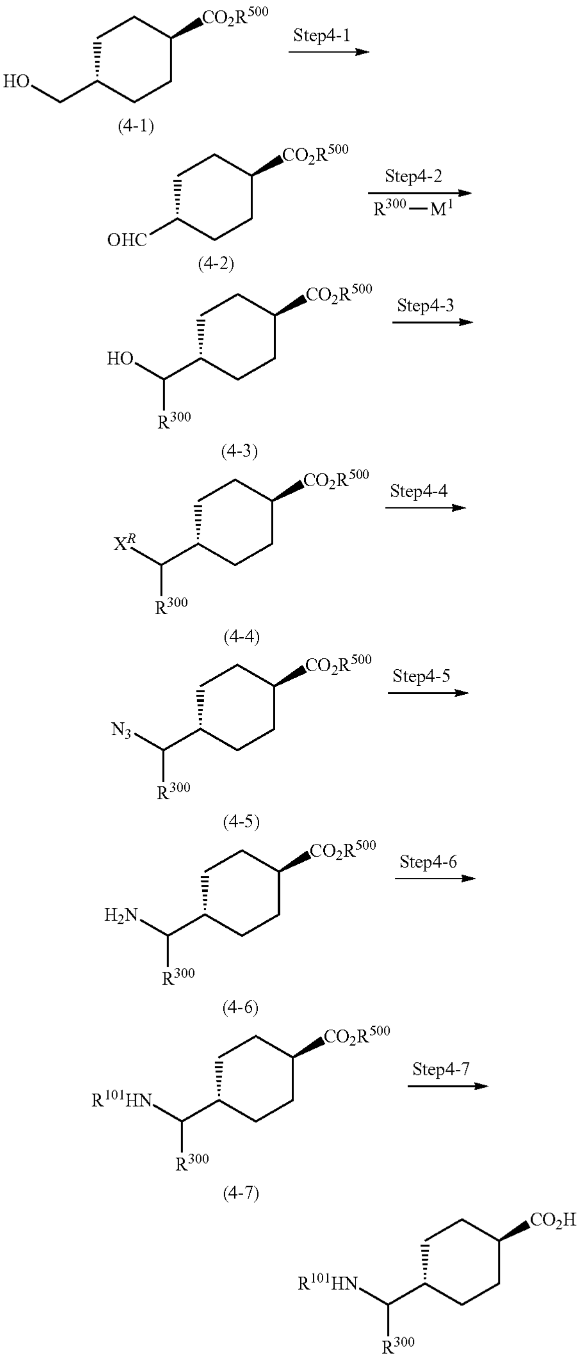

(4-1) (4-2) (4-3) (4-4) (4-5) (4-6) (4-7) (4-8)

wherein $R^{500}$ represents a $C_{1-4}$ alkyl group, a benzyl group, a 4-methoxybenzyl group, or a 2,4-dimethoxybenzyl group, $R^{300}$ represents optionally substituted $C_{1-6}$ alkyl or optionally substituted $C_{3-10}$ cycloalkyl, $X^R$ represents a leaving group (e.g., a methanesulfonyloxy group, a chloromethanesulfonyloxy group, a trifluoromethanesulfonyloxy group, a benzenesulfonyloxy group, a p-toluenemethanesulfonyloxy group, a chlorine atom, a bromine atom, and an iodine atom), $M^1$ represents lithium or magnesium halide, and $R^{101}$ represents a Cbz group, a Boc group, an Alloc group, a benzyl group, or an Fmoc group.

The compound represented by formula (4-1) can be a commercially available product or can be prepared by appropriately protecting a functional group in commercially available trans-4-(hydroxymethyl)cyclohexanecarboxylic acid by a production method known in the art (e.g., Protective Groups in Organic Synthesis $3^{rd}$ Edition (John Wiley & Sons, Inc.)).

Step 4-1: Step of Producing Compound (4-2)

Compound (4-2) is produced by oxidizing compound (4-1) in the same way as a method known in the art (e.g., Comprehensive Organic Transformation, R. C. Larock et al., VCH publisher Inc., 1989). Dess-Martin oxidation, Swern oxidation, Parikh-Doering oxidation, TPAP oxidation, PCC oxidation, PDC oxidation, or the like is preferably used as the oxidation method.

Step 4-2: Step of Producing Compound (4-3)

Compound (4-3) is produced by reacting compound (4-2) with alkyllithium or a Grignard reagent in an inert solvent. Also, a Lewis acid may be added, if necessary.

Specific examples of the Lewis acid include lithium chloride, lithium bromide, lithium iodide, titanium(IV) tetraisopropoxide, zinc chloride, zinc bromide, aluminum chloride, bismuth(III) chloride, and manganese(II) chloride. The amount of the Lewis acid used is usually 0.01 to 100 equivalents, preferably 0.1 to 3 equivalents, with respect to compound (4-2).

Specific examples of the alkyllithium include methyllithium, ethyllithium, n-propyllithium, n-pentyllithium, n-hexyllithium, isopropyllithium, isobutyllithium, sec-butyllithium, tert-butyllithium, neopentyllithium, and cyclopentyllithium.

Specific examples of the Grignard reagent include methyl magnesium chloride, ethyl magnesium chloride, propyl magnesium chloride, n-butyl magnesium chloride, n-pentyl magnesium chloride, n-hexyl magnesium chloride, isopropyl magnesium chloride, isobutyl magnesium chloride, tert-butyl magnesium chloride, sec-butyl magnesium chloride, cyclopropyl magnesium chloride, cyclobutyl magnesium chloride, cyclopentyl magnesium chloride, cyclohexyl magnesium chloride, cycloheptyl magnesium chloride, 1,1-dimethylpropyl magnesium chloride, 2,2-dimethylpropyl magnesium chloride, 3,3-dimethyl-1-butyl magnesium chloride, 3-methylbutyl magnesium chloride, 2-methyl-2-pentyl magnesium chloride, 2-methylpentyl magnesium chloride, methyl magnesium bromide, ethyl magnesium bromide, propyl magnesium bromide, n-butyl magnesium bromide, n-pentyl magnesium bromide, n-hexyl magnesium bromide, isopropyl magnesium bromide, isobutyl magnesium bromide, tert-butyl magnesium bromide, sec-butyl magnesium bromide, cyclopropyl magnesium bromide, cyclobutyl magnesium bromide, cyclopentyl magnesium bromide, cyclohexyl magnesium bromide, cycloheptyl magnesium bromide, 1,1-dimethylpropyl magnesium bromide, 2,2-dimethylpropyl magnesium bromide, 3,3-dimethyl-1-butyl magnesium bromide, 3-methylbutyl magnesium bromide, 2-methyl-2-pentyl magnesium bromide, 2-methylpentyl magnesium bromide, methyl magnesium iodide, ethyl magnesium iodide, n-propyl magnesium iodide, isopropyl magnesium iodide, n-butyl magnesium iodide, and isobutyl magnesium iodide.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; and halogenated hydrocarbon solvents such as dichloromethane, chloroform, and 1,2-dichloroethane. A mixed solvent thereof may be used. The reaction temperature is not particularly limited and is preferably selected from the range of approximately −100° C. to 100° C., more preferably −100° C. to 0° C.

Step 4-3: Step of Producing Compound (4-4)

Compound (4-4) wherein $X^R$ represents a methanesulfonyloxy group, a chloromethanesulfonyloxy group, a trifluoromethanesulfonyloxy group, a benzenesulfonyloxy group, or a p-toluenemethanesulfonyloxy group is produced by reacting compound (4-3) with methanesulfonyl chloride, methanesulfonic anhydride, chloromethanesulfonyl chloride, trifluoromethanesulfonyl chloride, trifluoromethanesulfonic anhydride, benzenesulfonyl chloride, benzenesulfonic anhydride, p-toluenesulfonyl chloride, or p-toluenesulfonic anhydride in the presence of a base in an inert solvent.

The base is not particularly limited as long as the base can be used in usual reaction. Examples thereof include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline; and inorganic bases such as sodium methoxide, sodium tert-butoxide, potassium tert-butoxide, lithium diisopropylamide, lithium bis(trimethylsilyl)amide, potassium bis(trimethylsilyl)amide, sodium bis(trimethylsilyl)amide, lithium amide, n-butyllithium, sodium bicarbonate, potassium bicarbonate, sodium carbonate, potassium carbonate, sodium hydroxide, and sodium hydride. The amount of the base used is usually 0.1 to 100 equivalents, preferably 0.8 to 3 equivalents, with respect to compound (4-3).

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; and aprotic solvents such as N,N-dimethylformamide, dimethyl sulfoxide, and hexamethylenephosphoramide. A mixed solvent thereof may be used. The reaction temperature is not particularly limited and is preferably selected from the range of approximately −20° C. to 40° C.

Compound (4-4) wherein $X^R$ represents a chlorine atom is produced by chlorinating compound (4-3) in the same way as a method known in the art (e.g., Comprehensive Organic Transformation, R. C. Larock et al., VCH publisher Inc., 1989). A chlorinating reagent such as oxalyl chloride, thionyl chloride, phosphorus oxychloride, sulfuryl chloride, cyanuryl trichloride, carbon tetrachloride, or N-chlorosuccinimide is preferably used.

Compound (4-4) wherein $X^R$ represents a bromine atom is produced by brominating compound (4-3) in the same way as a method known in the art (e.g., Comprehensive Organic Transformation, R. C. Larock et al., VCH publisher Inc., 1989). A brominating reagent such as phosphorus tribromide, carbon tetrabromide, bromine, or N-bromosuccinimide is preferably used.

Compound (4-4) wherein $X^R$ represents an iodine atom is produced by iodating compound (4-3) in the same way as a method known in the art (e.g., Comprehensive Organic Transformation, R. C. Larock et al., VCH publisher Inc., 1989). An iodating reagent such as iodine or N-iodosuccinimide is preferably used.

Step 4-4: Step of Producing Compound (4-5)

Compound (4-5) is produced by reacting compound (4-4) with sodium azide, potassium azide, or lithium azide in an inert solvent.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; and aprotic solvents such as N,N-dimethylformamide, dimethyl sulfoxide, and hexamethylenephosphoramide. A mixed solvent thereof may be used. The reaction temperature is not particularly limited and is preferably selected from the range of approximately 20° C. to 160° C.

Step 4-5: Step of Producing Compound (4-6)

Compound (4-6) is produced by reducing compound (4-5) in the same way as a method known in the art (e.g., Experimental Chemistry (edited by The Chemical Society of Japan, Maruzen Co., Ltd.), Vol. 14).

Step 4-6: Step of Producing Compound (4-7)

Compound (4-7) is produced by treating compound (4-6) by a method known in the art (e.g., Protective Groups in Organic Synthesis 3rd Edition (John Wiley & Sons, Inc.)).

Step 4-7: Step of Producing Compound (4-8)

Compound (4-8) is produced by hydrolyzing compound (4-7) in the same way as a method known in the art (e.g., Protective Groups in Organic Synthesis 3rd Edition (John Wiley & Sons, Inc.), and Comprehensive Organic Transformation, R. C. Larock et al., VCH publisher Inc., 1989).

Production Method 5

Among the compounds represented by formula (1-7), a compound represented by formula (5-8) is produced by, for example, a method shown below.

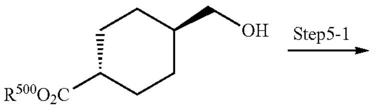

(4-1)

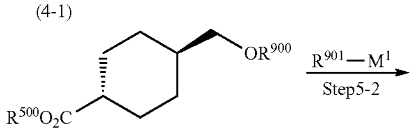

(5-1)

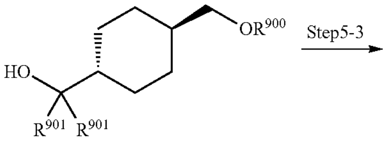

(5-2)

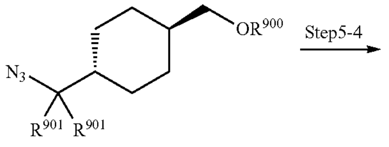

(5-3)

-continued

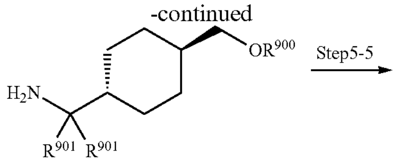

(5-4)

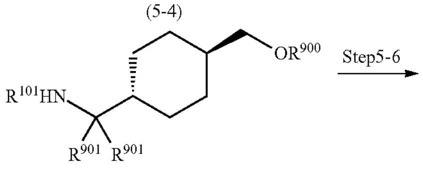

(5-5)

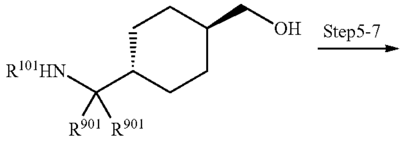

(5-6)

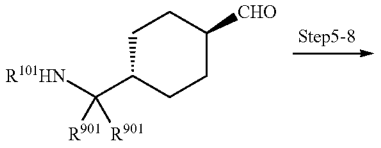

(5-7)

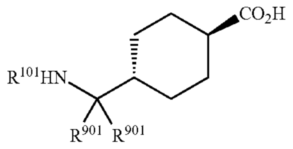

(5-8)

wherein $R^{500}$ represents a $C_{1-4}$ alkyl group, a benzyl group, a 4-methoxybenzyl group, or a 2,4-dimethoxybenzyl group, $R^{900}$ represents a trimethylsilyl group, a triethylsilyl group, a tert-butyldimethylsilyl group, a tert-butyldiphenylsilyl group, a triisopropylsilyl group, a diethylisopropylsilyl group, or an optionally substituted benzyl group, $R^{901}$ represents optionally substituted $C_{1-6}$ alkyl or optionally substituted $C_{3-10}$ cycloalkyl, $M^1$ represents lithium or magnesium halide, and $R^{101}$ represents a Cbz group, a Boc group, an Alloc group, a benzyl group, or an Fmoc group.

Step 5-1: Step of Producing Compound (5-1)

Compound (5-1) is produced in the same way as a method known in the art (e.g., Protective Groups in Organic Synthesis 3rd Edition (John Wiley & Sons, Inc.)) using compound (4-1).

Step 5-2: Step of Producing Compound (5-2)

Compound (5-2) is produced by reacting compound (5-1) with alkyllithium or a Grignard reagent in an inert solvent. Also, a Lewis acid may be added, if necessary.

Specific examples of the Lewis acid include lithium chloride, lithium bromide, lithium iodide, titanium(IV) tetraisopropoxide, zinc chloride, zinc bromide, aluminum chloride, bismuth(III) chloride, and manganese(II) chloride. The amount of the Lewis acid used is usually 0.01 to 100 equivalents, preferably 0.1 to 3 equivalents, with respect to compound (5-1).

Specific examples of the alkyllithium include methyllithium, ethyllithium, n-propyllithium, n-pentyllithium, n-hexyllithium, isopropyllithium, isobutyllithium, sec-butyllithium, tert-butyllithium, neopentyllithium, and cyclopentyllithium.

Specific examples of the Grignard reagent include methyl magnesium chloride, ethyl magnesium chloride, propyl magnesium chloride, n-butyl magnesium chloride, n-pentyl magnesium chloride, n-hexyl magnesium chloride, isopropyl magnesium chloride, isobutyl magnesium chloride, tert-butyl magnesium chloride, sec-butyl magnesium chloride, cyclopropyl magnesium chloride, cyclobutyl magnesium chloride, cyclopentyl magnesium chloride, cyclohexyl magnesium chloride, cycloheptyl magnesium chloride, 1,1-dimethylpropyl magnesium chloride, 2,2-dimethylpropyl magnesium chloride, 3,3-dimethyl-1-butyl magnesium chloride, 3-methylbutyl magnesium chloride, 2-methyl-2-pentyl magnesium chloride, 2-methylpentyl magnesium chloride, methyl magnesium bromide, ethyl magnesium bromide, propyl magnesium bromide, n-butyl magnesium bromide, n-pentyl magnesium bromide, n-hexyl magnesium bromide, isopropyl magnesium bromide, isobutyl magnesium bromide, tert-butyl magnesium bromide, sec-butyl magnesium bromide, cyclopropyl magnesium bromide, cyclobutyl magnesium bromide, cyclopentyl magnesium bromide, cyclohexyl magnesium bromide, cycloheptyl magnesium bromide, 1,1-dimethylpropyl magnesium bromide, 2,2-dimethylpropyl magnesium bromide, 3,3-dimethyl-1-butyl magnesium bromide, 3-methylbutyl magnesium bromide, 2-methyl-2-pentyl magnesium bromide, 2-methylpentyl magnesium bromide, methyl magnesium iodide, ethyl magnesium iodide, n-propyl magnesium iodide, isopropyl magnesium iodide, n-butyl magnesium iodide, and isobutyl magnesium iodide.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; and halogenated hydrocarbon solvents such as dichloromethane, chloroform, and dichloroethane. A mixed solvent thereof may be used. The reaction temperature is not particularly limited and is preferably selected from the range of approximately −20° C. to 50° C.

Step 5-3: Step of Producing Compound (5-3)

Compound (5-3) is produced by reacting compound (5-2) with hydrogen azide, sodium azide, or trimethylsilyl azide in the presence or absence of an acid in an inert solvent. Also, an additive may be added, if necessary.

Specific examples of the acid include trifluoroacetic acid, sulfuric acid, and hydrochloric acid. The amount of the acid used is usually 0.01 to 100 equivalents, preferably 0.1 to 20 equivalents, with respect to compound (5-2).

Specific examples of the additive include boron trifluoride-diethyl ether complexes, 15-crown-5, 18-crown-6, and HY-zeolite. The amount of the additive used is usually 0.01 to 100 equivalents, preferably 0.1 to 20 equivalents, with respect to compound (5-2).

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; and aprotic solvents such as acetonitrile, N,N-dimethylformamide, dimethyl sulfoxide, hexamethylenephosphoramide, and pyridine. A mixed solvent thereof may be used. The reaction temperature is not particularly limited and is preferably selected from the range of approximately −20° C. to 100° C.

Step 5-4: Step of Producing Compound (5-4)

Compound (5-4) is produced in the same way as in step 4-5 using compound (5-3).

Step 5-5: Step of Producing Compound (5-5)

Compound (5-5) is produced in the same way as in step 4-6 using compound (5-4).

Step 5-6: Step of Producing Compound (5-6)

Compound (5-6) is produced by deprotecting compound (5-5) in the same way as a method known in the art (e.g., Protective Groups in Organic Synthesis $3^{rd}$ Edition (John Wiley & Sons, Inc.), and Comprehensive Organic Transformation, R. C. Larock et al., VCH publisher Inc., 1989).

Step 5-7: Step of Producing Compound (5-7)

Compound (5-7) is produced by oxidizing compound (5-6) in the same way as a method known in the art (e.g., Comprehensive Organic Transformation, R. C. Larock et al., VCH publisher Inc., 1989). Dess-Martin oxidation, Swern oxidation, TPAP oxidation, PCC oxidation, or the like is preferably used as the oxidation method.

Step 5-8: Step of Producing Compound (5-8)

Compound (5-8) is produced by oxidizing compound (5-7) in the same way as a method known in the art (e.g., Comprehensive Organic Transformation, R. C. Larock et al., VCH publisher Inc., 1989). Pinnick oxidation, PDC oxidation, or the like is preferably used as the oxidation method.

Production Method 6

Among the compounds represented by formula (1-7), a compound represented by formula (6-9) is produced by, for example, a method shown below.

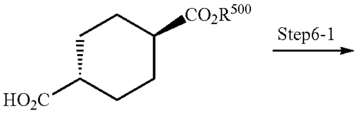

(6-1)

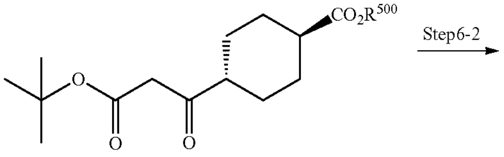

(6-2)

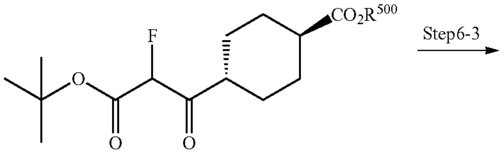

(6-3)

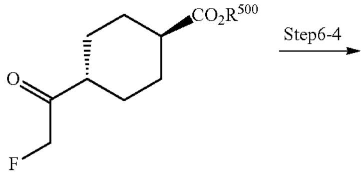

(6-4)

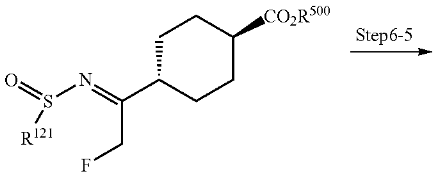

(6-5)

-continued

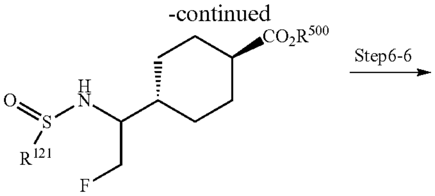

(6-6)

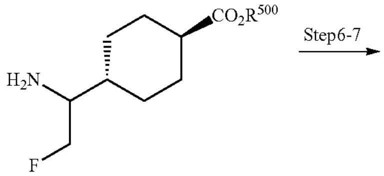

(6-7)

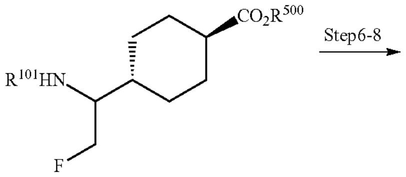

(6-8)

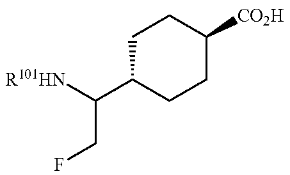

(6-9)

wherein $R^{500}$ represents a $C_{1-4}$ alkyl group, a benzyl group, a 4-methoxybenzyl group, or a 2,4-dimethoxybenzyl group, $R^{121}$ represents a 4-methylphenyl group or a tert-butyl group, and $R^{101}$ represents a Cbz group, a Boc group, an Alloc group, a benzyl group, or an Fmoc group.

Step 6-1: Step of Producing Compound (6-2)

Compound (6-2) is produced by, for example, a production method shown below (i. or ii.).

i. Compound (6-2) is produced in the same way as a method known in the art (e.g., J. Org. Chem., 1997, 62, 2292) by reacting compound (6-1) with N,N'-carbonyldiimidazole, oxalyl chloride, thionyl chloride, ethyl chloroformate, isobutyl chloroformate, propyl chloroformate, or isopropyl chloroformate in a range of −10° C. to 50° C., subsequently adding metal enolate of tert-butyl acetate to this reaction mixture, and reacting the resulting mixture in the range of −80° C. to approximately 50° C.

ii. Compound (6-2) is also produced in the same way as a method known in the art (e.g., Org. Lett., 2011, 13, 6284) by reacting compound (6-1) with N,N'-carbonyldiimidazole in the range of −20° C. to 50° C., subsequently adding isopropyl magnesium bromide or isopropyl magnesium chloride to this reaction mixture, and reacting the resulting mixture in the range of −20° C. to 50° C.

Step 6-2: Step of Producing Compound (6-3)

Compound (6-3) is produced by reacting compound (6-2) with Selectfluor, N-fluorobenzenesulfonimide, N-fluoromethanesulfonimide, N-fluorotrifluoromethanesulfonimide, or fluorine in an inert solvent.

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; and acetonitrile. A mixed solvent thereof may be used. The reaction temperature is not particularly limited and is preferably selected from the range of approximately −40° C. to 50° C.

Step 6-3: Step of Producing Compound (6-4)

Compound (6-4) is produced by decarboxylating compound (6-3) in the same way as a method known in the art (e.g., Comprehensive Organic Trans Formation, R. C. Larock et al.).

Step 6-4: Step of Producing Compound (6-5)

Compound (6-5) is produced by reacting compound (6-4) with (R)-2-methyl-2-propanesulfinamide, (S)-2-methyl-2-propanesulfinamide, (R)-4-methylbenzene-1-sulfinamide, or (S)-4-methylbenzene-1-sulfinamide in the presence of titanium tetrabutoxide, titanium tetraethoxide, or titanium tetraisopropoxide in an inert solvent.

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; and hydrocarbon solvents such as hexane, heptane, toluene, benzene, and xylene. A mixed solvent thereof may be used. The reaction temperature is not particularly limited and is preferably selected from the range of approximately −20° C. to 100° C.

Step 6-5: Step of Producing Compound (6-6)

Compound (6-6) is produced by, for example, a production method shown below (i. or ii.). Also, optically active compound (6-6) can be produced by using optically active sulfinamide in step 6-4.

i. Compound (6-6) is produced by reducing compound (6-5) using borane, sodium borohydride, sodium triacetoxyborohydride, sodium cyanoborohydride, L-Selectride, K-Selectride, diisobutyl aluminum hydride, lithium borohydride, lithium aluminum hydride, lithium triethylborohydride, zinc borohydride, sodium bis(2-methoxyethoxy) aluminum hydride, or 9-BBN in an inert solvent.

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; and aprotic solvents such as acetonitrile, N,N-dimethylformamide, dimethyl sulfoxide, hexamethylenephosphoramide, and pyridine. A mixed solvent thereof may be used. The reaction temperature is not particularly limited and is preferably selected from the range of approximately −100° C. to 100° C.

ii. Compound (6-6) is also produced by reacting compound (6-5) with a dichloro(cymene)ruthenium dimer or a ligand, if necessary in the presence of a base and a molecular sieve 4 Å in an isopropanol solvent.

Examples of the ligand include 2-amino-2-methyl-1-propanol, 2-aminoethanol, (1R,2S)-2-amino-1,2-diphenylethanol, (1 S,2R)-2-amino-1,2-diphenylethanol, (1 S,2R)-cis-1-amino-2-indanol, (1R,2S)-cis-1-amino-2-indanol, L-prolinol, R-prolinol, (S)-diphenyl(pyrrolidin-2-yl)methanol, and (R)-diphenyl(pyrrolidin-2-yl)methanol. The amount of the ligand used is usually 0.01 to 2 equivalents, preferably 0.01 to 0.2 equivalents, with respect to compound (6-5). Examples of the base include tert-butoxypotassium and potassium hydroxide. The amount of the base used is usually 0.01 to 2 equivalents, preferably 0.01 to 1.0 equivalents, with respect to compound (6-5). The reaction temperature is not particularly limited and is preferably selected from the range of approximately −100° C. to 100° C.

Step 6-6: Step of Producing Compound (6-7)

Compound (6-7) is produced by reacting compound (6-6) with an acid in an inert solvent.

Examples of the acid include hydrochloric acid, hydrobromic acid, sulfuric acid, trifluoroacetic acid, benzenesulfonic acid, p-toluenesulfonic acid, and acetic acid.

Examples of the inert solvent include: ether solvents such as tetrahydrofuran, diethyl ether, 1,4-dioxane, and 1,2-dimethoxyethane; halogenated hydrocarbon solvents such as dichloromethane, chloroform, and dichloroethane; hydrocarbon solvents such as hexane, heptane, toluene, benzene, and xylene; alcohol solvents such as ethanol, methanol, and isopropanol; and aprotic solvents such as acetonitrile, N,N-dimethylformamide, dimethyl sulfoxide, hexamethylenephosphoramide, and pyridine. A mixed solvent thereof may be used. The reaction temperature is not particularly limited and is preferably selected from the range of approximately −100° C. to 100° C.

Step 6-7: Step of Producing Compound (6-8)

Compound (6-8) is produced by treating compound (6-7) by a method known in the art (e.g., Protective Groups in Organic Synthesis 3$^{rd}$ Edition (John Wiley & Sons, Inc.)).

Step 6-8: Step of Producing Compound (6-9)

Compound (6-9) is produced by hydrolyzing compound (6-8) by a method known in the art (e.g., Protective Groups in Organic Synthesis 3$^{rd}$ Edition (John Wiley & Sons, Inc.), and Comprehensive Organic Transformation, R. C. Larock et al., VCH publisher Inc., 1989).

Production Method 7

The compound represented by formula (1-6) is also produced by, for example, a method shown below.

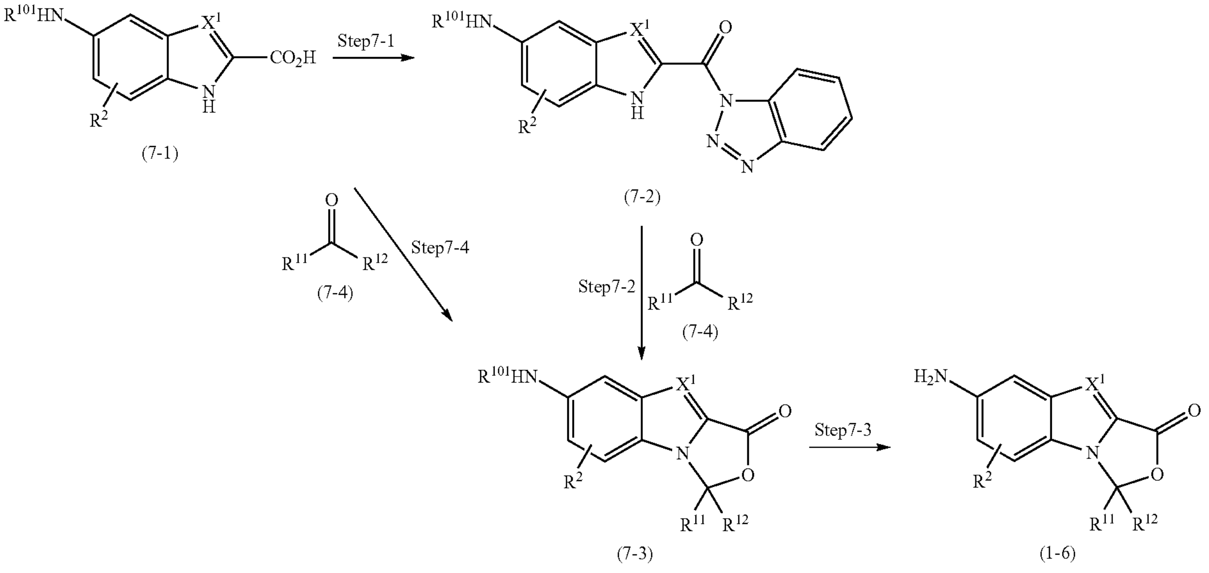

(7-1) (7-2) (7-4) (7-4) (7-3) (1-6)

wherein $R^{11}$, $R^{12}$, $R^2$, and $X^1$ are the same as defined above in [1], and $R^{101}$ represents a Cbz group, a Boc group, an Alloc group, a benzyl group, or an Fmoc group.

Step 7-1: Step of Producing Compound (7-2)

Compound (7-2) can be produced by, for example, a production method shown below (i. or ii.).

i. Compound (7-2) is produced by converting compound (7-1) to the corresponding acid chloride by the action of a halogenating reagent and then reacting the acid chloride with benzotriazole, if necessary in the presence of a base, in an inert solvent.

Examples of the halogenating reagent include 1-chloro-N,N,2-trimethylpropenylamine, phosphorus oxychloride, phosphorus trichloride, thionyl chloride, phosphorus pentachloride, and oxalyl chloride.

Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; ester solvents such as ethyl acetate and isopropyl acetate; ketone solvents such as methyl ethyl ketone and acetone; and aprotic solvents such as acetonitrile, N,N-dimethylformamide, dimethyl sulfoxide, and hexamethylenephosphoramide.

Examples of the base include organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline.

ii. Compound (7-2) is also produced by reacting compound (7-1) with benzotriazole using a condensing agent, if necessary in the presence of a base, in an inert solvent.

The base is not particularly limited as long as the base can be used in usual reaction. Examples thereof include: organic bases such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, dimethylaminopyridine, and picoline; and inorganic bases such as sodium bicarbonate, potassium bicarbonate, sodium carbonate, potassium carbonate, sodium hydroxide, and sodium hydride. The amount of the base used is usually 0.1 to 100 equivalents, preferably 1 to 5 equivalents, with respect to compound (7-1).

Examples of the condensing agent include those described in Experimental Chemistry (edited by The Chemical Society of Japan, Maruzen Co., Ltd.), Vol. 22. Examples thereof include: phosphoric acid esters such as diethyl cyanophosphate and diphenylphosphorylazide; carbodiimides such as 1-ethyl-3-(3-dimethylaminopropyl)-carbodiimide hydrochloride (WSC.HCl) and dicyclohexylcarbodiimide (DCC); combinations of disulfides such as 2,2'-dipyridyl disulfide and phosphines such as triphenylphosphine; phosphorus halides such as N,N'-bis(2-oxo-3-oxazolidinyl)phosphinic chloride (BOPCl); combinations of azodicarboxylic acid diesters such as diethyl azodicarboxylate and phosphines such as triphenylphosphine; 2-halo-1-lower alkylpyridinium halides such as 2-chloro-1-methylpyridinium iodide; 1,1'-carbonyldiimidazole (CDI); diphenylphosphorylazide (DPPA); diethylphosphorylcyanide (DEPC); tetrafluoroborates such as 2-(1H-benzotriazol-1-yl)-1,1,3,3-tetramethyluronium tetrafluoroborate (TBTU) and 2-chloro-1,3-dimethylimidazolidinium tetrafluoroborate (CIB); and phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino) phosphonium hexafluorophosphate (PYBOP), and 2-(7-aza-1H-benzotriazol-1-yl)-1,1,3,3-tetramethyluronium hexafluorophosphate (HATU). The amount of the condensing agent used is usually 0.8 to 100 equivalents, preferably 1 to 5 equivalents, with respect to compound (7-1). Examples of the inert solvent include: ether solvents such as tetrahydrofuran, diethyl ether, 1,4-dioxane, and 1,2-dimethoxyethane; hydrocarbon solvents such as hexane, heptane, toluene, benzene, and xylene; halogenated hydrocarbon solvents such as dichloromethane, chloroform, and dichloroethane; ketone solvents such as acetone; and aprotic solvents such as acetonitrile, N,N-dimethylformamide, dimethyl sulfoxide, and hexamethylenephosphoramide. A mixed solvent thereof may be used. The reaction temperature is not particularly limited and is preferably selected from the range of approximately −70° C. to 100° C., more preferably 0° C. to 50° C.

Step 7-2: Step of Producing Compound (7-3)

Compound (7-3) is produced by reacting compound (7-2) with compound (7-4) in the presence of DBU in a THF solvent in the same way as a method known in the art (e.g., J. Org. Chem., 2004, 69, 9313.).

Step 7-3: Step of Producing Compound (1-6)

Compound (1-6) is produced by treating compound (7-3) according to a method described in the literature (Protective Groups in Organic Synthesis 3$^{rd}$ Edition (John Wiley & Sons, Inc.)).

Step 7-4: Step of Producing Compound (7-3)

Compound (7-3) is also produced by reacting compound (7-1) with a condensing agent in an inert solvent, subsequently adding a base and compound (7-4) to this reaction mixture, and reacting the resulting mixture.

Specific examples of the condensing agent include N,N'-carbonyldiimidazole, oxalyl chloride, thionyl chloride, ethyl chloroformate, isobutyl chloroformate, propyl chloroformate, and isopropyl chloroformate. The amount of the condensing agent used is 0.5 to 100 equivalents, preferably 0.8 to 5 equivalents, with respect to compound (7-1).

Specific examples of the inert solvent include: halogenated hydrocarbons such as chloroform and dichloromethane; aromatic hydrocarbons such as benzene and toluene; ether solvents such as diethyl ether, tetrahydrofuran (THF), 1,4-dioxane, dimethoxyethane, tert-butyl methyl ether, and cyclopentyl methyl ether, aprotic polar solvents such as N,N-dimethylformamide, N-methylpyrrolidone, and dimethyl sulfoxide; and mixed solvents thereof. Preferred examples thereof include tetrahydrofuran and N,N-dimethylformamide.

Specific examples of the base include 1,8-diazabicyclo [4.3.0]non-5-ene, 1,4-diazabicyclo[5.4.0]undec-7-ene, tetramethylguanidine, 7-methyl-1,5,7-triazabicyclo[4.4.0] dec-5-ene, 1,5,7-triazabicyclo[4.4.0]dec-5-ene, 2-tert-butylimino-2-diethylamino-1,3-dimethylperhydro-1,3,2-diazaphospholine, and heptamethyl phosphorimidic triamide. The amount of the base used is usually 0.1 to 100 equivalents, preferably 1 to 5 equivalents, with respect to compound (7-1).

The reaction temperature is not particularly limited and is preferably selected from the range of approximately −70° C. to 100° C., more preferably 0° C. to 70° C.

Production Method 8

The compound represented by formula (1-2) is also produced by, for example, a method shown below.

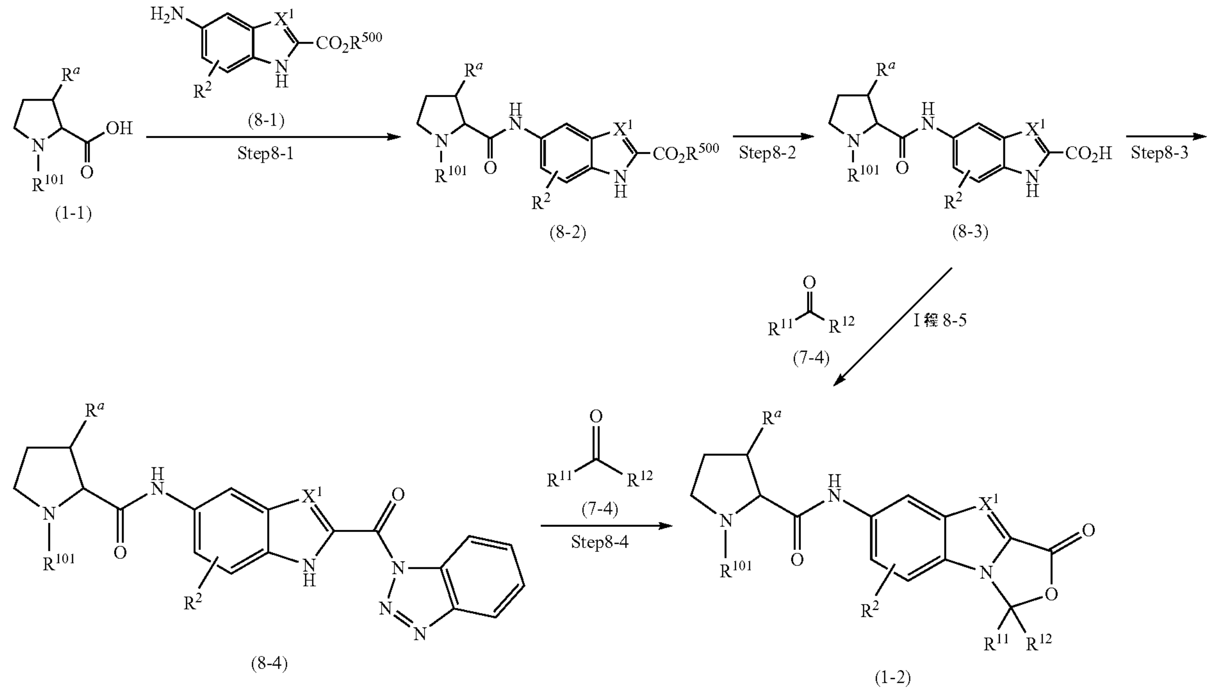

(1-1) (8-1) (8-2) (8-3) (7-4) (8-4) (7-4) (1-2)

wherein $R^a$, $R^{11}$, $R^{12}$, $R^2$, and X are the same as defined above in [1], $R^{500}$ represents a $C_{1-4}$ alkyl group, a benzyl group, a 4-methoxybenzyl group, or a 2,4-dimethoxybenzyl group, and $R^{101}$ represents a Cbz group, a Boc group, an Alloc group, a benzyl group, or an Fmoc group.

Step 8-1: Step of Producing Compound (8-2)

Compound (8-2) is produced in the same way as in step 1-1 using compound (1-1) and compound (8-1) which is a commercially available produced or is synthesized by a method known in the art (e.g., Chem. Commun. 2009, 48, 7581, and WO2008/012782).

Step 8-2: Step of Producing Compound (8-3)

Compound (8-3) can be produced by hydrolyzing compound (8-2) by a method known in the art (e.g., Protective Groups in Organic Synthesis 3$^{rd}$ Edition (John Wiley & Sons, Inc.), and Comprehensive Organic Trans Formation, R. C. Larock et al., VCH publisher Inc., 1989).

Step 8-3: Step of Producing Compound (8-4)

Compound (8-4) is produced in the same way as in step 7-1 using compound (8-3).

Step 8-4: Step of Producing Compound (1-2)

Compound (1-2) is produced in the same way as in step 7-2 using compound (8-4).

Step 8-5: Step of Producing Compound (1-2)

Compound (1-2) is also produced in the same way as in step 7-4 using compound (8-3).

Production Method 9

The compound represented by formula (1-4) is also produced by, for example, a method shown below.

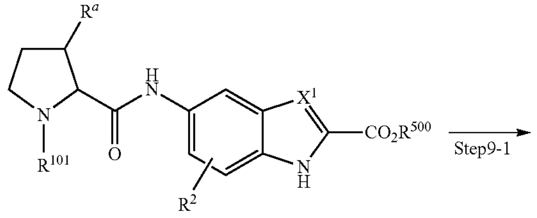

(8-2)

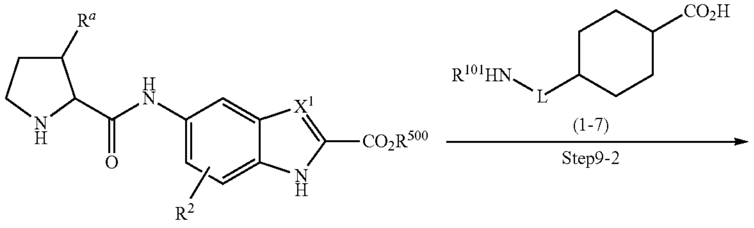

(9-1)

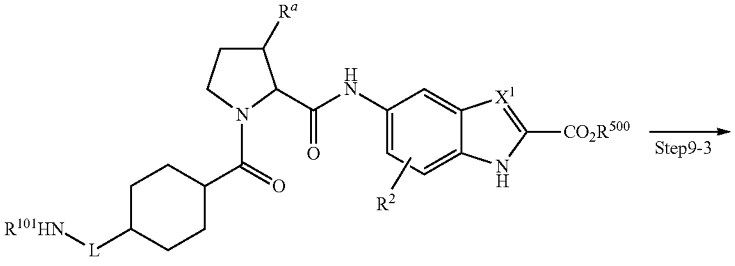

(9-2)

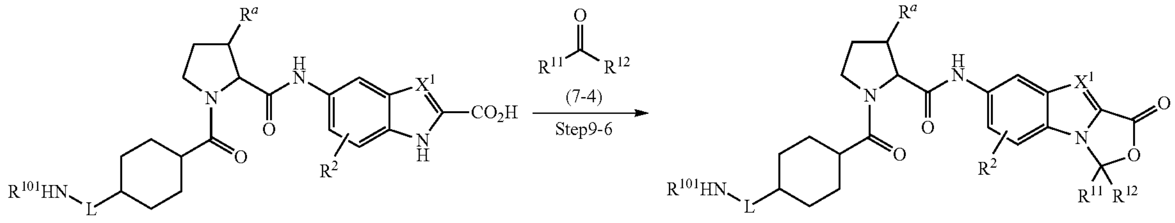

(9-3) (1-4)

-continued

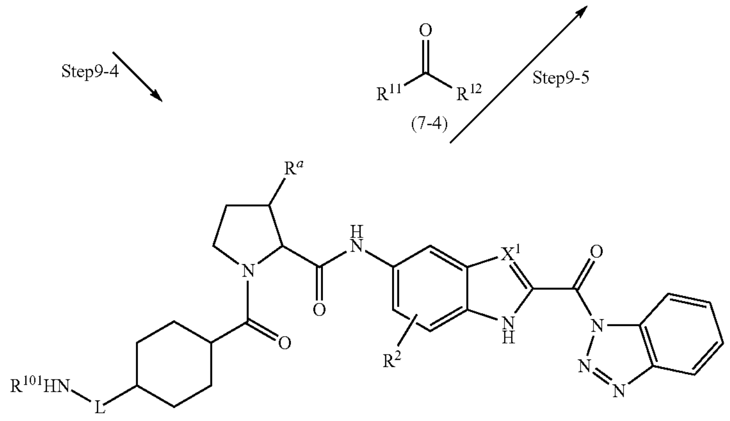

(9-4)

wherein L, $R^a$, $R^{11}$, $R^{12}$, $R^2$, and $X^1$ are the same as defined above in [1], $R^{500}$ represents a $C_{1-4}$ alkyl group, a benzyl group, a 4-methoxybenzyl group, or a 2,4-dimethoxybenzyl group, and $R^{101}$ represents a Cbz group, a Boc group, an Alloc group, a benzyl group, or an Fmoc group.

Step 9-1: Step of Producing Compound (9-1)

Compound (9-1) is produced by treating compound (8-2) according to a method described in the literature (Protective Groups in Organic Synthesis $3^{rd}$ Edition (John Wiley & Sons, Inc.)).

Step 9-2: Step of Producing Compound (9-2)

Compound (9-2) is produced in the same way as in step 1-1 using compound (9-1) and compound (1-7).

Step 9-3: Step of Producing Compound (9-3)

Compound (9-3) can be produced by hydrolyzing compound (9-2) in the same way as a method known in the art (e.g., Protective Groups in Organic Synthesis $3^{rd}$ Edition (John Wiley & Sons, Inc.), and Comprehensive Organic Transformation, R. C. Larock et al., VCH publisher Inc., 1989).

Step 9-4: Step of Producing Compound (9-4)

Compound (9-4) is produced in the same way as in step 7-1 using compound (9-3).

Step 9-5: Step of Producing Compound (1-4)

Compound (1-4) is produced in the same way as in step 7-2 using compound (9-4).

Step 9-6: Step of Producing Compound (1-4)

Compound (1-4) is also produced in the same way as in step 7-4 using compound (9-3) and compound (7-4).

Production Method 10

The compound represented by formula (1-4) is also produced by, for example, a method shown below.

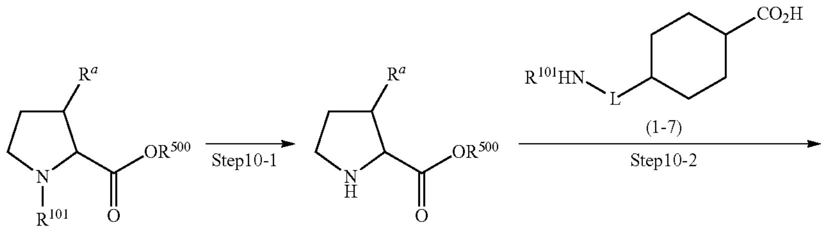

(10-1) (10-2)

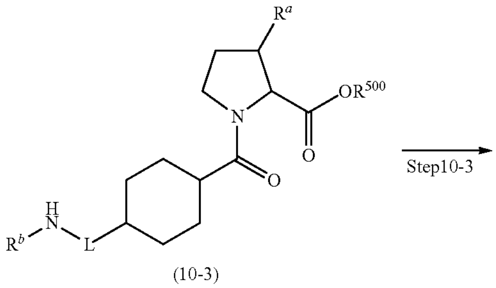

(10-3)

-continued

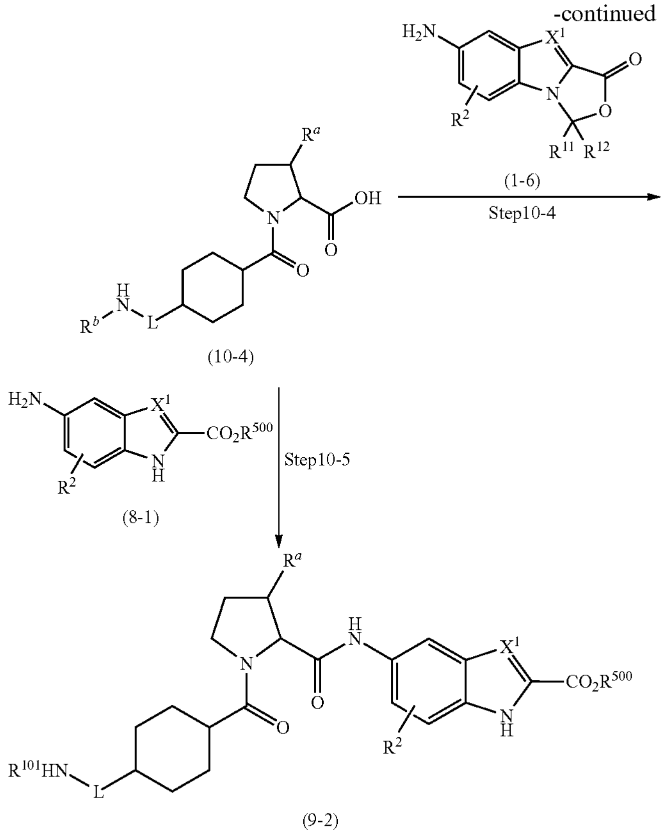

(1-6) (10-4) (1-4) (8-1) (9-2)

wherein L, $R^a$, $R^{11}$, $R^{12}$, $R^2$, and $X^1$ are the same as defined above in [1], $R^{500}$ represents a $C_{1-4}$ alkyl group, a benzyl group, a 4-methoxybenzyl group, or a 2,4-dimethoxybenzyl group, and $R^{101}$ represents a Cbz group, a Boc group, an Alloc group, a benzyl group, or an Fmoc group.

Starting Compound

The compound represented by formula (10-1) or (10-2) may be a commercially available product or can be produced by a known synthesis method (e.g., Tetrahedron Lett. 2010, 51, 6745, Org. Lett. 2009, 11, 4056, and Bioorg. Med. Chem. 2011, 19, 5833.).

Step 10-1: Step of Producing Compound (10-2)

Compound (10-2) can be produced in the same way as a method described in the literature (Protective Groups in Organic Synthesis 3rd Edition (John Wiley & Sons, Inc.)) using compound (10-1) as a starting material.

Step 10-2: Step of Producing Compound (10-3)

Compound (10-3) is produced in the same way as in step 1-3 using compound (10-2) and compound (1-7).

Step 10-3: Step of Producing Compound (10-4)

Compound (10-4) can be produced by hydrolyzing compound (10-3) by a method known in the art (e.g., Protective Groups in Organic Synthesis 3rd Edition (John Wiley & Sons, Inc.), and Comprehensive Organic Transformation, R. C. Larock et al., VCH publisher Inc., 1989).

Step 10-4: Step of Producing Compound (1-4)

Compound (1-4) is produced in the same way as in step 1-1 using compound (10-4) and compound (1-6).

Step 10-5: Step of Producing Compound (9-2)

Compound (9-2) is produced in the same way as in step 1-1 using compound (10-4) and compound (8-1).

Production Method 11

The compound represented by formula (11-2) is produced by, for example, a method shown below. This production method is an excellent synthesis method that can produce the tricyclic compound of interest in one step and at high yields.

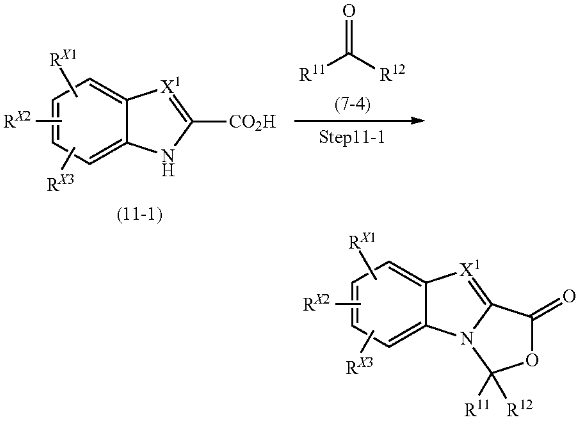

(11-1) (11-2)

wherein $R^{11}$, $R^{12}$, and $X^1$ are the same as defined above in [1], and $R^{X1}$, $R^{X2}$, and $R^{X3}$ each independently represent a hydrogen atom, a halogen atom, a $C_{1-6}$ alkoxy group, a $C_{1-6}$ alkyl group, a cyano group, an amino group, a hydroxy group, a $C_{1-6}$ alkylcarbonyl group, a $C_{1-6}$ alkoxycarbonyl group, an aminocarbonyl group, a $C_{1-6}$ alkoxycarbonylamino group, a nitro group, an alkylcarbonylamino group, an alkoxycarbonylamino group, a $C_{1-6}$ alkylsulfonyl group, a $C_3$ cycloalkyl group, a $C_{4-7}$ cycloalkoxy group, a phenyl group, a 5- or 6-membered heteroaryl group, a 3- to 8-membered saturated heterocyclic group, or an aminosulfonyl group.

Step 11-1: Step of Producing Compound (11-2)

Compound (11-2) is produced in the same way as in step 7-4 using compound (11-1).

The intermediates and the final products in these production methods are converted to other compounds included in the present invention by appropriately converting their functional groups, particularly elongating various side chains from a scaffold such as an amino group, an amidino group, a hydroxy group, a carbonyl group, or a halogen group, converting a scaffold such as a nitro group, a carboxyl group, a halogen group, or a hydroxy group to an amino group, or converting a scaffold such as a carboxyl group to an ester and an amide group, and appropriately performing protection and deprotection according to the operation. The conversion of functional groups and the elongation of side chains are carried out by usually performed general methods (e.g., Comprehensive Organic Transformation, R. C. Larock et al.).

The intermediate or the compound of interest in each of the production methods can be isolated and purified by a purification method routinely used in organic synthetic chemistry, for example, neutralization, filtration, extraction, washing, drying, concentration, recrystallization, and various chromatography techniques. Alternatively, the intermediate may be subjected to the next reaction without being particularly purified.

Particularly, optical isomers and atropisomers of the present compound are each obtained as a racemate or as an optically active form in the case of using an optically active starting material or intermediate. If necessary, at an appropriate stage of the production methods, a racemate of the corresponding starting material, intermediate, or final product can be resolved physically or chemically into its optical enantiomers by a resolution method known in the art such as a method using an optically active column or a fractional crystallization method. Geometric isomers such as a cis form and a trans from may be synthetically converted or can be resolved using a column. Specifically, for example, in a diastereomer method, two diastereomers or diastereomer salts are formed from the racemate using an optically active resolving agent. These different diastereomers generally differ in physical properties and can therefore be resolved by a method known in the art such as fractional crystallization.

The compound represented by formula (1) may be obtained in the form of a salt depending on the type of a functional group present in the structural formula, a selected starting compound, and reaction treatment conditions. This salt can be converted to the compound of formula (1) according to a routine method. On the other hand, the compound of formula (1) having a group capable of forming an acid-addition salt in the structural formula can be converted to an acid-addition salt by treatment with various acids according to a routine method. The pharmaceutically acceptable salt of the compound of the present invention represented by formula (1) can be produced, for example, by mixing the compound represented by formula (1) having basicity or acidity sufficient for forming a salt with a pharmaceutically acceptable acid or base in a solvent such as water, methanol, ethanol, or acetone.

Features of the compound represented by formula (1) and the pharmaceutically acceptable salt thereof are to exhibit excellent oral absorbability and to act as a prodrug that is converted to a highly active form by in vivo metabolism. Specifically, as shown in the following formulas (12) and (13):

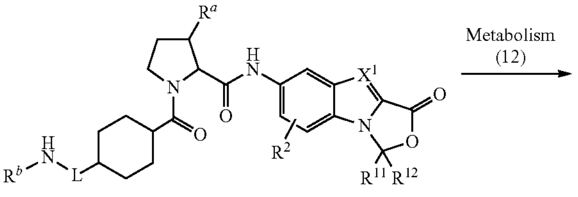

(1)

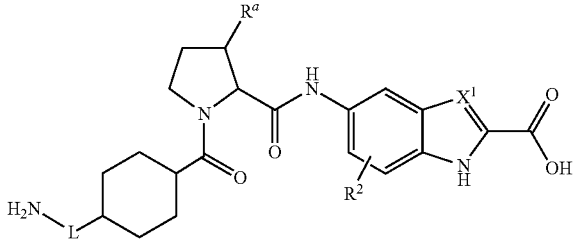

(8)

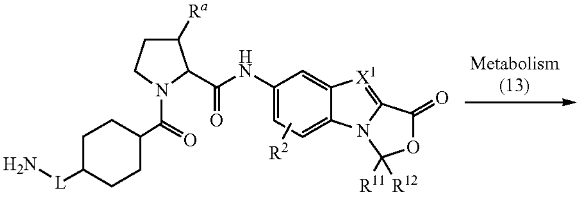

(1')

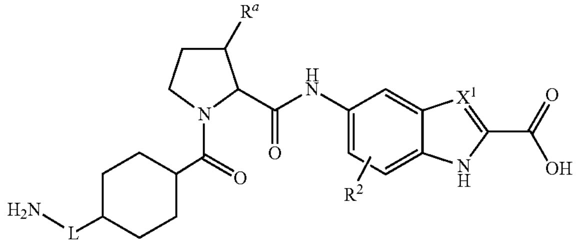

(8)

wherein L, $R^a$, $R^b$, R, $R^{12}$, $R^2$, and $X^1$ are the same as defined above in [1], the compound represented by formula (1) is metabolized in vivo by an enzyme (particularly, an enzyme in plasma) and converted to a metabolite represented by formula (8). In the case of oral administration, the compound represented by formula (8) exhibits excellent FXIa inhibition activity in vivo.

The present compound is applicable to the treatment of various diseases by virtue of its inhibitory effect on FXIa or/and anticoagulant effect. The compounds described in the present specification are useful as drugs for preventing or treating thromboembolism (venous thrombosis, myocardial infarction, pulmonary embolism, brain embolism, slowly progressive cerebral thrombosis, etc.). These compounds are expected to be effective for arterial thrombosis, venous thrombosis, and thrombosis t caused by sepsis, or the exposure of blood to an artificial surface such as a prosthetic valve, an indwelling catheter, a stent, a heart-lung machine, or hemodialysis. Also, these compounds are expected to be effective for inflammatory diseases such as rheumatoid arthritis and ulcerative colitis. In addition, these compounds are effective in the improvement in therapeutic effects on these diseases, etc.

The compound represented by formula (1) or the pharmaceutically acceptable salt thereof is preferably orally administered as a systemic administration agent or parenterally administered as a local administration agent. Also, the compound represented by formula (8) or the pharmaceutically acceptable salt thereof is preferably parenterally administered. Such an oral formulation can be administered in a dosage form usually used. The parenteral formulation can be administered in the form of, for example, a local administration agent, an injection, a transdermal agent, or a transnasal agent. Examples of the oral agent or the rectal administration agent include capsules, tablets, pills, powders, cachets, suppositories, and liquid preparations. Examples of the injection include sterile solutions and suspensions. Examples of the local administration agent include creams, ointments, lotions, and transdermal agents (usual patches and matrixes).

These dosage forms are formulated together with a pharmaceutically acceptable excipient and additive by an ordinary method. Examples of the pharmaceutically acceptable excipient and additive include carriers, binders, flavors, buffers, thickeners, colorants, stabilizers, emulsifiers, dispersants, suspending agents, and antiseptics.

Examples of the pharmaceutically acceptable carriers include magnesium carbonate, magnesium stearate, talc, sugar, lactose, pectin, dextrin, starch, gelatin, tragacanth, methylcellulose, sodium carboxymethylcellulose, low-melting wax, and cacao butter. The capsules can be formulated by putting the present compound together with pharmaceutically acceptable carriers into capsule shells. The present compound can be contained in the capsules as a mixture with pharmaceutically acceptable excipients or without these excipients. The cachets can also be produced by a similar method.

Examples of the liquid preparations for injection include solutions, suspensions, and emulsions. Examples thereof include aqueous solutions and water-propylene glycol solutions. These liquid preparations can also be produced in the form of a solution of polyethylene glycol or/and propylene glycol that may contain water. The liquid preparations suitable for oral administration can be produced by adding the present compound to water and, if necessary, adding a colorant, a flavor, a stabilizer, a sweetener, a solubilizer, a thickener, or the like to the mixture. Alternatively, the liquid preparations suitable for oral administration can also be produced by adding the present compound together with a dispersant to water for thickening. Examples of the thickener include pharmaceutically acceptable natural or synthetic gums, resins, methylcellulose, sodium carboxymethylcellulose, and suspending agents known in the art.

The dose differs depending on individual compounds or the disease, age, body weight, sex, symptoms, administration route, etc., of a patient. Typically, the present compound is administered at a dose of 0.1 to 1000 mg/day, preferably 1 to 300 mg/day, once a day or in two or three portions per day to an adult (body weight: 50 kg). Alternatively, the present compound may be administered once a few days to once a few weeks.

The present compound can also constitute a medicament in combination with or including an additional drug. This can bring about additive and/or synergistic pharmacological effects. For example, the present compound can be used in combination with any of various drugs such as anticoagulants or antiplatelet agents (hereinafter, referred to as a concomitant drug). The combination of the compound according to the present invention with an additional drug can constitute a single pharmaceutical composition containing the compound of the present invention together with the additional drug. Alternatively, a first pharmaceutical composition containing the compound of the present invention and a second pharmaceutical composition containing an additional drug may be provided separately. More specifically, such a pharmaceutical composition may be a single preparation containing these active ingredients together (i.e., a combination drug) or may be a plurality of preparations formulated by separately using these individual active ingredients. Such a plurality of preparations separately formulated can be administered separately or concurrently. Also, these preparations separately formulated can be mixed using a diluent or the like before use and administered concurrently. Alternatively, for example, a pharmaceutical composition containing the present compound may be prepared as a preparation for oral administration, and a concomitant drug may be prepared as a preparation for parenteral administration. These preparations can be separately administered orally and parenterally, respectively. The administration timings of the present compound and a concomitant drug are not limited. They may be administered concurrently to a recipient or may be administered separately over time or at intervals. Furthermore, the present compound and a concomitant drug may be formulated as a combination drug. The dose of a concomitant drug can be appropriately selected on the basis of a dose clinically used. The mixing ratio between the present compound and a concomitant drug can be appropriately selected dependent on a recipient, an administration route, a target disease, symptoms, a combination, etc. When the recipient is, for example, a human, a concomitant drug can be used at 0.01 to 100 parts by weight with respect to 1 part by weight of the present compound.

Examples of the anticoagulant include thrombin inhibitors (e.g., dabigatran, AZD-0837, MPC-0920, Org-27306, and NU-172), other FXIa inhibitors (e.g., ISIS-FXIRx), other plasma kallikrein inhibitors, FVIIa inhibitors (e.g., PCI-27483), FIXa inhibitors (e.g., TTP-889, REGI, and REG2), and FXa inhibitors (e.g., rivaroxaban, apixaban, edoxaban, YM-150, TAK-442, betrixaban, eribaxaban, LY-517717, AVE-3247, GW-813893, R-1663, and DB-772d). Examples of the antiplatelet agent include GPIIb/IIIa blockers (e.g., abciximab, eptifibatide, and tirofiban), P2Y1 and P2Y12 antagonists (e.g., clopidogrel, prasugrel, ticagrelor, and elinogrel), thromboxane receptor antagonists, and aspirin.

The concomitant drug is preferably an antiplatelet agent. Two or more of these concomitant drugs may be used in combination at an appropriate ratio.

When the present compound is used in combination with the concomitant drug, the amounts of these drugs used can be reduced within safe ranges in consideration of the adverse reactions of the drugs. Thus, the adverse reactions that might be caused by these drugs can be prevented safely.

EXAMPLES

The present invention will be described in further detail below with reference to Reference Examples, Examples, and Test Examples, but the present invention is not limited thereto at all. Note that not all the names of the compounds described in the following Reference Examples and Examples are in accordance with the International Union of Pure and Applied Chemistry (IUPAC) nomenclature. Note that abbreviations may be used herein for simplification of description and have the same meanings as those described above.

The following abbreviations may be used herein.

The following abbreviations are used in NMR data of Reference Examples and Examples.

Me: methyl group
Et: ethyl group
Bu: butyl group
tert-: tertiary
Boc: tert-butoxycarbonyl group
Tf: trifluoromethanesulfonyl group
THF: tetrahydrofuran
DMF: N,N-dimethylformamide
TFA: trifluoroacetic acid
DBU: 1,8-diazabicyclo[5.4.0]undec-7-ene
WSC.HCl: 1-ethyl-3-(3-dimethylaminopropyl)carbodiimide hydrochloride
HATU: 2-(7-aza-1H-benzotriazol-1-yl)-1,1,3,3-tetramethyluronium hexafluorophosphate
LHMDS: lithium bis(trimethylsilyl)amide
s: singlet
brs: broad singlet
d: doublet
t: triplet
m: multiplet
br: broad
J: coupling constant
Hz: Hertz:
$CDCl_3$: deuterochloroform
DMSO-$d_6$: deuterodimethyl sulfoxide
aPTT: activated partial thromboplastin time
pNA: p-nitroaniline
pyroGlu: pyroglutamic acid
PT: prothrombin time The conditions for measurement with a high-performance liquid chromatography mass spectrometer are as follows, and values observed by mass spectrometry [MS (m/z)] are expressed by "MH+" and the retention time is expressed by "Rt" (min). Note that for each observed value, the measurement condition used in the high-performance liquid chromatography mass spectrometry is followed by "A" or "B" according to the following measurement condition A or B.

Measurement Condition A
Detection device: Waters ACQUITY UPLC
Column: ACQUITY UPLC BEH C18 1.7 μm 2.1×50 mm column
Solvent: liquid A: 0.05% $HCOOH/H_2O$, liquid B: $CH_3CN$
Gradient conditions:
0.0 to 1.3 min; A/B=90:10 to 1:99 (linear gradient)
1.35 to 1.5 min; A/B=1:99
1.5 to 2 min; A/B=90:10
Flow rate: 0.75 mL/min.
UV: 220 nm, 254 nm
Column temperature: 50° C.

Measurement Condition B
Detection device: Shimadzu LC20AD
Column: Kinetex 1.7μ C18 100 A
Solvent: liquid A: 0.05% $TFA/H_2O$, liquid B: 0.05% $TFA/CH_3CN$
Gradient conditions:
0 to 6.0 min; A/B=60:40 to 1:99 (linear gradient)
6.0 to 8.0 min; A/B=1:99
8.0 to 9.9 min; A/B=99:1
Flow rate: 0.90 mL/min.
UV: 220/254 nm
Column temperature: 40° C.

Reference Example 1 tert-Butyl {(1S)-1-[trans-4-({(2S,3S)-3-cyclohexyl-2-[(3,3-dimethyl-1-oxo-1H-[1,3]oxazolo[3,4-a]indol-7-yl)carbamoyl]piperidin-1-yl}carbonyl)cyclohexyl]-2-fluoroethyl}carbamate

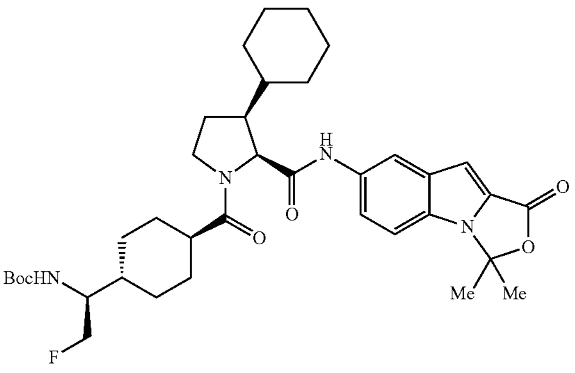 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C(C)(C)OC2=O)CC1]

A mixture of the compound of Reference Example 1-8 (77.4 mg, 0.179 mmol), the compound of Reference Example 1-3 (57.0 mg, 0.200 mmol), 1-hydroxybenzotriazole (41.1 mg, 0.269 mmol), WSC.HCl (51.5 mg, 0.269 mmol), triethylamine (62.3 μl, 0.448 mmol), and DMF (3 mL) was stirred at room temperature for 3 hours. A saturated aqueous solution of ammonium chloride was added to the reaction mixture, and the resulting mixture was extracted with ethyl acetate. The organic layer was washed twice with a saturated aqueous solution of ammonium chloride and once with a saturated aqueous solution of sodium hydrogencarbonate and a saturated saline solution, then dried over anhydrous sodium sulfate, filtered, and concentrated under reduced pressure. The obtained residue was purified by silica gel column chromatography to obtain the title compound (58.4 mg, 49%).

MS (ESI+) 667 (M+1, 100%)

Reference Example 1-1

Methyl trans-4-(3-tert-butoxy-3-oxopropanoyl)cyclohexanecarboxylate

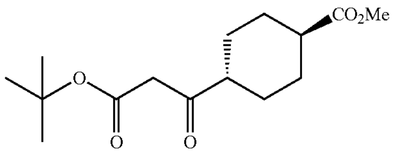 [SMILES: COC(=O)[C@H]1CC[C@H](C(=O)CC(=O)OC(C)(C)C)CC1]

Carbonyldiimidazole (28.7 g, 177 mmol) was added to a solution of trans-1,4-cyclohexanedicarboxylic acid monomethyl ester (30.00 g, 161.1 mmol) in tetrahydrofuran (180 mL), in an ice bath, and the resulting mixture was stirred at room temperature for 1 hour. Separately, tert-butyl acetate (19.65 g, 169.2 mmol) was added dropwise at −78° C. to LHMDS (1.0 mol/L in THF, 338 mL, 338 mmol) and the resulting solution was stirred for 1 hour. A reaction solution of trans-1,4-cyclohexanedicarboxylic acid monomethyl ester and carbonyldiimidazole was added dropwise thereto at −78° C., and the resulting mixture was stirred for 3 hours. A saturated aqueous solution of ammonium chloride was added to the reaction solution, and the reaction solvent was concentrated under reduced pressure. The residue was extracted with diethyl ether, the organic layer was washed with a 0.1 mol/L aqueous solution of sodium hydroxide and a saturated saline solution, then dried over anhydrous sodium sulfate, filtered, and concentrated under reduced pressure to obtain the title compound (34.25 g, 75%).

$^1$H NMR ($CDCl_3$, 300 MHz) δ 3.66 (s, 3H), 3.38 (s, 2H), 2.46 (m, 1H), 2.27-2.23 (m, 1H), 2.09-1.98 (m, 5H), 1.52-1.31 (m, 12H).

Reference Example 1-2

Methyl trans-4-(fluoroacetyl)cyclohexanecarboxylate

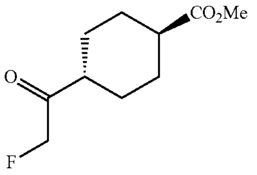 [SMILES: COC(=O)[C@H]1CC[C@H](C(=O)CF)CC1]

Selectfluor (13.08 g, 36.92 mmol) was added to a solution of the compound of Reference Example 1-1 (7.00 g, 24.62 mmol) in acetonitrile (50 mL) at room temperature and the resulting mixture was stirred at 40° C. for 4 hours and then at room temperature for 13 hours. A saturated aqueous solution of sodium thiosulfate was added to the reaction solution, and the resulting mixture was extracted with ethyl acetate. The organic layer was washed with a saturated aqueous solution of sodium hydrogencarbonate, a saturated aqueous solution of ammonium chloride, and a saturated saline solution, then dried over anhydrous sodium sulfate, filtered, and concentrated under reduced pressure to obtain a crude product (6.78 g).

Trifluoroacetic acid (15.02 g, 131.7 mmol) was added to a solution of the obtained crude product (6.64 g, 21.96 mmol) in chloroform (30 mL) at room temperature, and the resulting mixture was stirred at 40° C. for 4 hours. The reaction solution was concentrated under reduced pressure, a saturated aqueous solution of sodium hydrogencarbonate was added to the residue, and the resulting mixture was extracted with chloroform. The organic layer was dried over anhydrous sodium sulfate, filtered, and concentrated under reduced pressure. The obtained residue was purified by silica gel column chromatography to obtain the title compound (2.92 g, 59%).

$^1$H NMR ($CDCl_3$, 300 MHz) δ 4.96 (s, 1H), 4.80 (s, 1H), 3.67 (s, 3H), 2.69-2.61 (m, 1H), 2.33-2.24 (m, 1H), 2.11-2.07 (m, 2H), 1.99-1.95 (m, 2H), 1.58-1.34 (m, 4H).

Reference Example 1-3 trans-4-{(1S)-1-[(tert-Butoxycarbonyl)amino]-2-fluoroethyl}cyclohexanecarboxylic acid

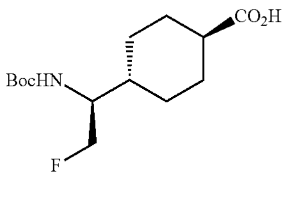 [SMILES: CC(C)(C)OC(=O)N[C@H](CF)[C@H]1CC[C@H](C(=O)O)CC1]

Titanium tetraisopropoxide (2.53 g, 8.90 mmol) and (S)-(−)-2-methyl-2-propanesulfinamide (467 mg, 3.85 mmol) were added to a solution of the compound of Reference Example 1-2 (599.1 mg, 2.96 mmol) in tetrahydrofuran (5 mL) and the resulting mixture was heated to reflux for 8 hours. The reaction solution was allowed to stand to cool, a saturated aqueous solution of sodium hydrogencarbonate and ethyl acetate were added thereto, and the resulting mixture was stirred at room temperature for 15 minutes, and then filtered through Celite. The mixed solution was separated, then the organic layer was washed with a saturated aqueous solution of sodium hydrogencarbonate and a saturated saline solution, then dried over anhydrous sodium sulfate and filtered. The filtrate was concentrated under reduced pressure to obtain a crude product.

K-selectride (1.0 M in THF, 3.84 mL, 3.84 mmol) was added dropwise at −78° C. to a solution of the obtained crude product in tetrahydrofuran (3 mL), and the resulting mixture was stirred for 1 hour. A saturated aqueous solution of ammonium chloride was added to the reaction solution, and the resulting mixture was allowed to stand to cool to room temperature and extracted with ethyl acetate. The organic layer was washed with a saturated aqueous solution of sodium hydrogencarbonate and a saturated saline solution, then dried over anhydrous sodium sulfate, filtered, and concentrated under reduced pressure. 4 mol/L hydrochloric acid in dioxane (10 mL) was added dropwise to a solution of the obtained crude product in methanol (10 mL) in an ice bath, and the resulting mixture was stirred for 30 minutes. The reaction solution was concentrated under reduced pressure, toluene was added thereto, and the resulting mixture was concentrated under reduced pressure, which was carried out twice. Diethyl ether was added to the generated solid, and the resulting mixture was filtered, washed successively with diethyl ether and hexane, and dried. The residue was dissolved in tetrahydrofuran (3 mL) and a saturated aqueous solution of sodium hydrogencarbonate (3 mL), di-tert-butyl dicarbonate (434.8 mg, 1.99 mmol) was added thereto, and the resulting mixture was stirred at room temperature for 12 hours. Water was added to the reaction solution, and the resulting mixture was extracted with ethyl acetate. The organic layer was washed with a saturated aqueous solution of ammonium chloride and a saturated saline solution, then dried over anhydrous sodium sulfate, filtered, and concentrated under reduced pressure. The obtained residue was dissolved in tetrahydrofuran (2 mL) and ethanol (2 mL), a 10% aqueous solution of sodium hydroxide (2 mL) was added thereto, and the resulting mixture was heated to reflux. 12 hours later, the reaction solution was allowed to stand to cool to room temperature, and concentrated under reduced pressure. Diethyl ether was added to the residue, the resulting mixture was separated, and a 5% aqueous solution of potassium hydrogensulfate was added to the aqueous layer to adjust the pH to <5. The reaction mixture was extracted with chloroform, dried over anhydrous sodium sulfate, filtered, and concentrated under reduced pressure to obtain the title compound (348.0 mg, 41% for 5 steps, 90% ee).

$^1$H NMR (DMSO-$d_6$, 300 MHz) δ 6.87 (m, 1H), 4.48-4.37 (m, 1H), 4.32-4.21 (m, 1H), 3.45-3.34 (m, 1H), 2.11-2.03 (m, 1H), 1.89-1.86 (m, 2H), 1.71-1.67 (m, 2H), 1.37-1.30 (m, 10H), 1.23-1.17 (m, 2H), 1.13-0.95 (m, 2H).

Purification by Fractional Crystallization (R)-(+) a phenyl ethylamine (10.68 g, 88.13 mmol) was added to a solution of the compound of Reference Example 1-3 (25.50 g, 88.13 mmol, 89% ee) in isopropyl acetate (230 g) at 80° C., and the resulting mixture was stirred for 1 hour.

The reaction solution was cooled to room temperature over 1.5 hours, filtered, and washed with hexane/ethyl acetate=3. The obtained residue was dried, and a 5% aqueous solution of potassium hydrogensulfate was then added to the obtained solid to adjust the PH to <5, and the resulting mixture was extracted with chloroform. The organic layer was washed with a saturated saline solution, then dried over anhydrous sodium sulfate, filtered, and concentrated under reduced pressure to obtain the title compound (20.32 g, 80%, 97.3% ee).

Reference Example 1-4 tert-Butyl (3,3-dimethyl-1-oxo-1H-[1,3]oxazolo[3,4-a]indol-7-yl)carbamate

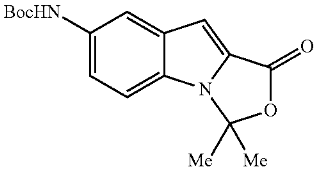 [SMILES: CC(C)(C)OC(=O)Nc1ccc2c(c1)cc1n2C(C)(C)OC1=O]

Carbonyldiimidazole (2.21 g, 13.62 mmol) was added to a solution of commercial 5-(tert-butoxycarbonylamino)-1H-indole-2-carboxylic acid (2.51 g, 9.08 mmol) in tetrahydrofuran (20 mL) in an ice bath, and the resulting mixture was stirred at room temperature for 1.5 hours. Acetone (20 mL) and DBU (3.51 mL, 23.47 mmol) were added to the reaction mixture at room temperature, and the resulting mixture was stirred for 1.5 hours. A 5% aqueous solution of potassium hydrogensulfate was added to the reaction mixture, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (2.49 g, 87%).

MS (ESI+) 317 (M+1, 27%)

Reference Example 1-5

7-Amino-3,3-dimethyl-1H-[1,3]oxazolo[3,4-a]indol-1-one hydrochloride

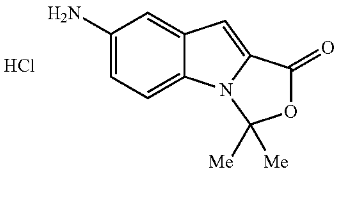 [SMILES: Cl ; CC1(C)OC(=O)c2cc3cc(N)ccc3n21]

4 mol/L hydrochloric acid in 1,4-dioxane (60 mL) was added to a solution of the compound of Reference Example 1-4 (4.00 g, 11.00 mmol) in chloroform (60 mL), and the resulting mixture was stirred at 45° C. for 4 hours. The solvent in the reaction solution was distilled off under reduced pressure, hexane-ethyl acetate (1:1) was added to the residue, and the solid was filtered out to obtain the title compound (2.82 g, 100%).

MS (ESI+) 217 (M+1, 100%)

Reference Example 1-6

(2S,3S)-1-tert-Butoxycarbonyl-3-cyclohexylpyrrolidine-2-carboxylic acid

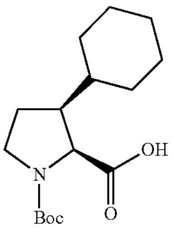 [SMILES: CC(C)(C)OC(=O)N1CC[C@@H](C2CCCCC2)[C@H]1C(=O)O]

Platinum oxide (274 mg) was added to a solution of (2S,3S)-1-tert-butoxycarbonyl-3-phenylpyrrolidine-2-carboxylic acid (632 mg, 2.17 mmol) known from documents (e.g., Org. Lett, 2009, 11, 18, 4056) in acetic acid (10 mL), and the resulting mixture was stirred at a pressure of 0.4 Mpa for 3.5 hours in a hydrogen atmosphere. The reaction solution was filtered through Celite and concentrated under reduced pressure to obtain the title compound (627.8 mg, 97%).

MS (ESI+) 298 (M+1, 15%)

Reference Example 1-7 tert-Butyl (2S,3S)-3-cyclohexyl-2-[(3,3-dimethyl-1-oxo-1H-[1,3]oxazolo[3,4-a]indol-7-yl)carbamoyl]pyrrolidine-1-carboxylate

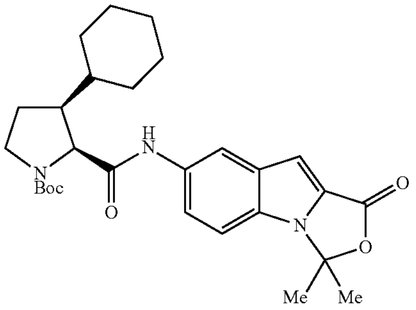 [SMILES: CC(C)(C)OC(=O)N1CC[C@@H](C2CCCCC2)[C@H]1C(=O)Nc1ccc2c(c1)cc1n2C(C)(C)OC1=O]

HATU (12.11 g, 31.86 mmol) and diisopropylethylamine (11.23 g, 86.88 mmol) were added to a solution of the compound of Reference Example 1-6 (9.04 g, 30.41 mmol) in DMF (40 mL), and the resulting mixture was stirred at room temperature for 1 hour. A solution of the compound of Reference Example 1-5 (2.82 g, 28.96 mmol) in DMF (40 mL) was added to the reaction mixture, and the temperature of the resulting mixture was gradually raised up to 80° C. over 2 hours. The reaction mixture was stirred for 4 hours, then a saturated aqueous solution of ammonium chloride was added to the reaction mixture, and the resulting mixture was extracted with ethyl acetate. The organic layer was washed twice with a saturated aqueous solution of ammonium chloride and with a saturated sodium hydrogencarbonate and a saturated saline solution, then dried over anhydrous sodium sulfate, filtered, and concentrated under reduced pressure. The obtained residue was purified by silica gel column chromatography to obtain the title compound (12.70 g, 89%).

MS (ESI+) 496 (M+1, 100%)

Reference Example 1-8

(3S)-3-Cyclohexyl-N-(3,3-dimethyl-1-oxo-1H-[1,3]oxazolo[3,4-a]indol-7-yl)-L-prolinamide hydrochloride

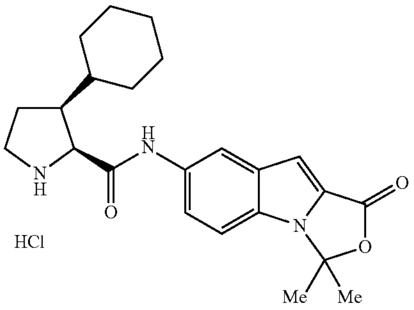 [SMILES: CC1(C)OC(=O)c2cc3cc(NC(=O)[C@H]4NCC[C@H]4C4CCCCC4)ccc3n21 ; Cl]

4 mol/L hydrochloric acid in 1,4-dioxane (4 mL) was added to a solution of the compound of Reference Example 1-7 (88.8 mg, 0.179 mmol), and the resulting mixture was stirred for 2 hours. The solvent in the reaction solution was distilled off under reduced pressure to obtain the title compound (77.4 mg, 100%).

MS (ESI+) 396 (M+1, 100%)

Reference Example 2 tert-Butyl {(1S)-1-[trans-4-({(2S,3S)-3-cyclohexyl-2-[(1'-oxo-1'H-spiro[cyclopentane-1,3'-[1,3]oxazolo[3,4-a]indol]-7'-yl)carbamoyl]pyrrolidin-1-yl}carbonyl)cyclohexyl]-2-fluoroethyl}carbamate

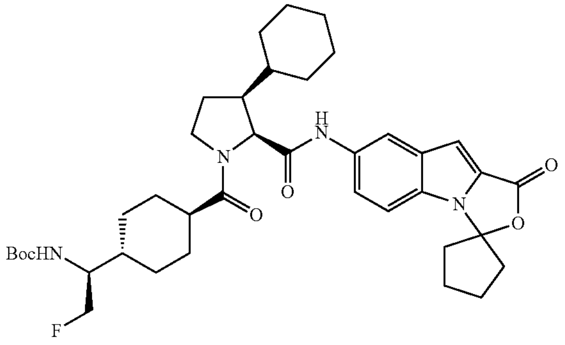 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C3(CCCC3)OC2=O)CC1]

Cyclopentanone (10 mL) and DBU (937 μL, 6.27 mmol) were added to the compound of Reference Example 2-5 (1.12 g, 1.62 mmol), and the resulting mixture was stirred at 50° C. for 3 hours. The reaction solution was allowed to stand to cool, filtered through Celite, and concentrated under reduced pressure. The obtained residue was purified by silica gel column chromatography to obtain the title compound (31.2 mg, 2.8%).

MS (ESI+) 693 (M+1, 100%)

Reference Example 2-1

Ethyl 5-{[(3S)-(tert-butoxycarbonyl)-3-cyclohexyl-L-prolyl]amino}-1H-indole-2-carboxylate

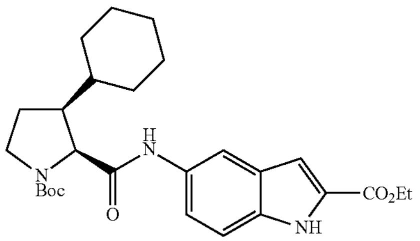 [SMILES: CCOC(=O)c1cc2cc(NC(=O)[C@@H]3[C@H](C4CCCCC4)CCN3C(=O)OC(C)(C)C)ccc2[nH]1]

In the same manner as in Reference Example 1, the title compound (12.73 g, 81%) was obtained from the compound of Reference Example 1-6 (9.84 g, 33.09 mmol) and commercial ethyl 5-amino-1H-indole-2-carboxylate (6.75 g, 33.09 mmol).

MS (ESI+) 484 (M+1, 100%)

Reference Example 2-2

Ethyl 5-{[(3S)-3-cyclohexyl-L-prolyl]amino}-1H-indole-2-carboxylate hydrochloride

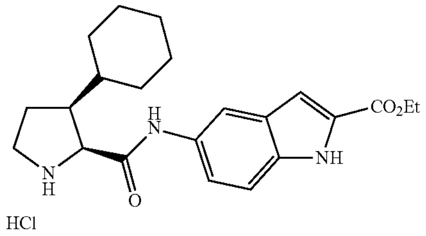 [SMILES: CCOC(=O)c1cc2cc(NC(=O)[C@H]3NCC[C@H]3C3CCCCC3)ccc2[nH]1 ; Cl]

In the same manner as in Reference Example 1-8, the title compound (11.97 g, 100%) was obtained from the compound of Reference Example 2-1 (12.71 g, 26.28 mmol).

MS (ESI+) 384 (M+1, 100%)

Reference Example 2-3

Ethyl 5-({(3S)-1-[(trans-4-{((1R)-1-[(tert-butoxycarbonyl)amino]-2-fluoroethyl}cyclohexyl)carbonyl]-3-cyclohexyl-L-prolyl}amino)-1H-indole-2-carboxylate

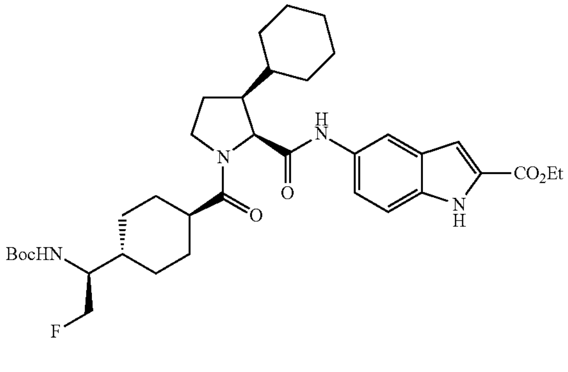 [SMILES: CCOC(=O)c1cc2cc(NC(=O)[C@@H]3[C@H](C4CCCCC4)CCN3C(=O)[C@H]3CC[C@H]([C@@H](CF)NC(=O)OC(C)(C)C)CC3)ccc2[nH]1]

In the same manner as in Reference Example 1, the title compound (15.72 g, 91%) was obtained from the compound of Reference Example 2-2 (11.97 g, 26.28 mmol) and the compound of Reference Example 1-3 (7.98 g, 26.28 mmol).

MS (ESI+) 655 (M+1, 100%)

Reference Example 2-4

5-({(3S)-1-[(trans-4-{(1R)-1-[(tert-Butoxycarbonyl)amino]-2-fluoroethyl}cyclohexyl)carbonyl]-3-cyclohexyl-L-prolyl}amino)-1H-indole-2-carboxylic acid

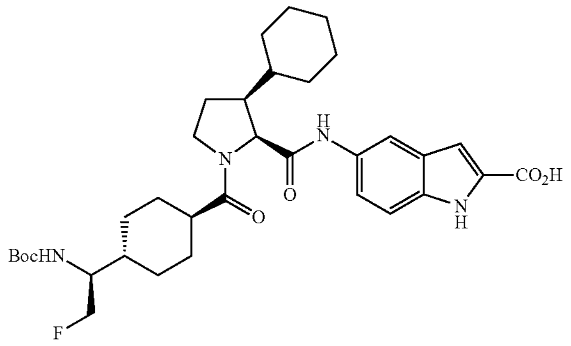

The compound of Reference Example 2-3 (15.72 g, 24.01 mmol) was dissolved in tetrahydrofuran (50 mL) and ethanol (50 mL), a 1 mol/L aqueous solution of sodium hydroxide (50 mL) was added thereto, and the resulting mixture was stirred at room temperature overnight. A 5% aqueous solution of potassium hydrogensulfate was added to the reaction solution, and the resulting mixture was extracted with chloroform. The organic layer was washed with a saturated saline solution, then dried over anhydrous sodium sulfate, filtered, and concentrated under reduced pressure to obtain the title compound (13.55 g, 90%).

MS (ESI+) 627 (M+1, 100%)

Reference Example 2-5 tert-Butyl [(1S)-1-(trans-4-{[(2S,3S)-2-{[2-(1H-benzotriazol-1-ylcarbonyl)-1H-indol-5-yl]carbamoyl}-3-cyclohexylpyrrolidin-1-yl]carbonyl}cyclohexyl)-2-fluoroethyl]carbamate

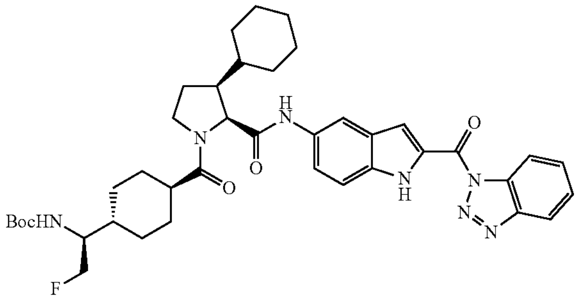 [SMILES: CC(C)(C)OC(=O)N[C@H](CF)[C@H]1CC[C@H](C(=O)N2CC[C@@H](C3CCCCC3)[C@H]2C(=O)Nc2ccc3[nH]c(C(=O)n4nnc5ccccc54)cc3c2)CC1]

Benzotriazole (824.8 mg, 6.92 mmol) and WSC.HCl (1.33 g, 6.92 mmol) were added to a solution of the compound of Reference Example 2-4 (2.17 g, 3.46 mmol) in dichloromethane (15 mL), and the resulting mixture was stirred at room temperature for 3 hours. A 1 mol/L aqueous solution of sodium hydroxide was added to the reaction mixture, and the resulting mixture was extracted with chloroform. The organic layer was washed with a 1 mol/L aqueous solution of sodium hydroxide and a saturated saline solution, then dried over anhydrous sodium sulfate, filtered, and concentrated under reduced pressure. The obtained residue was purified by silica gel column chromatography to obtain the title compound (1.55 g, 62%).

MS (ESI+) 728 (M+1, 100%)

Reference Example 2-6

5-{[(3S)-1-({trans-4-[(1S)-1-Amino-2-fluoroethyl]cyclohexyl}carbonyl)-3-cyclohexyl-L-prolyl]amino}-1H-indole-2-carboxylic acid hydrochloride

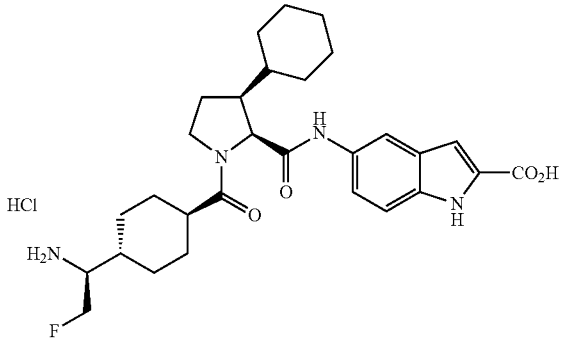 [SMILES: Cl ; N[C@H](CF)[C@H]1CC[C@H](C(=O)N2CC[C@@H](C3CCCCC3)[C@H]2C(=O)Nc2ccc3[nH]c(C(=O)O)cc3c2)CC1]

In the same manner as in Reference Example 1-8, the title compound (2.40 g, 87%) was obtained from the compound of Reference Example 2-4 (3.06 g, 4.88 mmol).

MS (ESI+) 527 (M+1, 100%)

Reference Example 3 tert-Butyl {(1S)-1-[trans-4-({(2S,3S)-3-cyclohexyl-2-[(1'-oxo-1'H-spiro[cyclohexane-1,3'-[1,3]oxazolo[3,4-a]indol]-7'-yl)carbamoyl]pyrrolidin-1-yl}carbonyl)cyclohexyl]-2-fluoroethyl}carbamate

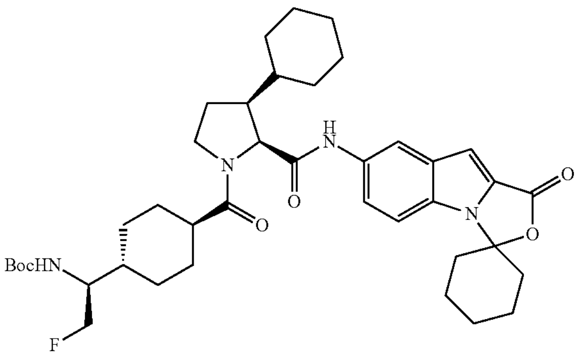 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C3(CCCCC3)OC2=O)CC1]

In the same manner as in Reference Example 1, the title compound (90.5 mg, 55%) was obtained from the compound of Reference Example 3-5 (110.0 mg, 0.232 mmol) and the compound of Reference Example 1-3 (73.8 mg, 0.255 mmol).

MS (ESI+) 707 (M+1, 100%)

Reference Example 3-1 tert-Butyl [2-(1H-benzotriazol-1-ylcarbonyl)-1H-indol-5-yl]carbamate

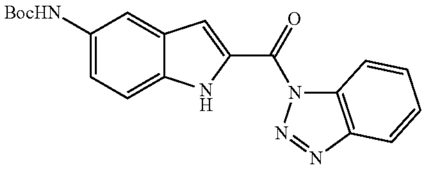 [SMILES: CC(C)(C)OC(=O)Nc1ccc2[nH]c(C(=O)n3nnc4ccccc43)cc2c1]

In the same manner as in Reference Example 2-5, the title compound (7.93 g, 58%) was obtained from commercial 5-(tert-butoxycarbonylamino)-1H-indole-2-carboxylic acid (10.0 g, 3.62 mmol).

MS (ESI+) 378 (M+1, 100%)

Reference Example 3-2 tert-Butyl (1'-oxo-1'H-spiro[cyclohexane-1,3'-[1,3]oxazolo[3,4-a]indol]-7'-yl)carbamate

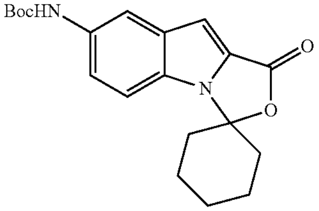 [SMILES: CC(C)(C)OC(=O)Nc1ccc2c(c1)cc1n2C2(CCCCC2)OC1=O]

Cyclohexanone (1.16 μL, 10.8 mmol) and DBU (1.04 mL, 6.95 mmol) were added to a solution of the compound of Reference Example 3-1 (1.02 g, 2.70 mmol) in tetrahydrofuran (20 mL) at room temperature, and the resulting mixture was stirred at 50° C. for 4 hours. The reaction solution was allowed to stand to cool, filtered through Celite, and concentrated under reduced pressure. The obtained residue was purified by silica gel column chromatography to obtain the title compound (101.8 mg, 11%).

MS (ESI+) 357 (M+1, 100%)

Reference Example 3-3

7'-Amino-1'H-spiro[cyclohexane-1,3'-[1,3]oxazolo[3,4-a]indol]-1'-one hydrochloride

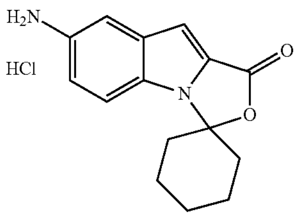 [SMILES: Cl ; Nc1ccc2c(c1)cc1n2C2(CCCCC2)OC1=O]

In the same manner as in Reference Example 1-8, the title compound (83.9 mg, 100%) was obtained from the compound of Reference Example 3-2 (101.8 mg, 0.286 mmol).

MS (ESI+) 257 (M+1, 100%)

Reference Example 3-4 tert-Butyl (2S,3S)-3-cyclohexyl-2-[(1'-oxo-1'H-spiro[cyclohexane-1,3'-[1,3]oxazolo[3,4-a]indol]-7'-yl)carbamoyl]pyrrolidine-1-carboxylate

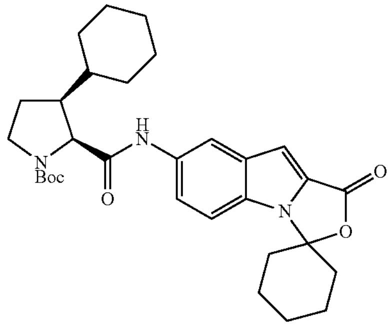 [SMILES: CC(C)(C)OC(=O)N1CC[C@@H](C2CCCCC2)[C@H]1C(=O)Nc1ccc2c(c1)cc1n2C2(CCCCC2)OC1=O]

In the same manner as in Reference Example 1-7, the title compound (124.2 mg, 81%) was obtained from the compound of Reference Example 3-3 (83.9 mg, 0.286 mmol) and the compound of Reference Example 1-6 (85.1 mg, 0.286 mmol).

MS (ESI+) 536 (M+1, 100%)

Reference Example 3-5

(3S)-3-Cyclohexyl-N-(1'-oxo-1'H-spiro[cyclohexane-1,3'-[1,3]oxazolo[3,4-a]indol]-7'-yl)-L-prolinamide hydrochloride

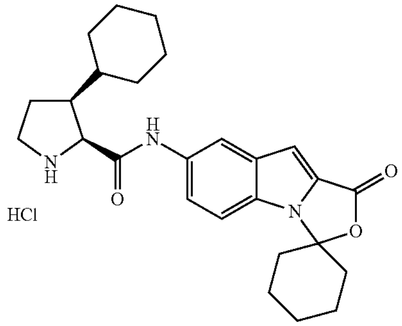 [SMILES: Cl ; O=C1OC2(CCCCC2)n2c1cc1cc(NC(=O)[C@H]3NCC[C@H]3C3CCCCC3)ccc12]

In the same manner as in Reference Example 1-8, the title compound (110.0 mg, 100%) was obtained from the compound of Reference Example 3-4 (124.2 mg, 0.232 mmol).

MS (ESI+) 436 (M+1, 100%)

Reference Example 4 tert-Butyl [(1S)-1-(trans-4-{[(2S,3S)-2-({3,3-bis[($^2H_3$)methyl)-1-oxo-1H-[1,3]oxazolo[3,4-a]indol-7-yl]carbamoyl}-3-cyclohexylpyrrolidin-1-yl)carbonyl]cyclohexyl}-2-fluoroethyl]carbamate

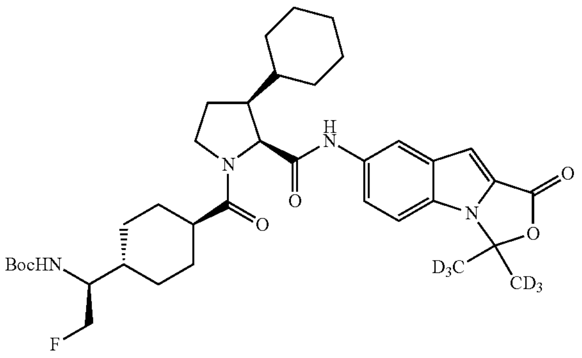 [SMILES: [2H]C([2H])([2H])C1(C([2H])([2H])[2H])OC(=O)c2cc3cc(NC(=O)[C@@H]4[C@H](C5CCCCC5)CCN4C(=O)[C@H]4CC[C@H]([C@@H](CF)NC(=O)OC(C)(C)C)CC4)ccc3n21]

In the same manner as in Reference Example 1, the title compound (14.1 mg, 57%) was obtained from the compound of Reference Example 4-4 (16.2 mg, 0.0369 mmol) and the compound of Reference Example 1-3 (12.8 mg, 0.0442 mmol).

MS (ESI+) 673 (M+1, 100%)

Reference Example 4-1

5-{[(3S)-1-(tert-Butoxycarbonyl)-3-cyclohexyl-L-proline]amino}-1H-indole-2-carboxylic acid

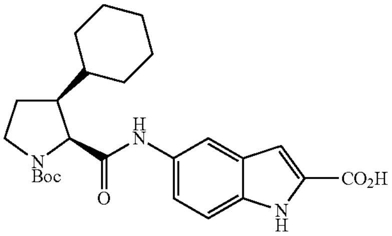 [SMILES: CC(C)(C)OC(=O)N1CC[C@@H](C2CCCCC2)[C@H]1C(=O)Nc1ccc2[nH]c(C(=O)O)cc2c1]

In the same manner as in Reference Example 2-4, the title compound (57.40 g, 100%) was obtained from the compound of Reference Example 2-1 (60.95 g, 0.126 mol).

MS (ESI+) 456 (M+1, 100%)

Reference Example 4-2 tert-Butyl (2S,3S)-2-{[2-(1H-benzotriazol-1-ylcarbonyl)-1H-indol-5-yl]carbamoyl}-3-cyclohexylpyrrolidine-1-carboxylate

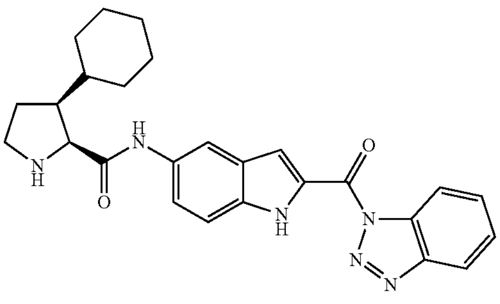 [SMILES: O=C(Nc1ccc2[nH]c(C(=O)n3nnc4ccccc43)cc2c1)[C@H]1NCC[C@H]1C1CCCCC1]

In the same manner as in Reference Example 2-5, the title compound (823 mg, 54%) was obtained from the compound of Reference Example 4-1 (1.25 g, 2.74 mmol).

MS (ESI+) 557 (M+1, 100%)

Reference Example 4-3 tert-Butyl (2S,3S)-2-({3,3-bis[(2H3)methyl]-1-oxo-1H-[1,3]oxazolo[3,4-a]indol-7-yl}carbamoyl)-3-cyclohexylpyrrolidine-1-carboxylate

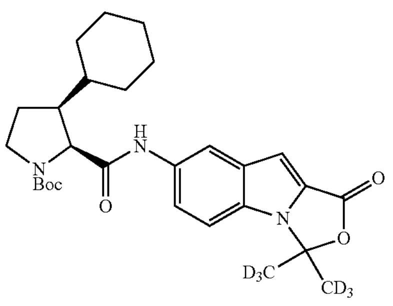 [SMILES: [2H]C([2H])([2H])C1(C([2H])([2H])[2H])OC(=O)c2cc3cc(NC(=O)[C@@H]4[C@H](C5CCCCC5)CCN4C(=O)OC(C)(C)C)ccc3n21]

In the same manner as in Reference Example 3-2, the title compound (18.5 mg, 4.7%) was obtained from the compound of Reference Example 4-2 (433 mg, 0.778 mmol) and deuteroacetone (750 μL, 10.29 mmol).

MS (ESI+) 502 (M+1, 100%)

Reference Example 4-4

(3S)—N-{3,3-bis[($^2H_3$)Methyl]-1-oxo-1H-[1,3]oxazolo[3,4-a]indol-7-yl}-3-cyclohexyl-L-prolinamide

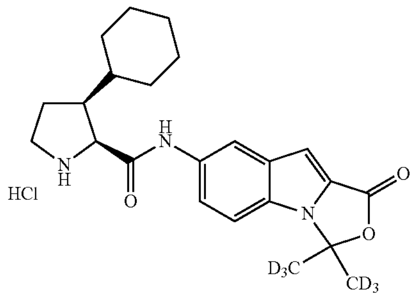 [SMILES: Cl ; [2H]C([2H])([2H])C1(C([2H])([2H])[2H])OC(=O)c2cc3cc(NC(=O)[C@H]4NCC[C@H]4C4CCCCC4)ccc3n21]

In the same manner as in Reference Example 1-8, the title compound (16.2 mg, 0.0369 mmol) was obtained from the compound of Reference Example 4-3 (18.5 mg, 0.0369 mmol).

MS (ESI+) 402 (M+1, 100%)

Reference Example 5 tert-Butyl {(1S)-1-[trans-4-({(2S,3S)-3-cyclohexyl-2-[(4,4-difluoro-1'-oxo-1'H-spiro[cyclohexane-1,3'-[1,3]oxazolo[3,4-a]indol]-7'-yl)carbamoyl]pyrrolidin-1-yl}carbonyl)cyclohexyl]-2-fluoroethyl}carbamate

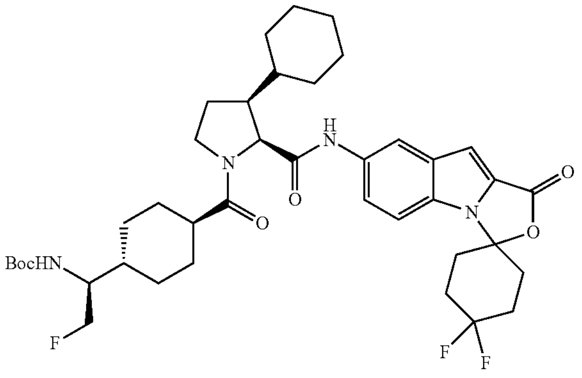 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C3(CCC(F)(F)CC3)OC2=O)CC1]

According to the methods described in the above Reference Examples 4-3 and 4-4 and Reference Example 4, the title compound was obtained from the compound of Reference Example 4-2.

MS (ESI+) 743 (M+1, 100%)

Reference Example 6 tert-Butyl [(1S)-1-(trans-4-{[(2S,3S)-2-{[3,3-bis(fluoroethyl)-1-oxo-1H-[1,3]oxazolo[3,4-a]indol-7-yl)carbamoyl]-3-cyclohexylpyrrolidin-1-yl]carbonyl}cyclohexyl)-2-fluoroethyl]carbamate

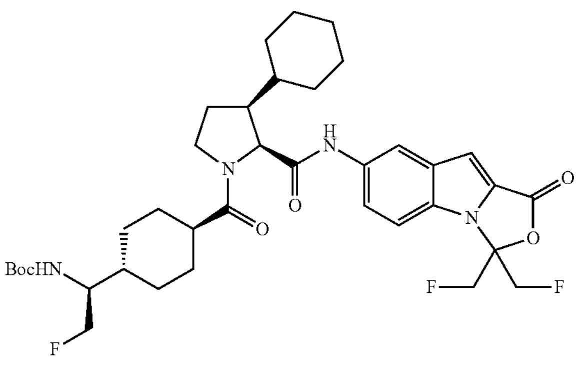 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C(CF)(CF)OC2=O)CC1]

In the same manner as in Reference Example 1, the title compound (1.02 g, 59%) was obtained from the compound of Reference Example 6-2 (1.15 g, 2.46 mmol) and the compound of Reference Example 1-3 (782 mg, 2.71 mmol).

MS (ESI+) 703 (M+1, 100%)

Reference Example 6-1 tert-Butyl (2S,3S)-2-{[3,3-bis(fluoroethyl)-1-oxo-1H-[1,3]oxazolo[3,4-a]indol-7-yl]carbamoyl}-3-cyclohexylpyrrolidine-1-carbamate

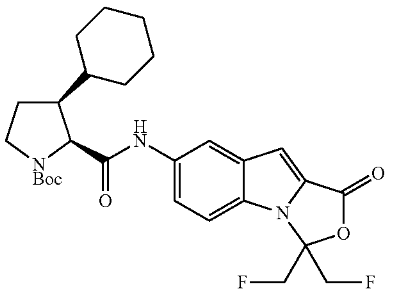 [SMILES: CC(C)(C)OC(=O)N1CC[C@@H](C2CCCCC2)[C@H]1C(=O)Nc1ccc2c(c1)cc1n2C(CF)(CF)OC1=O]

Carbonyldiimidazole (1.63 g, 10.05 mmol) was added to a solution of the compound of Reference Example 4-1 (3.05 g, 6.70 mmol) in tetrahydrofuran (25 mL) in an ice bath, and the resulting mixture was stirred at room temperature for 1.5 hours. 1,3-Difluoroacetone (945 mg, 10.05 mmol) and DBU (2.0 mL, 13.4 mmol) were added to the reaction mixture at room temperature, and the resulting mixture was stirred for 5 hours. A 5% aqueous solution of potassium hydrogensulfate was added to the reaction mixture, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (1.59 g, 45%).

MS (ESI+) 532 (M+1, 100%)

Reference Example 6-2

(3S)—N-[3,3-bis(Fluoroethyl)-1-oxo-1H-[1,3]oxazolo[3,4-a]indol-7-yl]-3-cyclohexyl-L-prolinamide hydrochloride

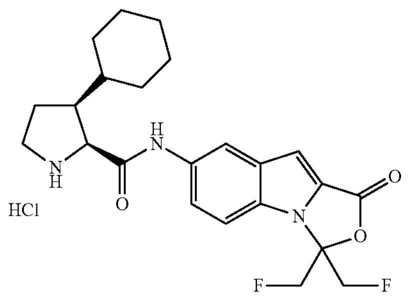 [SMILES: Cl ; O=C1OC(CF)(CF)n2c1cc1cc(NC(=O)[C@H]3NCC[C@H]3C3CCCCC3)ccc12]

In the same manner as in Reference Example 1-8, the title compound (1.61 g, 100%) was obtained from the compound of Reference Example 6-1 (1.59 g, 2.99 mmol).

MS (ESI+) 432 (M+1, 100%)

Reference Example 7 tert-Butyl {(1S)-1-[trans-4-({(2S,3S)-3-cyclohexyl-2-[(1'-oxo-1'H-spiro[cyclobutane-1,3'-[1,3]oxazolo[3,4-a]indol]-7'-yl)carbamoyl]pyrrolidin-1-yl}carbamoyl)cyclohexyl]-2-fluoroethyl}carbamate

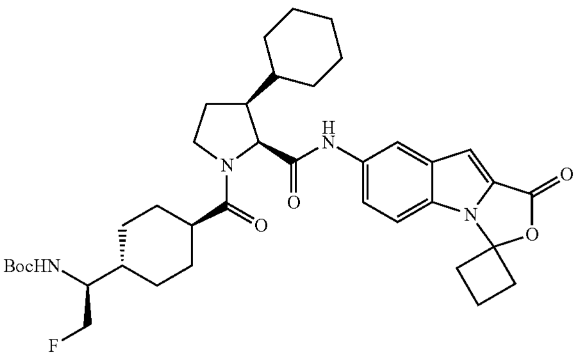 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C3(CCC3)OC2=O)CC1]

A mixture of the compound of Reference Example 7-2 (200 mg, 0.452 mmol), the compound of Reference Example 1-3 (144 mg, 0.498 mmol), 1-hydroxybenzotriazole (104 mg, 0.679 mmol), WSC.HCl (130 mg, 0.679 mmol), triethylamine (157 μL, 1.13 mmol), and DMF (4 mL) was stirred at room temperature for 3 hours. A saturated aqueous solution of ammonium chloride was added to the reaction mixture, and the resulting mixture was extracted with ethyl acetate. The organic layer was washed twice with a saturated aqueous solution of ammonium chloride and once with an aqueous solution of saturated sodium hydrogencarbonate and a saturated saline solution, then dried over anhydrous sodium sulfate, filtered, and concentrated under reduced pressure. The obtained residue was purified by silica gel column chromatography to obtain the title compound (279.4 mg, 91%).

RT 5.462 min (Kinetex 1.7μ C18 100 A, 0.1% trifluoroacetic acid in water/acetonitrile, acetonitrile 1 to 99% 7.0 min, 0.9 mL/min)

MS (ESI+) 679 (M+1, 100%) RT 1.242 min

Reference Example 7-1

(3S)-3-Cyclohexyl-N-(1'-oxo-1'H-spiro[cyclobutane-1,3'-[1,3]oxazolo[3,4-a]indol]-7'-yl)-L-prolinamide hydrochloride

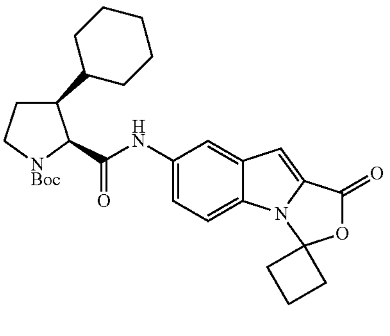 [SMILES: CC(C)(C)OC(=O)N1CC[C@@H](C2CCCCC2)[C@H]1C(=O)Nc1ccc2c(c1)cc1n2C2(CCC2)OC1=O]

Carbonyldiimidazole (164.9 mg, 1.02 mmol) was added to a solution of the compound of Reference Example 4-1 (309 mg, 0.678 mmol) in tetrahydrofuran (3 mL) in an ice bath, and the resulting mixture was stirred at room temperature for 1.5 hours. Cyclobutanone (76.2 μL, 1.02 mmol) and DBU (262 μL, 1.36 mmol) were added to the reaction mixture at room temperature, and the resulting mixture was stirred for 3 hours. A saturated aqueous solution of ammonium chloride was added to the reaction mixture, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (229.2 mg, 67%).

RT 5.441 min (Kinetex 1.7μ C18 100 A, 0.1% trifluoroacetic acid in water/acetonitrile, acetonitrile 1 to 99% 7.0 min, 0.9 mL/min)

MS (ESI+) 508 (M+1, 100%) RT 1.192 min

Reference Example 7-2

(3S)—N-[3,3-bis(Fluoroethyl)-1-oxo-1H-[1,3]oxazolo[3,4-a]indol-7-yl]-3-cyclohexyl-L-prolinamide hydrochloride

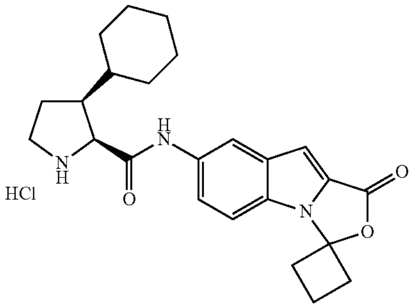 [SMILES: Cl ; O=C1OC2(CCC2)n2c1cc1cc(NC(=O)[C@H]3NCC[C@H]3C3CCCCC3)ccc12]

4 mol/L hydrochloric acid in 1,4-dioxane (5 mL) was added to the compound of Reference Example 7-1 (229.2 mg, 0.452 mmol), and the resulting mixture was stirred for 2 hours. The solvent in the reaction solution was distilled off under reduced pressure to obtain the title compound (200 mg, 100%).

MS (ESI+) 408 (M+1, 100%) RT 0.718 min

Reference Example 8 tert-Butyl {(1S)-1-[trans-4-({(2S,3S)-3-cyclohexyl-2-[(1-oxo-2',3',5',6'-tetrahydro-1H-spiro[1,3-oxazolo[3,4-a]indole-3,4'-pyran]-7-yl}carbamoyl]pyrrolidin-1-yl}carbonyl)cyclohexyl]-2-fluoroethyl}carbamate

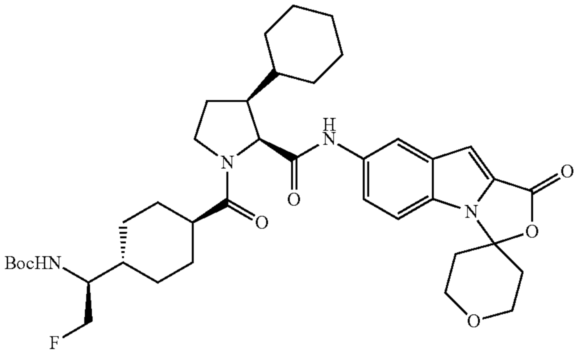

In the same manner as in Reference Example 2, the title compound (100 mg, 18%) was obtained from the compound of Reference Example 2-5 (581 mg, 0.798 mmol).

MS (ESI+) 709 (M+1, 38%)

Reference Example 9 tert-Butyl {(1S)-1-[trans-4-({(2S,3S)-3-cyclohexyl-2-[(3,3-diethyl-1-oxo-1H-[1,3]oxazolo[3,4-a]indol-7-yl)carbamoyl]pyrrolidin-1-yl)}carbonyl)cyclohexyl]-2-fluoroethyl}carbamate

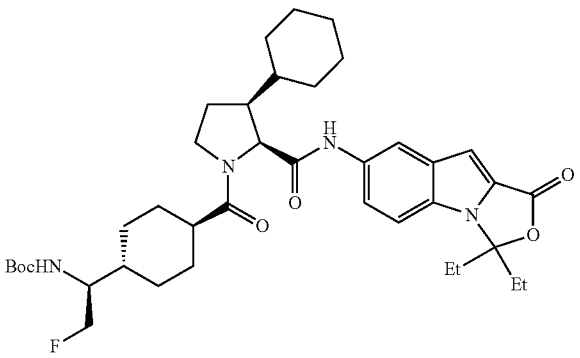 [SMILES: CCC1(CC)OC(=O)c2cc3cc(NC(=O)[C@@H]4[C@H](C5CCCCC5)CCN4C(=O)[C@H]4CC[C@H]([C@@H](CF)NC(=O)OC(C)(C)C)CC4)ccc3n21]

According to the methods described in the above Reference Examples 3-2, 3-3, 3-4, and 3-5 and Reference Example 3, the title compound was obtained from the compound of Reference Example 3-1.

MS (ESI+) 695 (M+1, 100%)

Reference Example 10 tert-Butyl [(1S)-1-(trans-4-{[(2S,3S)-2-[(3,3-dimethyl-1-oxo-1H-[1,3]oxazolo[3,4-a]indol-7-yl)carbamoyl]-3-(trans-4-methoxycyclohexyl)pyrrolidin-1-yl]carbonyl}cyclohexyl)-2-fluoroethyl]carbamate

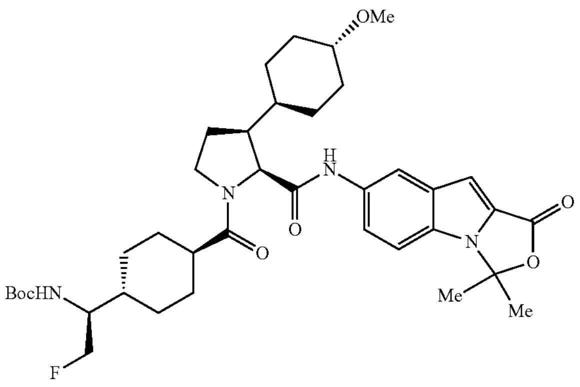 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3c(c2)cc2n3C(C)(C)OC2=O)CC1]

In the same manner as in Reference Example 2, the title compound (17.7 mg, 14%) was obtained from the compound of Reference Example 10-5 (137 mg, 0.181 mmol) and acetone (3.0 mL).

MS (ESI+) 697 (M+1, 100%)

Reference Example 10-1

Ethyl 5-{[(3S)-1-(tert-butoxycarbonyl)-3-(trans-4-methoxycyclohexyl)-L-prolyl]amino}-1H-indole-2-carboxylate

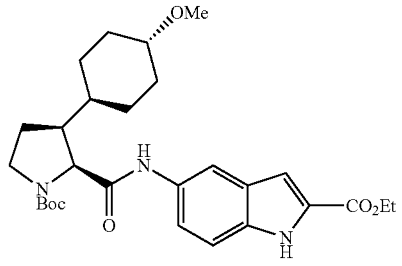 [SMILES: CCOC(=O)c1cc2cc(NC(=O)[C@@H]3[C@H]([C@H]4CC[C@H](OC)CC4)CCN3C(=O)OC(C)(C)C)ccc2[nH]1]

In the same manner as in Reference Example 1-7, the title compound (7.15 g, 92%) was obtained from the compound of Reference Example 11-3 (6.2 g, 18.94 mmol) and commercial ethyl 5-amino-1H-indole-2-carboxylate (3.87 g, 18.94 mmol).

MS (ESI+) 514 (M+1, 100%)

Reference Example 10-2

Ethyl 5-{[(3S)-3-(trans-4-methoxycyclohexyl)-L-prolyl]amino}-1H-indole-2-carboxylate hydrochloride

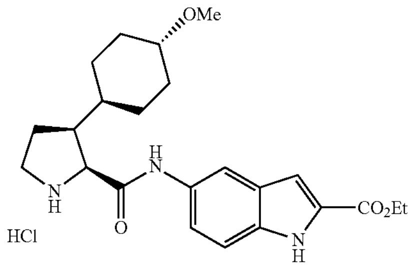 [SMILES: Cl ; CCOC(=O)c1cc2cc(NC(=O)[C@H]3NCC[C@H]3[C@H]3CC[C@H](OC)CC3)ccc2[nH]1]

In the same manner as in Reference Example 1-8, the title compound (7.15 g, 99%) was obtained from the compound of Reference Example 10-1 (7.15 g, 17.29 mmol).

MS (ESI+) 414 (M+1, 100%)

Reference Example 10-3

Ethyl 5-{[(3S)-1-[(trans-4-{(1R)-1-[(tert-butoxycarbonyl)amino]-2-fluoroethyl}cyclohexyl)carbonyl]-3-(trans-4-methoxycyclohexyl)-L-prolyl]amino}-1H-indole-2-carboxylate

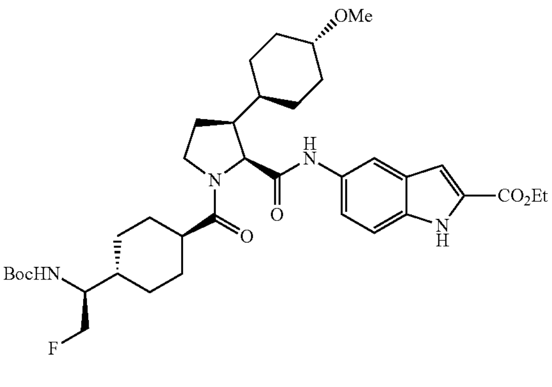 [SMILES: CCOC(=O)c1cc2cc(NC(=O)[C@@H]3[C@H]([C@H]4CC[C@H](OC)CC4)CCN3C(=O)[C@H]3CC[C@H]([C@@H](CF)NC(=O)OC(C)(C)C)CC3)ccc2[nH]1]

In the same manner as in Reference Example 1, the title compound (5.11 g, 44%) was obtained from the compound of Reference Example 10-2 (7.15 g, 17.29 mmol) and the compound of Reference Example 1-3 (5.5 g, 19.0 mmol).

MS (ESI+) 685 (M+1, 100%)

Reference Example 10-4

5-{[(3S)-1-[(trans-4-{(1R)-1-[(tert-Butoxycarbonyl)amino]-2-fluoroethyl}cyclohexyl)carbonyl]-3-(trans-4-methoxycyclohexyl)-L-prolyl]amino}-1H-indole-2-carboxylic acid

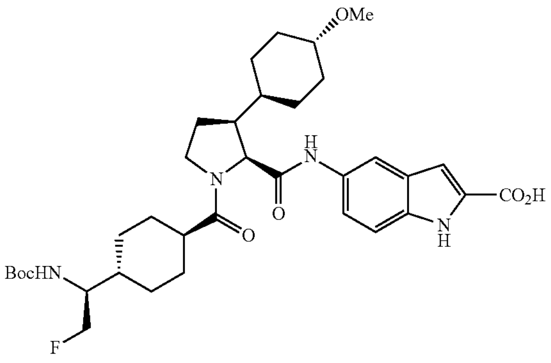 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3[nH]c(C(=O)O)cc3c2)CC1]

In the same manner as in Reference Example 2-4, the title compound (2.22 g, 83%) was obtained from the compound of Reference Example 10-3 (2.81 g, 4.10 mmol).

MS (ESI+) 657 (M+1, 100%)

Reference Example 10-5 tert-Butyl [(1S)-1-(trans-4-{[(2S,3S)-2-{[2-(1H-benzotriazol-1-ylcarbonyl)-1H-indol-5-yl]carbamoyl}-3-(trans-4-methoxycyclohexyl)pyrrolidin-1-yl]carbonyl}cyclohexyl)-2-fluoroethyl]carbamate

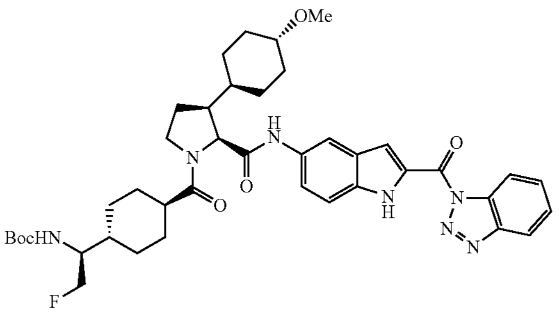 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3[nH]c(C(=O)n4nnc5ccccc54)cc3c2)CC1]

In the same manner as in Reference Example 2-5, the title compound (261.8 mg, 55%) was obtained from the compound of Reference Example 10-4 (410.4 mg, 0.625 mmol).

MS (ESI+) 758 (M+1, 100%)

Reference Example 11 tert-Butyl {(1S)-2-fluoro-1-[trans-4-({(2S,3S)-3-(trans-4-methoxycyclohexyl)-2-[(1'-oxo-1'H-spiro[cyclohexane-1,3'-[1,3]oxazoio[3,4-a]indol]-7'-yl)carbamoyl]pyrrolidin-1-yl}carbonyl)cyclohexyl]ethyl carbamate

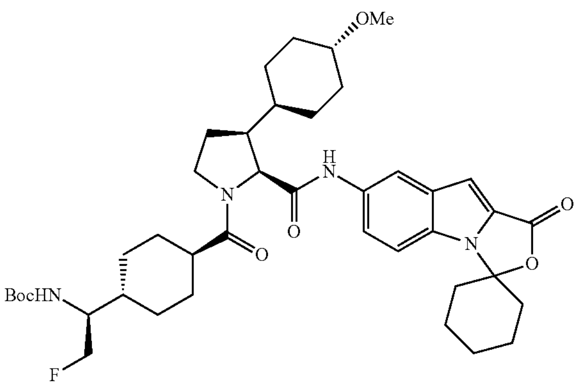 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3c(c2)cc2n3C3(CCCCC3)OC2=O)CC1]

According to the methods described in the above Reference Examples 1-7 and 1-8 and Reference Example 1, the title compound was obtained from the compound of Reference Example 3-3 and the compound of Reference Example 11-3.

MS (ESI+) 737 (M+1, 100%)

Reference Example 11-1 tert-Butyl (2S,3S)-2-(hydroxymethyl)-3-(4-methoxyphenyl)pyrrolidine-1-carboxylate

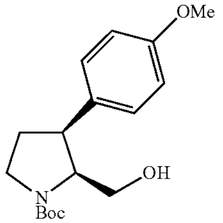 [SMILES: COc1ccc([C@@H]2CCN(C(=O)OC(C)(C)C)[C@@H]2CO)cc1]

(2S)-2-[Diphenyl[(trimethylsilyl)oxy]methyl]pyrrolidine (2.95 g, 9.06 mmol), nitroethanol (24.71 g, 0.272 mol), and benzoic acid (2.21 g, 18.1 mmol) were added to a solution of trans-4-methoxycinnamaldehyde (29.35 g, 0.181 mol) in methanol (145 mL), and the resulting mixture was stirred at 40° C. for 10 hours in a nitrogen atmosphere. The reaction solution was allowed to stand to cool to room temperature, and the precipitated solid was filtered out and washed with ethyl acetate and hexane to obtain (4S,5S)-4-(2-methoxyphenyl)-5-nitrotetrahydro-2H-pyran-2-ol (28.20 g, 62%).

Zinc (145.6 g, 2.23 mol) and ammonium chloride (119.2 g, 2.23 mol) were added to a solution of the obtained (4S,5S)-4-(2-methoxyphenyl)-5-nitrotetrahydro-2H-pyran-2-ol (28.20 g, 111.4 mol) in ethanol (400 ml)-water (200 ml), and the resulting mixture was stirred at 60° C. for 1 hour. The reaction solution was allowed to stand to cool, a saturated aqueous solution of sodium hydrogencarbonate (500 mL) was added thereto, and the resulting mixture was stirred for 15 minutes and filtered through Celite. Ethyl acetate was added to the filtrate for separation, and di-tert-butyl dicarbonate (59.30 g, 271.7 mmol) was added to the aqueous layer, and the resulting mixture was stirred at room temperature overnight. Ethyl acetate was added to the reaction solution for separation, the obtained organic layer was washed with a saturated saline solution, then dried over anhydrous sodium sulfate, filtered, and concentrated under reduced pressure. Hexane was added to the obtained residue, and the precipitated solid was filtered out to obtain the title compound (30.34 g, 89%).

MS (ESI+) 308 (M+1, 100%)

Reference Example 11-2 tert-Butyl (2S,3S)-2-(hydroxymethyl)-3-(trans-4-methoxycyclohexyl)pyrrolidine-1-carboxylate

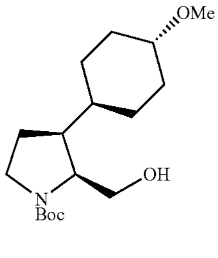 [SMILES: CO[C@H]1CC[C@H]([C@@H]2CCN(C(=O)OC(C)(C)C)[C@@H]2CO)CC1]

Platinum oxide (2.12 g) was added to a solution of the compound of Reference Example 11-1 (21.11 g, 68.68 mmol) in acetic acid (120 mL), and the resulting mixture was stirred for 4 hours at a pressure of 0.4 Mpa in a hydrogen atmosphere. The reaction solution was filtered through Celite, toluene was added thereto, and the resulting mixture was concentrated under reduced pressure. The obtained residue was purified by silica gel column chromatography to obtain the title compound (1.09 g, 5.1%).

MS (ESI+) 314 (M+1, 28%)

Reference Example 11-3

(3S)-1-(tert-Butoxycarbonyl)-3-(trans-4-methoxycyclohexyl)-L-proline

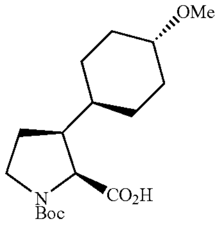 [SMILES: CO[C@H]1CC[C@H]([C@@H]2CCN(C(=O)OC(C)(C)C)[C@@H]2C(=O)O)CC1]

AZADOL (registered trademark) (531 mg, 3.47 mmol) and iodobenzene diacetate (55.80 g, 173 mmol) were added to a solution of the compound of Reference Example 11-2 (21.72 g, 69.30 mmol) in dichloromethane (80 mL)/pH 7.0 phosphoric acid buffer (80 mL) in an ice bath, and the resulting mixture was stirred at room temperature for 2 hours. A 1 M aqueous solution of sodium thiosulfate and a 1 mol/L aqueous solution of sodium hydroxide were added thereto in an ice bath to adjust the pH to >8. Chloroform was added to the resulting mixture for separation, and the organic layer was washed 3 times with a 1 mol/L aqueous solution of sodium hydroxide. The aqueous layers were combined, a 5% aqueous solution of potassium hydrogensulfate was added thereto to adjust the pH to <4, and the resulting mixture was extracted with chloroform 8 times. The organic layers were combined, dried over anhydrous sodium sulfate, filtered, and concentrated under reduced pressure to obtain the title compound (16.68 g, 74%).

MS (ESI+) 328 (M+1, 0.75%)

Reference Example 12 tert-Butyl [(1S)-1-(trans-4-{[(2S,3S)-2-[(4,4-difluoro-1'-oxo-1'H-spiro[cyclohexane-1,3'-[1,3]oxazolo[3,4-a]indol]-7'-yl]carbamoyl)-3-(trans-4-methoxycyclohexyl)pyrrolidin-1-yl]carbonyl]}-2-fluoroethyl)carbamate

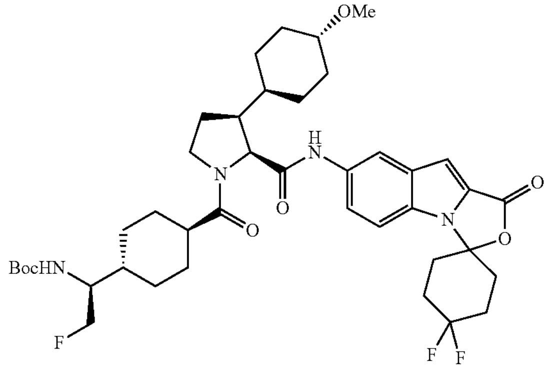 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3c(c2)cc2n3C3(CCC(F)(F)CC3)OC2=O)CC1]

In the same manner as in Reference Example 3-2, the title compound (141.4 mg, 53%) was obtained from the compound of Reference Example 10-5 (261.8 mg, 0.345 mmol).

MS (ESI+) 773 (M+1, 100%)

Reference Example 13 tert-Butyl [(1S)-1-(trans-4-{[(2S,3S)-2-{[3,3-bis(fluoromethyl)-1-oxo-1H-[1,3]oxazolo[3,4-a]indol-7-yl]carbamoyl}-3-(trans-4-methoxycyclohexyl)pyrrolidin-1-yl]carbonyl}cyclohexyl)-2-fluoroethyl]carbamate

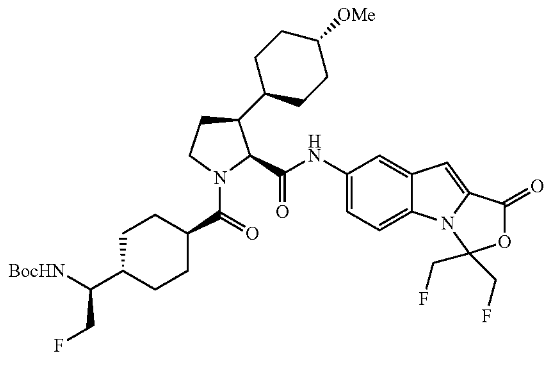 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3c(c2)cc2n3C(CF)(CF)OC2=O)CC1]

According to the methods described in the above Reference Examples 3-2, 3-3, 3-4, and 3-5 and Reference Example 3, the title compound was obtained from the compound of Reference Example 3-1 and the compound of Reference Example 11-3.

MS (ESI+) 733 (M+1, 100%)

Reference Example 14 tert-Butyl {(1S)-2-fluoro-1-[trans-4-({(2S,3S)-3-(trans-4-methoxycyclohexyl)-2-[(1'-oxo-1'H-spiro[cyclobutane-1,3'-[1,3]oxazolo[3,4-a]indol]-7'-yl)carbamoyl]pyrrolidin-1-yl}carbonyl)cyclohexyl]ethyl}carbamate

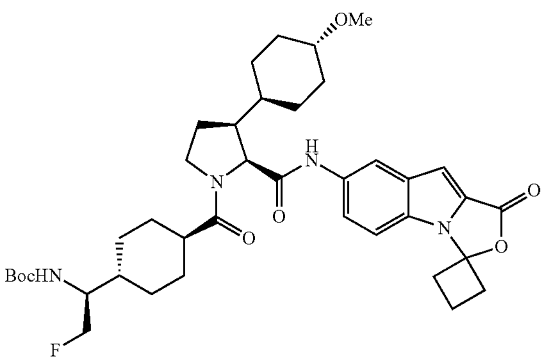 [SMILES: CO[C@H]1CC[C@H]([C@@H]2CCN(C(=O)[C@H]3CC[C@H]([C@@H](CF)NC(=O)OC(C)(C)C)CC3)[C@@H]2C(=O)Nc2ccc3c(c2)cc2n3C3(CCC3)OC2=O)CC1]

In the same manner as in Reference Example 6-1, the title compound (464 mg, 19%) was obtained from the compound of Reference Example 10-4 (255 mg, 0.388 mmol).

MS (ESI+) 709 (M+1, 100%)

Reference Example 15 tert-Butyl [(1S)-1-(trans-4-{(2S,3R)-2-[(3,3-dimethyl-1-oxo-1H-[1,3]oxazolo[3,4-a]indol-7-yl)carbamoyl]-3-(piperidin-1-yl)pyrrolidin-1-yl]carbonyl}cyclohexyl)-2-fluoroethyl]carbamate

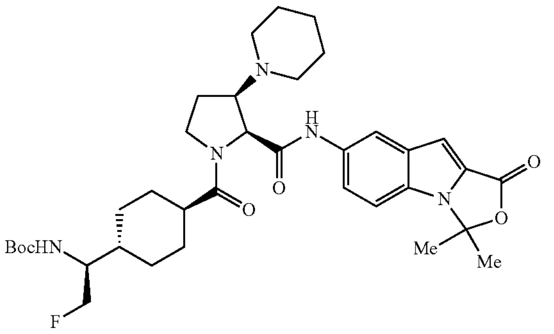 [SMILES: CC(C)(C)OC(=O)N[C@H](CF)[C@H]1CC[C@H](C(=O)N2CC[C@@H](N3CCCCC3)[C@H]2C(=O)Nc2ccc3c(c2)cc2n3C(C)(C)OC2=O)CC1]

DBU (43.4 mL, 0.291 mmol) was added to a solution of the compound of Reference Example 15-8 (70.6 mg, 0.097 mmol) in acetone (2 mL) at room temperature, and the resulting mixture was stirred at 60° C. for 2 hours. The reaction solution was allowed to stand to cool, a saturated aqueous solution of ammonium chloride was added thereto, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (17.0 mg, 20%).

MS (ESI+) 668 (M+1, 100%)

Reference Example 15-1

(rac.)-1-tert-Butyl 2-ethyl (2S,3R)-3-(piperidin-1-yl)pyrrolidine-1,2-dicarboxylate

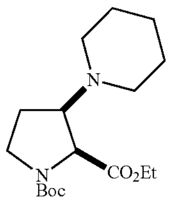 [SMILES: CCOC(=O)[C@@H]1[C@H](N2CCCCC2)CCN1C(=O)OC(C)(C)C]

Acetic acid (2 mL), and subsequently, sodium tri(acetoxy)borohydride (2.72 g, 12.8 mmol) were added to a solution of 1-tert-butyl 2-ethyl (2S)-3-oxopyrrolidine-1,2-dicarboxylate (1.1 g, 4.27 mmol) known from documents (e.g., J. Org. Chem. 1985, 50, 25, 5223) and piperidine (845 μL, 8.55 mmol) in dichloromethane (17 mL) in an ice bath, and the resulting mixture was stirred at room temperature for 15 hours. A saturated aqueous solution of sodium hydrogencarbonate was added to the reaction mixture, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (600 mg, 43%).

MS (ESI+) 327 (M+1, 100%)

Reference Example 15-2

1-tert-Butyl 2-ethyl (2S,3R)-3-(piperidin-1-yl)pyrrolidine-1,2-dicarboxylate

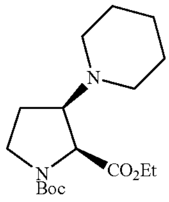 [SMILES: CCOC(=O)[C@@H]1[C@H](N2CCCCC2)CCN1C(=O)OC(C)(C)C]

A racemate of the compound of Reference Example 15-1 was collected by HPLC under the following conditions to obtain the title compound. CHIRALPAK AY-H (0.46 cmI.D.×25 cmL), moving bed: n-hexane/ethanol (90/10), flow rate: 1.0 mL/min, wavelength: 206 nm, RT 4.473 min Reference Example 15-3

(3R)-1-(tert-Butoxycarbonyl)-3-piperidin-1-yl-L-proline

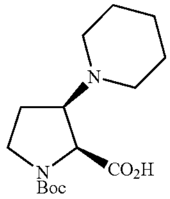 [SMILES: CC(C)(C)OC(=O)N1CC[C@@H](N2CCCCC2)[C@H]1C(=O)O]

The compound of Reference Example 15-2 (803 mg, 2.46 mmol) was dissolved in ethanol (4 mL) and THF (4 mL), a 2 mol/L aqueous solution of sodium hydroxide (3.7 mL, 7.38 mmol) was added to the resulting mixture, and the resulting mixture was stirred at 90° C. for 10 hours. The reaction solution was allowed to stand to cool to room temperature and concentrated under reduced pressure. Water was added to the residue, and the aqueous layer was washed with diethyl ether. A 2 mol/L hydrochloric acid was added to the aqueous layer for neutralization, and the resulting mixture was concentrated under reduced pressure. THF was added to the residue, then the insolubles were filtered, and the obtained filtrate was concentrated under reduced pressure to obtain the title compound (746.4 mg, 100%).

MS (ESI+) 299 (M+1, 100%)

Reference Example 15-4

Ethyl 5-{[(3R)-1-(tert-butoxycarbonyl)-3-(piperidin-1-yl)-L-prolyl]amino]-1H-indole-2-carboxylate

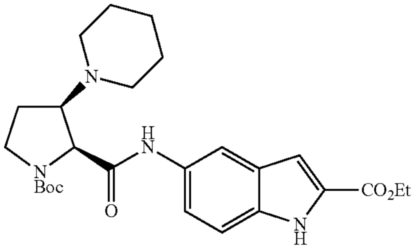 [SMILES: CCOC(=O)c1cc2cc(NC(=O)[C@@H]3[C@H](N4CCCCC4)CCN3C(=O)OC(C)(C)C)ccc2[nH]1]

In the same manner as in Reference Example 1, the title compound (976 mg, 82%) was obtained from the compound of Reference Example 15-3 (746.4 mg, 2.46 mmol) and ethyl 5-amino-1H-indole-2-carboxylate (552.6 mg, 2.71 mmol).

MS (ESI+) 485 (M+1, 100%)

Reference Example 15-5

Ethyl 5-{[(3R)-3-(piperidin-1-yl)-L-prolyl]amino}-1H-indole-2-carboxylate hydrochloride

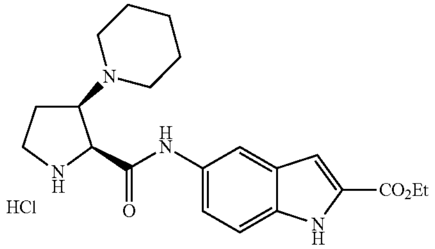 [SMILES: Cl ; CCOC(=O)c1cc2cc(NC(=O)[C@H]3NCC[C@H]3N3CCCCC3)ccc2[nH]1]

In the same manner as in Reference Example 1-8, the title compound (756.9 mg, 100%) was obtained from the compound of Reference Example 15-4 (822 mg, 1.70 mmol).

MS (ESI+) 385 (M+1, 100%)

Reference Example 15-6

Ethyl 5-{[(3R)-1-[(trans-4-{(1S)-1-[(tert-Butoxycarbonyl)amino]-2-fluoroethyl}cyclohexyl)carbonyl]-3-(piperidin-1-yl)-L-prolyl]amino}-1H-indole-2-carboxylate

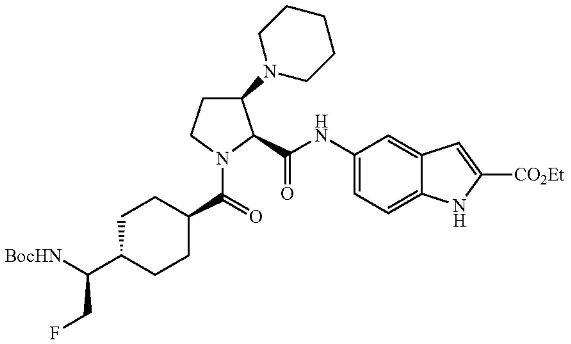 [SMILES: CCOC(=O)c1cc2cc(NC(=O)[C@@H]3[C@H](N4CCCCC4)CCN3C(=O)[C@H]3CC[C@H]([C@@H](CF)NC(=O)OC(C)(C)C)CC3)ccc2[nH]1]

In the same manner as in Reference Example 1, the title compound (792 mg, 98%) was obtained from the compound of Reference Example 15-5 (518 mg, 1.23 mmol) and the compound of Reference Example 1-3 (391.7 mg, 1.35 mmol).

MS (ESI+) 656 (M+1, 100%)

Reference Example 15-7

5-{[(3R)-1-[(trans-4-{(1S)-1 I-[(tert-Butoxycarbonyl)amino]-2-fluoroethyl}cyclohexyl)carbonyl]-3-(piperidin-1-yl)-L-prolyl]amino}-1H-indole-2-carboxylic acid

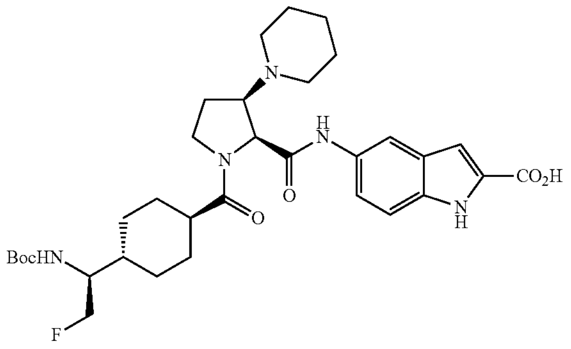 [SMILES: CC(C)(C)OC(=O)N[C@H](CF)[C@H]1CC[C@H](C(=O)N2CC[C@@H](N3CCCCC3)[C@H]2C(=O)Nc2ccc3[nH]c(C(=O)O)cc3c2)CC1]

In the same manner as in Reference Example 15-3, the title compound (643 mg, 86%) was obtained from the compound of Reference Example 15-6 (779 mg, 1.19 mmol).

MS (ESI+) 628 (M+1, 100%)

Reference Example 15-8 tert-Butyl [(1S)-1-(trans-4-{[(2S,3R)-2-{[2-(1H-benzotriazol-1-ylcarbonyl)-1H-indol-5-yl]carbamoyl}-3-(piperidin-1-yl)pyrrolidin-1-yl]carbonyl}cyclohexyl)-2-fluoroethyl]carbamate

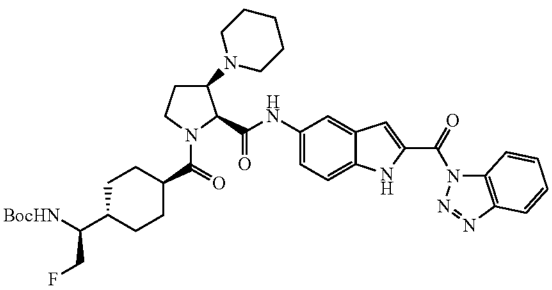 [SMILES: CC(C)(C)OC(=O)N[C@H](CF)[C@H]1CC[C@H](C(=O)N2CC[C@@H](N3CCCCC3)[C@H]2C(=O)Nc2ccc3[nH]c(C(=O)n4nnc5ccccc54)cc3c2)CC1]

In the same manner as in Reference Example 2-5, the title compound (138 mg, 49%) was obtained from the compound of Reference Example 15-7 (255 mg, 0.389 mmol).

MS (ESI+) 729 (M+1, 100%)

Reference Example 16 tert-Butyl [(1S)-1-(trans-4-{[(2S,3R)-2-[(3,3-diethyl-1-oxo-1H-[1,3]oxazolo[3,4-a]indol-7-yl)carbamoyl]-3-(piperidin-1-yl)pyrrolidin-1-yl]carbonyl}cyclohexyl)-2-fluoroethyl]carbamate

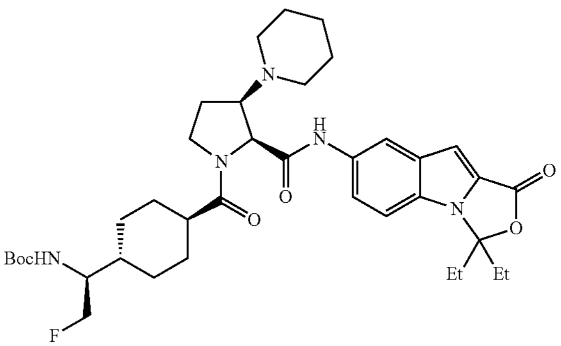 [SMILES: CCC1(CC)OC(=O)c2cc3cc(NC(=O)[C@@H]4[C@H](N5CCCCC5)CCN4C(=O)[C@H]4CC[C@H]([C@@H](CF)NC(=O)OC(C)(C)C)CC4)ccc3n21]

According to the methods described in the above Reference Examples 1-7, 1-8, 4, 2-4, 2-5, 3-2, and 1-8 and Reference Example 1, the title compound was obtained from the compound of Reference Example 15-3.

MS (ESI+) 696 (M+1, 100%)

Reference Example 17 tert-Butyl {[trans-4-({(2S,3S)-3-cyclohexyl-2-[(3,3-dimethyl-1-oxo-1H-[1,3]oxazolo[3,4-a]indol-7-yl)carbamoyl]pyrrolidin-1-yl}carbonyl)cyclohexyl]methyl}carbamate

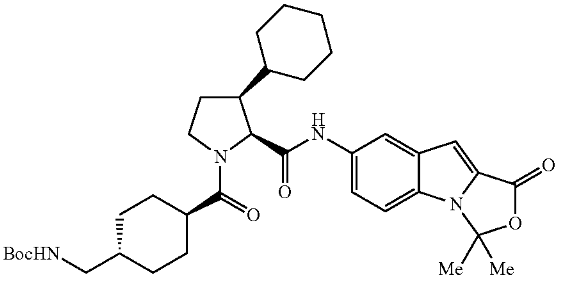 [SMILES: CC(C)(C)OC(=O)NC[C@H]1CC[C@H](C(=O)N2CC[C@@H](C3CCCCC3)[C@H]2C(=O)Nc2ccc3c(c2)cc2n3C(C)(C)OC2=O)CC1]

In the same manner as in Reference Example 1, the title compound (334.4 mg, 76%) was obtained from the compound of Reference Example 1-8 (299.8 mg, 0.693 mmol) and trans-4-{[(tert-butoxycarbonyl)amino]methyl} cyclohexyl carboxylic acid (196 mg, 0.762 mmol).

MS (ESI+) 635 (M+1, 100%)

Reference Example 18 tert-Butyl [(trans-4-{[(2S,3S)-2-{[3,3-bis(fluoromethyl)-1-oxo-1H-[1,3]oxazolo[3,4-a]indol-7-yl]carbamoyl}-3-cyclohexylpyrrolidin-1-yl]carbonyl}cyclohexyl)methyl]carbamate

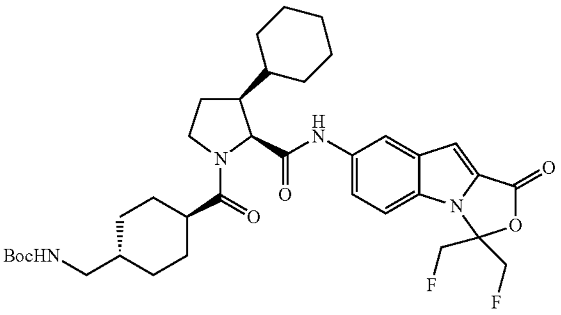 [SMILES: CC(C)(C)OC(=O)NC[C@H]1CC[C@H](C(=O)N2CC[C@@H](C3CCCCC3)[C@H]2C(=O)Nc2ccc3c(c2)cc2n3C(CF)(CF)OC2=O)CC1]

In the same manner as in Reference Example 1, the title compound (1.02 g, 59%) was obtained from the compound of Reference Example 6-2 (1.15 g, 2.46 mmol) and trans-4-{[(tert-butoxycarbonyl)amino]methyl}cyclohexyl carboxylic acid (782 mg, 2.71 mmol).

MS (ESI+) 703 (M+1, 100%)

Reference Example 19 tert-Butyl {(1S)-1-[trans-4-({(2S,3S)-2-[(3,3-dimethyl-1-oxo-1H-[1,3]oxazolo[3,4-a]indol-7-yl)carbamoyl]-3-phenylpyrrolidin-1-yl}carbonyl)cyclohexyl]-2-fluoroethyl}carbamate

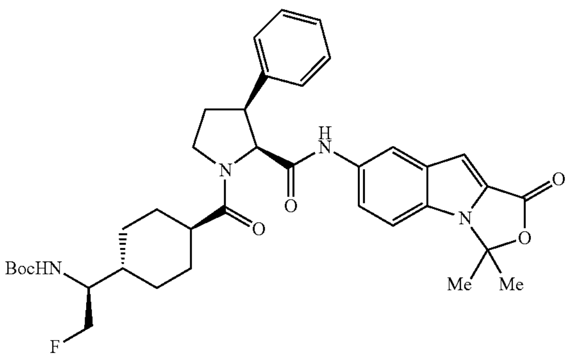 [SMILES: CC(C)(C)OC(=O)N[C@H](CF)[C@H]1CC[C@H](C(=O)N2CC[C@@H](c3ccccc3)[C@H]2C(=O)Nc2ccc3c(c2)cc2n3C(C)(C)OC2=O)CC1]

According to the methods described in the above Reference Examples 1-7 and 1-8 and Reference Example 1, the title compound was obtained from the compound of Reference Example 1-5 and (2S,3S)-1-tert-butoxycarbonyl-3-phenylpyrrolidine-2-carboxylic acid known from documents (e.g., Org. Lett, 2009, 11, 18, 4056.).

MS (ESI+) 661 (M+1, 100%)

Reference Example 19-1

5-{[(3S)-1-({trans-4-[(1S)-1-Amino-2-fluoroethyl]cyclohexyl}carbonyl)-3-phenyl-L-prolyl]amino}-1H-indole-2-carboxylic acid hydrochloride

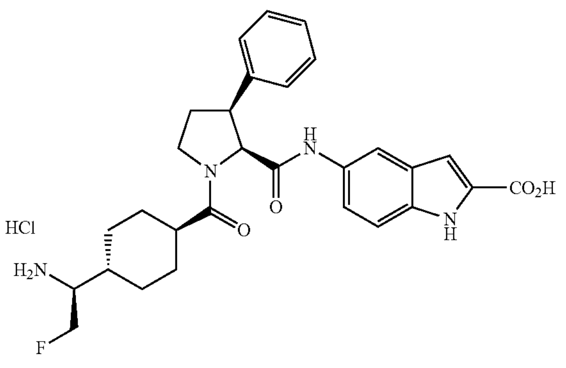 [SMILES: Cl ; N[C@H](CF)[C@H]1CC[C@H](C(=O)N2CC[C@@H](c3ccccc3)[C@H]2C(=O)Nc2ccc3[nH]c(C(=O)O)cc3c2)CC1]

According to the methods described in the above Reference Examples 1-7, 1-8, 1, and 2-4 and Reference Example 1-8, the title compound was obtained from commercial ethyl 5-amino-1H-indole-2-carboxylate and (2S,3S)-1-tert-butoxycarbonyl-3-phenylpyrrolidine-2-carboxylic acid known from documents (e.g., Org. Lett, 2009, 11, 18, 4056.).

MS (ESI+) 521 (M+1, 100%)

Reference Example 20 tert-Butyl {(1S)-1-[trans-4-({(2S,3R)-2-[(3,3-dimethyl-1-oxo-1H-[1,3]oxazolo[3,4-a]indol-7-yl)carbamoyl]-3-phenylpyrrolidin-1-yl}carbonyl)cyclohexyl]-2-fluoroethyl}carbamate

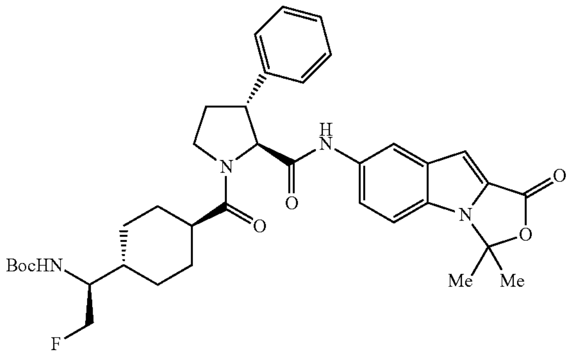 [SMILES: CC(C)(C)OC(=O)N[C@H](CF)[C@H]1CC[C@H](C(=O)N2CC[C@H](c3ccccc3)[C@H]2C(=O)Nc2ccc3c(c2)cc2n3C(C)(C)OC2=O)CC1]

According to the methods described in the above Reference Examples 1-7 and 1-8, and Reference Example 1, the title compound was obtained from the compound of Reference Example 1-5 and the compound of Reference Example 20-4.

MS (ESI+) 661 (M+1, 100%)

Reference Example 20-1 tert-Butyl (2R,3R)-2-(hydroxymethyl)-3-phenylpyrrolidine-1-carboxylate

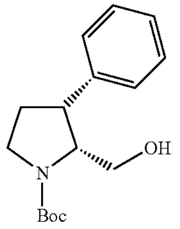

(2R)-2-[Diphenyl[(trimethylsilyl)oxy]methyl]pyrrolidine (16.5 g, 50.6 mmol), nitroethanol (138.8 g, 1.524 mol), and benzoic acid (12.4 g, 101.5 mmol) were added to a solution of trans-cinnamaldehyde (134.2 g, 1.015 mol) in methanol (2 L), and the resulting mixture was stirred in a nitrogen atmosphere at room temperature for 3 days. Sodium hydrogencarbonate (424.2 g, 5.05 mol) was added thereto and the resulting mixture was further stirred for 12 hours. The reaction solution was concentrated under reduced pressure, distilled water was added thereto, and the resulting mixture was extracted with ethyl acetate. The obtained organic layer was dried over anhydrous sodium sulfate, filtered, and concentrated under reduced pressure. The residue was dissolved in a mixed solvent of ethyl acetate and hexane (1:1) under heating at 80° C., then the resulting solution was stirred while being allowed to gradually cool to room temperature. 3 hours later, the precipitated solid was filtered out to obtain (4R,5R)-4-phenyl-5-nitrotetrahydro-2H-pyran-2-ol (128.68 g, 0.576 mol, >99% ee).

Palladium hydroxide (15.0 g) were added to a solution of (4R,5R)-4-phenyl-5-nitrotetrahydro-2H-pyran-2-ol (15.0 g, 67.0 mmol) in methanol (1.5 L), and the resulting mixture was stirred in a hydrogen atmosphere overnight. The reaction solution was filtered through Celite and concentrated under reduced pressure. This residue was dissolved in acetonitrile (225 mL), di-tert-butyl dicarbonate (21.9 g, 101 mmol) was added thereto, and the resulting mixture was stirred overnight. The reaction solution was concentrated under reduced pressure and then purified by silica gel column chromatography to obtain the title compound (10.2 g, 55%).

MS (ESI+) 278 (M+1, 2.8%)

Reference Example 20-2 tert-Butyl (2R,3R)-2-formyl-3-phenylpyrrolidine-1-carboxylate

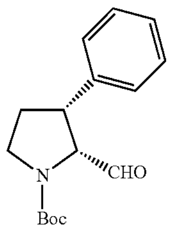 [SMILES: CC(C)(C)OC(=O)N1CC[C@H](c2ccccc2)[C@@H]1C=O]

N-Methylmorpholine N-oxide (13.2 g, 113 mmol) and molecular sieves 4 Å (10.5 g) were added to a solution of the compound of Reference Example 20-1 (20.9 g, 75 mmol) in dichloromethane (200 mL), and the resulting mixture was stirred for 10 minutes. Then tetrapropylammonium perruthenate (1.32 g, 3.75 mmol) was added thereto, and the resulting mixture was stirred overnight. The reaction solution was filtered through silica gel and concentrated under reduced pressure. The obtained residue was purified by silica gel column chromatography to obtain the title compound (13.7 g, 66%).

MS (ESI+) 276 (M+1, 3.7%)

Reference Example 20-3 tert-Butyl (2S,3R)-2-formyl-3-phenylpyrrolidine-1-carboxylate

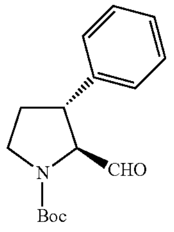 [SMILES: CC(C)(C)OC(=O)N1CC[C@H](c2ccccc2)[C@H]1C=O]

DBU (7.56 g, 50 mmol) was added to a solution of the compound of Reference Example 20-2 (13.7 g, 50 mmol) in dichloromethane (170 mL), and the resulting mixture was stirred at room temperature overnight. A pH 7 phosphate buffer was added to the reaction mixture, and the resulting mixture was extracted with ethyl acetate. The organic layer was washed with a saturated saline solution, then dried over anhydrous sodium sulfate, filtered, and concentrated under reduced pressure to obtain the title compound (13.7 g, 100%).

MS (ESI+) 276 (M+1, 5%)

Reference Example 20-4

(3R)-1-(tert-Butoxycarbonyl)-3-phenyl-L-proline

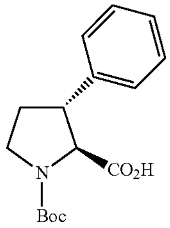

The compound of Reference Example 20-3 (12.45 g, 45.1 mmol) was dissolved in a mixed solvent of tert-butanol and distilled water (3:1, 240 mL), sodium dihydrogenphosphate dihydrate (21.1 g, 135 mmol), 2-methyl-2-butene (15.8 g, 226 mmol), and sodium chlorite (11.7 g, 90 mmol) were added thereto, and the resulting mixture was stirred for 1 hour. A pH 7 phosphate buffer was added to the reaction solution, and the resulting mixture was extracted with ethyl acetate. The organic layer was dried over anhydrous sodium sulfate, filtered, and concentrated under reduced pressure. The obtained residue was recrystallized with a chloroform/hexane mixed solution to obtain the title compound (5.3 g, 40%).

MS (ESI+) 292 (M+1, 17%)

Reference Example 20-5

5-{[(3R)-1-({trans-4-[(1S)-1-Amino-2-fluoroethyl]cyclohexyl}carbonyl)-3-phenyl-L-prolyl]amino}-1H-indole-2-carboxylic acid hydrochloride

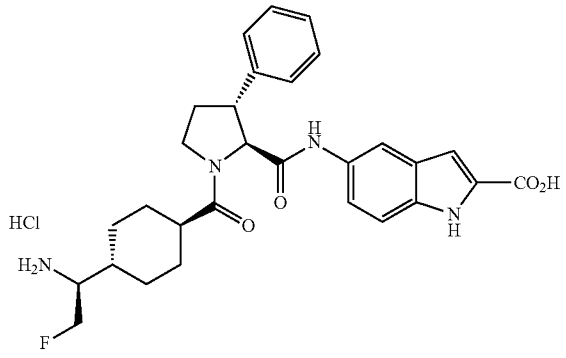 [SMILES: Cl ; N[C@H](CF)[C@H]1CC[C@H](C(=O)N2CC[C@H](c3ccccc3)[C@H]2C(=O)Nc2ccc3[nH]c(C(=O)O)cc3c2)CC1]

According to the methods described in the above Reference Examples 1-7, 1-8, 1, and 2-4 and Reference Example 1-8, the title compound was obtained from commercial ethyl 5-amino-1H-indole-2-carboxylate and the compound of Reference Example 20-4.

MS (ESI+) 521 (M+1, 100%)

Reference Example 21 tert-Butyl [(1S)-1-(trans-4-{[(2S,3S)-2-{[3,3-bis(fluoromethyl)-1-oxo-1H-[1,3]oxazolo[3,4-a]indol-7-yl]carbamoyl}-3-phenylpyrrolidin-1-yl]carbonyl}cyclohexyl)-2-fluoroethyl]carbamate

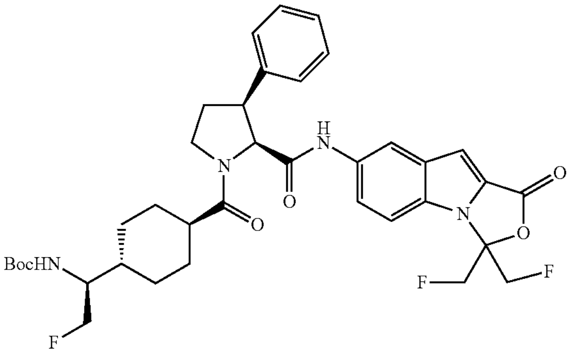 [SMILES: CC(C)(C)OC(=O)N[C@H](CF)[C@H]1CC[C@H](C(=O)N2CC[C@@H](c3ccccc3)[C@H]2C(=O)Nc2ccc3c(c2)cc2n3C(CF)(CF)OC2=O)CC1]

According to the methods described in the above Reference Examples 1-7, 2-4, 6-1, and 1-8 and Reference Example 1, the title compound was obtained from commercial ethyl 5-amino-1H-indole-2-carboxylate and (2S,3S)-1-tert-butoxycarbonyl-3-phenylpyrrolidine-2-carboxylic acid known from documents (e.g., Org. Lett, 2009, 11, 18, 4056.).

MS (ESI+) 697 (M+1, 100%)

Reference Example 22 tert-Butyl [(1S)-1-(trans-4-{[(2S,3R)-2-{[3,3-bis(fluoromethyl)-1-oxo-1H-[1,3]oxazolo[3,4-a]indol-7-yl]carbamoyl}-3-phenylpyrrolidin-1-yl]carbonyl}cyclohexyl)-2-fluoroethyl]carbamate

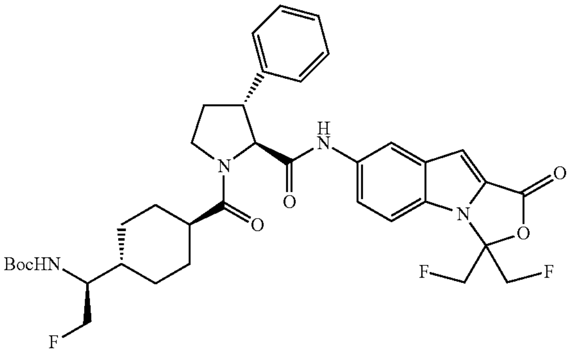 [SMILES: CC(C)(C)OC(=O)N[C@H](CF)[C@H]1CC[C@H](C(=O)N2CC[C@H](c3ccccc3)[C@H]2C(=O)Nc2ccc3c(c2)cc2n3C(CF)(CF)OC2=O)CC1]

According to the methods described in the above Reference Examples 1-7, 2-4, 6-1, and 1-8 and Reference Example 1, the title compound was obtained from commercial ethyl 5-amino-1H-indole-2-carboxylate and the compound of Reference Example 20-4.

MS (ESI+) 697 (M+1, 100%)

Reference Example 23

5-({(3S)-1-[(trans-4-{[(tert-Butoxycarbonyl)amino]methyl}cyclohexyl)carbonyl]-3-cyclohexyl-L-prolyl} amino)-1H-indole-2-carboxylic acid

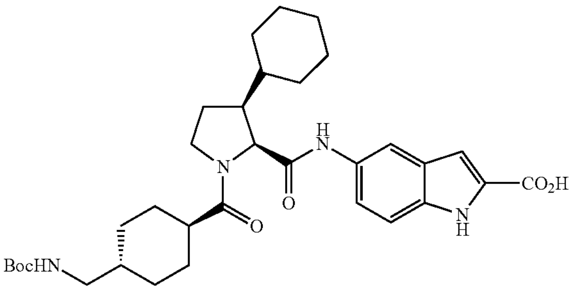 [SMILES: CC(C)(C)OC(=O)NC[C@H]1CC[C@H](C(=O)N2CC[C@@H](C3CCCCC3)[C@H]2C(=O)Nc2ccc3[nH]c(C(=O)O)cc3c2)CC1]

In the same manner as in Reference Example 2-4, the title compound (176.6 mg, 91%) was obtained from the compound of Reference Example 17 (206.9 mg, 0.326 mmol).

MS (ESI+) 595 (M+1, 100%)

Reference Example 24 tert-Butyl (2S,3S)-3-cyclohexyl-2-[(3,3-dimethyl-1-oxo-1H-[1,3]oxazolo[3,4-a]indol-7-yl)carbamoyl]pyrrolidine-1-carboxylate

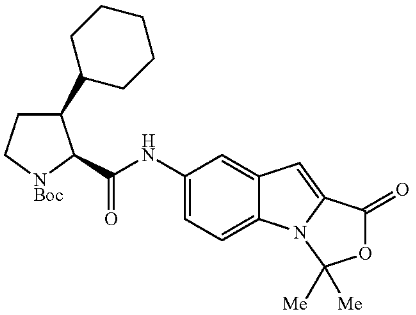 [SMILES: CC(C)(C)OC(=O)N1CC[C@@H](C2CCCCC2)[C@H]1C(=O)Nc1ccc2c(c1)cc1n2C(C)(C)OC1=O]

In the same manner as in Reference Example 1-4, the title compound (343.6 mg, 88%) was obtained from the compound of Reference Example 4-1 (360.0 mg, 0.790 mmol).

MS (ESI+) 496 (M+1, 100%)

Reference Example 25 tert-Butyl {(1S)-1-[trans-4-({(2S,3S)-3-cyclohexyl-2-[(1'-oxo-1'H-spiro[cyclobutane-1,3'-[1,3]oxazolo[3,4-a]indol]-7'-yl)carbamoyl]pyrrolidin-1-yl}carbamoyl)cyclohexyl]-2-fluoroethyl}carbamate

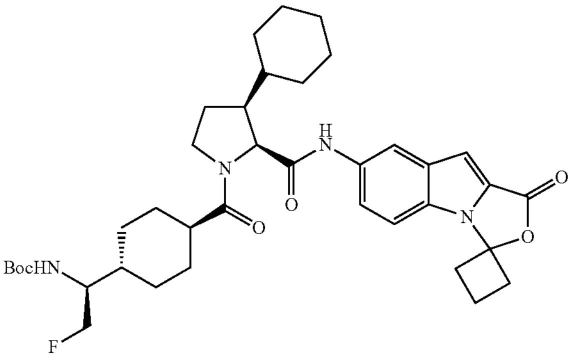 [SMILES: CC(C)(C)OC(=O)N[C@H](CF)[C@H]1CC[C@H](C(=O)N2CC[C@@H](C3CCCCC3)[C@H]2C(=O)Nc2ccc3c(c2)cc2n3C3(CCC3)OC2=O)CC1]

In the same manner as in Reference Example 7-1, the title compound (6.41 g, 80%) was obtained from the compound of Reference Example 2-4 (7.38 g, 11.77 mmol) and cyclobutanone (4.12 g, 58.78 mmol).

MS (ESI+) 679 (M+1, 100%)

Reference Example 26

5-[(2S,3S)-1-{trans-4-[1-(tert-Butoxycarbonyl)amino-2-fluoroethyl]cyclohexanecarbonyl}-3-cyclohexylpyrrolidine-2-carboxamide]-3-fluoro-1H-indole-2-carboxylic acid

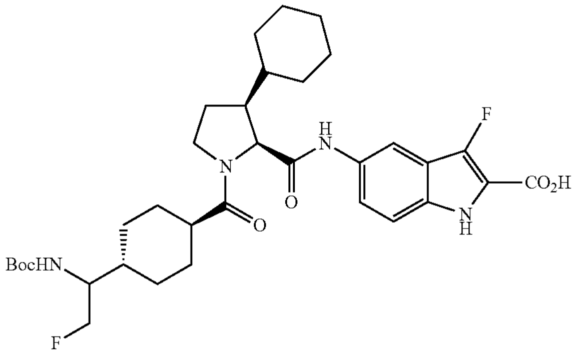 [SMILES: CC(C)(C)OC(=O)NC(CF)[C@H]1CC[C@H](C(=O)N2CC[C@@H](C3CCCCC3)[C@H]2C(=O)Nc2ccc3[nH]c(C(=O)O)c(F)c3c2)CC1]

In the same manner as in Reference Example 2-4, the title compound (7.0 mg, 68%) was obtained from the compound of Reference Example 26-8 (8.0 mg, 0.016 mmol).

MS (ESI+) 645 (M+1, 100%)

Reference Example 26-1

Ethyl 5-[(2S,3S)-1-tert-butoxycarbonyl-3-cyclohexylpyrrolidine-2-carboxamide]-3-fluoro-1H-indole-2-carboxylate

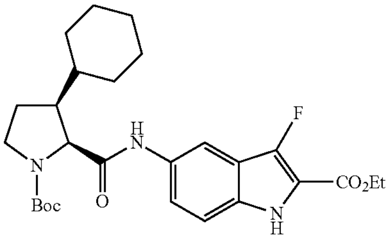 [SMILES: CCOC(=O)c1[nH]c2ccc(NC(=O)[C@@H]3[C@H](C4CCCCC4)CCN3C(=O)OC(C)(C)C)cc2c1F]

1-Fluoro-2,4,6-trimethylpyridinium trifluoromethanesulfonate (191 mg, 0.662 mmol) was added to a solution of the compound of Reference Example 2-1 (100 mg, 0.207 mmol) in dichloethane (2 mL), and the resulting mixture was stirred at 90° C. for 8 hours. The reaction solution was allowed to stand to cool, then water was added thereto and extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (8.0 mg, 8%).

MS (ESI+) 502 (M+1, 100%)

Reference Example 26-2

Ethyl 5-[(2S,3S)-3-cyclohexylpyrrolidine-2-carboxamide]-3-fluoro-1H-indole-2-carboxylate trifluoroacetate

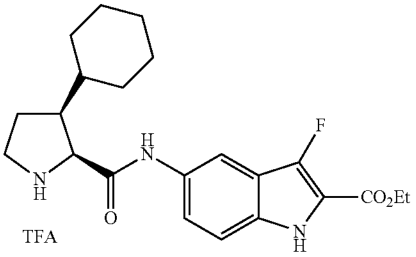 [SMILES: CCOC(=O)c1[nH]c2ccc(NC(=O)[C@H]3NCC[C@H]3C3CCCCC3)cc2c1F ; "TFA"]

According to the method described in Example 15, the title compound (8.0 mg, 100%) was obtained from the compound of Reference Example 26-1 (8.0 mg, 0.016 mmol).

MS (ESI+) 402 (M+1, 100%)

Reference Example 26-3

Methyl trans-4-(bromoacetyl))cyclohexanecarboxylate

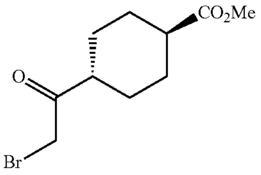 [SMILES: COC(=O)[C@H]1CC[C@H](C(=O)CBr)CC1]

Oxalyl chloride (10.20 mL, 119 mmol) and DMF (50 μL) were added to a solution of trans-1,4-cyclohexanedicarboxylic acid monomethyl ester (9.98 g, 53.60 mmol) in dichloromethane (60 mL) at room temperature. The reaction solution was heated to reflux for 1 hour and allowed to stand to cool to room temperature, and then concentrated under reduced pressure. Toluene was added to the residue and the residue was distilled off under reduced pressure, THF (30 mL) and acetonitrile (30 mL) were added thereto, and (trimethylsilyl)diazomethane (32.2 mL, 64.32 mmol) was added dropwise thereto in an ice bath. The resulting mixture was stirred for 1 hour in an ice bath, then further stirred for 1 hour at room temperature. The reaction solution was ice-cooled, 48% hydrobromic acid (11.75 g, 69.7 mmol) was added dropwise, and the resulting mixture was stirred for 15 minutes. A saturated aqueous solution of sodium hydrogencarbonate was added to the reaction mixture and, and the reaction mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (7.89 g, 56%).

$^1$H NMR ($CDCl_3$, 300 MHz) δ 3.96 (s, 2H), 3.67 (s, 3H), 2.77-2.69 (m, 1H), 2.32-2.25 (m, 1H), 2.11-1.98 (m, 4H), 1.58-1.40 (m, 4H).

Reference Example 26-4

Methyl trans-4-(fluoroacetyl)cyclohexanecarboxylate

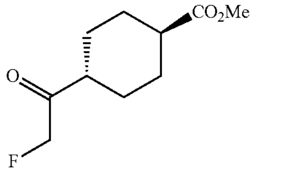 [SMILES: COC(=O)[C@H]1CC[C@H](C(=O)CF)CC1]

Potassium fluoride (8.71 g, 150 mmol) and 18-crown-6 (3.96 g, 14.98 mmol) were added to a solution of the compound of Reference Example 26-3 (7.89 g, 30.0 mmol) in acetonitrile (50 mL). The resulting mixture was heated to reflux for 5 hours, and then allowed to stand to cool, a saturated aqueous solution of ammonium chloride was added to the reaction mixture, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (5.29 g, 87%).

$^1$H NMR ($CDCl_3$, 300 MHz) δ 4.96 (s, 1H), 4.80 (s, 1H), 3.67 (s, 3H), 2.69-2.61 (m, 1H), 2.33-2.24 (m, 1H), 2.11-2.07 (m, 2H), 1.99-1.95 (m, 2H), 1.58-1.34 (m, 4H).

Reference Example 26-5

Methyl trans-4-(2-fluoro-1-hydroxyethyl)cyclohexanecarboxylate

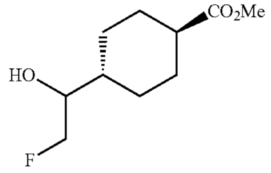 [SMILES: COC(=O)[C@H]1CC[C@H](C(O)CF)CC1]

Sodium borohydride (693 mg, 18.32 mmol) was added to a solution of the compound of Reference Example 26-4 (5.29 g, 26.16 mmol) in methanol (50 mL) in an ice bath, and the resulting mixture was stirred for 45 minutes. 0.5 mol/L hydrochloric acid was added to the reaction mixture in an ice bath, and the resulting mixture was extracted with ethyl acetate. The organic layer was washed with a saturated aqueous solution of sodium hydrogencarbonate and a saturated saline solution, then dried over anhydrous sodium sulfate, filtered, and concentrated under reduced pressure. The obtained residue was purified by silica gel column chromatography to obtain the title compound (4.76 g, 89%).

$^1$H NMR ($CDCl_3$, 400 MHz) δ 4.58-4.55 (m, 0.5H), 4.48-4.23 (m, 1H), 4.36-4.32 (m, 0.5H), 3.66 (s, 3H), 3.65-3.59 (m, 1H), 2.28-2.21 (m, 1H), 2.07-1.96 (m, 3H), 1.78-1.73 (m, 1H), 1.54-1.38 (m, 3H), 1.22-1.12 (m, 2H).

Reference Example 26-6

Methyl trans-4-[1-(tert-butoxycarbonyl)amino-2-fluoroethyl]cyclohexanecarboxylate

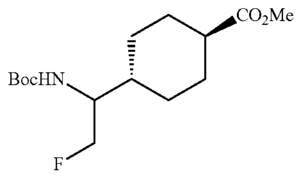 [SMILES: COC(=O)[C@H]1CC[C@H](C(CF)NC(=O)OC(C)(C)C)CC1]

Triethylamine (4.72 g, 46.65 mmol) and methanesulfonyl chloride (4.00 g, 34.90 mmol) were added to a solution of the compound of Reference Example 26-5 (4.76 g, 23.31 mmol) in THF (50 mL) in an ice bath. The resulting mixture was stirred at room temperature for 2 hours, then a saturated aqueous solution of ammonium chloride was added thereto, and the resulting mixture was extracted with ethyl acetate. The organic layer was washed with a saturated sodium hydrogencarbonate and a saturated saline solution, then dried over anhydrous sodium sulfate, filtered, and concentrated under reduced pressure.

The obtained residue was dissolved in DMF (40 mL), and sodium azide (2.27 g, 34.90 mmol) was added. The resulting mixture was stirred at 90° C. for 4 hours and then allowed to stand to cool, a saturated aqueous solution of ammonium chloride was added thereto, and the resulting mixture was extracted with ethyl acetate. The organic layer was washed twice with a saturated aqueous solution of ammonium chloride and with a saturated saline solution, then dried over anhydrous sodium sulfate, filtered, and concentrated under reduced pressure.

The obtained residue was dissolved in THF (40 mL) and water (4 mL), triphenylphosphine (9.17 g, 34.96 mmol) was added thereto, and the resulting mixture was heated to reflux. 3 hours later, the reaction solution was allowed to stand to cool, a saturated aqueous solution of sodium hydrogencarbonate (40 mL) and di-tert-butyl dicarbonate (7.63 g, 34.96 mmol) were added thereto, and the resulting mixture was stirred for 2 hours. Water was added to the reaction solution, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (6.04 g, 85%).

$^1$H NMR ($CDCl_3$, 400 MHz) δ 4.72-4.70 (m, 1H), 4.62-4.59 (m, 0.5H), 4.50-4.47 (m, 1H), 4.38-4.35 (m, 0.5H), 3.66 (s, 3H), 3.65-3.48 (m, 1H), 2.28-2.20 (m, 1H), 2.05-2.02 (m, 2H), 1.94-1.86 (m, 2H), 1.55-1.48 (m, 1H), 1.45-1.42 (m, 10H), 1.40-1.36 (m, 1H), 1.17-1.03 (m, 2H).

Reference Example 26-7 trans-4-[1-(tert-Butoxycarbonyl)amino-2-fluoroethyl]cyclohexanecarboxylic acid

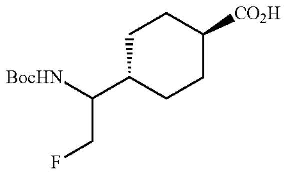 [SMILES: CC(C)(C)OC(=O)NC(CF)[C@H]1CC[C@H](C(=O)O)CC1]

The compound of Reference Example 26-6 (11.94 g, 39.36 mmol) was dissolved in methanol (115 mL) and THF (115 mL), and a 1 mol/L aqueous solution of sodium hydroxide (115 mL) was added thereto, and the resulting mixture was stirred at room temperature for 6 hours. A 5% aqueous solution of potassium hydrogensulfate was added to the reaction solution and the resulting mixture was extracted with chloroform. The organic layer was dried over anhydrous sodium sulfate and filtered, and then the solvent was distilled off under reduced pressure to obtain the title compound (11.21 g, 98%).

$^1H$ NMR (DMSO-$d_6$, 300 MHz) δ 6.87 (m, 1H), 4.48-4.37 (m, 1H), 4.32-4.21 (m, 1H), 3.45-3.34 (m, 1H), 2.11-2.03 (m, 1H), 1.89-1.86 (m, 2H), 1.71-1.67 (m, 2H), 1.37-1.30 (m, 10H), 1.23-1.17 (m, 2H), 1.13-0.95 (m, 2H).

Reference Example 26-8

Ethyl 5-[(2S,3S)-1-{trans-4-[1-(tert-butoxycarbonyl)amino-2-fluoroethyl]cyclohexanecarbonyl}-3-cyclohexylpyrrolidine-2-carboxamide]-3-fluoro-1H-indole-2-carboxylate

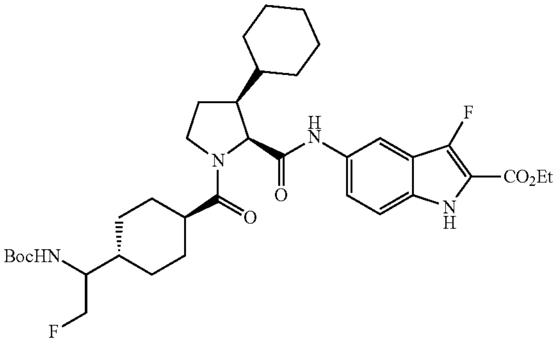 [SMILES: CCOC(=O)c1[nH]c2ccc(NC(=O)[C@@H]3[C@H](C4CCCCC4)CCN3C(=O)[C@H]3CC[C@H](C(CF)NC(=O)OC(C)(C)C)CC3)cc2c1F]

In the same manner as in Reference Example 1, the title compound (8.0 mg, 74%) was obtained from the compound of Reference Example 26-2 (8.0 mg, 0.016 mmol) and the compound of Reference Example 26-7 (6.0 mg, 0.021 mmol).

MS (ESI+) 673 (M+1, 100%)

Reference Example 27

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-chloro-1H-indole-2-carboxylic acid

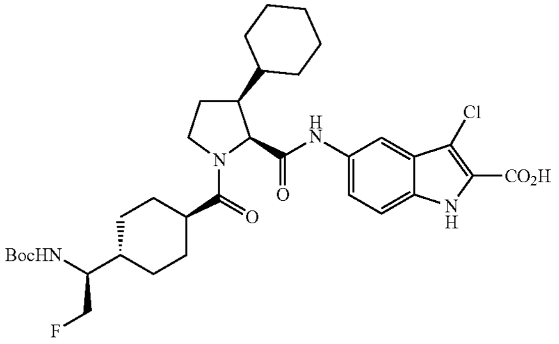 [SMILES: CC(C)(C)OC(=O)N[C@H](CF)[C@H]1CC[C@H](C(=O)N2CC[C@@H](C3CCCCC3)[C@H]2C(=O)Nc2ccc3[nH]c(C(=O)O)c(Cl)c3c2)CC1]

NCS (61.4 mg, 0.460 mmol) was added to a solution of the compound of Reference Example 2-3 (298 mg, 0.455 mmol) in DMF (9 mL), and the resulting mixture was heated and stirred at 60° C. for 7 days. Water was added thereto and the resulting solution was extracted with ethyl acetate and washed with water and a saturated saline solution. The resulting solution was dried over anhydrous sodium sulfate, filtered, and concentrated under reduced pressure. The obtained residue was purified by silica gel chromatography (ethyl acetate/hexane). The obtained solid was processed in the same manner as in Reference Example 2-4 to obtain the title compound (246 mg, 82%).

MS (ESI+) 661 (M+1, 100%)

Reference Example 28

5-[(2S,3S)-1-{trans-4-[1-(tert-Butoxycarbonyl)amino-2-fluoroethyl]cyclohexanecarbonyl}-3-(4-fluorophenyl)pyrrolidine-2-carboxamide]-1H-indole-2-carboxylic acid

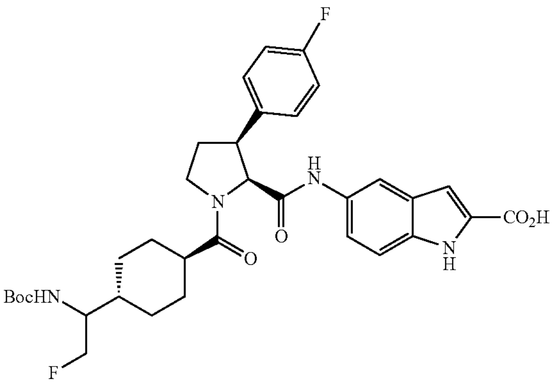 [SMILES: CC(C)(C)OC(=O)NC(CF)[C@H]1CC[C@H](C(=O)N2CC[C@@H](c3ccc(F)cc3)[C@H]2C(=O)Nc2ccc3[nH]c(C(=O)O)cc3c2)CC1]

In the same manner as in Reference Example 2-4, the title compound (41 mg, 86%) was obtained from the compound of Reference Example 28-4 (50 mg, 0.075 mmol).

MS (ESI+) 639 (M+1, 100%)

Reference Example 28-1

(2S,3S)-1-tert-Butoxycarbonyl-3-(4-fluorophenyl)pyrrolidine-2-carboxylic acid

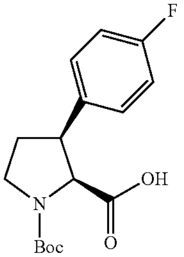 [SMILES: CC(C)(C)OC(=O)N1CC[C@@H](c2ccc(F)cc2)[C@H]1C(=O)O]

In the same manner as in Reference Examples 11-1 and 20-2 and Reference Example 20-4, the title compound (2.6 g, 91%) was obtained from trans-p-fluorocinnamaldehyde (5.0 g, 33.3 mmol).

MS (ESI+) 310 (M+1, 5%)

Reference Example 28-2

Ethyl 5-[(2S,3S)-1-tert-butoxycarbonyl-3-(4-fluorophenyl)pyrrolidine-2-carboxamide]-1H-indole-2-carboxylate

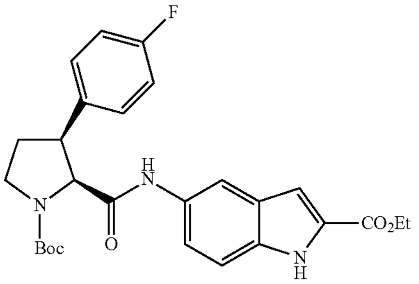 [SMILES: CCOC(=O)c1cc2cc(NC(=O)[C@@H]3[C@H](c4ccc(F)cc4)CCN3C(=O)OC(C)(C)C)ccc2[nH]1]

In the same manner as in Reference Example 1, the title compound (308 mg, 64%) was obtained from the compound of Reference Example 28-1 (300 mg, 0.97 mmol) and ethyl 5-amino-1H-indole-2-carboxylate (238 mg, 0.98 mmol).

MS (ESI+) 496 (M+1, 100%)

Reference Example 28-3

Ethyl 5-[(2S,3S)-3-(4-fluorophenyl)pyrrolidine-2-carboxamide]-1H-indole-2-carboxylate trifluoroacetate

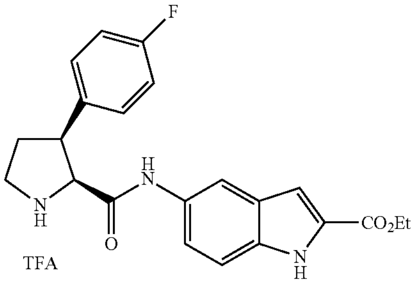 [SMILES: CCOC(=O)c1cc2cc(NC(=O)[C@H]3NCC[C@H]3c3ccc(F)cc3)ccc2[nH]1 ; "TFA"]

According to the method described in Example 15, the title compound (199 mg, 100%) was obtained from the compound of Reference Example 28-2 (200 mg, 0.404 mmol).

MS (ESI+) 396 (M+1, 100%)

Reference Example 28-4

Ethyl 5-[(2S,3S)-1-{trans-4-[1-(tert-butoxycarbonyl)amino-2-fluoroethyl]cyclohexanecarbonyl}-3-(4-fluorophenyl)pyrrolidine-2-carboxamide]-1H-indole-2-carboxylate

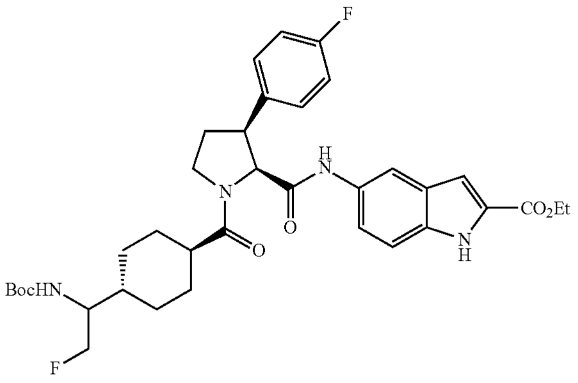 [SMILES: CCOC(=O)c1cc2cc(NC(=O)[C@@H]3[C@H](c4ccc(F)cc4)CCN3C(=O)[C@H]3CC[C@H](C(CF)NC(=O)OC(C)(C)C)CC3)ccc2[nH]1]

In the same manner as in Reference Example 1, the title compound (153 mg, 57%) was obtained from the compound of Reference Example 28-3 (199 mg, 0.404 mmol) and the compound of Reference Example 26-7 (140 mg, 0.484 mmol).

MS (ESI+) 667 (M+1, 100%)

Reference Example 29

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-methyl 1H-indole-2-carboxylic acid

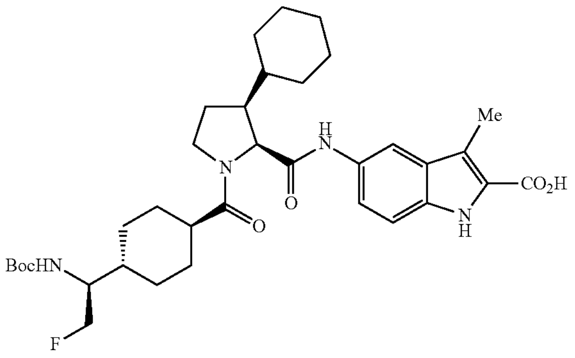 [SMILES: Cc1c(C(=O)O)[nH]c2ccc(NC(=O)[C@@H]3[C@H](C4CCCCC4)CCN3C(=O)[C@H]3CC[C@H]([C@@H](CF)NC(=O)OC(C)(C)C)CC3)cc12]

In the same manner as in Reference Example 2-4, the title compound (60.6 mg, 90%) was obtained from the compound of Reference Example 29-5 (50.0 mg, 0.075 mmol).

MS (ESI+) 641 (M+1, 100%)

Reference Example 29-1

Ethyl 3-methyl-5-nitro-1H-indole-2-carboxylate

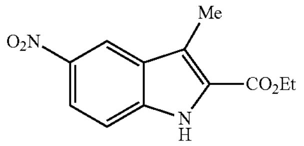 [SMILES: CCOC(=O)c1[nH]c2ccc([N+](=O)[O-])cc2c1C]

Potassium carbonate (755 mg, 5.46 mmol) and ethyl iodide (284 mg, 2.20 mmol) were added to a solution of commercial 3-methyl-5-nitro-1H-indole-2-carboxylic acid (400 mg, 1.82 mmol) in DMF (5 mL), and the resulting mixture was stirred at room temperature for 6 hours. Water was added to the reaction solution, and the resulting mixture was extracted twice with ethyl acetate. The organic layer was washed with a saturated saline solution, dried over anhydrous sodium sulfate and filtered, and then the solvent was distilled off under reduced pressure to obtain the title compound (440 mg, 100%).

MS (ESI−) 247 (M−1, 97%)

Reference Example 29-2

Ethyl 5-amino-3-methyl-1H-indole-2-carboxylate

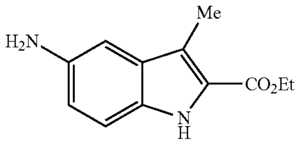 [SMILES: CCOC(=O)c1[nH]c2ccc(N)cc2c1C]

Palladium-carbon (300 mg) was added to a solution of the compound of Reference Example 29-1 (440 mg, 1.77 mmol) in methanol (15 mL), and the resulting mixture was stirred for 5.5 hours in a hydrogen atmosphere. The reaction solution was filtered through Celite and concentrated under reduced pressure to obtain the title compound (320 mg, 81%).

MS (ESI+) 219 (M+1, 100%)

Reference Example 29-3

Ethyl 5-[(2S,3S)-1-tert-butoxycarbonyl-3-cyclohexylpyrrolidine-2-carboxamide]-3-methyl-1H-indole-2-carboxylate

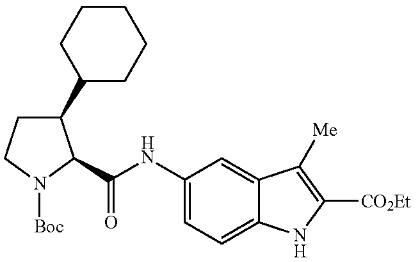 [SMILES: CCOC(=O)c1[nH]c2ccc(NC(=O)[C@@H]3[C@H](C4CCCCC4)CCN3C(=O)OC(C)(C)C)cc2c1C]

In the same manner as in Reference Example 1-7, the title compound (305 mg, 80%) was obtained from the compound of Reference Example 1-6 (227 mg, 0.764 mmol) and the compound of Reference Example 29-2 (200 mg, 0.916 mmol).

MS (ESI+) 498 (M+1, 100%)

Reference Example 29-4

Ethyl 5-[(2S,3S)-3-cyclohexylpyrrolidine-2-carboxamide]-3-methyl-1H-indole-2-carboxylate trifluoroacetate

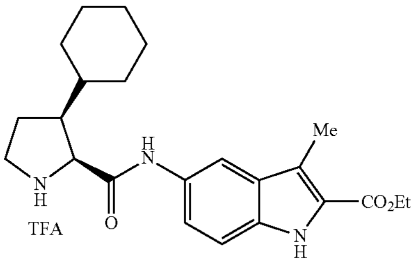 [SMILES: CCOC(=O)c1[nH]c2ccc(NC(=O)[C@H]3NCC[C@H]3C3CCCCC3)cc2c1C]

According to the method described in Example 15, the title compound (119 mg, 100%) was obtained from the compound of Reference Example 29-3 (200 mg, 0.241 mmol).

MS (ESI+) 398 (M+1, 100%)

Reference Example 29-5

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-3-methyl 1H-indole-2-carboxylate

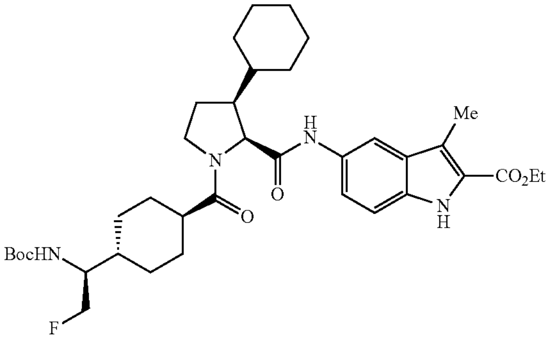 [SMILES: CCOC(=O)c1[nH]c2ccc(NC(=O)[C@@H]3[C@H](C4CCCCC4)CCN3C(=O)[C@H]3CC[C@H]([C@@H](CF)NC(=O)OC(C)(C)C)CC3)cc2c1C]

In the same manner as in Reference Example 1, the title compound (98.0 mg, 61%) was obtained from the compound of Reference Example 29-4 (119.0 mg, 0.241 mmol) and the compound of Reference Example 1-3 (84.0 mg, 0.289 mmol).

MS (ESI+) 669 (M+1, 100%)

Reference Example 30

5-{(2S,3S)-1-[trans-4-(tert-Butoxycarbonylaminomethyl)cyclohexanecarbonyl]-3-phenylpyrrolidine-2-carboxamide}-1H-indole-2-carboxylic acid

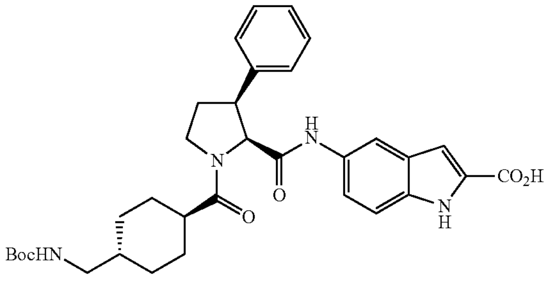 [SMILES: CC(C)(C)OC(=O)NC[C@H]1CC[C@H](C(=O)N2CC[C@@H](c3ccccc3)[C@H]2C(=O)Nc2ccc3[nH]c(C(=O)O)cc3c2)CC1]

By using (2S,3S)-1-tert-butoxycarbonyl-3-phenylpyrrolidine-2-carboxylic acid, commercial ethyl 5-amino-1H-indole-2-carboxylate, and 4-(tert-butoxycarbonylaminomethyl)-cyclohexanecarboxylic acid as starting materials, the title compound was obtained according to the methods described in Reference Example 28-2, Reference Example 1-8, Reference Example 1, and Reference Example 2-4 in this order.

MS (ESI+) 589 (M+1, 54%)

Reference Example 31

5-({(3S)-1-[(trans-4-{(1R)-1-[(tert-Butoxycarbonyl)amino]-2-fluoroethyl cyclohexyl)carbonyl]-3-cyclohexyl-L-prolyl}amino)-1H-benzimidazole-2-carboxylic acid

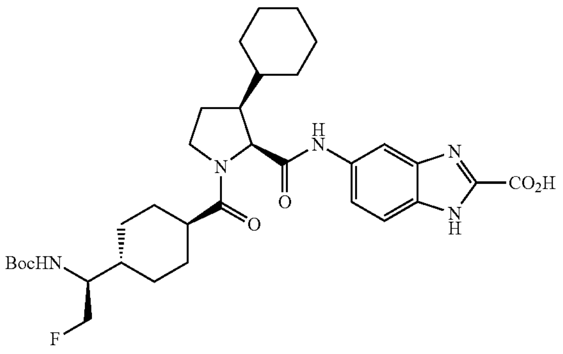

In the same manner as in Reference Example 2-4, the title compound (242.1 mg, 86%) was obtained from the compound of Reference Example 31-4 (293.2 mg, 0.447 mmol).

MS (ESI+) 628 (M+1, 100%)

Reference Example 31-1

Ethyl 5-amino-1H-benzimidazole-2-carboxylate

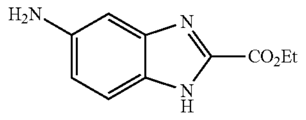 [SMILES: CCOC(=O)c1nc2cc(N)ccc2[nH]1]

Palladium-carbon (720 mg) was added to a solution of commercial ethyl 5-nitro-1H-benzimidazole-2-carboxylate (717.7 mg, 3.05 mmol) in methanol (10 mL), and the resulting mixture was stirred in a hydrogen atmosphere for 2 hours. The reaction solution was filtered through Celite and concentrated under reduced pressure to obtain the title compound (589.8 mg, 94%).

MS (ESI+) 206 (M+1, 100%)

Reference Example 31-2

Ethyl 5-{[(3S)-1-(tert-butoxycarbonyl)-3-cyclohexyl-L-prolyl]amino}-1H-benzimidazole-2-carboxylate

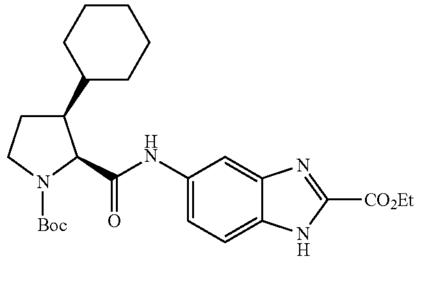 [SMILES: CCOC(=O)c1nc2cc(NC(=O)[C@@H]3[C@H](C4CCCCC4)CCN3C(=O)OC(C)(C)C)ccc2[nH]1]

In the same manner as in Reference Example 1-7, the title compound (565.3 mg, 45%) was obtained from the compound of Reference Example 31-1 (589.8 mg, 2.87 mmol) and the compound of Reference Example 1-6 (777 mg, 2.61 mmol).

MS (ESI+) 485 (M+1, 100%)

Reference Example 31-3

Ethyl 5-{[(3S)-3-cyclohexyl-L-prolyl]amino}-1H-benzimidazole-2-carboxylate trifluoroacetate

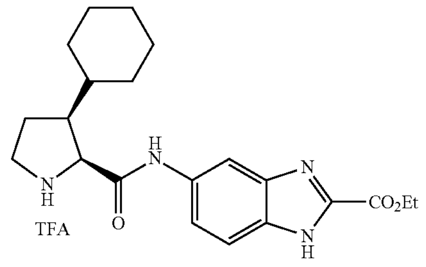 [SMILES: CCOC(=O)c1nc2cc(NC(=O)[C@H]3NCC[C@H]3C3CCCCC3)ccc2[nH]1]

The compound of Reference Example 31-2 (565.3 mg, 1.17 mmol) was dissolved in chloroform (4 mL), trifluoroacetic acid (4 mL) was added thereto, and the resulting mixture was stirred at room temperature for 1 hour. The solvent in the reaction solution was distilled off under reduced pressure to obtain the title compound (585 mg, 100%).

MS (ESI+) 385 (M+1, 100%)

Reference Example 31-4

Ethyl 5-({(3S)-1-[(trans-4-{(1R)-1-[(tert-butoxycarbonyl)amino]-2-fluoroethyl}cyclohexyl)carbonyl]-3-cyclohexyl-L-prolyl}amino)-1H-benzimidazole-2-carboxylate

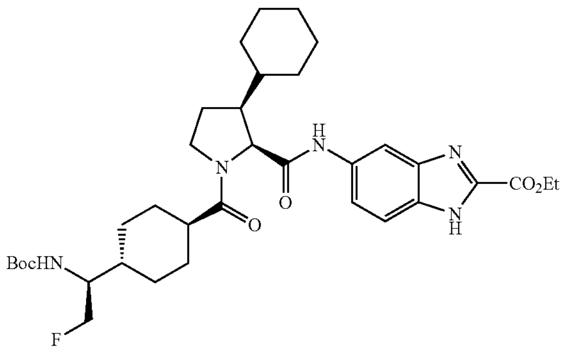 [SMILES: CCOC(=O)c1nc2cc(NC(=O)[C@@H]3[C@H](C4CCCCC4)CCN3C(=O)[C@H]3CC[C@H]([C@@H](CF)NC(=O)OC(C)(C)C)CC3)ccc2[nH]1]

In the same manner as in Reference Example 1, the title compound (293.2 mg, 38%) was obtained from the compound of Reference Example 31-3 (585 mg, 1.17 mmol) and the compound of Reference Example 1-3 (372 mg, 1.29 mmol).

MS (ESI+) 656 (M+1, 100%)

Reference Example 32

5-({(3S)-1-[(trans-4-{(1S)-1-[(tert-Butoxycarbonyl)amino]-2-fluoroethyl}cyclohexyl)carbonyl]-3-cyclohexyl-L-prolyl}amino)-3-ethyl-1H-indole-2-carboxylic acid

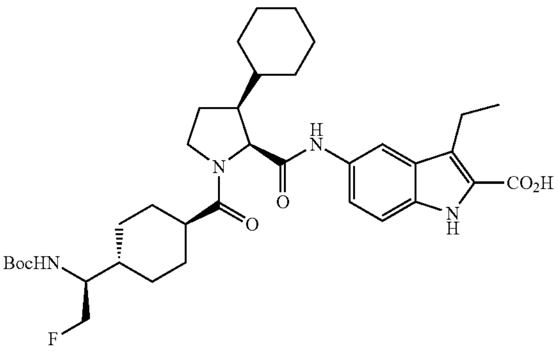 [SMILES: CCc1c(C(=O)O)[nH]c2ccc(NC(=O)[C@@H]3[C@H](C4CCCCC4)CCN3C(=O)[C@H]3CC[C@H]([C@@H](CF)NC(=O)OC(C)(C)C)CC3)cc12]

In the same manner as in Reference Example 2-4, the title compound (7.0 mg, 68%) was obtained from the compound of Reference Example 32-7 (11.0 mg, 0.016 mmol).

MS (ESI+) 655 (M+1, 100%)

Reference Example 32-1

Ethyl 5-[(tert-butoxycarbonyl)amino]-1H-indole-2-carboxylate

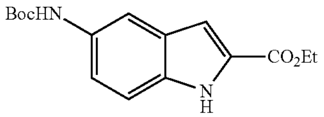 [SMILES: CCOC(=O)c1cc2cc(NC(=O)OC(C)(C)C)ccc2[nH]1]

Commercial ethyl 5-aminoindole-2-carboxylate (250 mg, 1.22 mmol) was dissolved in dichloromethane (15 mL), triethylamine (0.51 ml, 3.66 mmol) and di-tert-butyl dicarbonate (666 mg, 3.05 mmol) were added thereto, and the resulting mixture was stirred at room temperature for 14 hours. A saturated aqueous solution of ammonium chloride was added to the reaction solution and the resulting mixture was extracted with ethyl acetate. The organic layer was washed with a saturated saline solution, then dried over anhydrous sodium sulfate, filtered, and concentrated under reduced pressure to obtain the title compound (247 mg, 67%).

MS (ESI+) 609 (2M+1, 100%)

Reference Example 32-2

Ethyl 3-bromo-5-[(tert-butoxycarbonyl)amino]-1H-indole-2-carboxylate

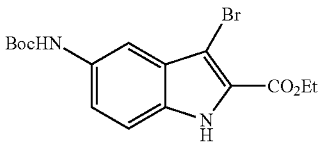 [SMILES: CCOC(=O)c1[nH]c2ccc(NC(=O)OC(C)(C)C)cc2c1Br]

The compound of Reference Example 32-1 (247 mg, 0.812 mmol) was dissolved in dichloromethane (10 mL), N-bromo succinimide (145 mg, 0.815 mmol) was added thereto, and the resulting mixture was stirred at room temperature for 14 hours. The reaction solution was concentrated under reduced pressure, water was added to the obtained residue, and the resulting mixture was extracted with ethyl acetate. The organic layer was washed with a saturated saline solution, then dried over anhydrous sodium sulfate, filtered, and concentrated under reduced pressure to obtain the title compound (318 mg, 100%).

MS (ESI+) 327 (M+1)-$^{t}$Bu, 100%)

Reference Example 32-3

Ethyl 5-[(tert-butoxycarbonyl)amino]-3-ethyl-1H-indole-2-carboxylate

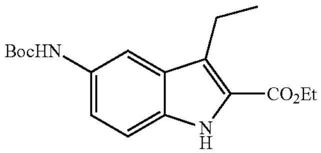 [SMILES: CCOC(=O)c1[nH]c2ccc(NC(=O)OC(C)(C)C)cc2c1CC]

A commercial diethylzinc hexane solution (3.3 ml, 3.28 mmol) was added dropwise to a commercial zinc chloride THF solution (13.2 ml, 6.56 mmol), and the resulting mixture was stirred at 70° C. for 1.5 hours. The obtained solution was added to a solution of the compound of Reference Example 32-2 (318 mg, 0.82 mmol), bis(tri-tert-butylphosphine) palladium(0) (84.0 mg, 0.164 mmol) in THF (26 ml), and the resulting mixture was stirred at room temperature for 1.5 hours. Water was added to the reaction solution, and the resulting mixture was extracted with ethyl acetate. The organic layer was washed with a saturated saline solution, then dried over anhydrous sodium sulfate, filtered, and concentrated under reduced pressure. The obtained residue was purified by silica gel column chromatography to obtain the title compound (238.0 mg, 87%).

MS (ESI+) 277 (M+1)-$^{t}$Bu, 100%)

Reference Example 32-4

Ethyl 5-amino-3-ethyl-1H-indole-2-carboxylate hydrochloride

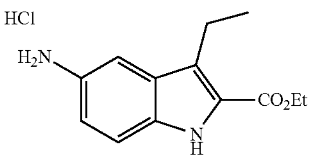 [SMILES: Cl ; CCOC(=O)c1[nH]c2ccc(N)cc2c1CC]

In the same manner as in Reference Example 1-5, the title compound (62.3 mg, 100%) was obtained from the compound of Reference Example 32-3 (77.0 mg, 0.232 mmol).

MS (ESI+) 233 (M+1, 100%)

Reference Example 32-5

Ethyl 5-{[(3S)-(tert-butoxycarbonyl)-3-cyclohexyl-L-prolyl]amino}-3-ethyl-1H-indole-2-carboxylate

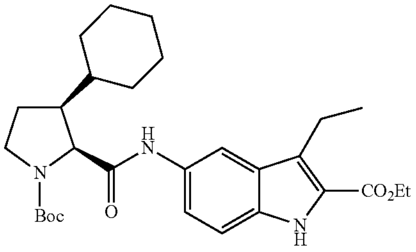 [SMILES: CCOC(=O)c1[nH]c2ccc(NC(=O)[C@@H]3[C@H](C4CCCCC4)CCN3C(=O)OC(C)(C)C)cc2c1CC]

In the same manner as in Reference Example 1-7, the title compound (20.0 mg, 17%) was obtained from the compound of Reference Example 1-6 (62.0 mg, 0.208 mmol) and the compound of Reference Example 32-4 (62.3 mg, 0.232 mmol).

MS (ESI+) 512 (M+1, 100%)

Reference Example 32-6

Ethyl 5-{[(3S)-3-cyclohexyl-L-prolyl]amino}-3-ethyl-1H-indole-2-carboxylate trifluoroacetate

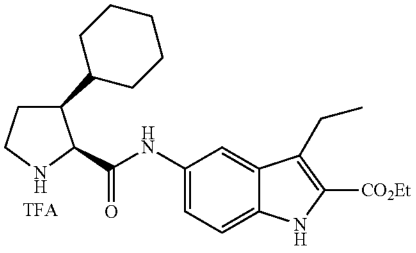 [SMILES: CCOC(=O)c1[nH]c2ccc(NC(=O)[C@H]3NCC[C@H]3C3CCCCC3)cc2c1CC ; "TFA"]

In the same manner as in Reference Example 31-3, the title compound (20.0 mg, 100%) was obtained from the compound of Reference Example 32-5 (20.0 mg, 0.039 mmol).

MS (ESI+) 412 (M+1, 100%)

Reference Example 32-7

Ethyl 5-({(3S)-1-[(trans-4-{(1S)-1-[(tert-butoxycarbonyl)amino]-2-fluoroethyl}cyclohexyl)carbonyl]-3-cyclohexyl-L-prolyl}amino)-3-ethyl-1H-indole-2-carboxylate

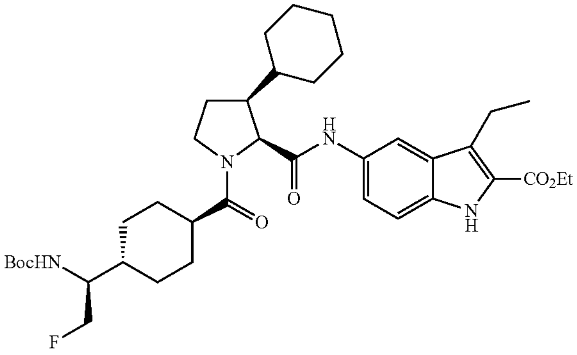 [SMILES: CCOC(=O)c1[nH]c2ccc(NC(=O)[C@@H]3[C@H](C4CCCCC4)CCN3C(=O)[C@H]3CC[C@H]([C@@H](CF)NC(=O)OC(C)(C)C)CC3)cc2c1CC]

In the same manner as in Reference Example 1, the title compound (11.0 mg, 41%) was obtained from the compound of Reference Example 32-6 (20.0 mg, 0.039 mmol) and the compound of Reference Example 1-3 (14.0 mg, 0.047 mmol).

MS (ESI+) 683 (M+1, 100%)

Reference Example 33

5-{[(3R)-1-[(trans-4-{(1S)-1-[(tert-Butoxycarbonyl)amino]-2-fluoroethyl}cyclohexyl)carbonyl]-3-(4-methoxyphenyl)-L-prolyl]amino}-1H-indole-2-carboxylic acid

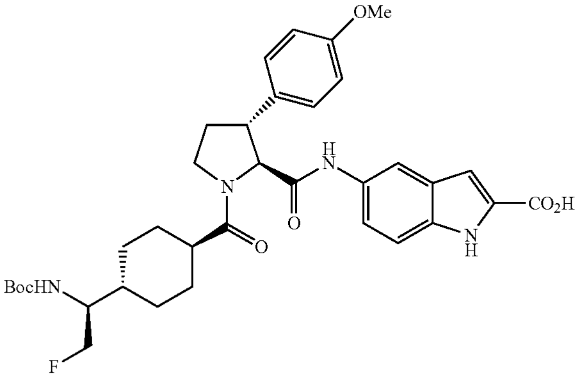 [SMILES: COc1ccc([C@H]2CCN(C(=O)[C@H]3CC[C@H]([C@@H](CF)NC(=O)OC(C)(C)C)CC3)[C@@H]2C(=O)Nc2ccc3[nH]c(C(=O)O)cc3c2)cc1]

In the same manner as in Reference Example 2-4, the title compound (290.0 mg, 86%) was obtained from the compound of Reference Example 33-4 (352.6 mg, 0.519 mmol).

MS (ESI+) 651 (M+1, 100%)

Reference Example 33-1

(2S,3R)-1-(tert-Butoxycarbonyl)-3-(4-methoxyphenyl)pyrrolidine-2-carboxylic acid

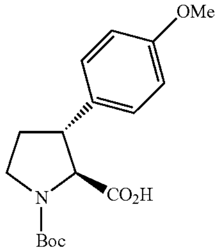 [SMILES: COc1ccc([C@H]2CCN(C(=O)OC(C)(C)C)[C@@H]2C(=O)O)cc1]

According to the method described in a document (Org. Lett. 2009, 11, 4056-4059) and by using (2R)-2-[diphenyl[(trimethylsilyl])oxy]methyl]pyrrolidine as a catalyst, (4R,5R)-4-(2-methoxyphenyl)-5-nitrotetrahydro-2H-pyran-2-ol (4.45 g, 83%, >99% ee) was obtained from 4-methoxycinnamaldehyde (3.43 g, 21.1 mmol).

Palladium hydroxide (2.50 g) was added to a solution of the obtained (4R,5R)-4-(2-methoxyphenyl)-5-nitrotetrahydro-2H-pyran-2-ol (4.45 g, 17.6 mmol) in methanol (150 ml), and the resulting mixture was stirred at a pressure of 0.4 MPa in a hydrogen atmosphere overnight. The reaction solution was filtered through Celite and concentrated under reduced pressure. The residue was dissolved in acetonitrile (200 mL), di-tert-butyl dicarbonate (7.70 g, 35.2 mmol) was added thereto, and the resulting mixture was stirred overnight. The reaction solution was concentrated under reduced pressure, and then purified by silica gel column chromatography to obtain tert-butyl (4R,5R)-3-(4-methoxyphenyl)-2-(hydroxymethyl)pyrrolidine-1-carboxylate (3.65 g, 67%). N-methylmorpholine N-oxide (629 mg, 5.37 mmol) and molecular sieves 4 Å (600 mg) were added to a solution of the obtained (4R,5R)-3-(4-methoxyphenyl)-2-(hydroxymethyl)pyrrolidine-1-carboxylate (1.1 g, 3.58 mmol) in acetonitrile (20 mL), and the resulting mixture was stirred for 10 minutes. Then tetrapropylammonium perruthenate (377 mg, 1.07 mmol) was added, and the resulting mixture was stirred for 4.5 hours. The reaction solution was filtered through Celite and silica gel, and the obtained filtrate was concentrated under reduced pressure to obtain tert-butyl (2R,3R)-3-(4-methoxyphenyl)-2-formylpyrrolidine-1-carboxylate (830 mg, 2.72 g).

DBU (0.43 mL, 2.86 mmol) was added to a solution of the obtained tert-butyl (2R,3R)-3-(4-methoxyphenyl)-2-formylpyrrolidine-1-carboxylate (830 mg, 2.72 mmol) in dichloromethane (10 mL), and the resulting mixture was stirred at room temperature overnight. A pH 7 phosphate buffer was added to the reaction mixture, and the resulting mixture was extracted with ethyl acetate. The organic layer was washed with a saturated saline solution, then dried over anhydrous sodium sulfate, filtered, and concentrated under reduced pressure to obtain tert-butyl (2S,3R)-2-formyl-3-(4-methoxyphenyl)-pyrrolidine-1-carboxylate (845 mg, 100%).

tert-Butyl (2S,3R)-2-formyl-3-(4-methoxyphenyl)-pyrrolidine-1-carboxylate (845 mg, 2.72 mmol) was dissolved in a mixed solvent of tert-butanol and distilled water (3:1, 20 mL), sodium dihydrogenphosphate dihydrate (1.27 mg, 8.16 mmol), 2-methyl-2-butene (1.45 mL, 13.6 mmol), and sodium chlorite (703 mg, 5.44 mmol) were added thereto, and the resulting mixture was stirred for 1 hour. Ethyl acetate and a 1 mol/L aqueous solution of sodium hydroxide were added to the reaction solution, the pH was adjusted to 8 to 9, and a separation operation was carried out to collect the aqueous layer. Ethyl acetate and 1 mol/L hydrochloric acid was added to the aqueous layer, the pH was adjusted to 6, and the organic layer was extracted and concentrated under reduced pressure to obtain the title compound (760 mg, 87%).

MS (ESI+) 322 (M+1, 17%)

Reference Example 33-2

Ethyl 5-{[(3R)-1-(tert-butoxycarbonyl)-3-(4-methoxyphenyl)-L-prolyl]amino}-1H-indole-2-carboxylate

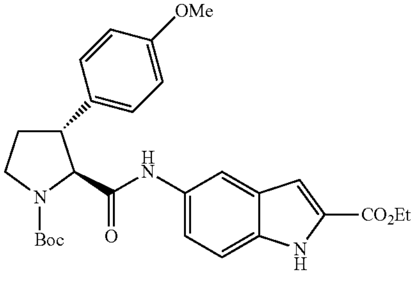 [SMILES: CCOC(=O)c1cc2cc(NC(=O)[C@@H]3[C@@H](c4ccc(OC)cc4)CCN3C(=O)OC(C)(C)C)ccc2[nH]1]

In the same manner as in Reference Example 1-7, the title compound (345.0 mg, 81%) was obtained from the compound of Reference Example 33-1 (270.4 mg, 0.841 mmol) and ethyl 5-amino-1H-indole-2-carboxylate (171.7 mg, 0.841 mmol).

MS (ESI+) 508 (M+1, 100%)

Reference Example 33-3

Ethyl 5-{[(3R)-3-(4-methoxyphenyl)-L-prolyl]amino}-1H-indole-2-carboxylate trifluoroacetate

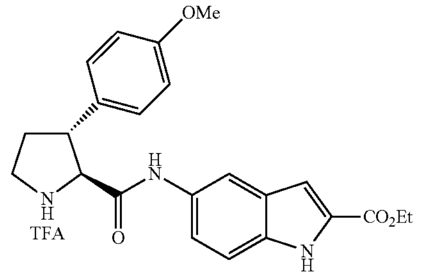 [SMILES: CCOC(=O)c1cc2cc(NC(=O)[C@H]3NCC[C@@H]3c3ccc(OC)cc3)ccc2[nH]1 ; "TFA"]

In the same manner as in Reference Example 31-3, the title compound (357 mg, 100%) was obtained from the compound of Reference Example 33-2 (345.0 mg, 0.68 mmol).

MS (ESI+) 408 (M+1, 100%)

Reference Example 33-4

Ethyl 5-{[(3R)-1-[(trans-4-{(1S)-1-[(tert-butoxycarbonyl)amino]-2-fluoroethyl}cyclohexyl)carbonyl]-3-(4-methoxyphenyl)-L-prolyl]amino}-1H-indole-2-carboxylate

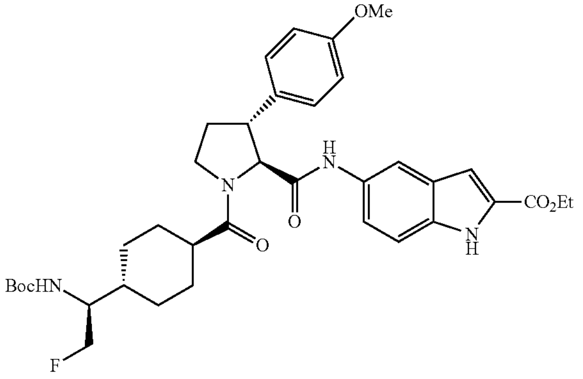 [SMILES: CCOC(=O)c1cc2cc(NC(=O)[C@@H]3[C@@H](c4ccc(OC)cc4)CCN3C(=O)[C@H]3CC[C@H]([C@@H](CF)NC(=O)OC(C)(C)C)CC3)ccc2[nH]1]

In the same manner as in Reference Example 1, the title compound (352.6 mg, 76%) was obtained from the compound of Reference Example 33-3 (357 mg, 0.68 mmol) and the compound of Reference Example 1-3 (216 mg, 0.748 mmol).

MS (ESI+) 679 (M+1, 100%)

Reference Example 34

5-{[(3R)-1-[(trans-4-{(1S)-1-[(tert-Butoxycarbonyl)amino]-2-fluoroethyl}cyclohexyl)carbonyl]-3-(4-fluorophenyl)-L-prolyl]amino}-1H-indole-2-carboxylic acid 20 [0486]

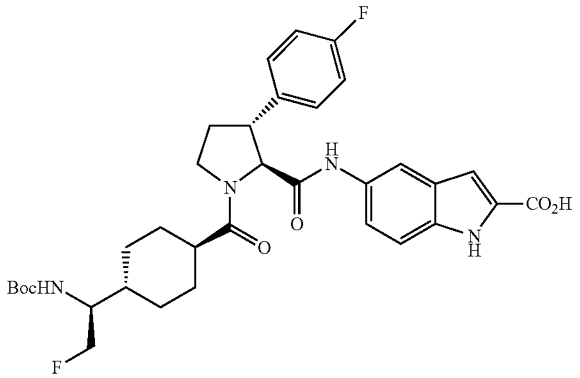 [SMILES: CC(C)(C)OC(=O)N[C@H](CF)[C@H]1CC[C@H](C(=O)N2CC[C@H](c3ccc(F)cc3)[C@H]2C(=O)Nc2ccc3[nH]c(C(=O)O)cc3c2)CC1]

In the same manner as in Reference Example 2-4, the title compound (35.0 mg, 100%) was obtained from the compound of Reference Example 34-4 (65.2 mg, 0.0978 mmol).

MS (ESI+) 639 (M+1, 100%)

Reference Example 34-1

(3R)-1-(tert-Butoxycarbonyl)-3-(4-fluorophenyl)-L-proline

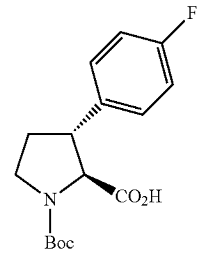 [SMILES: CC(C)(C)OC(=O)N1CC[C@H](c2ccc(F)cc2)[C@H]1C(=O)O]

In the same manner as in Reference Example 20-1, Reference Example 20-2, Reference Example 20-3, and Reference Example 20-4, the title compound (49.6 mg, 0.39%) was obtained from 4-fluorocinnamaldehyde (6.26 g, 40.86 mmol).

MS (ESI+) 310 (M+1, 1.2%)

Reference Example 34-2

Ethyl 5-{[(3R)-1-(tert-butoxycarbonyl)-3-(4-fluorophenyl)-L-prolyl]amino}-1H-indole-2-carboxylate

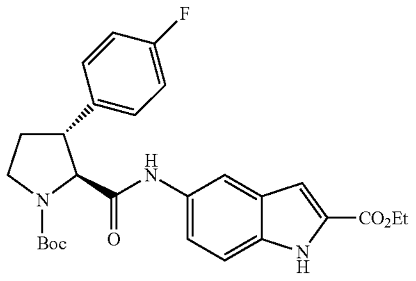 [SMILES: CCOC(=O)c1cc2cc(NC(=O)[C@@H]3[C@@H](c4ccc(F)cc4)CCN3C(=O)OC(C)(C)C)ccc2[nH]1]

In the same manner as in Reference Example 1-7, the title compound (72.3 mg, 91%) was obtained from the compound of Reference Example 34-1 (49.6 mg, 0.16 mmol) and ethyl 5-amino-1H-indole-2-carboxylate (32.7 mg, 0.16 mmol).

MS (ESI+) 496 (M+1, 100%)

Reference Example 34-3

Ethyl 5-{[(3R)-3-(4-fluorophenyl)-L-prolyl]amino}-1H-indole-2-carboxylate

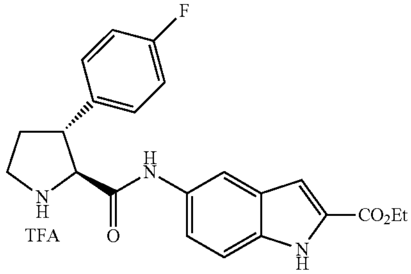 [SMILES: CCOC(=O)c1cc2cc(NC(=O)[C@H]3NCC[C@@H]3c3ccc(F)cc3)ccc2[nH]1 ; "TFA"]

In the same manner as in Reference Example 31-3, the title compound (75.0 mg, 100%) was obtained from the compound of Reference Example 34-2 (72.3 mg, 0.146 mmol).

MS (ESI+) 396 (M+1, 100%)

Reference Example 34-4

Ethyl 5-{[(3R)-1-[(trans-4-{(1S)-1-[(tert-butoxycarbonyl)amino]-2-fluoroethyl}cyclohexyl)carbonyl]-3-(4-fluorophenyl)-L-prolyl]amino}-1H-indole-2-carboxylate

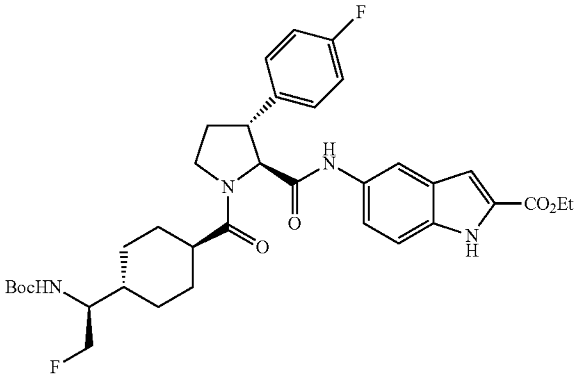 [SMILES: CCOC(=O)c1cc2cc(NC(=O)[C@@H]3[C@@H](c4ccc(F)cc4)CCN3C(=O)[C@H]3CC[C@H]([C@@H](CF)NC(=O)OC(C)(C)C)CC3)ccc2[nH]1]

In the same manner as in Reference Example 1, the title compound (65.2 mg, 67%) was obtained from the compound of Reference Example 34-3 (75.0 mg, 0.146 mmol) and the compound of Reference Example 1-3 (50.7 mg, 0.175 mmol).

MS (ESI+) 668 (M+1, 100%)

Reference Example 35

5-({(3R)-1-[(trans-4-{(1S)-1-[(tert-Butoxycarbonyl)amino]-2-fluoroethyl}cyclohexyl)carbonyl]-3-phenyl-L-prolyl}amino)-3-chloro-1H-indole-2-carboxylic acid

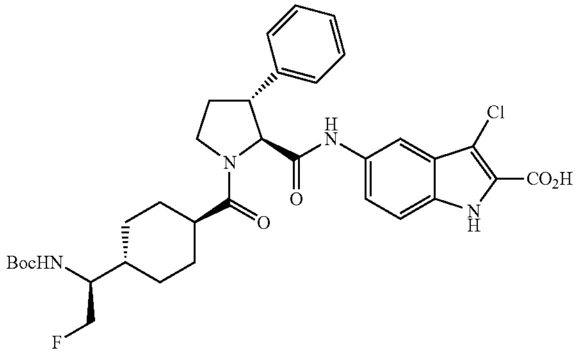 [SMILES: CC(C)(C)OC(=O)N[C@H](CF)[C@H]1CC[C@H](C(=O)N2CC[C@H](c3ccccc3)[C@H]2C(=O)Nc2ccc3[nH]c(C(=O)O)c(Cl)c3c2)CC1]

According to the methods described in the above Reference Examples 1-7 and 1-8, 1 and 27, the title compound was obtained from the compound of Reference Example 20-4 and ethyl 5-amino-1H-indole-2-carboxylate (644 mg, 20%).

MS (ESI+) 655 (M+1, 100%)

Reference Example 36 to 45

In the same manner as in Reference Example 1-8, the compounds of Reference Examples 36 to 39 and Reference Example 42 to 44 were obtained from the compounds of Reference Examples 26 to 29 and Reference Examples 32 to 34. In addition, In the same manner as in Reference Example 1-8, the compounds of Reference Examples 40, 41, and 45 were obtained from the compounds of Reference Examples 30, 31, and 35, respectively.

TABLE 1

| Reference Example | Structural formula | Device analysis data |
|---|---|---|
| 36 | 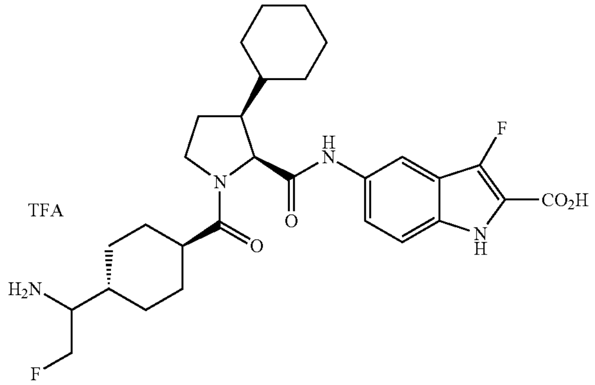 [SMILES: NC(CF)[C@H]1CC[C@H](C(=O)N2CC[C@@H](C3CCCCC3)[C@H]2C(=O)Nc2ccc3[nH]c(C(=O)O)c(F)c3c2)CC1] | RT 3.609 min (Condition A)<br>MS (ESI+) 545 (M + 1, 100%) |
| 37 | 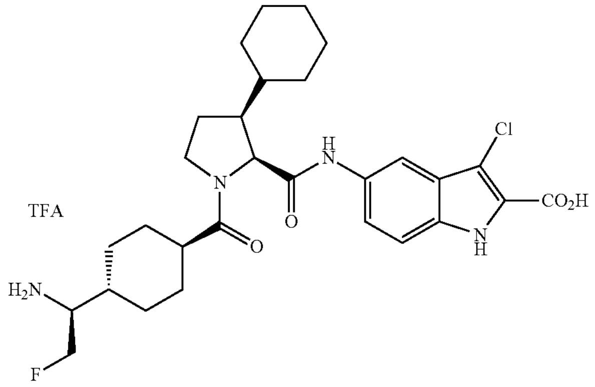 [SMILES: N[C@H](CF)[C@H]1CC[C@H](C(=O)N2CC[C@@H](C3CCCCC3)[C@H]2C(=O)Nc2ccc3[nH]c(C(=O)O)c(Cl)c3c2)CC1] | RT 4.080 min (Condition B)<br>MS (ESI+) 561 (M + 1, 100%) |

TABLE 1-continued
| Reference Example | Structural formula | Device analysis data |
|---|---|---|
| 38 | 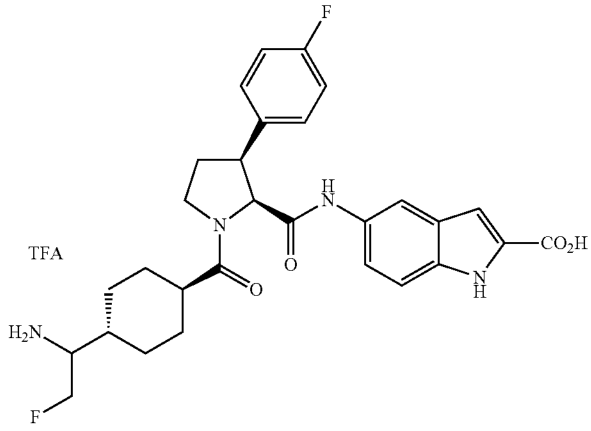 [SMILES: NC(CF)[C@H]1CC[C@H](C(=O)N2CC[C@@H](c3ccc(F)cc3)[C@H]2C(=O)Nc2ccc3[nH]c(C(=O)O)cc3c2)CC1] | RT 3.165 min (Condition A)<br>MS (ESI+) 539 (M + 1, 100%) |
| 39 | 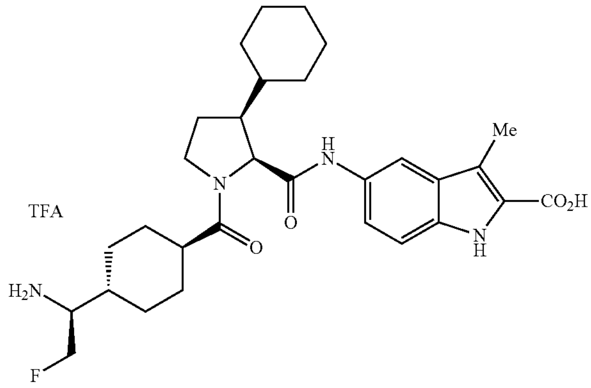 [SMILES: Cc1c(C(=O)O)[nH]c2ccc(NC(=O)[C@@H]3[C@H](C4CCCCC4)CCN3C(=O)[C@H]3CC[C@H]([C@H](N)CF)CC3)cc12] | RT 4.028 min (Condition B)<br>MS (ESI+) 541 (M + 1, 100%) |
| 40 | 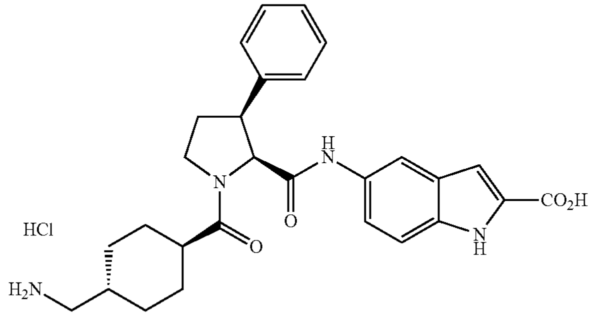 [SMILES: Cl ; NC[C@H]1CC[C@H](C(=O)N2CC[C@@H](c3ccccc3)[C@H]2C(=O)Nc2ccc3[nH]c(C(=O)O)cc3c2)CC1] | RT 3.274 min (Condition A)<br>MS (ESI+) 489 (M + 1, 100%) |
| 41 | 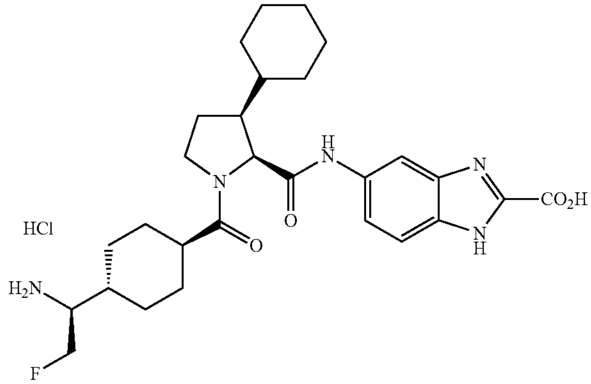 [SMILES: Cl ; N[C@H](CF)[C@H]1CC[C@H](C(=O)N2CC[C@@H](C3CCCCC3)[C@H]2C(=O)Nc2ccc3[nH]c(C(=O)O)nc3c2)CC1] | RT 4.847 min (Condition A)<br>MS (ESI+) 528 (M + 1, 100%) |

TABLE 1-continued
| Reference Example | Structural formula | Device analysis data |
|---|---|---|
| 42 | 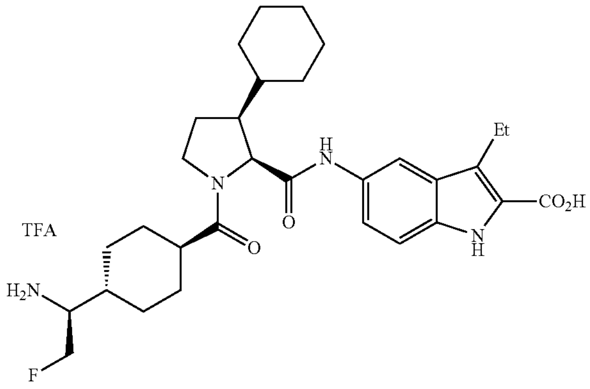 [SMILES: CCc1c(C(=O)O)[nH]c2ccc(NC(=O)[C@@H]3[C@H](C4CCCCC4)CCN3C(=O)[C@H]3CC[C@H]([C@H](N)CF)CC3)cc12 ; "TFA"] | RT 4.134 min (Condition B)<br>MS (ESI+) 555 (M + 1, 100%) |
| 43 | 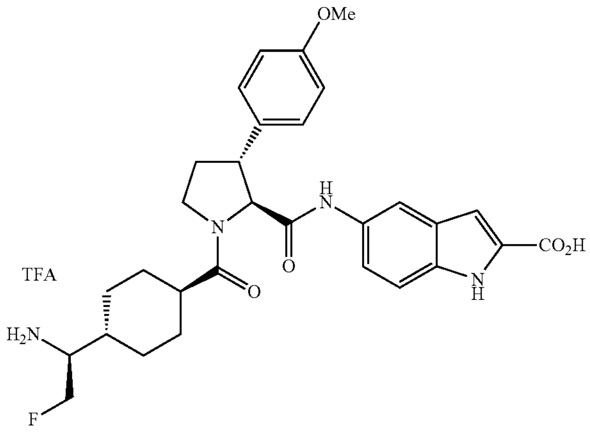 [SMILES: COc1ccc([C@H]2CCN(C(=O)[C@H]3CC[C@H]([C@H](N)CF)CC3)[C@@H]2C(=O)Nc2ccc3[nH]c(C(=O)O)cc3c2)cc1 ; "TFA"] | RT 3.571 min (Condition B)<br>MS (ESI+) 551 (M + 1, 100%) |
| 44 | 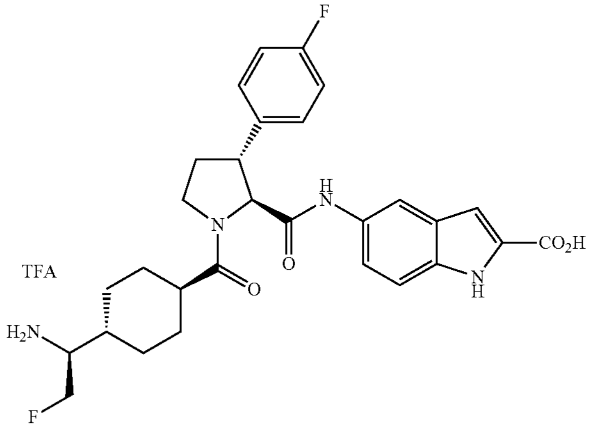 [SMILES: N[C@H](CF)[C@H]1CC[C@H](C(=O)N2CC[C@H](c3ccc(F)cc3)[C@H]2C(=O)Nc2ccc3[nH]c(C(=O)O)cc3c2)CC1 ; "TFA"] | RT 3.645 min (Condition B)<br>MS (ESI+) 539 (M + 1, 100%) |

TABLE 1-continued

| Reference Example | Structural formula | Device analysis data |
|---|---|---|
| 45 | 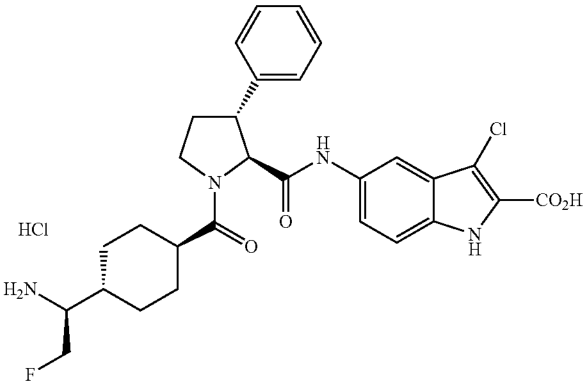 [SMILES: Cl ; N[C@H](CF)[C@H]1CC[C@H](C(=O)N2CC[C@H](c3ccccc3)[C@H]2C(=O)Nc2ccc3[nH]c(C(=O)O)c(Cl)c3c2)CC1] | RT 3.644 min (Condition A) MS (ESI+) 555 (M + 1, 100%) |

Example 1

(2S,3S)-1-({trans-4-[(1S)-1-Amino-2-fluoroethyl] cyclohexyl}carbonyl)-N-(3,3-dimethyl-1-oxo-1H-[1,3]oxazolo[3,4-a]indol-7-yl)-3-cyclohexylpyrrolidine-2-carboxamide hydrochloride

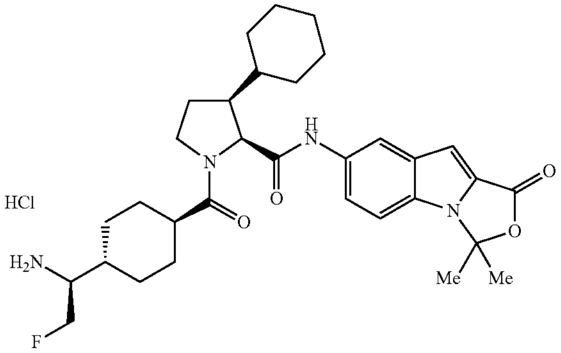 [SMILES: Cl ; CC1(C)OC(=O)c2cc3cc(NC(=O)[C@@H]4[C@H](C5CCCCC5)CCN4C(=O)[C@H]4CC[C@H]([C@H](N)CF)CC4)ccc3n21]

A 4 mol/L hydrochloric acid/1,4-dioxane solution (3 mL) was added to the compound of Reference Example 1 (58.4 mg, 0.0886 mmol), and the resulting mixture was stirred at room temperature for 1 hour. The solvent in the reaction solution was distilled off under reduced pressure, then toluene (2 mL) was added to the residue for removal of the solvent. Further, chloroform (3 mL) and hexane (3 mL) were added and the residue was distilled off under reduced pressure and this process was repeated twice to obtain the title compound (55.9 mg, 100%).

RT 4.068 min (Kinetex 1.7 pt C18 100 A, 0.1% trifluoroacetic acid in water/acetonitrile, acetonitrile 1-99% 7.0 min, 0.9 mL/min (condition A))

MS (ESI+) 567 (M+1, 100%)

$^1$H NMR (DMSO-d6, 400 MHz) δ 10.74 (s, 0.36H), 10.13 (s, 0.64H), 8.31 (s, 1H), 8.16-8.12 (m, 1H), 7.79-7.75 (m, 1H), 7.53-7.45 (m, 1H), 7.15-7.12 (m, 1H), 4.80-4.52 (m, 3H), 3.85-3.66 (m, 1H), 3.58-3.45 (m, 2H), 3.33-3.17 (m, 2H), 2.68-2.37 (m, 1H), 2.15-2.13 (m, 2H), 2.01-1.77 (m, 9H), 1.64-1.51 (m, 6H), 1.41-0.94 (m, 10H).

Examples 2 to 9

According to the method described in Example 1, the compounds of Examples 2 to 9 were obtained from the compounds of Reference Examples 2 to 9.

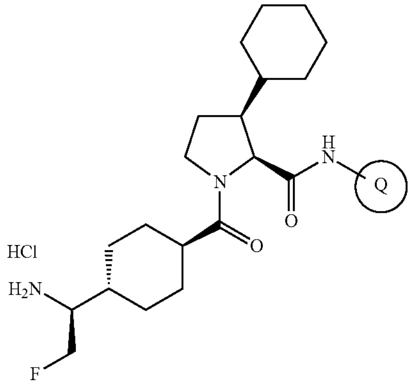

TABLE 2

| Example | Q | Device analysis data |
|---|---|---|
| 2 | 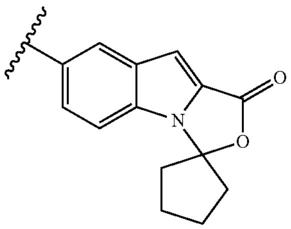 [SMILES: *c1ccc2c(c1)cc1n2C2(CCCC2)OC1=O] | RT 4.262 min (Condition A) MS (ESI+) 593 (M + 1, 100%) |
| 3 | 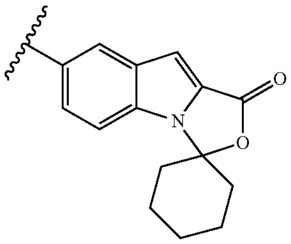 [SMILES: *c1ccc2c(c1)cc1n2C2(CCCCC2)OC1=O] | RT 4.415 min (Condition A) MS (ESI+) 607 (M + 1, 100%) |

TABLE 2-continued

| Example | Q | Device analysis data |
|---|---|---|
| 4 | 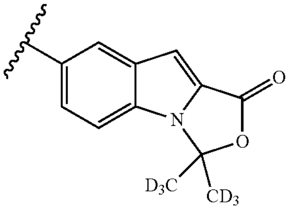 [SMILES: *c1ccc2c(c1)cc1n2C(C([2H])([2H])[2H])(C([2H])([2H])[2H])OC1=O] | RT 4.058 min (Condition A) MS (ESI+) 573 (M + 1, 100%) |
| 5 | 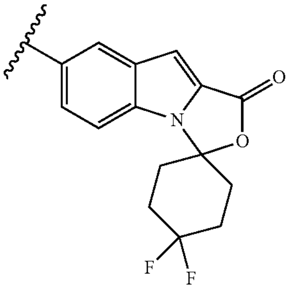 [SMILES: *c1ccc2c(c1)cc1n2C2(CCC(F)(F)CC2)OC1=O] | RT 4.354 min (Condition A) MS (ESI+) 643 (M + 1, 100%) |
| 6 | 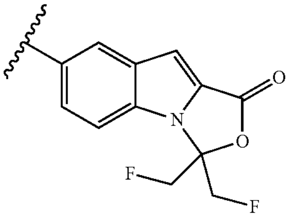 [SMILES: *c1ccc2c(c1)cc1n2C(CF)(CF)OC1=O] | RT 4.084 min (Condition A) MS (ESI+) 603 (M + 1, 100%) $^1$H NMR (DMSO-d6, 400 MHz) δ 10.44 (s, 0.28H), 10.19 (s, 0.72H), 8.20-8.11 (m, 4H), 7.84-7.79 (m, 1H), 7.51-7.47 (m, 1H), 7.35-7.32 (m, 1H), 5.31-5.08 (m, 4H), 4.69-4.49 (m, 3H), 3.77-3.73 (m, 2H), 3.57-3.21 (m, 3H), 2.42-2.37 (m, 1H), 2.18-2.12 (m, 1H), 2.01-1.87 (m, 4H), 1.64-1.50 (m, 6H), 1.43-0.91 (m, 10H). |
| 7 | 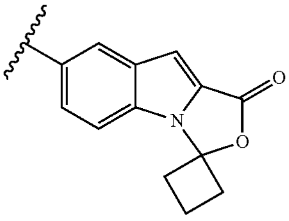 [SMILES: *c1ccc2c(c1)cc1n2C2(CCC2)OC1=O] | RT 4.107 min (Condition A) MS (ESI+) 579 (M + 1, 100%) $^1$H NMR (DMSO-d6, 400 MHz) δ 10.71 (s, 0.33H), 10.17 (s, 0.67H), 8.27 (s, 3H), 8.20-8.14 (m, 1H), 7.89-7.84 (m, 1H), 7.59-7.51 (m, 1H), 7.18-7.15 (m, 1H), 4.79-4.52 (m, 3H), 3.74-3.47 (m, 2H), 3.24-3.03 (m, 3H), 2.77-2.64 (m, 2H), 2.46-2.37 (m, 1H), 2.21-1.79 (m, 9H), 1.65-1.50 (m, 6H), 1.41-0.91 (m, 10H). |

TABLE 2-continued

| Example | Q | Device analysis data |
|---|---|---|
| 8 | 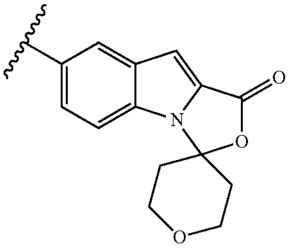 [SMILES: *c1ccc2c(c1)cc1n2C2(CCOCC2)OC1=O] | RT 3.968 min (Condition A) MS (ESI+) 609 (M + 1, 100%) |
| 9 | 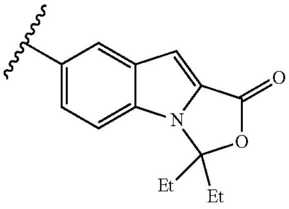 [SMILES: *c1ccc2c(c1)cc1n2C(CC)(CC)OC1=O] | RT 4.266 min (Condition A) MS (ESI+) 595 (M + 1, 100%) |

Examples 10 to 14

According to the method described in Example 1, the compounds of Examples 10 to 14 were obtained from the compounds of Reference Examples 10 to 14.

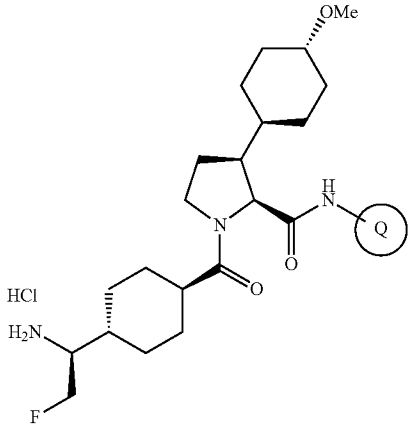

TABLE 3

| Example | Q | Device analysis data |
|---|---|---|
| 10 | 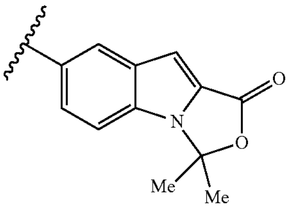 [SMILES: *c1ccc2c(c1)cc1n2C(C)(C)OC1=O] | RT 3.528 min (Condition A) MS (ESI+) 597 (M + 1, 100%) |

TABLE 3-continued

| Example | Q | Device analysis data |
|---|---|---|
| 11 | 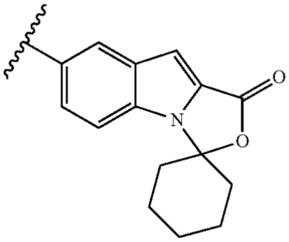 [SMILES: *c1ccc2c(c1)cc1n2C2(CCCCC2)OC1=O] | RT 3.923 min (Condition A) MS (ESI+) 637 (M + 1, 100%) |
| 12 | 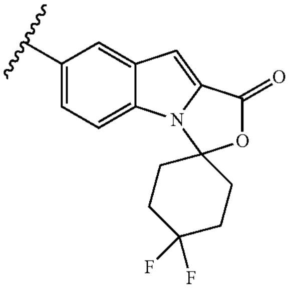 [SMILES: *c1ccc2c(c1)cc1n2C2(CCC(F)(F)CC2)OC1=O] | RT 3.871 min (Condition A) MS (ESI+) 673 (M + 1, 100%) |
| 13 | 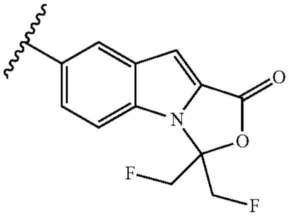 [SMILES: *c1ccc2c(c1)cc1n2C(CF)(CF)OC1=O] | RT 3.600 min (Condition A) MS (ESI+) 633 (M + 1, 100%) |
| 14 | 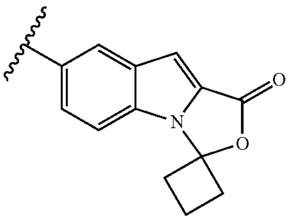 [SMILES: *c1ccc2c(c1)cc1n2C2(CCC2)OC1=O] | RT 3.670 min (Condition A) MS (ESI+) 609 (M + 1, 100%) |

Example 15

(2S,3R)-1-({trans-4-[(1S)-1-Amino-2-fluoroethyl] cyclohexyl}carbonyl)-N-(3,3-dimethyl-1-oxo-1H-[1,3]oxazolo[3,4-a]indol-7-yl)-3-(piperidin-1-yl)pyrrolidine-2-carboxamide 2-trifluoroacetate

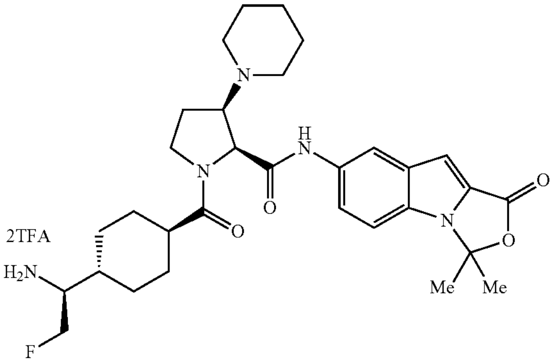 [SMILES: "2TFA" ; CC1(C)OC(=O)c2cc3cc(NC(=O)[C@@H]4[C@H](N5CCCCC5)CCN4C(=O)[C@H]4CC[C@H]([C@H](N)CF)CC4)ccc3n21]

Trifluoroacetic acid (0.5 mL) was added to a solution of the compound of Reference Example 15 (17.0 mg, 0.019 mmol) in chloroform (1 mL), and the resulting mixture was stirred for 45 minutes. The solvent in the reaction solution was distilled off under reduced pressure, then toluene (2 mL) was added to the residue to distill off the residue under reduced pressure. Further, chloroform (1 mL) and hexane (1 mL) were added thereto and the residue was distilled off under reduced pressure and this process was repeated twice to obtain the title compound (21.2 mg, 100%).

RT 2.844 min (condition A) MS (ESI+) 568 (M+1, 38%)

Example 16

(2S,3R)-1-({trans-4-[(1S)-1-Amino-2-fluoroethyl] cyclohexyl}carbonyl)-N-(3,3-diethyl-1-oxo-1H-[1,3] oxazolo[3,4-a]indol-7-yl)-3-(piperidin-1-yl)pyrrolidine-2-carboxamide 2-trifluoroacetate

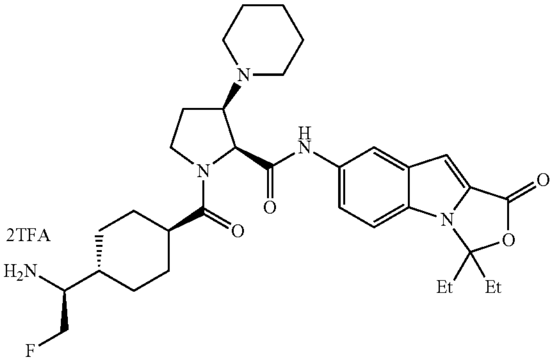 [SMILES: "2TFA" ; CCC1(CC)OC(=O)c2cc3cc(NC(=O)[C@@H]4[C@H](N5CCCCC5)CCN4C(=O)[C@H]4CC[C@H]([C@H](N)CF)CC4)ccc3n21]

In the same manner as in Example 15, the title compound (27.2 mg, 100%) was obtained from the compound of Reference Example 16 (23.4 mg, 0.029 mmol).

RT 3.136 min (condition A) MS (ESI+) 596 (M+1, 13%)

Examples 17 to 23

According to the method described in Example 1, the compounds of Examples 17 to 23 were obtained from the compounds of Reference Examples 17 to 23.

TABLE 4
| Example | Structural formula | Device analysis data |
|---|---|---|
| 17 | 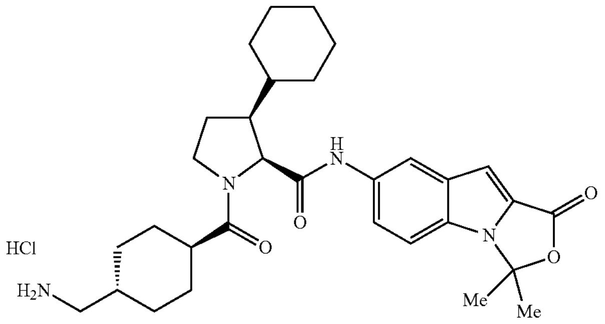 [SMILES: Cl ; CC1(C)OC(=O)c2cc3cc(NC(=O)[C@@H]4[C@H](C5CCCCC5)CCN4C(=O)[C@H]4CC[C@H](CN)CC4)ccc3n21] | RT 3.973 min (Condition A) MS (ESI+) 535 (M + 1, 100%) |
| 18 | 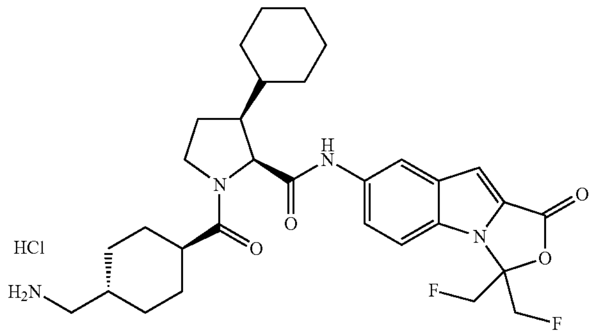 [SMILES: Cl ; NC[C@H]1CC[C@H](C(=O)N2CC[C@@H](C3CCCCC3)[C@H]2C(=O)Nc2ccc3c(c2)cc2n3C(CF)(CF)OC2=O)CC1] | RT 4.051 min (Condition A) MS (ESI+) 571 (M + 1, 100%) |
| 19 | 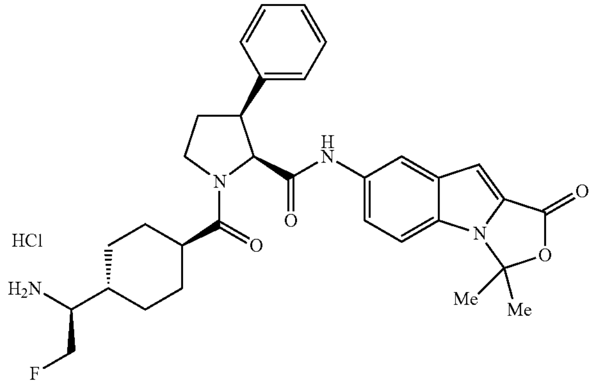 [SMILES: Cl ; CC1(C)OC(=O)c2cc3cc(NC(=O)[C@@H]4[C@H](c5ccccc5)CCN4C(=O)[C@H]4CC[C@H]([C@H](N)CF)CC4)ccc3n21] | RT 1.401 min (Kinetex 1.7 µ C18 100A, 0.1% trifluoroacetic acid in water/acetonitrile, acetonitrile 40-99% 10.0 min, 0.9 mL/min (condition B)) MS (ESI+) 561 (M + 1, 100%) |
| 20 | 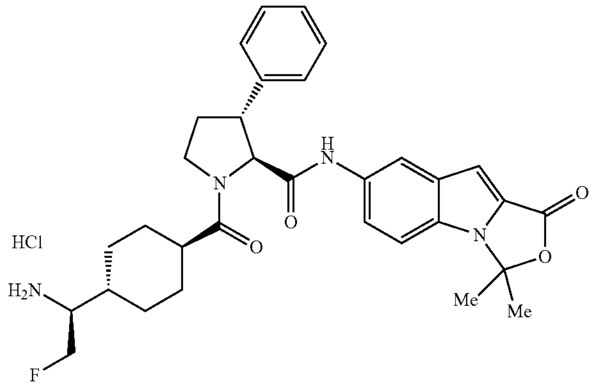 [SMILES: Cl ; CC1(C)OC(=O)c2cc3cc(NC(=O)[C@@H]4[C@@H](c5ccccc5)CCN4C(=O)[C@H]4CC[C@H]([C@H](N)CF)CC4)ccc3n21] | RT 1.474 min (Condition B) MS (ESI+) 561 (M + 1, 100%) |

TABLE 4-continued
| Example | Structural formula | Device analysis data |
|---|---|---|
| 21 | 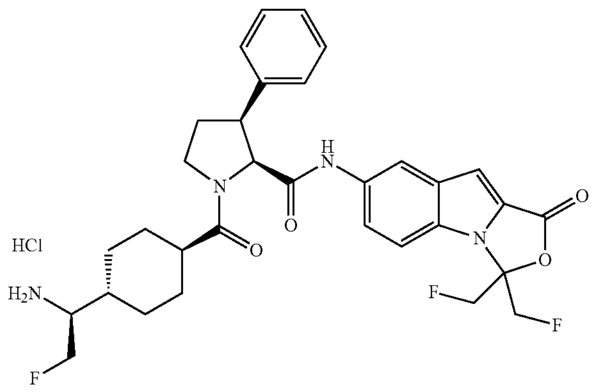 [SMILES: Cl ; N[C@H](CF)[C@H]1CC[C@H](C(=O)N2CC[C@@H](c3ccccc3)[C@H]2C(=O)Nc2ccc3c(c2)cc2n3C(CF)(CF)OC2=O)CC1] | RT 3.594 min (Condition A)<br>MS (ESI+) 597 (M + 1, 100%) |
| 22 | 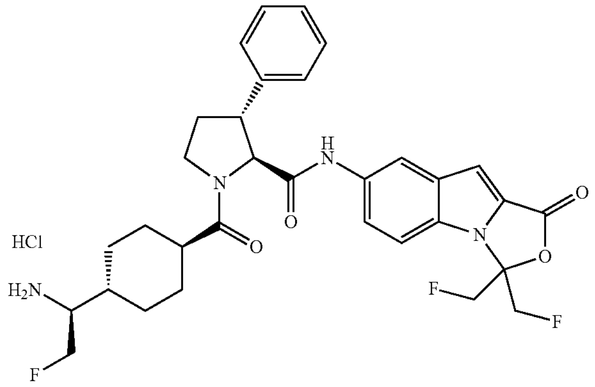 [SMILES: Cl ; N[C@H](CF)[C@H]1CC[C@H](C(=O)N2CC[C@H](c3ccccc3)[C@H]2C(=O)Nc2ccc3c(c2)cc2n3C(CF)(CF)OC2=O)CC1] | RT 3.672 min (Condition A)<br>MS (ESI+) 597 (M + 1, 100%) |
| 23 | 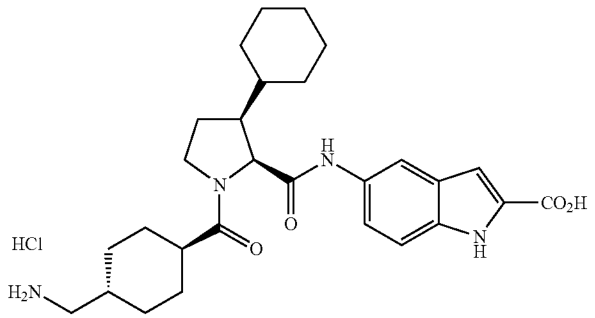 [SMILES: Cl ; NC[C@H]1CC[C@H](C(=O)N2CC[C@@H](C3CCCCC3)[C@H]2C(=O)Nc2ccc3[nH]c(C(=O)O)cc3c2)CC1] | RT 3.504 min (Condition A)<br>MS (ESI+) 495 (M + 1, 100%) |

Example 24

5-[(2S,3S)-1-({trans-4-[(1S)-1-Amino-2-fluoroethyl]cyclohexyl}carbonyl)-3-(trans-4-methoxycyclohexyl)pyrrolidine-2-carboxamide]-1H-indole-2-carboxylic acid hydrochloride

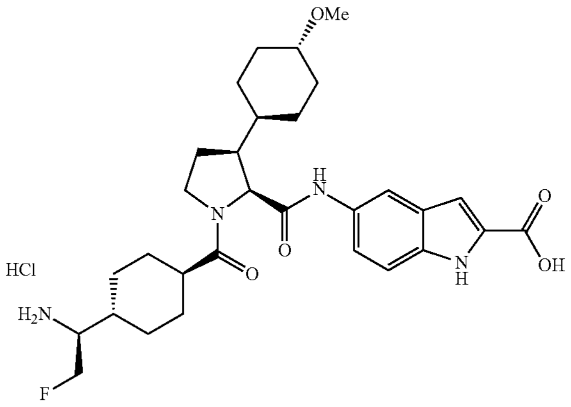

According to the method described in Example 1, title compound (85 mg, 95%) was obtained from the compound of Reference Example 10-4 (100 mg, 0.152 mmol).

RT 3.079 min (condition A) MS (ESI+) 557 (M+1, 100%)

Example 25

5-[(2S,3R)-1-({trans-4-[(1S)-1-Amino-2-fluoroethyl]cyclohexyl}carbonyl)-3-(piperidin-1-yl)pyrrolidine-2-carboxamide]-1H-indole-2-carboxylic acid 2-trifluoroacetate

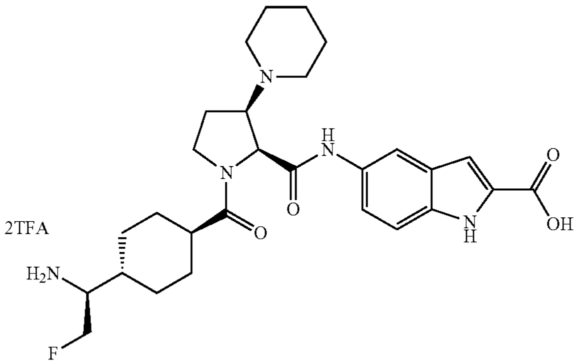 [SMILES: "2TFA" ; N[C@H](CF)[C@H]1CC[C@H](C(=O)N2CC[C@@H](N3CCCCC3)[C@H]2C(=O)Nc2ccc3[nH]c(C(=O)O)cc3c2)CC1]

According to the method described in Example 15, the title compound (48.1 mg, 50%) was obtained from the compound of Reference Example 15-7 (80.0 mg, 0.127 mmol). RT 2.287 min (Kinetex 1.7μ C18 100 A, 0.1% trifluoroacetic acid in water/acetonitrile, acetonitrile 1-99% 10.0 min, 0.9 mL/min (condition A)

MS (ESI+) 528 (M+1, 100%)

Example 26

(5-Methyl-2-oxo-1,3-dioxol-4-yl)methyl {(1S)-1-[trans-4-({(2S,3S)-3-cyclohexyl-2-[(1'-oxo-1'H-spiro[cyclobutane-1,3'-[1,3]oxazolo[3,4-a]indol]-7'-yl)carbamoyl]pyrrolidin-1-yl}carbonyl)cyclohexyl]-2-fluoroethyl}carbamate

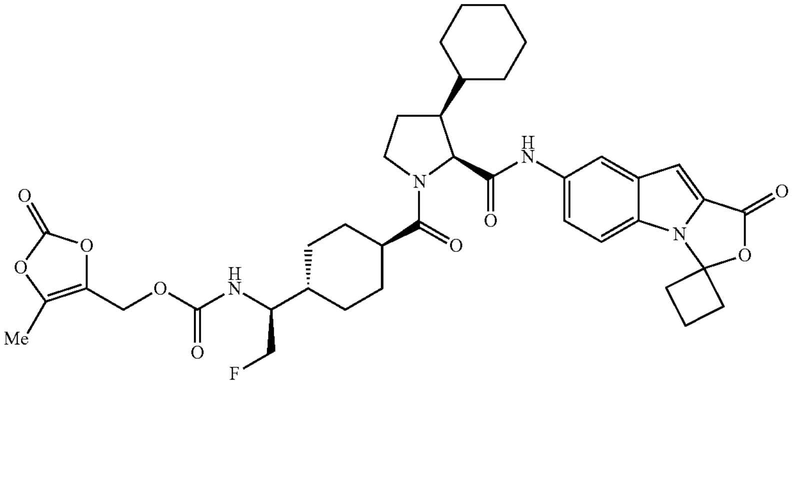 [SMILES: Cc1oc(=O)oc1COC(=O)N[C@H](CF)[C@H]1CC[C@H](C(=O)N2CC[C@@H](C3CCCCC3)[C@H]2C(=O)Nc2ccc3c(c2)cc2n3C3(CCC3)OC2=O)CC1]

Triethylamine (36.1 μL, 0.259 mmol), dimethylaminopyridine (5.3 mg, 0.0434 mmol), and (5-methyl-2-oxo-1,3-dioxol-4-yl)methyl 4-nitrophenyl carbonate (70.2 mg, 0.238 mmol) known from documents (e.g., WO 2010/150840 A1) were added to a solution of the compound of Example 7 (133 mg, 0.216 mmol) in tetrahydrofuran (4 mL), and the resulting mixture was stirred at 25° C. for 2 hours. A saturated aqueous solution of ammonium chloride was added to the reaction solution, the resulting mixture was extracted with ethyl acetate, the organic layer was washed with a saturated saline solution and then dried over anhydrous sodium sulfate, filtered, and concentrated under reduced pressure. The obtained residue was purified by silica gel column chromatography to obtain the title compound (113.5 mg, 72%).

RT 5.166 min (condition A) MS (ESI+) 733 (M+1, 100%)

Test Example 1

In Vitro Activated Factor XI (FXIa) Inhibition Test

Human FXIa (manufactured by Enzyme Research Laboratories) was reacted at a final concentration of 0.35 μg/mL with a substrate and a test compound at 37° C. for 10 minutes in a 30 mmol/L HEPES buffer solution (pH 7.4) containing 145 mmol/L NaCl, 5 mmol/L KCl, and 1 mg/mL PEG8000 (manufactured by Qiagen N.V.). S-2366 (pyro-Glu-Pro-Arg-pNA.HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (nM).

TABLE 5

| Compound | FXIa Inhibition activity $IC_{50}$ (nmol/l) |
|---|---|
| Reference Example 2-6 | 6 |
| Reference Example 19-1 | 15 |
| Reference Example 20-5 | 20 |
| Example 23 | 3 |
| Example 24 | 11 |
| Example 25 | 19 |
| Reference Example 36 | 45 |
| Reference Example 37 | 18 |
| Reference Example 38 | 30 |
| Reference Example 39 | 145 |
| Reference Example 40 | 9 |
| Reference Example 41 | 34 |
| Reference Example 42 | 91 |
| Reference Example 43 | 76 |
| Reference Example 44 | 33 |
| Reference Example 45 | 60 |

Test Example 2

Test to Study Specific Difference of Factor XIa

The compound of Reference Example 2-6 dissolved in DMSO was added at final concentrations of 0.03 to 200 μmol/L to the plasma of each animal species prepared using 3.2% sodium citrate. The solution was incubated at 37° C. for 6 minutes. Then, an STA reagent Cephascreen (for aPTT assay; manufactured by Roche Diagnostics K.K.) was added thereto in an amount equal to the total amount of the plasma and the DMSO solution, and the mixture was further incubated for 4 minutes. Then, STA calcium chloride (manufactured by Roche Diagnostics K.K.) was added thereto in an amount equal to the total amount of the plasma and the DMSO solution, and the time required for coagulation was measured. The concentration at which the coagulation time was prolonged two times ($EC_{2x}$) was calculated for each plasma. The results are shown in Table 6.

From the results of this test, the compound of Reference Example 2-6 was confirmed to most strongly prolong aPTT in human plasma.

TABLE 6

| Animal species | $EC_{2x}$ of Reference Example 2-6 (μM) |
|---|---|
| Human | 0.6 |
| Cynomolgus monkey | 2.6 |
| Rabbit | 34.2 |
| Rat | >200 |
| Mouse | >200 |
| Dog | 34.4 |

Test Example 3

Enzyme Selectivity Evaluation Test

1) Thrombin 0.005 μg/mL human thrombin (manufactured by Enzyme Research Laboratories) was reacted at a final concentration of 0.005 μg/mL with a substrate and a test compound at 37° C. for 60 minutes in a 30 mmol/L HEPES buffer solution (pH 7.4) containing 145 mmol/L NaCl, 5 mmol/L KCl, and 1 mg/mL PEG8000 (Qiagen N.V.). S-2366 (pyroGlu-Pro-Arg-pNA.HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

2) Tissue Factor (TF):Factor VIIa (FVIIa) Complex

Human FVIIa (manufactured by Enzyme Research Laboratories) and recombinant human coagulation factor III/TF (manufactured by R&D Systems, Inc.) were reacted at final concentrations of 0.8 μg/mL and 0.4 μg/mL, respectively, at 37° C. for 30 minutes in a 30 mmol/L HEPES buffer solution (pH 7.4) containing 145 mmol/L NaCl, 5 mmol/L KCl, and 1 mg/mL PEG8000 (Qiagen N.V.), and then reacted by the addition of a substrate and a test compound at 37° C. for 30 minutes. S-2288 (H-D-Ile-Pro-Arg-pNA.2HCl) (manufactured by Chromogenix) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

3) Factor IXa (FIXa)

Human FIXαβ (manufactured by Enzyme Research Laboratories) was reacted at a final concentration of 5 μg/mL with a substrate and a test compound at 37° C. for 90 minutes in a 30 mmol/L HEPES buffer solution (pH 7.4) containing 145 mmol/L NaCl, 5 mmol/L $CaCl_2$, and 1 mg/mL PEG8000 (Qiagen N.V.). SPECTROZYME® FIXa (D-Leu-Ph'Gly-Arg-pNA.2AcOH) (manufactured by American Diagnostica Inc.) was added as the substrate at a final concentration of 800 μmol/L. After progression of the reaction, the absorbance was measured at OD 405 nm. Change in OD in case of no addition of the test compound was defined as 100%, and the concentration at which a rise in OD value was reduced by 50% was calculated as TGm 4) Factor Xa (FXa)

Human FXa (manufactured by Enzyme Research Laboratories) was added at a final concentration of 0.2 μg/mL to a 30 mmol/L HEPES buffer solution (pH 7.4) containing 145 mmol/L NaCl, 5 mmol/L KCl, and 1 mg/mL PEG8000 (Qiagen N.V.), and reacted with a substrate and a test compound at 37° C. for 30 minutes. S-2222 (Bz-Ile-Glu(γ-OR)-Gly-Arg-pNAHC1 (SEQ ID NO: 1), R═H (50%) and R═$CH_3$ (50%)) (manufactured by Chromogenix) was added as the substrate at a final concentration of 150 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

5) Factor XIIa (FXIIa)

Human FXIIa (manufactured by Enzyme Research Laboratories) was added at a final concentration of 0.5 μg/mL to a 30 mmol/L HEPES buffer solution (pH 7.4) containing 145 mmol/L NaCl, 5 mmol/L KCl, and 1 mg/mL PEG8000 (Qiagen N.V.), and reacted with a substrate and a test compound at 37° C. for 30 minutes. S-2288 (H-D-Ile-Pro-Arg-pNA.2HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

6) Plasmin

Human plasmin (manufactured by Sekisui Diagnostics, LLC) was added at a final concentration of 0.5 μg/mL to a 30 mmol/L HEPES buffer solution (pH 7.4) containing 145 mmol/L NaCl, 5 mmol/L KCl, and 1 mg/mL PEG8000 (Qiagen N.V.), and reacted with a substrate and a test compound at 37° C. for 30 minutes. S-2288 (H-D-Ile-Pro-Arg-pNA.2HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

7) Urokinase

Human urokinase (manufactured by Calbiochem) was added at a final concentration of 25 U/mL to a 30 mmol/L HEPES buffer solution (pH 7.4) containing 145 mmol/L NaCl, 5 mmol/L KCl, and 1 mg/mL PEG8000 (Qiagen N.V.), and reacted with a substrate and a test compound at 37° C. for 60 minutes. S-2444 (pyroGlu-Gly-Arg-pNA.HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

8) Tissue Plasminogen Activator t-PA

Human t-PA (manufactured by Calbiochem) was reacted at a final concentration of 2 μg/mL with a substrate and a test compound at 37° C. for 30 minutes in a 30 mmol/L HEPES buffer solution (pH 7.4) containing 145 mmol/L NaCl, 5 mmol/L KCl, and 1 mg/mL PEG8000 (Qiagen N.V.). S-2288 (H-D-Ile-Pro-Arg-pNA.2HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

9) Plasma Kallikrein

Human kallikrein (manufactured by Enzyme Research Laboratories) was reacted at a final concentration of 0.1 μg/mL with a substrate and a test compound at 37° C. for 30 minutes in a 30 mmol/L HEPES buffer solution (pH 7.4) containing 145 mmol/L NaCl, 5 mmol/L KCl, and 1 mg/mL PEG8000 (Qiagen N.V.). S-2288 (H-D-Ile-Pro-Arg-pNA.2HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

10) Tryptase

Human tryptase (manufactured by Calbiochem) was reacted at a final concentration of 0.06 μg/mL with a substrate and a test compound at 37° C. for 20 minutes in a 30 mmol/L HEPES buffer solution (pH 7.4) containing 145 mmol/L NaCl, 5 mmol/L KCl, and 1 mg/mL PEG8000 (Qiagen N.V.). S-2288 (H-D-Ile-Pro-Arg-pNA.2HCl) was added as the substrate at a final concentration of 300 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

11) Trypsin

Human Trypsin (manufactured by Athens Research & Technology, Inc.) was reacted at a final concentration of 0.016 μg/mL with a substrate and a test compound at 37° C. for 30 minutes in a 30 mmol/L HEPES buffer solution (pH 7.4) containing 145 mmol/L NaCl, 5 mmol/L KCl, and 1 mg/mL PEG8000 (Qiagen N.V.). S-2222 (Bz-Ile-Glu(γ-OR)-Gly-Arg-pNA.HCl (SEQ ID NO: 1), R═H (50%) and R═$CH_3$ (50%)) was added as the substrate at a final concentration of 150 μmol/L. After progression of the reaction, the absorbance was measured at OD 405 nm. Change in OD in case of no addition of the test compound was defined as 100%, and the concentration at which a rise in OD value was reduced by 50% was calculated as $IC_{50}$ (μM).

From this test and Test Example 1, the compound of Reference Example 2-6 was confirmed to be an FXIa-selective inhibitor.

TABLE 7

| Enzyme | $IC_{50}$ of Reference Example 2-6 (μM) |
|---|---|
| Thrombin | >10 |
| TF:FVIIa complex | >10 |
| FIXa | >10 |
| FXa | >10 |
| FXIIa | >10 |
| Plasmin | >10 |
| Urokinase | >10 |
| t-PA | >10 |
| Plasma kallikrein | 0.43 |
| Tryptase | >10 |
| Trypsin | >10 |

Test Example 4

In Vivo Antithrombotic Effect Evaluation Test Using Rabbit

Rabbit venous thrombus models were prepared by a modification of the report of Wong et al. (Wong P C. et al., J. Pharmacol. Exp. Ther. 292: 351-357 (2000)). Male rabbits (JW, 2 to 4 kg) were anesthetized by the inhalation of isoflurane (ISOFLU®, manufactured by DS Pharma Animal Health Co., Ltd.) (introduced anesthesia: 4%, continuous anesthesia: 1.5 to 2.5%). A tracheostomy tube was inserted to each rabbit, which was then ventilated using a respirator. For the intravenous administration of a test drug and blood collection, catheters were inserted to the right femoral vein and the right femoral artery, respectively. An arteriovenous shunt filled with saline was inserted to the carotid artery and the jugular vein. The arteriovenous shunt was prepared by connecting Atom extension tubes (4Fr) having lengths of 15 cm and 13 cm to the artery side and the vein side, respectively, of a polyethylene tube (length: 60 cm, outside diameter: 11.1 mm, inside diameter: 7.9 mm). Also, 4-0 silk thread having a length of 5 cm was indwelled in the arteriovenous shunt. Blood was sent for 30 minutes from the carotid artery to the jugular vein via the arteriovenous shunt. The shunt was removed, and the weight of the silk thread covered with thrombus was measured. The weight of the silk thread measured before the experiment was subtracted from the measured weight, and the obtained value was used as a wet thrombus weight. One hour before the open of the arteriovenous shunt, the test drug or a vehicle was promptly intravenously administered (0.67 mL/kg) and then continuously intravenously administered (1 mL/kg/hr). The continuous injection was continued throughout the experiment. Further, an existing anticoagulant dabigatran (antithrombin drug) and rivaroxaban (FXa inhibitor) were tested as control drugs.

In order to measure aPTT of blood samples as an index for the intrinsic coagulation pathway, blood was collected before administration and immediately before cessation of blood flow, and plasma was prepared using 3.2% sodium citrate. After incubation at 37° C. for 6 minutes, an STA reagent Cephascreen (for aPTT assay; manufactured by Roche Diagnostics K.K.) was added in an amount equal thereto, and the mixture was further incubated for 4 minutes. STA calcium chloride (manufactured by Roche Diagnostics K.K.) was added in an amount equal thereto, and the time required for coagulation was measured.

In order to measure prothrombin time (PT) of blood samples as an index for the extrinsic coagulation pathway, blood was collected before administration and immediately before cessation of blood flow, and plasma was prepared using 3.2% sodium citrate. After incubation at 37° C. for 10 minutes, Neoplastin Plus (for PT assay; manufactured by Roche Diagnostics K.K.) was added in a double amount, and the time required for coagulation was measured.

In this test, the compound of Reference Example 2-6 prolonged aPTT without influencing the PT time, suggesting that this compound lowered the thrombus weight via the inhibition of FXIa, one of the intrinsic coagulation factors (see FIG. 1 and Table 8). Thus, this compound is expected to be able to serve as a novel anticoagulant.

TABLE 8

| Compound | Vehicle1 | Dabigatran etexilate | | |
|---|---|---|---|---|
| Dose (mg/kg + mg/kg/h) Prompt intravenous administration + continuous intravenous administration | 0 + 0 | 0.01 + 0.015 | 0.03 + 0.045 | 0.1 + 0.15 |
| Thrombus weight (mg) | 103 ± 2 | 62 ± 18 | 32 ± 9 | 12 ± 4 |
| aPTT (ratio) | 0.98 ± 0.04 | 1.28 ± 0.07 | 1.58 ± 0.15 | 2.34 ± 0.12 |
| PT (ratio) | 0.99 ± 0.01 | 1.07 ± 0.02 | 1.23 ± 0.10 | 2.29 ± 0.29 |
| **Compound** | **Vehicle2** | **Rivaroxaban** | | |
| Dose (mg/kg + mg/kg/h) Prompt intravenous administration + continuous intravenous administration | 0 + 0 | 0.03 + 0.045 | 0.1 + 0.15 | 0.3 + 0.45 |
| Thrombus weight (mg) | 112 ± 14 | 92 ± 19 | 58 ± 9 | 29 ± 10 |
| aPTT (ratio) | 1.00 ± 0.04 | 1.22 ± 0.06 | 1.50 ± 0.09 | 1.87 ± 0.14 |
| PT (ratio) | 0.99 ± 0.02 | 1.23 ± 0.05 | 1.73 ± 0.15 | 2.87 ± 0.33 |
| **Compound** | **Compound of Reference Example 2-6** | | | |
| Dose (mg/kg + mg/kg/h) Prompt intravenous administration + continuous intravenous administration | 0.15 + 0.225 | 0.5 + 0.75 | 1.5 + 2.25 | 5.0 + 7.5 |

TABLE 8-continued

| | | | | |
|---|---|---|---|---|
| Thrombus weight (mg) | 81 ± 12 | 66 ± 22 | 36 ± 6 | 16 ± 6 |
| aPTT (ratio) | 1.24 ± 0.08 | 1.59 ± 0.15 | 1.84 ± 0.10 | 2.35 ± 0.09 |
| PT (ratio) | 1.01 ± 0.02 | 1.00 ± 0.02 | 1.01 ± 0.00 | 1.02 ± 0.02 |

Data is indicated by mean ± standard deviation (n = 27 only for vehicle 2, n = 3 to 8/group for the others). The vehicle for dabigatran etexilate was vehicle 1, and the vehicle for rivaroxaban and Reference Example 2-6 was vehicle 2.

Test Example 5

Bleeding Time Evaluation Test Using Rabbit Nail Bleeding Model

Rabbit nail bleeding models were prepared by a modification of the report of Wong et al. (Wong P C. et al., J. Thromb. Haemost. 7: 1313-1320 (2009)). Male rabbits (JW, 1.5 to 3.5 kg) were anesthetized by the inhalation of isoflurane (ISOFLU®, manufactured by DS Pharma Animal Health Co., Ltd.) (introduced anesthesia: 4%, continuous anesthesia: 2 to 3%).

For the intravenous administration of a test drug or a vehicle, an indwelling needle was inserted to the auricular vein, and the test drug or the vehicle was promptly intravenously administered (0.67 mL/kg) and then continuously intravenously administered (1 mL/kg/hr). One hour after the start of administration, three posterior toenails were cut and dipped in saline heated to approximately 37° C., and the bleeding time was measured. The bleeding time was defined as a time from the cutting to the arrest of bleeding, and an average value from the three nails was used. The measurement time was 30 minutes at the maximum for experiment 1 and 60 minutes at the maximum for experiment 2. In each experiment, if bleeding for 30 minutes or 60 minutes or longer was confirmed, the bleeding time was regarded as 30 minutes or 60 minutes.

In this test, the compound of Reference Example 2-6 had smaller influence on the bleeding time than that of the existing anticoagulants dabigatran and rivaroxaban. Thus, this compound is expected to be able to serve as a novel anticoagulant with a reduced risk of bleeding (see Table 9).

TABLE 9

Experiment 1

| Compound | Vehicle1 | Dabigatran etexilate | | |
|---|---|---|---|---|
| Dose (mg/kg + mg/kg/h) Prompt intravenous administration + continuous intravenous administration | 0 + 0 | 0.03 + 0.045 | 0.1 + 0.15 | 0.3 + 0.45 |
| Bleeding time (sec) | 479 ± 84 | 1276 ± 353 | 1800 ± 0 | 1800 ± 0 |
| Bleeding time (fold-increase) | 1.0 | 2.7 ± 0.7 | 3.8 ± 0.0 | 3.8 ± 0.0 |

| Compound | Vehicle2 | Rivaroxaban | | |
|---|---|---|---|---|
| Dose (mg/kg + mg/kg/h) Prompt intravenous administration + continuous intravenous administration | 0 + 0 | 0.03 + 0.045 | 0.1 + 0.15 | 0.3 + 0.45 |
| Bleeding time (sec) | 458 ± 113 | 1031 ± 319 | 1369 ± 334 | 1733 ± 110 |
| Bleeding time (fold-increase) | 1.0 | 2.3 ± 0.7 | 3.0 ± 0.7 | 3.8 ± 0.2 |

Experiment 2

| Compound | Vehicle2 | Compound of Reference Example 2-6 | | | |
|---|---|---|---|---|---|
| Dose (mg/kg + mg/kg/h) Prompt intravenous administration + continuous intravenous administration | 0 + 0 | 0.5 + 0.75 | 1.5 + 2.25 | 5.0 + 7.5 | 15 + 22..5 |
| Bleeding time (sec) | 576 ± 152 | 843 ± 270 | 772 ± 234 | 768 ± 236 | 656 ± 198 |
| Bleeding time (fold-increase) | 1.0 | 1.5 ± 0.5 | 1.3 ± 0.4 | 1.3 ± 0.4 | 1.1 ± 0.3 |

Data is indicated by mean ± standard deviation (n = 3 to 14/group). The vehicle for dabigatran etexilate was vehicle 1, and the vehicle for rivaroxaban and Reference Example 2-6 was vehicle 2. The bleeding time (fold-increase) was calculated as a ratio to the average value of the vehicle administration group.

Test Example 6

Ester Metabolism Stability Test (1) Stability Test in Human Liver

A reaction solution containing 5 μL of human liver S9 (manufactured by Sekisui XenoTech, LLC, 20 mg/mL) mixed with 20 μL of 500 mmol/L Kpi (pH 7.4), 40 μL of a 5 mmol/L aqueous solution of NADPH (manufactured by Oriental Yeast Co., Ltd.), and 133 μL of ion-exchange water was added to 2 μL of a DMSO solution containing a 100 μmol/L test substance, and the mixture was incubated at 37° C. for 20 minutes. After the incubation, the metabolic reaction was terminated by the addition of 600 μL of acetonitrile. The residual rate of the test substance was measured using LC (LC-20A manufactured by Shimadzu Corp.)-MS (API4000 manufactured by AB Sciex Pte Ltd.). The results are shown in Table 10.

(2) Stability Test in Human Plasma

198 μL of human plasma (manufactured by Cosmo Bio Inc.) was added to 2 μL of a DMSO solution containing a 100 μmol/L test substance, and the mixture was incubated at 37° C. for 20 minutes. After the incubation, the metabolic reaction was terminated by the addition of 600 μL of acetonitrile. The residual rate of the test substance was measured using LC (LC-20A manufactured by Shimadzu Corp.)-MS (API4000 manufactured by AB Sciex Pte Ltd.). The results are shown in Table 10.

In these tests, the present compound was excellent in metabolic properties in human plasma and is therefore expected to effectively exert intended FXIa inhibition activity and the like by oral administration.

TABLE 10

| | Residual rate (%) | |
|---|---|---|
| Example | Human liver S9 | Human plasma |
| 1 | 87 | 29 |
| 4 | 91 | 26 |
| 6 | 67 | 7.9 |
| 7 | 71 | <1 |
| 10 | 98 | 6.7 |
| 13 | 69 | 21 |
| 14 | 47 | <1 |
| 15 | 82 | 14 |
| 17 | >99 | 50 |
| 18 | 78 | 15 |
| 19 | 93 | 15 |
| 20 | 93 | 11 |

In this test, the compounds of Examples 1, 4, 6, and 7 were found to be converted to the compound of Reference Example 2-6 by metabolism in the human body. Likewise, the compounds of Examples 10, 13, and 14 were found to be converted to the compound of Example 24. Furthermore, the compounds of Examples 17 and 18 were found to be converted to the compound of Example 23 by metabolism in the human body. Likewise, the compounds of Examples 15, 19, and 20 were found to be converted to the corresponding compounds of Example 25, Reference Example 19-1, and Reference Example 20-5. The metabolites were identified using LC (LC-Nexera X2 manufactured by Shimadzu Corp.)-MS (API4000 manufactured by AB Sciex Pte Ltd.).

Test Example 7

Dog PK Test (1) Intravenous Administration

The compound of Reference Example 2-6 was dissolved in a mixed solution of saline/0.1 N HCl=9/1, and this solution was intravenously administered at a dose of 1 mg/2 mL/kg to a male beagle. Blood collection was carried out 0.25, 0.5, 1, 2, 4, 6, and 24 hours after administration. 2 mL of blood was collected using a syringe packed with 20 μL of Novo-Heparin Injection, transferred to a centrifugal tube cooled in ice, and centrifuged at 3000 rpm at 4° C. for 10 minutes to prepare plasma. 200 μL of the prepared plasma was added to a tube containing 600 μL of acetonitrile and mixed for approximately 10 seconds using a vortex mixer. Then, the concentration of the compound of Reference Example 2-6 was measured.

Figure 2:
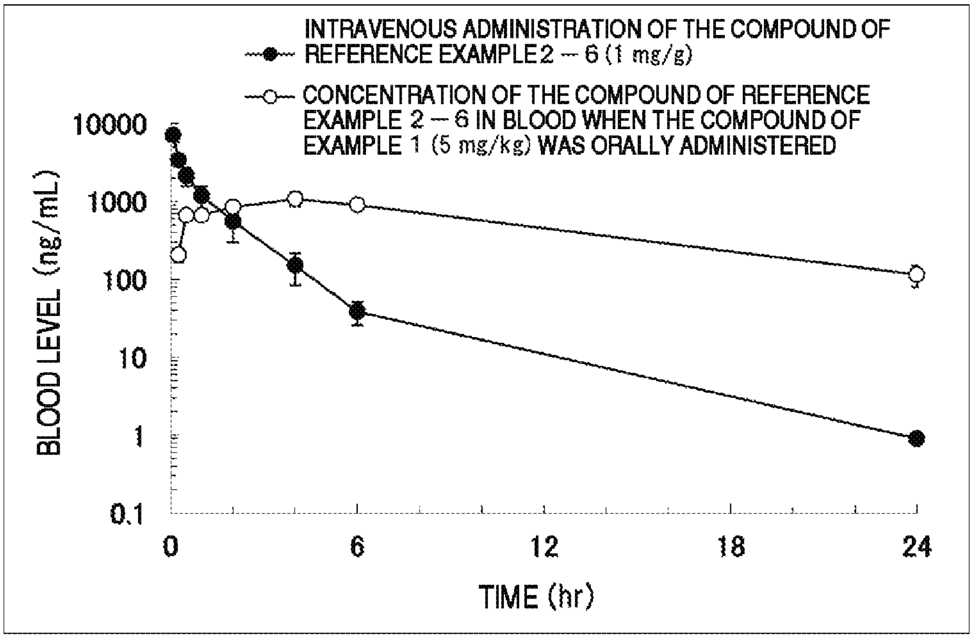
FIG. 2 shows change in the concentration of the compound of Reference Example 2-6 in blood by the administration of the compound of Reference Example 2-6 and a compound of Example 1 to dogs (Test Example 7).

The area under the plasma concentration-time curve (AUC) from 0 hours to 24 hours after the administration of the test sample was 5223 hr·ng/mL (see FIG. 2).

(2) Oral Administration in Fasting State

The compound of Example 1 was dissolved in a 0.5% aqueous methylcellulose solution, and this solution was orally administered at a dose of 5 mg/5 mL/kg to a male beagle fasted for 16 hours. Blood collection was carried out 0.5, 1, 2, 4, 6, and 24 hours after administration. 2 mL of blood was collected using a syringe packed with 20 μL of Novo-Heparin Injection, transferred to a centrifugal tube cooled in ice, and centrifuged at 3000 rpm at 4° C. for 10 minutes to prepare plasma. 200 μL of the prepared plasma was added to a tube containing 600 μL of acetonitrile and mixed for approximately 10 seconds using a vortex mixer. Then, the concentration of the compound of Reference Example 2-6 was measured.

The area under the plasma concentration-time curve (AUC) from 0 hours to 24 hours after the administration of the test sample was 15273 hr·ng/mL. Bioavailability (BA) was 62.8%, and Cmax was 1076.0 ng/mL (see FIG. 2). The compound of Example 1 was confirmed to be a prodrug having excellent oral absorbability.

Test Example 8

Rat PK Test

The compounds of Reference Example 2-6 and Examples 1, 6, and 7 were each suspended in a 0.5% aqueous methylcellulose solution, and each suspension was orally administered at a dose of 10 mg/5 mL/kg to a male rat. Blood collection was carried out 0.25, 0.5, 1, 2, 4, 6, and 24 hours after administration. 0.5 mL of blood was collected from the jugular vein using a 1 mL heparinized syringe without anesthesia, transferred to a centrifugal tube cooled in ice, and centrifuged at 3000 rpm at 4° C. for 10 minutes to prepare plasma. 200 μL of the prepared plasma was added to a tube containing 600 μL of acetonitrile and mixed for approximately 10 seconds using a vortex mixer. Then, the concentration of the compound of Reference Example 2-6 was measured.

The area under the plasma concentration-time curve (AUC) from 0 hours to 24 hours after the administration of the test sample was calculated. From this test, the compounds of Examples 1, 6, and 7 were confirmed to be prodrugs having excellent oral absorbability as compared with the compound of Reference Example 2-6 orally administered directly (see Table 11).

TABLE 11

| Compound | AUC of compound of Reference Example 2-6 (hr · ng/mL) |
|---|---|
| Reference Example 2-6 | 144 |
| Example 1 | 281 |
| Example 6 | 374 |
| Example 7 | 690 |

Test Example 9

Dog PK Test (1) Intravenous Administration

The compound of Reference Example 2-6 was dissolved in a mixed solution of saline/0.1 N HCl=9/1, and this solution was intravenously administered at a dose of 1 mg/2 mL/kg to a male beagle. Blood collection was carried out 0.25, 0.5, 1, 2, 4, 6, and 24 hours after administration. 2 mL of blood was collected using a syringe packed with 20 μL of Novo-Heparin Injection, transferred to a centrifugal tube cooled in ice, and centrifuged at 3000 rpm at 4° C. for 10 minutes to prepare plasma. 200 μL of the prepared plasma was added to a tube containing 600 μL of acetonitrile and mixed for approximately 10 seconds using a vortex mixer. Then, the concentration of the compound of Reference Example 2-6 was measured.

Figure 3:
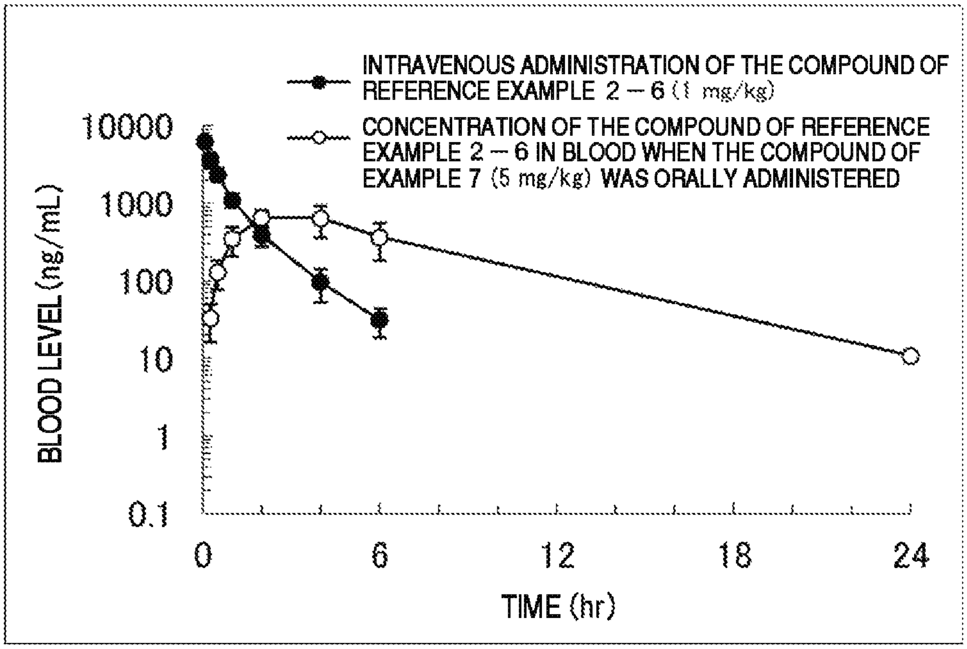
FIG. 3 shows change in the concentration of the compound of Reference Example 2-6 in blood by the administration of the compound of Reference Example 2-6 and a compound of Example 7 (Test Example 9).

The area under the plasma concentration-time curve (AUC) from 0 hours to 24 hours after the administration of the test sample was 4417 hr·ng/mL (see FIG. 3).

(2) Oral Administration in Fasting State

The compound of Example 7 was suspended in a 0.5% aqueous methylcellulose solution, and this suspension was orally administered at a dose of 5 mg/5 mL/kg to a male beagle fasted for 16 hours. Blood collection was carried out 0.5, 1, 2, 4, 6, and 24 hours after administration. 2 mL of blood was collected using a syringe packed with 20 μL of Novo-Heparin Injection, transferred to a centrifugal tube cooled in ice, and centrifuged at 3000 rpm at 4° C. for 10 minutes to prepare plasma. 200 μL of the prepared plasma was added to a tube containing 600 μL of acetonitrile and mixed for approximately 10 seconds using a vortex mixer. Then, the concentration of the compound of Reference Example 2-6 was measured.

The area under the plasma concentration-time curve (AUC) from 0 hours to 24 hours after the administration of the test sample was 6371 hr·ng/mL. Bioavailability (BA) was 31.6%, and Cmax was 726.4 ng/mL (see FIG. 3). The compound of Example 7 was confirmed to be a prodrug having excellent oral absorbability.

Test Example 10

Cynomolgus Monkey aPTT Evaluation Test

The compound of Example 7 was suspended in a 0.5% aqueous methylcellulose solution, and this suspension was orally administered at a dose of 10 mg/5 mL/kg or 30 mg/5 mL/kg to a male cynomolgus monkey fasted for 16 hours. Blood collection for aPTT evaluation was carried out before administration and 0.5, 1, 2, 4, 6, and 24 hours after administration. 0.9 mL of blood was collected using a syringe packed with 100 μL of 3.2% sodium citrate, transferred to a centrifugal tube cooled in ice, and centrifuged at 2100 g at 4° C. for 10 minutes to prepare plasma. After incubation at 37° C. for 6 minutes, an STA reagent Cephascreen (for aPTT assay; manufactured by Roche Diagnostics K.K.) was added in an amount equal to the amount of the plasma, and the mixture was further incubated for 4 minutes. STA calcium chloride (manufactured by Roche Diagnostics K.K.) was added in an amount equal to the amount of the plasma, and the time required for coagulation was measured. Blood collection for the measurement of the compound concentration was carried out 0.5, 1, 2, 4, 6, and 24 hours after administration. 1 mL of blood was collected using a syringe packed with 10 μL of Novo-Heparin Injection, transferred to a centrifugal tube cooled in ice, and centrifuged at 2100 g at 4° C. for 10 minutes to prepare plasma. 200 μL of the prepared plasma was added to a tube containing 600 μL of acetonitrile and mixed for approximately 10 seconds using a vortex mixer. Then, the concentration of the compound of Reference Example 2-6 (a value based on the free form) was measured. The results are shown in Table 12.

From this test, the compound of Example 7 was confirmed to exhibit an anticoagulant effect over time after oral administration.

TABLE 12

| | Compound of Example 7 | | | | | |
|---|---|---|---|---|---|---|
| | 10 mg/kg | | | 30 mg/kg | | |
| Time (hr) | aPTT (sec) | aPTT (ratio) | Concentration of compound of Reference Example 2-6 (ng/mL) | aPTT (sec) | aPTT (ratio) | Concentration of compound of Reference Example 2-6 (ng/mL) |
| 0 | 23.8 ± 2.2 | 1.00 ± 0.00 | — | 23.9 ± 1.6 | 1.00 ± 0.00 | — |
| 0.5 | 26.9 ± 3.3 | 1.13 ± 0.03 | 25.3 | 27.6 ± 3.2 | 1.15 ± 0.10 | 25.5 |
| 1 | 30.5 ± 3.0 | 1.29 ± 0.04 | 64.1 | 32.8 ± 2.8 | 1.37 ± 0.03 | 255.1 |
| 2 | 36.5 ± 4.1 | 1.53 ± 0.07 | 201.6 | 36.9 ± 0.8 | 1.55 ± 0.07 | 600.0 |
| 4 | 38.5 ± 3.5 | 1.62 ± 0.00 | 273.1 | 39.4 ± 1.4 | 1.65 ± 0.12 | 1061.4 |
| 6 | 37.5 ± 4.5 | 1.57 ± 0.06 | 221.5 | 39.4 ± 1.5 | 1.65 ± 0.12 | 1031.0 |
| 24 | 26.1 ± 3.2 | 1.10 ± 0.06 | 10.1 | 34.0 ± 3.3 | 1.42 ± 0.05 | 111.5 |

Data is indicated by mean ± standard deviation (n = 3/group)

Test Example 11

Test on Effect of Combined Use with Antiplatelet Drug Using Rabbit AVST Model

Rabbit venous thrombus models were prepared by a modification of the report of Wong et al. (Wong P C. et al., J. Pharmacol. Exp. Ther. 292: 351-357 (2000)). Male rabbits (JW, 2 to 4 kg) were anesthetized by the inhalation of isoflurane (ISOFLU®, manufactured by DS Pharma Animal Health Co., Ltd.) (introduced anesthesia: 4%, continuous anesthesia: 1.5 to 2.5%). A tracheostomy tube was inserted to each rabbit, which was then ventilated using a respirator. For the intravenous administration of a test drug and blood collection, catheters were inserted to the right femoral vein and the right femoral artery, respectively. An arteriovenous shunt filled with saline was inserted to the carotid artery and the jugular vein. The arteriovenous shunt was prepared by connecting Atom extension tubes (4Fr) having lengths of 15 cm and 13 cm to the artery side and the vein side, respectively, of a polyethylene tube (length: 60 cm, outside diameter: 11.1 mm, inside diameter: 7.9 mm). Also, 4-0 silk thread having a length of 5 cm was indwelled in the arteriovenous shunt. Blood was sent for 30 minutes from the carotid artery to the jugular vein via the arteriovenous shunt. The shunt was removed, and the weight of the silk thread covered with thrombus was measured. The weight of the silk thread measured before the experiment was subtracted from the measured weight, and the obtained value was used as a wet thrombus weight. One hour before the open of the arteriovenous shunt, the test drug or a vehicle was promptly intravenously administered (0.67 mL/kg) and then continuously intravenously administered (1 mL/kg/hr). The continuous injection was continued throughout the experiment.

In order to measure activated partial thromboplastin time of blood samples as an index for the intrinsic coagulation pathway, blood was collected before administration and immediately before cessation of blood flow, and plasma was prepared using 3.2% sodium citrate. After incubation at 37° C. for 6 minutes, an STA reagent Cephascreen (for aPTT assay; manufactured by Roche Diagnostics K.K.) was added in an amount equal thereto, and the mixture was further incubated for 4 minutes. STA calcium chloride (manufactured by Roche Diagnostics K.K.) was added in an amount equal thereto, and the time required for coagulation was measured.

In order to measure prothrombin time of blood samples as an index for the extrinsic coagulation pathway, blood was collected before administration and immediately before cessation of blood flow, and plasma was prepared using 3.2% sodium citrate. After incubation at 37° C. for 10 minutes, Neoplastin Plus (for PT assay; manufactured by Roche Diagnostics K.K.) was added in a double amount, and the time required for coagulation was measured. The results are shown in Table 13.

From this test, the compound of Reference Example 2-6 was confirmed to strongly lower thrombus weight by combined use with an antiplatelet drug.

TABLE 13

| Compound | Vehicle | Rivaroxaban | | Compound of Reference Example 2-6 | |
|---|---|---|---|---|---|
| Dose (mg/kg + mg/kg/h) Prompt intravenous administration + continuous intravenous administration | 0 + 0 | 0.03 + 0.045 | 0.1 + 0.15 | 0.5 + 0.75 | 1.5 + 2.25 |
| Thrombus weight (mg) | 112 ± 14 | 92 ± 19 | 58 ± 9 | 66 ± 22 | 36 ± 6 |
| aPTT (ratio) | 1.00 ± 0.04 | 1.22 ± 0.06 | 1.50 ± 0.09 | 1.59 ± 0.15 | 1.84 ± 0.10 |
| PT (ratio) | 0.99 ± 0.02 | 1.23 ± 0.05 | 1.73 ± 0.15 | 1.00 ± 0.02 | 1.01 ± 0.00 |
| **Compound** | **Aspirin** | **Aspirin + Rivaroxaban** | | **Aspirin + Compound of Reference Example 2-6** | |
| Dose (mg/kg + mg/kg/h) Prompt intravenous administration + continuous intravenous administration | 0.67 + 1.0 | (0.67 + 1.0) + (0.03 + 0.045) | (0.67 + 1.0) + (0.1 + 0.15) | (0.67 + 1.0) + (0.5 + 0.75) | (0.67 + 1.0) + (1.5 + 2.25) |
| Thrombus weight (mg) | 96 ± 9 | 87 ± 8 | 52 ± 11 | 54 ± 11 | 28 ± 4 |
| aPTT (ratio) | 0.97 ± 0.01 | 1.21 ± 0.02 | 1.50 ± 0.05 | 1.62 ± 0.13 | 1.90 ± 0.08 |
| PT (ratio) | 0.99 ± 0.01 | 1.25 ± 0.05 | 1.85 ± 0.08 | 1.01 ± 0.04 | 0.99 ± 0.01 |

Data is indicated by mean ± standard deviation (n = 27 only for vehicle 2, n = 5 to 8/group for the others).

Test Example 13

Study on Effect of Combined Use with Antiplatelet Drug Using Rabbit Nail Bleeding Model Rabbit nail bleeding models were prepared by a modification of the report of Wong et al. (Wong P C. et al., J. Thromb. Haemost. 7: 1313-1320 (2009)). Male rabbits (JW, 1.5 to 3.5 kg) were anesthetized by the inhalation of isoflurane (ISOFLU®, manufactured by DS Pharma Animal Health Co., Ltd.) (introduced anesthesia: 4%, continuous anesthesia: 2 to 3%). For the intravenous administration of a test drug or a vehicle, an indwelling needle was inserted to the auricular vein, and the test drug or the vehicle was promptly intravenously administered (0.67 mL/kg) and then continuously intravenously administered (1 mL/kg/hr). One hour after the start of administration, three posterior toenails were cut and dipped in saline heated to approximately 37° C., and the bleeding time was measured. The bleeding time was defined as a time from the cutting to the arrest of bleeding, and an average value from the three nails was used. The measurement time was 60 minutes at the maximum. If bleeding for 60 minutes or longer was confirmed, the bleeding time was regarded as 60 minutes. The results are shown in Table 14.

In this test, the combined use of the compound of Reference Example 2-6 with aspirin had smaller influence on the bleeding time than that of the existing anticoagulant rivaroxaban. Thus, this compound is able to serve as a novel anticoagulant with a small risk of bleeding even when used in combination with an antiplatelet drug.

TABLE 14

| Compound | Vehicle | Rivaroxaban | | Compound of Reference Example 2-6 | |
|---|---|---|---|---|---|
| Dose (mg/kg + mg/kg/h) Prompt intravenous administration + continuous intravenous administration | 0 + 0 | 0.03 + 0.045 | 0.1 + 0.15 | 1.5 + 2.25 | 5.0 + 7.5 |
| Bleeding time (sec) | 576 ± 152 | 1614 ± 869 | 2445 ± 964 | 772 ± 234 | 768 ± 236 |
| Bleeding time (fold-increase) | 1.0 | 2.8 ± 1.5 | 4.2 ± 1.7 | 1.3 ± 0.4 | 1.3 ± 0.4 |
| Compound | Aspirin | Aspirin + Rivaroxaban | | Aspirin + Compound of Reference Example 2-6 | |
| Dose (mg/kg + mg/kg/h) Prompt intravenous administration + continuous intravenous administration | 0.67 + 1.0 | (0.67 + 1.0) + (0.03 + 0.045) | (0.67 + 1.0) + (0.1 + 0.15) | (0.67 + 1.0) + (1.5 + 2.25) | (0.67 + 1.0) + (5.0 + 7.5) |
| Bleeding time (sec) | 1087 ± 522 | 1653 ± 463 | 2771 ± 606 | 1089 ± 546 | 965 ± 379 |
| Bleeding time (fold-increase) | 1.9 ± 0.9 | 2.9 ± 0.8 | 4.8 ± 1.1 | 1.9 ± 1.0 | 1.7 ± 0.7 |

Data is indicated by mean ± standard deviation (n = 5 to 14/group). The bleeding time (fold-increase) was calculated as a ratio to the average value of the vehicle administration group.

INDUSTRIAL APPLICABILITY

The present compound has an excellent anticoagulant effect and oral absorbability and is useful as a drug for treating thrombosis or the like. The contents of the references cited herein are incorporated herein by reference in their entirety.

The invention claimed is:

1. A compound represented by formula (1) or a pharmaceutically acceptable salt thereof:

(1)

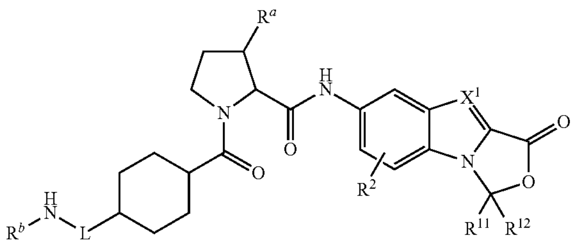

wherein

L represents an optionally substituted $C_{1-4}$ alkylene group;

$R^{11}$ and $R^{12}$ each independently represent a hydrogen atom, an optionally substituted $C_{1-6}$ alkyl group, an optionally substituted $C_{3-8}$ cycloalkyl group, an optionally substituted phenyl group, an optionally substituted 5- or 6-membered heteroaryl group, or an optionally substituted 3- to 8-membered saturated heterocyclic group, or together form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of a halogen atom, hydroxy, cyano, $C_{1-6}$ alkoxy, and $C_{1-6}$ alkyl;

$X^1$ represents N or $CR^1$;

$R^1$ and $R^2$ each independently represent a hydrogen atom, a halogen atom, a $C_{1-6}$ alkoxy group, or a $C_{1-6}$ alkyl group;

$R^a$ represents an optionally substituted $C_{4-7}$ cycloalkyl group, an optionally substituted phenyl group, an optionally substituted pyridyl group, an optionally substituted 4- to 7-membered saturated heterocyclic group, an optionally substituted $C_{1-6}$ alkoxy group, an optionally substituted $C_{4-7}$ cycloalkoxy group, an optionally substituted phenoxy group, or an optionally substituted 4- to 7-membered saturated heterocyclyloxy group; and $R^b$ represents a hydrogen atom, a $C_{1-6}$ alkoxycarbonyl group, a group represented by the following formula (2a):

(2a)

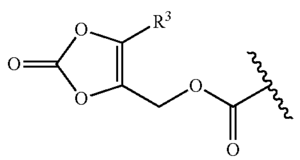

wherein $R^3$ represents a hydrogen atom or a $C_{1-6}$ alkyl group, or a group represented by the following formula (2b):

(2b)

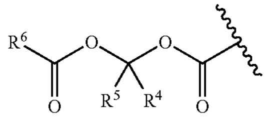

wherein $R^4$ and $R^5$ each independently represent a hydrogen atom or a $C_{1-6}$ alkyl group; and $R^6$ represents a $C_{1-6}$ alkyl group.

2. The compound according to claim 1 or a pharmaceutically acceptable salt thereof, wherein L is a $C_{1-4}$ alkylene group which may be optionally substituted by 1 to 3 identical or different groups selected from the group consisting of a halogen atom, an oxo group, a hydroxy group, and a $C_{1-6}$ alkoxy group;

$R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the $C_{3-8}$ cycloalkyl group (3), or (6) a 3- to 8-membered saturated heterocyclic group which may be optionally substituted by 1 to 4 identical or different groups selected from the group consisting of the substituents (a) to (f) in the $C_{3-8}$ cycloalkyl group (3), or $R^{11}$ and $R^{12}$ form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_{3-8}$ cycloalkyl group (3); and $R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (2) a phenyl group which may be optionally substituted by 1 to 4 identical or different groups selected from the group consisting of the substituents (a) to (e) in the $C_{4-7}$ cycloalkyl (1), (3) a pyridyl group which may be optionally substituted by 1 to 4 identical or different groups selected from the group consisting of the substituents (a) to (e) in the $C_{4-7}$ cycloalkyl (1), (4) a 4- to 7-membered saturated heterocyclic group which may be optionally substituted by 1 to 4 identical or different groups selected from the group consisting of the substituents (a) to (f) in the $C_{4-7}$ cycloalkyl (1), or (5) a $C_{1-6}$ alkoxy group which may be optionally substituted by (a) a halogen atom, (b) $C_{1-6}$ alkoxy, (c) $C_{4-7}$ cycloalkyl which may be optionally substituted by 1 to 4 identical or different groups selected from the group consisting of the substituents (a) to (f) in the $C_{4-7}$ cycloalkyl (1), (d) phenyl which may be optionally substituted by 1 to 4 identical or different groups selected from the group consisting of the substituents (a) to (e) in the $C_{4-7}$ cycloalkyl (1), (e) pyridyl which may be optionally substituted by 1 to 3 identical or different groups selected from the group consisting of the substituents (a) to (e) in the $C_{4-7}$ cycloalkyl (1), or (f) a 4- to 7-membered saturated heterocyclic ring which may be optionally substituted by 1 to 4 identical or different groups selected from the group consisting of the substituents (a) to (f) in the $C_{4-7}$ cycloalkyl (1), (6) a $C_{4-7}$ cycloalkoxy group which may be optionally substituted by 1 to 4 identical or different groups selected from the group consisting of the substituents (a) to (f) in the $C_{4-7}$ cycloalkyl (1), (7) a phenoxy group which may be optionally substituted by 1 to 4 identical or different groups selected from the group consisting of the substituents (a) to (e) in the $C_{4-7}$ cycloalkyl (1), or (8) a 4- to 7-membered saturated heterocyclyloxy group which may be optionally substituted by 1 to 4 identical or different groups selected from the group consisting of the substituents (a) to (f) in the $C_{4-7}$ cycloalkyl (1).

3. The compound according to claim 1 or a pharmaceutically acceptable salt thereof, wherein L is a $C_{1-4}$ alkylene group which may be optionally substituted by 1 to 3 fluorine atoms.

4. The compound according to claim 1 or a pharmaceutically acceptable salt thereof, wherein $R^b$ is a hydrogen atom or a group represented by the following formula (2a):

(2a)

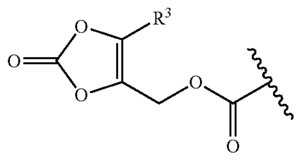

wherein $R^3$ represents a hydrogen atom or a $C_{1-6}$ alkyl group.

5. The compound according to claim 1 or a pharmaceutically acceptable salt thereof, wherein $R^a$ is (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, (2) a phenyl group which may be optionally substituted by 1 to 4 identical or different groups selected from the group consisting of the substituents (a) to (c) in the $C_{4-7}$ cycloalkyl group (1), or (3) a 4- to 7-membered saturated heterocyclic group which may be optionally substituted by 1 to 4 identical or different groups selected from the group consisting of the substituents (a) to (c) in the $C_{4-7}$ cycloalkyl group (1).

6. The compound according to claim 1 or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3).

7. The compound according to claim 1 or a pharmaceutically acceptable salt thereof, wherein $R^{11}$ and $R^{12}$ are each independently a hydrogen atom or a $C_{1-6}$ alkyl group which may be optionally substituted by 1 to 3 identical or different halogen atoms.

8. The compound according to claim 1 or a pharmaceutically acceptable salt thereof, wherein $R^{11}$ and $R^{12}$ form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and $C_{1-6}$ alkyl.

9. The compound according to claim 1 or a pharmaceutically acceptable salt thereof, wherein L is a $C_{1-4}$ alkylene group substituted by 1 to 3 fluorine atoms.

10. The compound according to claim 1 or a pharmaceutically acceptable salt thereof, wherein the compound is represented by formula (2):

(2)

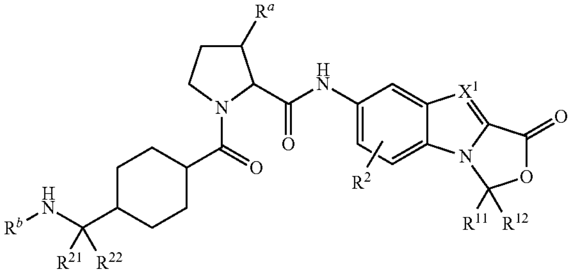

wherein $R^{11}$, $R^{12}$, $R^a$, $R^b$, $X^1$, and $R^2$ are the same as defined in claim 1, and $R^{21}$ and $R^{22}$ each independently represent a hydrogen atom, a fluorine atom, or a methyl group which may be optionally substituted by 1 to 3 fluorine atoms.

11. The compound according to claim 10 or a pharmaceutically acceptable salt thereof, wherein $R^{11}$ and $R^1$ are each independently (1) a hydrogen atom, (2) a $C_{1-6}$ alkyl group which may be optionally substituted by 1 to 3 identical or different groups selected from the group consisting of (a) a halogen atom, (b) hydroxy, (c) cyano, (d) $C_{1-6}$ alkoxy, and (e) $C_{4-7}$ cycloalkyl, (3) a $C_{3-8}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (4) a phenyl group which may be optionally substituted by 1 to 4 identical or different groups selected from the group consisting of the substituents (a) to (e) in the $C_{3-8}$ cycloalkyl group (3), (5) a 5- or 6-membered heteroaryl group which may be optionally substituted by 1 to 4 identical or different groups selected from the group consisting of the substituents (a) to (e) in the $C_{3-8}$ cycloalkyl group (3), or (6) a 3- to 8-membered saturated heterocyclic group which may be optionally substituted by 1 to 4 identical or different groups selected from the group consisting of the substituents (a) to (f) in the $C_{3-8}$ cycloalkyl group (3), or $R^{11}$ and $R^{12}$ optionally form, together with the carbon atom bonded thereto, a 3- to 8-membered cycloalkane ring or a 3- to 8-membered saturated heterocyclic ring wherein the 3- to 8-membered cycloalkane ring and the 3- to 8-membered saturated heterocyclic ring may be each optionally substituted by 1 to 4 identical or different groups selected from the group consisting of the substituents (a) to (e) in the $C_{3-8}$ cycloalkyl group (3); and $R^a$ is (1) a $C_{4-7}$ cycloalkyl group which may be optionally substituted by 1 to 4 identical or different groups selected from the group consisting of (a) a halogen atom, (b) hydroxy, (c) cyano, (d) $C_{1-6}$ alkoxy, (e) $C_{1-6}$ alkyl, and (f) oxo, (2) a phenyl group which may be optionally substituted by 1 to 4 identical or different groups selected from the group consisting of the substituents (a) to (e) in the $C_{4-7}$ cycloalkyl group (1), (3) a pyridyl group which may be optionally substituted by 1 to 4 identical or different groups selected from the group consisting of the substituents (a) to (e) in the $C_{4-7}$ cycloalkyl group (1), (4) a 4- to 7-membered saturated heterocyclic group which may be optionally substituted by 1 to 4 identical or different groups selected from the group consisting of the substituents (a) to (f) in the $C_{4-7}$ cycloalkyl group (1), (5) a $C_{4-7}$ cycloalkoxy group which may be optionally substituted by 1 to 4 identical or different groups selected from the group consisting of the substituents (a) to (f) in the $C_{4-7}$ cycloalkyl group (1), or (6) a phenoxy group which may be optionally substituted by 1 to 4 identical or different groups selected from the group consisting of the substituents (a) to (e) in the $C_{4-7}$ cycloalkyl group (1).

12. The compound according to claim 10 or a pharmaceutically acceptable salt thereof, wherein $R^a$ is (1) a $C_{4-7}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, (2) a phenyl group which may be optionally substituted by 1 to 4 identical or different groups selected from the group consisting of the substituents (a) to (c) in the $C_{4-7}$ cycloalkyl group (1), or (3) a 4- to 7-membered saturated heterocyclic group which may be optionally substituted by 1 to 4 identical or different groups selected from the group consisting of the substituents (a) to (c) in the $C_{4-7}$ cycloalkyl group (1).

13. The compound according to claim 10 or a pharmaceutically acceptable salt thereof, wherein $R^{11}$ and $R^{12}$ are each independently (1) a hydrogen atom, (2) a $C_{1-6}$ alkyl group which may be optionally substituted by 1 to 3 identical or different groups selected from the group consisting of (a) a halogen atom, (b) $C_{1-6}$ alkoxy, and (c) $C_{4-7}$ cycloalkyl, (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or (4) a phenyl group which may be optionally substituted by 1 to 4 identical or different groups selected from the group consisting of the substituents (a) to (c) in the $C_{3-8}$ cycloalkyl group (3).

14. The compound according to claim 10 or a pharmaceutically acceptable salt thereof, wherein $R^{11}$ and $R^{12}$ are each independently a hydrogen atom or a $C_{1-6}$ alkyl group which may be optionally substituted by 1 to 3 identical or different halogen atoms.

15. The compound according to claim 10 or a pharmaceutically acceptable salt thereof, wherein $R^{11}$ and $R^{12}$ form, together with the carbon atom bonded thereto, a 4- to 7-membered cycloalkane ring or a 4- to 7-membered saturated heterocyclic ring wherein the 4- to 7-membered cycloalkane ring and the 4- to 7-membered saturated heterocyclic ring may be each optionally substituted by 1 to 4 identical or different groups selected from the group consisting of a halogen atom and $C_{1-6}$ alkyl.

16. The compound according to claim 10 or a pharmaceutically acceptable salt thereof, wherein $R^b$ is a hydrogen atom or a group represented by the following formula (2a):

(2a)

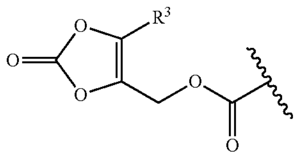

wherein $R^3$ represents a hydrogen atom or a $C_{1-6}$ alkyl group.

17. The compound according to claim 1 or a pharmaceutically acceptable salt thereof, wherein $R^{21}$ is a hydrogen atom, and $R^{22}$ is a methyl group substituted by 1 to 3 fluorine atoms.

18. The compound according to claim 1 or a pharmaceutically acceptable salt thereof, wherein $X^1$ is $CR^1$, and each of $R^1$ and $R^2$ is a hydrogen atom.

19. The compound according to claim 1 or a pharmaceutically acceptable salt thereof, wherein the compound is represented by formula (3):

(3)

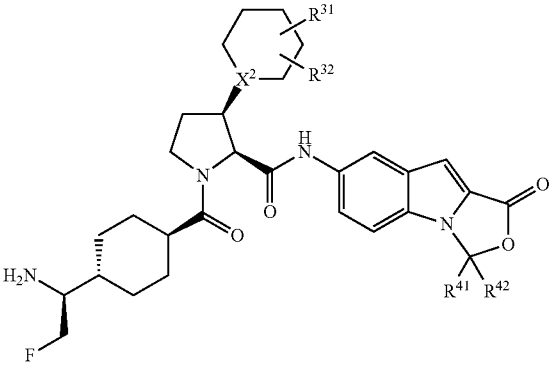

wherein $R^{41}$ and $R^{42}$ each independently represent (1) a hydrogen atom, (2) a $C_{1-6}$ alkyl group which may be optionally substituted by 1 to 4 identical or different groups selected from the group consisting of (a) a halogen atom, (b) $C_{1-6}$ alkoxy, and (c) $C_{4-7}$ cycloalkyl, or (3) a $C_{3-8}$ cycloalkyl group which may be optionally substituted by 1 to 4 identical or different groups selected from the group consisting of (a) a halogen atom, (b) $C_{1-6}$ alkoxy, and (c) $C_{1-6}$ alkyl, or $R^{41}$ and $R^{42}$ together form, together with the carbon atom bonded thereto, a 4- to 7-membered cycloalkane ring or a 4- to 6-membered saturated heterocyclic ring wherein the 4- to 7-membered cycloalkane ring and the 4- to 6-membered saturated heterocyclic ring may be each optionally substituted by 1 to 4 identical or different groups selected from the group consisting of the substituents (a) to (c) in the $C_{3-8}$ cycloalkyl group (3);

$X^2$ represents N or CH; and $R^{31}$ and $R^{32}$ each independently represent a hydrogen atom, a halogen atom, a $C_{1-6}$ alkoxy group, or a $C_{1-6}$ alkyl group.

20. The compound according to claim 19 or a pharmaceutically acceptable salt thereof, wherein $R^{41}$ and $R^{42}$ are each independently a hydrogen atom or a $C_{1-6}$ alkyl group which may be optionally substituted by 1 to 3 identical or different halogen atoms.

21. The compound according to claim 19 or a pharmaceutically acceptable salt thereof, wherein $R^{41}$ and $R^{42}$ form, together with the carbon atom bonded thereto, a 4- to 6-membered cycloalkane ring or a 4- to 6-membered saturated heterocyclic ring wherein the 4- to 6-membered cycloalkane ring and the 4- to 6-membered saturated heterocyclic ring may be each optionally substituted by 1 to 4 identical or different groups selected from the group consisting of a halogen atom and $C_{1-6}$ alkyl.

22. The compound according to claim 1 or a pharmaceutically acceptable salt thereof, wherein the compound is selected from the following compounds:

(2S,3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-cyclohexylpyrrolidine-2-carboxamide, (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-cyclohexyl-L-prolinamide, (3S)-1-({trans-4-[(1S)-1-amino-2-fluoroethyl]cyclohexyl}carbonyl)-3-cyclohexylhexy-N-(1'-oxo-1'H-spiro[cyclobutane-1,3'-[1,3]oxazolo[3,4-a]indol]-7'-yl)-L-prolinamide, (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-(trans-4-methoxycyclohexyl)-L-prolinamide, (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-(trans-4-methoxycyclohexyl)-L-prolinamide, (3S)-1-({trans-4-[(1S)-1-amino-2-fluoroethyl]cyclohexyl}carbonyl)-3-(trans-4-methoxycyclohexyl)-N-(1'-oxo-1'H-spiro[cyclobutane-1,3'-[1,3]oxazolo[3,4-a]indol]-7'-yl)-L-prolinamide, (3S)-1-{[trans-4-(aminomethyl)cyclohexyl]carbonyl}-3-cyclohexyl-N-(3,3-dimethyl-1-oxo-1H-[1,3]oxazolo[3,4-a]indol-7-yl)-L-prolinamide, (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-phenyl-L-prolinamide, (3R)-1-({trans-4-[(1 S)-1-amino-2-fluoroethyl]cyclohexyl}carbonyl)-N-(3,3-dimethyl-1-oxo-1H-[1,3]oxazolo[3,4-a]indol-7-yl)-3-phenyl-L-prolinamide, and (3R)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-phenyl-L-prolinamide.

23. The compound according to claim 1 or a pharmaceutically acceptable salt thereof, wherein the compound is (3S)-1-({trans-4-[(1S)-1-amino-2-fluoroethyl]cyclohexyl}carbonyl)-N-[3,3-bis(fluoromethyl)-1-oxo-1H-[1,3]oxazolo[3,4-a]indol-7-yl]-3-cyclohexyl-L-prolinamide.

24. The compound according to claim 1 or a pharmaceutically acceptable salt thereof, wherein the compound is (3S)-1-({trans-4-[(1S)-1-amino-2-fluoroethyl]cyclohexyl}carbonyl)-3-cyclohexyl-N-(1'-oxo-1'H-spiro[cyclobutane-1,3'-[1,3]oxazolo[3,4-a]indol]-7'-yl)-L-prolinamide.

25. The compound according to claim 1 or a pharmaceutically acceptable salt thereof, wherein the compound is (3S)-1-({trans-4-[(1S)-1-amino-2-fluoroethyl]cyclohexyl}carbonyl)-N-(3,3-dimethyl-1-oxo-1H-[1,3]oxazolo[3,4-a]indol-7-yl)-3-(trans-4-methoxycyclohexyl)-L-prolinamide.

26. A method for producing a compound represented by formula (8), comprising converting a compound according to any one of claims 1 to 25 or a pharmaceutically acceptable salt thereof to the compound represented by formula (8) through enzymatic reaction in plasma:

(8)

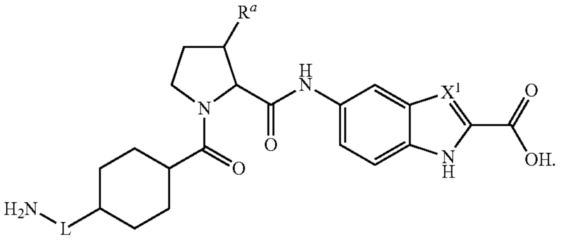

27. A pharmaceutical composition comprising a compound according to claim 1 or a pharmaceutically acceptable salt thereof.

28. A method for treating a disease caused by abnormal blood coagulation involving FXIa, comprising administering a therapeutically effective amount of a compound according to claim 1 or a pharmaceutically acceptable salt thereof to a patient in need of treatment.

29. A medicament comprising a compound according to claim 1, or a pharmaceutically acceptable salt thereof and at least one drug selected from an anticoagulant and an antiplatelet agent.

30. The method according to claim 28, wherein the disease caused by abnormal blood coagulation involving FXIa is thromboembolism.

31. The method according to claim 30, wherein the thromboembolism is venous thrombosis, myocardial infarction, pulmonary embolism, brain embolism, or slowly progressive cerebral thrombosis.

* * * * *

UNITED STATES PATENT AND TRADEMARK OFFICE

CERTIFICATE OF CORRECTION

PATENT NO. : 9,718,840 B2
APPLICATION NO. : 15/110811
DATED : August 1, 2017
INVENTOR(S) : Yohei Ikuma et al.

It is certified that error appears in the above-identified patent and that said Letters Patent is hereby corrected as shown below:

In the Claims

Column 156, Line 42 (Claim 11), please change "$R^{11}$ and $R^{1}$" to --$R^{11}$ and $R^{12}$--;

Column 160, Line 7 (Claim 22), please change "cyclohexyl}carbonyl)-3-cyclohexylhexy-N-(1'-oxo-" to --cyclohexyl}carbonyl)-3-cyclohexyl-N-(1'-oxo- --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Glu (gamma-OR), wherein R=H (50%) and R=CH3 (50%)

<400> SEQUENCE: 1

Ile Xaa Gly Arg
1